US008642774B2

(12) United States Patent
Grauert et al.

(10) Patent No.: US 8,642,774 B2

(45) **Date of Patent: *Feb. 4, 2014**

(54) COMPOUNDS

(71) Applicants: Matthias Grauert, Biberach an der Riss (DE); Daniel Bischoff, Biberach an der Riss (DE); Georg Dahmann, Warthausen-Birkenhard (DE); Raimund Kuelzer, Mittelbiberach (DE); Klaus Rudolf, Warthausen (DE); Bernd Wellenzohn, Friedrichshafen (DE)

(72) Inventors: Matthias Grauert, Biberach an der Riss (DE); Daniel Bischoff, Biberach an der Riss (DE); Georg Dahmann, Warthausen-Birkenhard (DE); Raimund Kuelzer, Mittelbiberach (DE); Klaus Rudolf, Warthausen (DE); Bernd Wellenzohn, Friedrichshafen (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/692,019

(22) Filed: Dec. 3, 2012

(65) Prior Publication Data

US 2013/0150341 A1 Jun. 13, 2013

(30) Foreign Application Priority Data

Dec. 8, 2011 (EP) .................................... 11192576

(51) Int. Cl.

| | |
|---|---|
| ***C07D 401/00*** | (2006.01) |
| ***C07D 211/00*** | (2006.01) |
| ***C07D 295/00*** | (2006.01) |
| ***C07D 421/00*** | (2006.01) |
| ***C07D 405/00*** | (2006.01) |
| ***C07D 409/00*** | (2006.01) |
| ***C07D 413/00*** | (2006.01) |
| ***C07D 213/02*** | (2006.01) |
| ***C07D 211/60*** | (2006.01) |

(52) U.S. Cl.

USPC ..................... 546/272.4; 546/184; 546/268.1; 546/192; 546/194; 546/245; 514/383; 514/315; 514/336; 514/252.05

(58) Field of Classification Search

USPC ....................................................... 546/272.4

See application file for complete search history.

(56) References Cited

U.S. PATENT DOCUMENTS

| | | | | |
|---|---|---|---|---|
| 7,582,635 | B2 | 9/2009 | Sun et al. | |
| 8,008,300 | B2 | 8/2011 | Sun et al. | |
| 8,048,890 | B2 * | 11/2011 | Buschmann et al. ......... | 514/278 |
| 2003/0055085 | A1 * | 3/2003 | Wagenen et al. ............. | 514/333 |
| 2004/0186111 | A1 | 9/2004 | Sun et al. | |
| 2005/0256130 | A1 | 11/2005 | Pennell et al. | |
| 2010/0004254 | A1 | 1/2010 | Sun et al. | |
| 2012/0004217 | A1 | 1/2012 | Sun et al. | |
| 2012/0015954 | A1 | 1/2012 | Sun et al. | |

FOREIGN PATENT DOCUMENTS

| | | | |
|---|---|---|---|
| WO | 9749395 | | 12/1997 |
| WO | 03051833 | A2 | 6/2003 |
| WO | 0353922 | A2 | 7/2003 |
| WO | 03105853 | A1 | 12/2003 |
| WO | 2004058754 | A1 | 7/2004 |
| WO | 2005030128 | A2 | 4/2005 |
| WO | 2005056015 | A1 | 6/2005 |
| WO | 2007021573 | A1 | 2/2007 |
| WO | 2007087135 | A2 | 8/2007 |
| WO | WO2008112440 | * | 9/2008 |
| WO | 2008145616 | A1 | 12/2008 |
| WO | 2008148840 | A1 | 12/2008 |
| WO | 2008156580 | A1 | 12/2008 |
| WO | 2009143404 | A1 | 11/2009 |
| WO | 2010124055 | A1 | 10/2010 |
| WO | 2010126811 | A1 | 11/2010 |
| WO | 2011002067 | A1 | 1/2011 |
| WO | 2011082010 | A1 | 7/2011 |

OTHER PUBLICATIONS

Commercial source information for 332916-18-4.*

Dorwald; Side Reactions in Organic Synthesis: A Guide to Successful Synthesis Design, 2005 Wiley-VCH Verlag GmbH & Co. KGaA, Wienheim.*

Wermuth; Practice of Medicinal Chemistry, Third edition, 2008, Elsevier, chapters 6, 15, 18 and 20.*

Lindsley, C.W., et al., "Discovery of Positive Allosteric Modulators for the Metabotropic Glutamate Receptor Subtype-5 from a Series of N-(1,3-Diphenyl-1H-pyrazol-5-yl) benzamides that Potentiate Receptor Function in Vivo", J. Med. Chem, 2004, 47, pp. 5825-5828.

(Continued)

*Primary Examiner* — John Mabry

*Assistant Examiner* — Daniel Carcanague

(74) *Attorney, Agent, or Firm* — Michael P. Morris; Anthony P. Bottino

(57) ABSTRACT

This invention relates to compounds of formula I

I

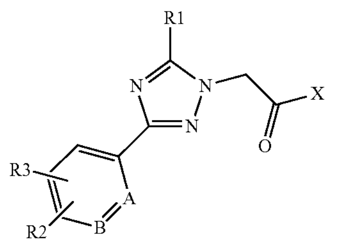

their use as positive allosteric modulators of mGlu5 receptor activity, pharmaceutical compositions containing the same, and methods of using the same as agents for treatment and/or prevention of neurological and psychiatric disorders associated with glutamate dysfunction such as schizophrenia or cognitive decline such as dementia or cognitive impairment. A, B, X, $R^1$, $R^2$, $R^3$ have meanings given in the description.

11 Claims, No Drawings

(56) References Cited

OTHER PUBLICATIONS

Shasheva. E. Y. et al., "Reactions of Hydroxyphenyl-substituted 1,2,4-Triazoles with Electrophylic Reagents", Russian Journal of General Chemistry, 2009, vol. 79, No. 10, pp. 2234-2243.

CHEMCATS: Accession No. 0046382561, Oct. 14, 2011.

Abstract in English for WO2011002067, Publication Date: Jan. 1, 2011.

* cited by examiner

COMPOUNDS

FIELD OF THE INVENTION

This invention relates to substituted triazoles and their use as positive allosteric modulators of mGlu5 receptor activity, pharmaceutical compositions containing the same, and methods of using the same as agents for treatment and/or prevention of neurological and psychiatric disorders associated with glutamate dysfunction such as schizophrenia or cognitive decline such as dementia or cognitive impairment.

BACKGROUND OF THE INVENTION

Glutamate is the primary excitatory amino acid in the mammalian central nervous system. Neurotransmission mediated by glutamate has been demonstrated to be critical in many physiological processes, such as synaptic plasticity, long term potentiation involved in both learning and memory as well as sensory perception (Riedel et al., Behay. Brain Res. 2003, 140:1-47). Furthermore, it has been demonstrated that an imbalance of glutamate neurotransmission plays a critical role in the pathophysiology of various neurological and psychiatric diseases.

The excitatory neurotransmission of glutamate is mediated through at least two different classes of receptors, the ionotropic glutamate receptors (NMDA, AMPA and kainate) and the metabotropic glutamate receptors (mGluR). The ionotropic receptors are ligand gated ion channels and are thought to be responsible for the regulating rapid neuronal transmission between two neurons. The metabotropic glutamate receptors are G-protein coupled receptors (GPCRs) which appear to mediate not only synaptic transmission, but also to regulate the extent of neurotransmitter release as well as post synaptic receptor activation.

Dysregulation in glutamatergic neurotransmission, for example through altered glutamate release or post-synaptic receptor activation, has been demonstrated in a variety of neurological ans well as psychiatric disorders. Hypofunction of the NMDA receptor has not only been demonstrated in Alzheimer's patients, but is increasingly accepted as the putative cause of schizophrenia (Farber et al., Prog. Brain Res., 1998, 116: 421-437, Coyle et al., Cell. and Mol. Neurobiol. 2006, 26: 365-384). This is supported by clinical studies showing that antagonists of the NMDA receptor induce symptoms indistinguishable to those suffered by schizophrenia patients (Javitt et al., Am J. Psychiatry, 1991, 148: 1301-1308). Therefore, approaches that could potentiate or normalize NMDA receptor signaling have the potential to treat neurological and psychiatric disorders. mGluR5 belongs to a superfamily of currently eight identified Type III GPCRs, which are unique in that the glutamate ligand binds to a large extracelullar amino-terminal protein domain. This superfamily is further divided into three gropus (Group I, II and III) based on amino acid homology as well as the intracellular signalling cascades they regulate (Schoepp et al., Neuropharma, 1999, 38:1431-1476). mGluR5 belongs to group I and is coupled to the phospholipase C signalling cascade which regulates intracellular calcium mobilization. In the CNS, mGluR5 has been demonstrared to be expressed mainly in the cortex, hippocampus, nucleus accumbens and the caudate-putamen. These brain regions are known to be involved in memory formation and cognitive function as well as emotional response. mGluR5 has been shown to be localized post-synaptically, adjacent to the post-synaptic density (Lujan et al., Eur. J. Neurosci. 1996, 8: 1488-1500). A functional interaction between mGluR5 and the NMDA receptor has also been demonstrated, where activation of mGluR5 potentiates the activation state of the NMDA receptor (Mannaioni et al, NeuroSci., 2001, 21:5925-5924, Rosenbrock et al., Eur. J. Pharma., 2010, 639:40-46). Furthermore, activation of mGluR5 has been demonstrated in pre-clinical in vivo models to rescue cognitive impairment as well as psychotic disturbance induced by NMDA receptor antagonists (Chan et al., Psychopharma. 2008, 198:141-148). Therefore, activation of mGluR5, and thereby potentiation or normalization of the NMDA receptor signaling, is a potential mechanism for the treatment of psychiatric and neurological disorders. Most agonists of mGluR5 bind the orthosteric glutamate binding site. Since the glutamate binding site between the mGluR family members is highly conserved, it has been challenging to develop selective mGluR5 agonists which have acceptable CNS penetration and demonstrate in vivo activity. An alternative approach to achieve selectivity between the mGluR family members is to develop compounds which bind to an allosteric site, which is not as highly conserved between the family members. These allosteric binding compounds would not interfere with the natural glutamate binding and signaling, but modulate the receptor activation state. Positive allosteric modulators of mGluR5 have recently been identified (O'Brien et al., Mol. Pharma. 2003, 64: 731-740, Lindsley et al., J. Med. Chem. 2004, 47: 5825-5828). These compounds potentiate mGluR5 activity in the presence of bound glutamate. In the absence of bound glutamate, the mGluR5 positive modulators do not demonstrate intrinsic activity. Therefore, these compounds potentiate the natural signaling of mGluR5 as opposed to agonists which activate the receptor in a permanent, unnatural manner. mGluR5 positive allosteric modulators therefore represent an approach to potentiate mGluR5 signaling which in turn potentiates and normalizes the NMDA receptor hypofunction detected in neurological and psychiatric disorders.

DETAILED DESCRIPTION OF THE INVENTION

The present invention is directed to compounds of formula I

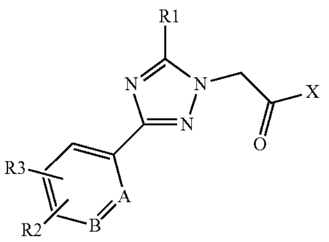

I in which

A and B independently represent CH or N;

$R^1$ represents aryl, heteroaryl, $C_{1-8}$alkyl, $C_{3-7}$cycloalkyl, —O—$C_{1-8}$alkyl which latter five groups are optionally substituted with one or more substituents selected from halogen, —CN, $C_{1-3}$alkyl, —O—$C_{1-3}$alkyl;

$R^2$ and $R^3$ independently represent —H, halogen, —CN, —COO—$C_{1-4}$alkyl, $C_{1-5}$alkyl, $C_{3-5}$cycloalkyl, —O—$C_{1-5}$alkyl which latter four groups are optionally substituted with one or more fluorine atoms;

X represents
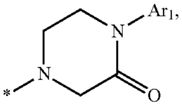
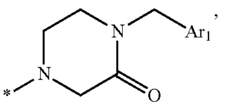
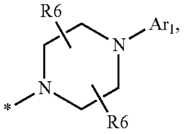
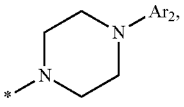
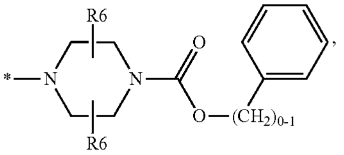
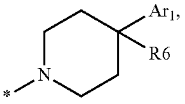
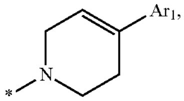
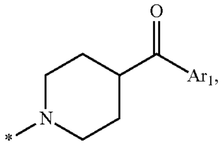
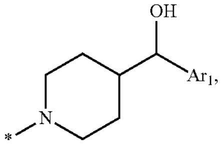
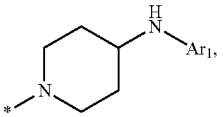
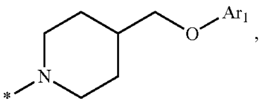
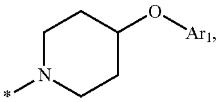
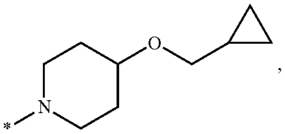
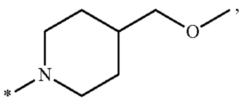
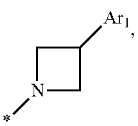
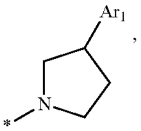
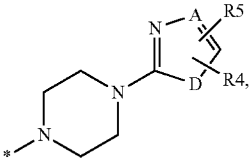
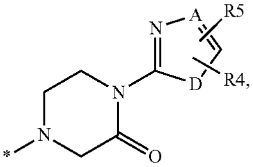
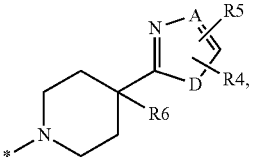
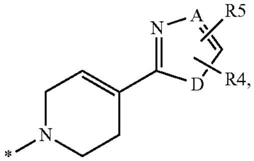
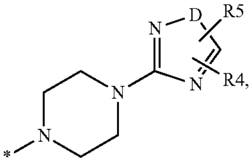
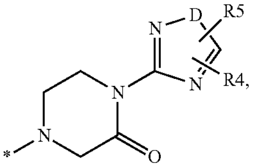
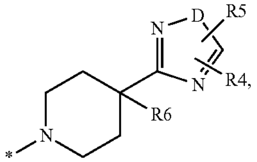
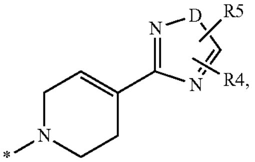
-continued
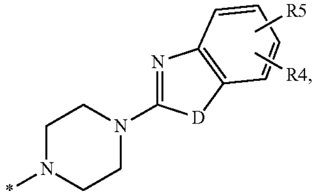
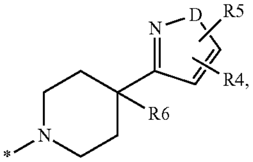
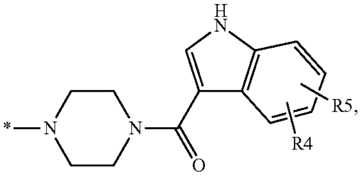
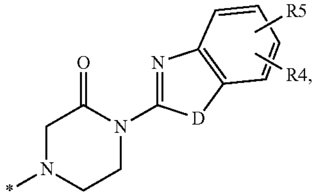
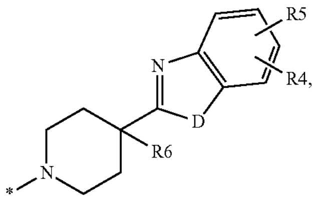
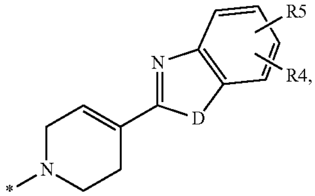
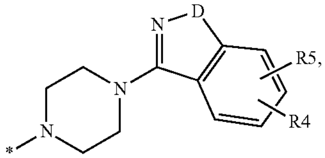
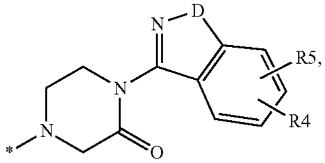
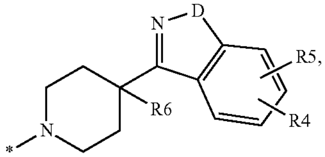

-continued
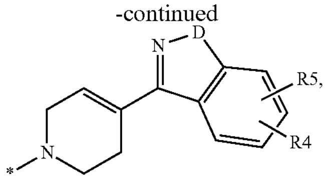
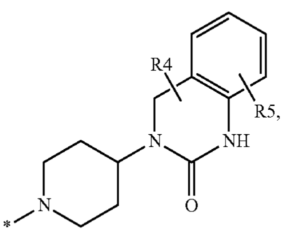
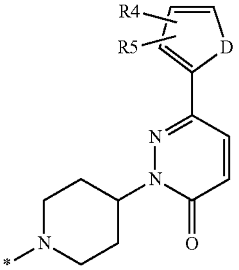
,
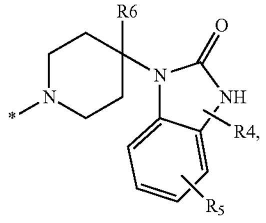
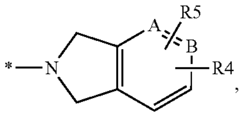
,
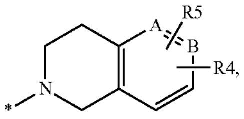
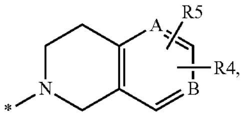
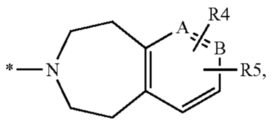
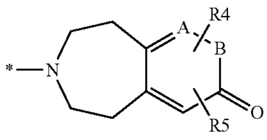
,
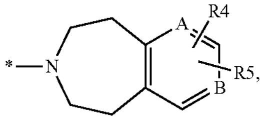
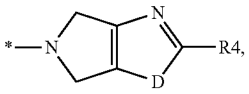
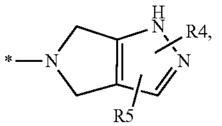
,
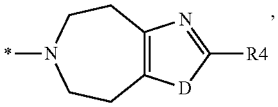
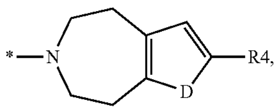
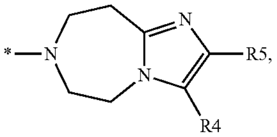
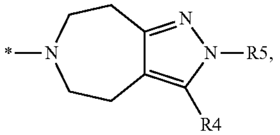
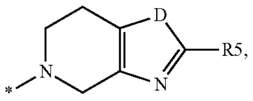
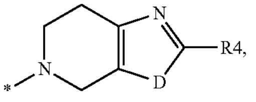
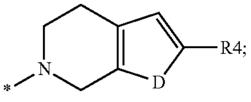
$Ar_1$ represents
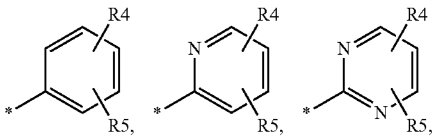
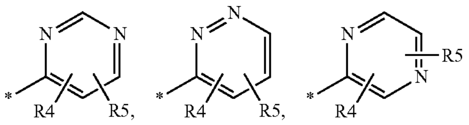
,
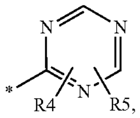
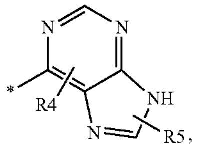
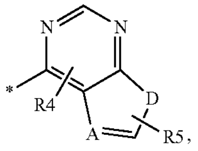
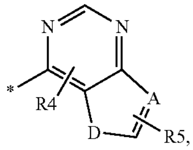
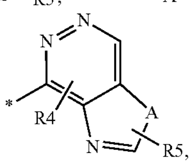
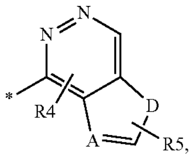
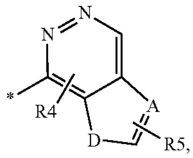
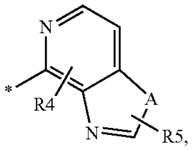
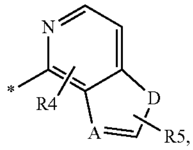
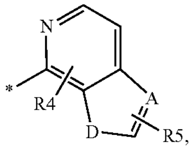
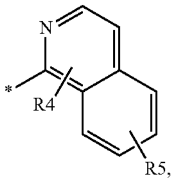
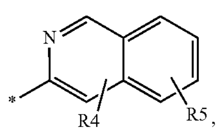
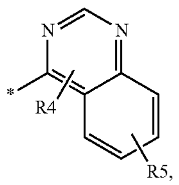
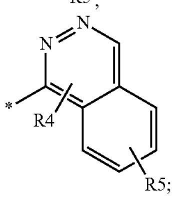
$Ar_2$ represents
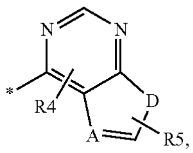
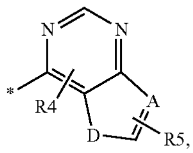

-continued

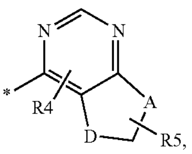
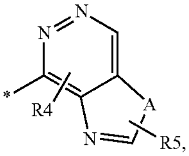
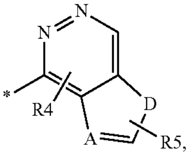
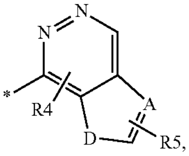
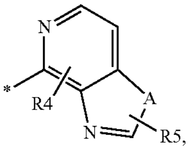
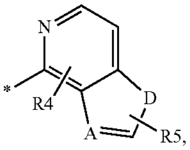
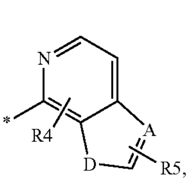
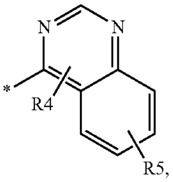
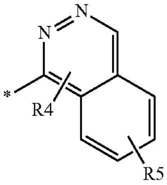

D represents S or O;

$R^4$ and $R^5$ independently represent —H, halogen, —OH, —CN, —$NH_2$, $C_{1-5}$alkyl, 3-7 membered heterocycloalkyl, phenyl, —NH-phenyl, —NH—$C_{1-5}$alkyl, —N($C_{1-5}$ alkyl)$_2$, —O—$C_{1-5}$ alkyl, —COO—$C_{1-5}$alkyl, —CONH ($C_{1-5}$alkyl), —CON($C_{1-5}$alkyl)$_2$, —NHCONH—$C_{1-5}$ alkyl, —NHCON($C_{1-5}$alkyl)$_2$, —NHCONH—$C_{3-5}$alkenyl, —NHCON($C_{3-5}$alkenyl)$_2$, —NHCO—$C_{1-5}$alkyl which latter fifteen groups are optionally substituted with one or more substituents selected from halogen, —OH; or together with the aromatic ring they are attached to form an 1,3-dioxolane ring.

$R^6$ represents —H, $C_{1-3}$ alkyl;

or a salt thereof, particularly a physiologically acceptable salt thereof.

In another embodiment, in the general formula I, A, B, D, X, $Ar^1$, $Ar^2$, $R^2$, $R^3$, $R^4$, $R^5$, $R^6$ have the same meaning as defined in any of the preceding embodiments, and $R^1$ represents phenyl, $C_{1-5}$alkyl, $C_{3-6}$cycloalkyl which latter four groups are optionally substituted with one or more substituents selected from fluoro, $C_{1-3}$alkyl, —O—$C_{1-3}$ alkyl.

In another embodiment, in the general formula I, A, B, D, $Ar^1$, $Ar^2$, $R^1$, $R^2$, $R^3$, $R^4$, $R^5$, $R^6$ have the same meaning as defined in any of the preceding embodiments, and X represents

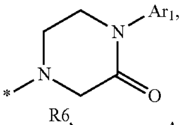
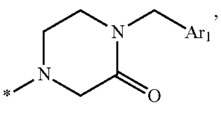
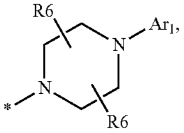
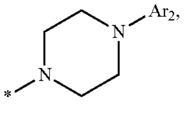

-continued

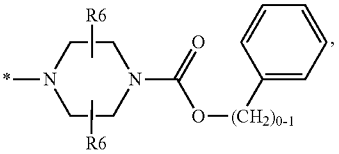
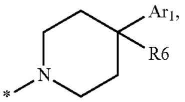
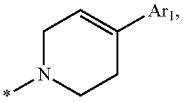
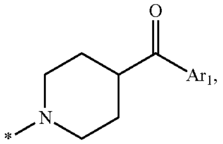
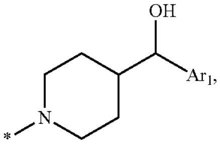
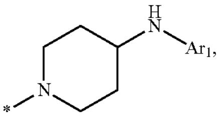
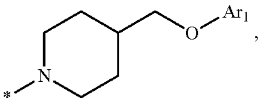
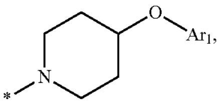
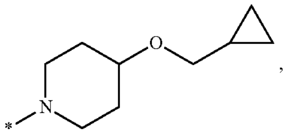
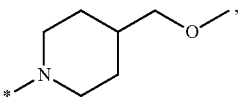
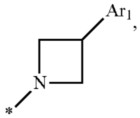
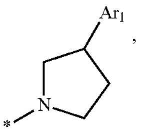
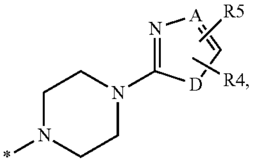
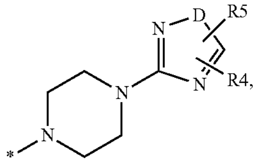
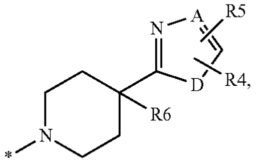
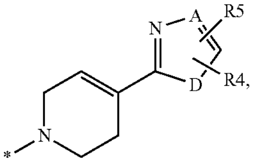
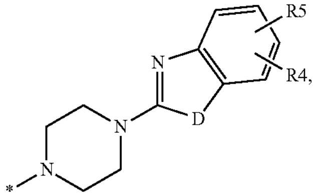
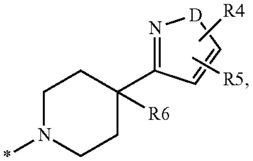
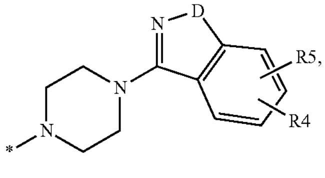

-continued
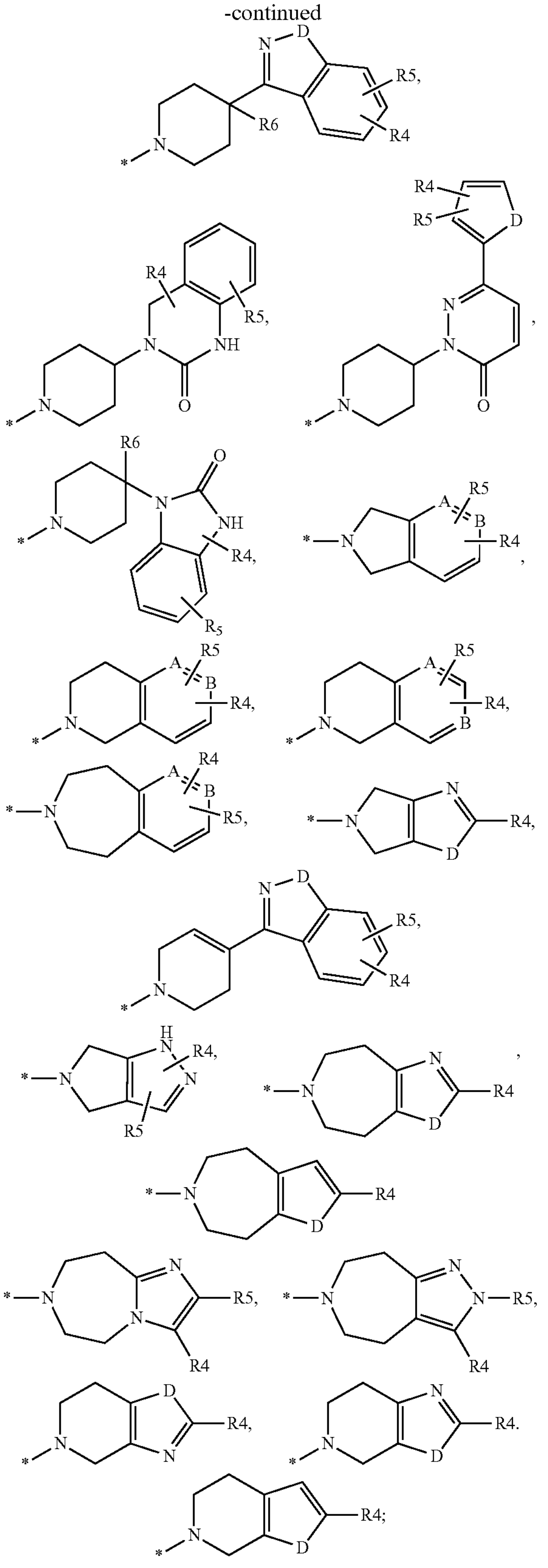
In another embodiment, in the general formula I, A, B, D, $Ar^1$, $Ar^2$, $R^1$, $R^2$, $R^3$, $R^4$, $R^5$, $R^6$ have the same meaning as defined in any of the preceding embodiments, and
X represents
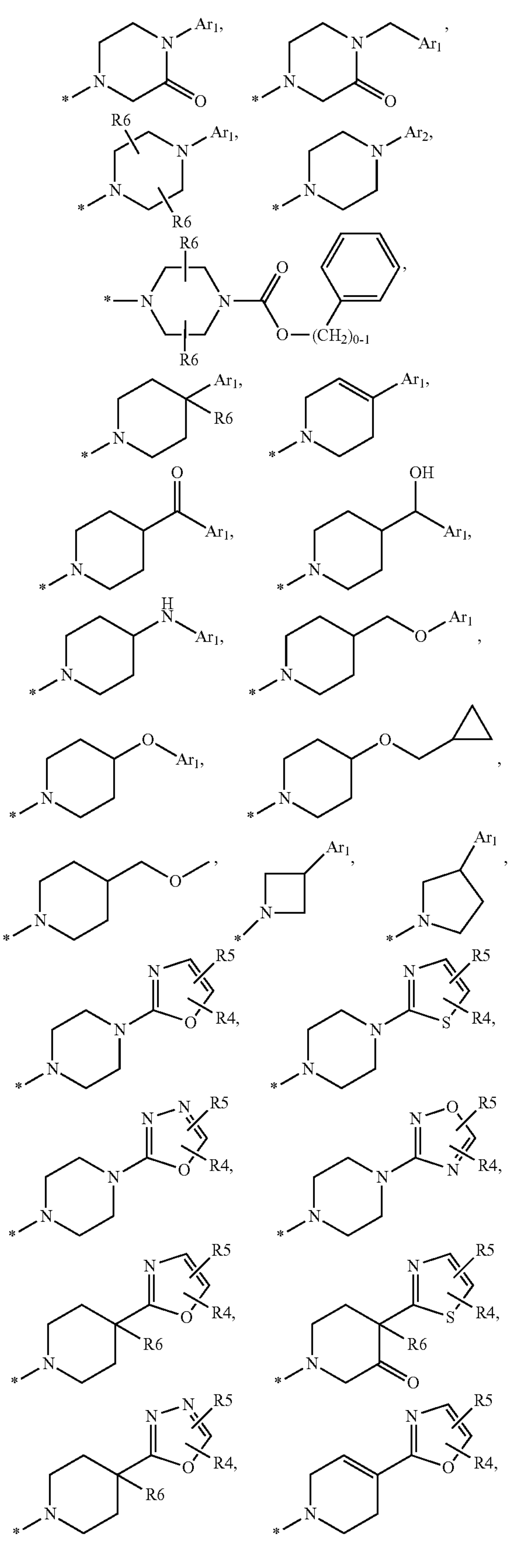

-continued

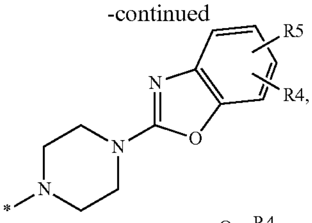

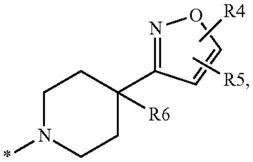

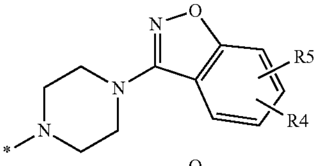

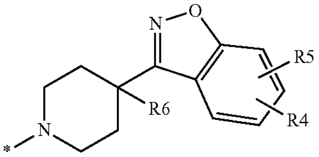

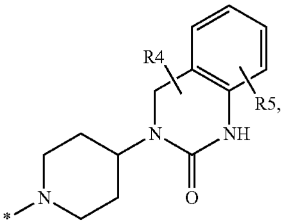

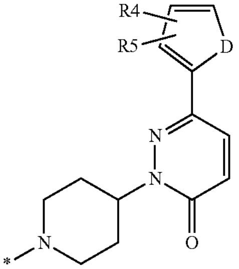

,

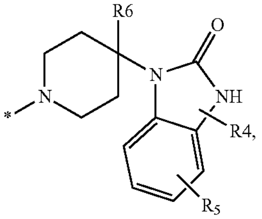

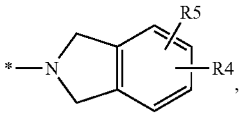

,

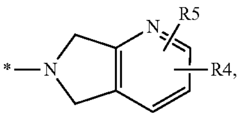

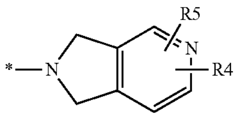

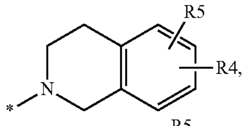

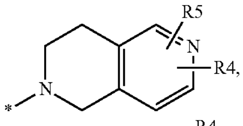

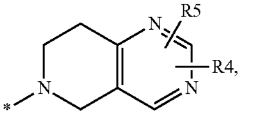

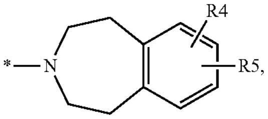

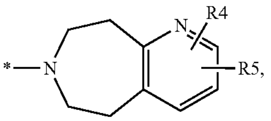

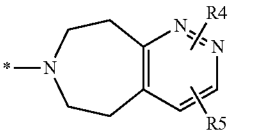

,

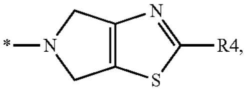

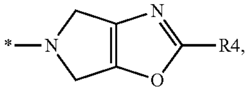

-continued

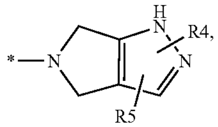

,

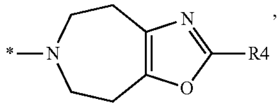

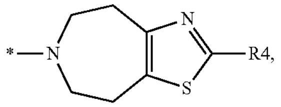

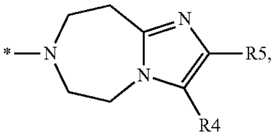

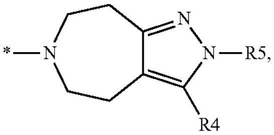

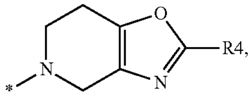

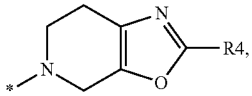

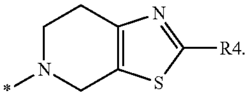

In another embodiment, in the general formula I, A, B, D, X, $Ar^2$, $R^1$, $R^2$, $R^3$, $R^4$, $R^5$, $R^6$ have the same meaning as defined in any of the preceding embodiments, and $Ar_1$ represents

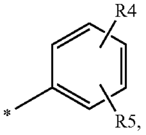

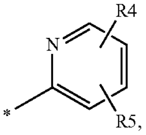

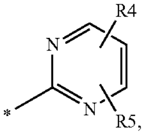

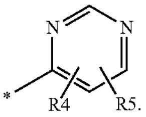

In another embodiment, in the general formula I, A, B, D, X, $Ar^1$, $R^1$, $R^2$, $R^3$, $R^4$, $R^5$, $R^6$ have the same meaning as defined in any of the preceding embodiments, and $Ar_2$ represents

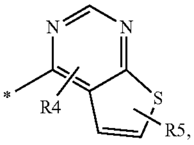

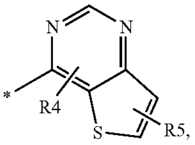

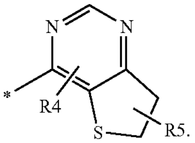

In another embodiment, in the general formula I, A, B, D, X, $Ar^1$, $Ar^2$, $R^1$, $R^2$, $R^3$, $R^4$, $R^5$ have the same meaning as defined in any of the preceding embodiments, and $R^6$ represents hydrogen, methyl.

In another embodiment, in the general formula I, A, B, D, X, $Ar^1$, $Ar^2$, $R^1$, $R^2$, $R^3$, $R^6$ have the same meaning as defined in any of the preceding embodiments, and $R^4$ and $R^5$ independently represent —H, —F, —Cl, —Br, —OH, —CN, —$NH_2$, $C_{1-3}$alkyl, 3-7 membered heterocycloalkyl, phenyl, —NH-phenyl, —NH—$C_{1-3}$alkyl, —N($C_{1-3}$alkyl)$_2$, —O—$C_{1-3}$alkyl, —COO—$C_{1-3}$alkyl, —CONH($C_{1-3}$alkyl), —CON($C_{1-3}$alkyl)$_2$, —NH-CONH—$C_{1-3}$alkyl, —NHCON($C_{1-3}$alkyl)$_2$, —NH-CONH-allyl, —NHCO—$C_{1-3}$alkyl which latter thirteen groups are optionally substituted with one or more fluorine atoms;

or together with the aromatic ring they are attached to form an 1,3-dioxolane ring.

In another embodiment, in the general formula I, X, $R^1$ have the same meaning as defined in any of the preceding embodiments, and the group

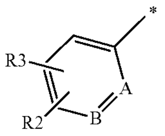

represents phenyl, 2-pyridyl which latter two groups are optionally substituted with one or more substituents selected from fluoro, chloro, bromo, —CN, $C_{1-3}$alkyl, $C_{3-5}$cycloalkyl, —O—$C_{1-3}$ alkyl, —COO—$C_{1-4}$alkyl which latter four groups are optionally substituted with one or more fluorine atoms.

In another embodiment, in the general formula I, A, B, D, X, $Ar^1$, $Ar^2$, $R^2$, $R^3$, $R^4$, $R^5$, $R^6$ have the same meaning as defined in any of the preceding embodiments, and $R^1$ represents phenyl, methyl, ethyl, propyl, iso-propyl, butyl, pentyl, cyclopentyl, cyclohexyl,

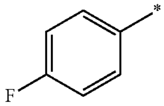 , 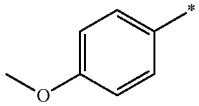 ,

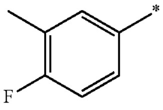 , 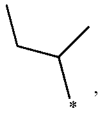 , 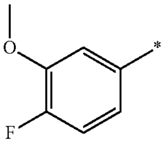 ,

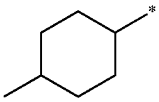 , 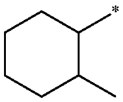 , 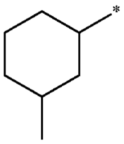 ,

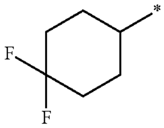 , 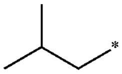 , 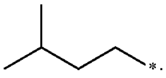 .

In another embodiment, in the general formula I, A, B, D, $Ar^1$, $Ar^2$, $R^1$, $R^2$, $R^3$, $R^4$, $R^5$, $R^6$ have the same meaning as defined in any of the preceding embodiments, and X represents

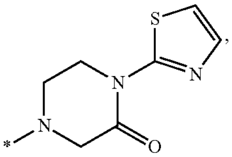 , 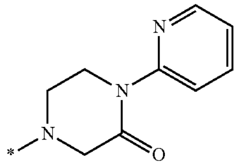 ,

-continued

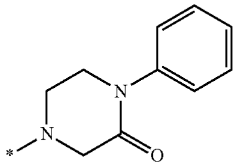 , 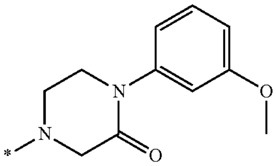 ,

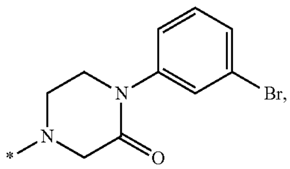 ,

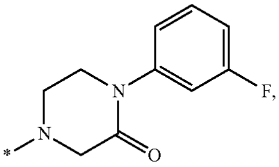 , 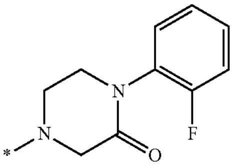 ,

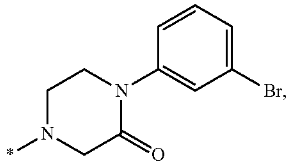 ,

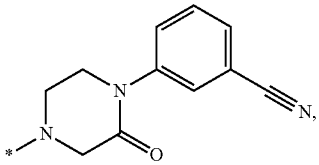 ,

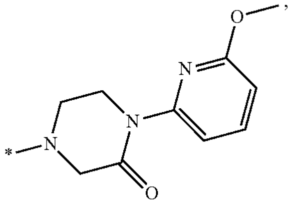 ,

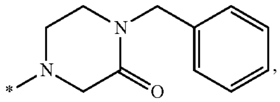 ,

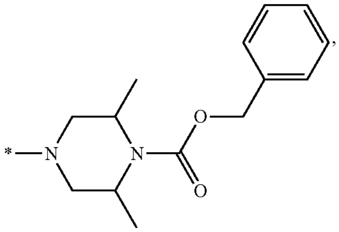 ,

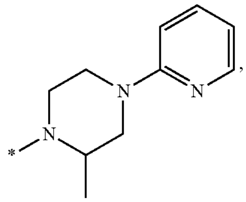 , 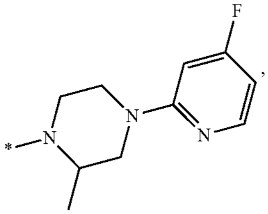 ,

-continued
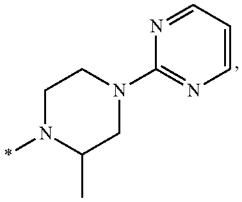,
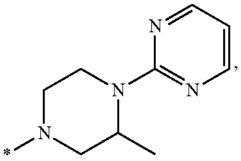,
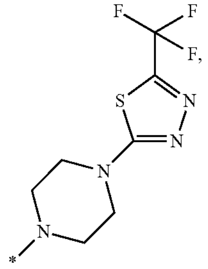
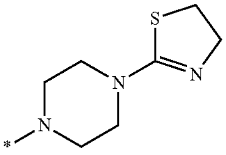,
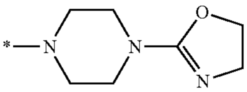,
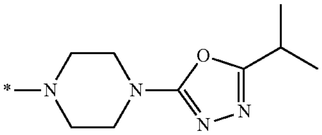,
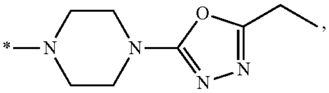,
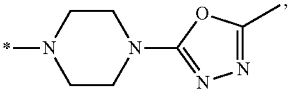,
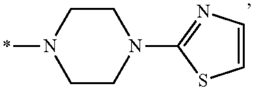,
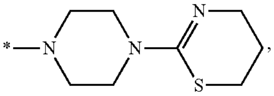,
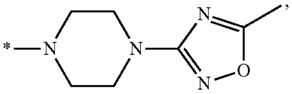,
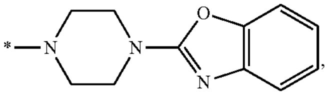,
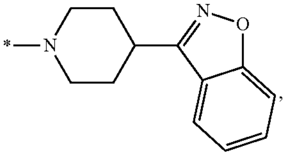,
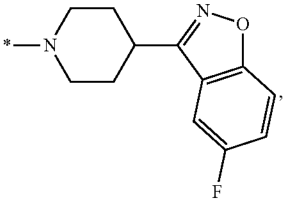
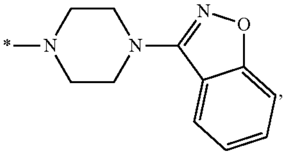,
-continued
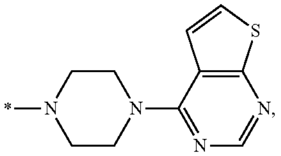
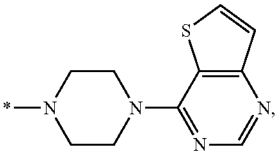
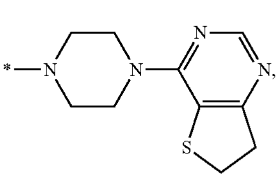
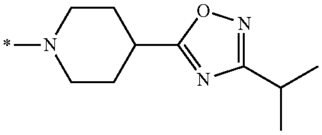,
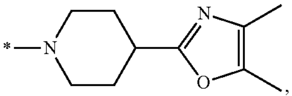,
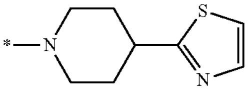,
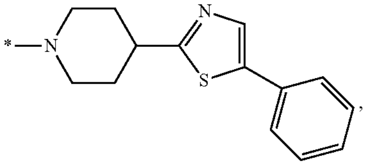,
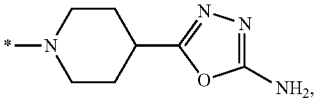
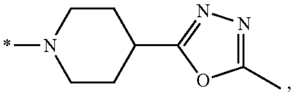,
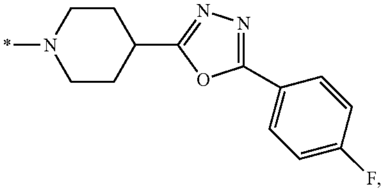
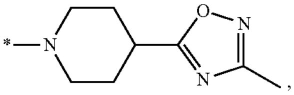,
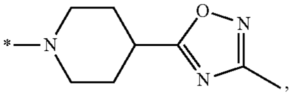,
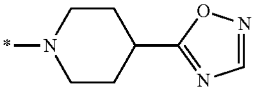,
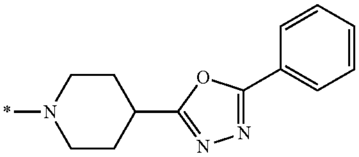,
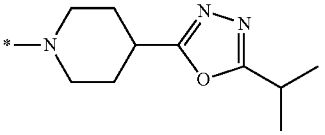,
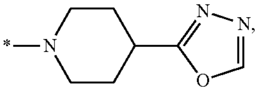
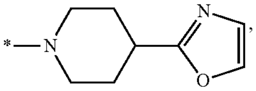, -continued
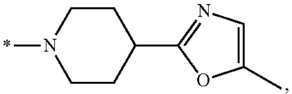,
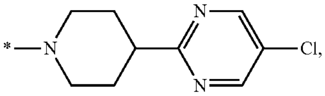,
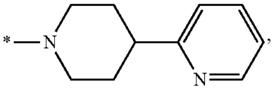,
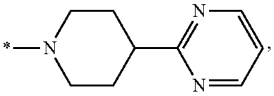,
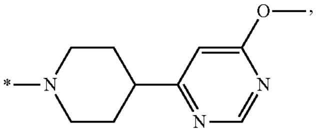,
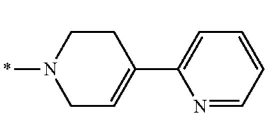, 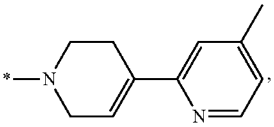,
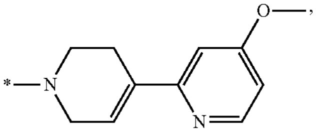,
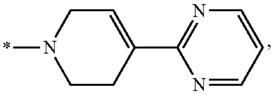,
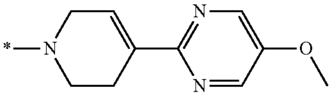,
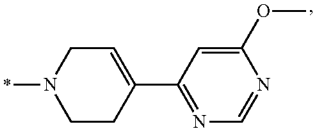,
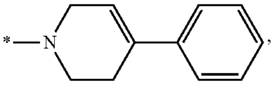,
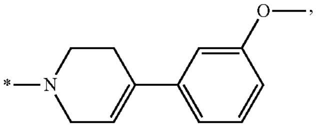,
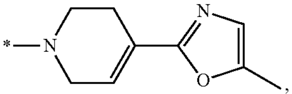,
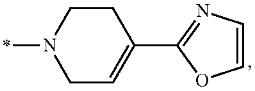,
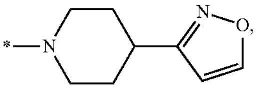, 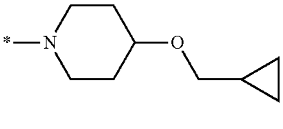,
-continued
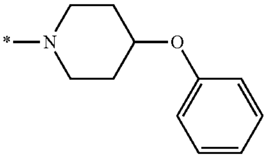, 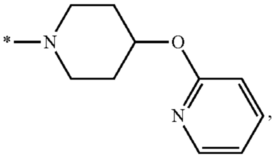,
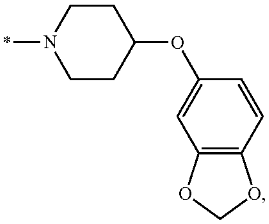,
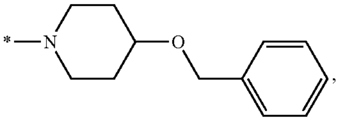,
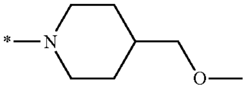, 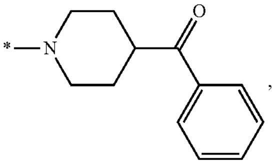,
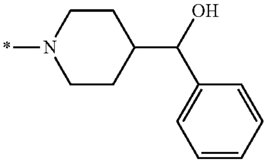, 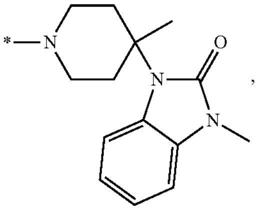,
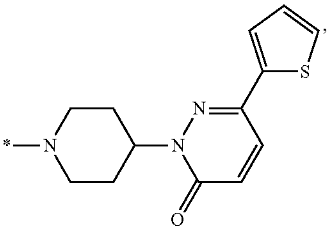,
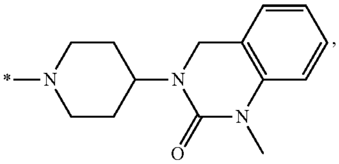,
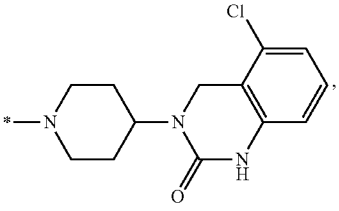,
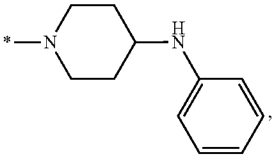, -continued
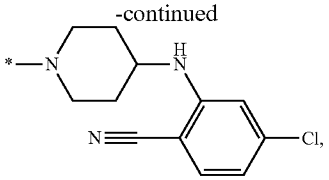
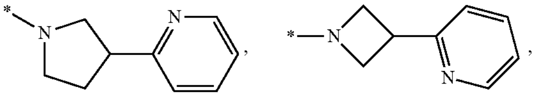
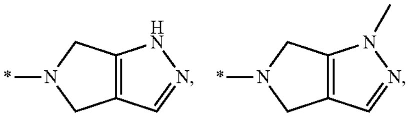
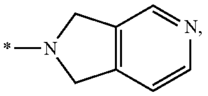
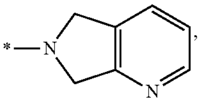
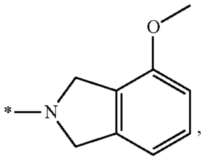
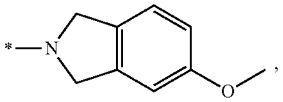
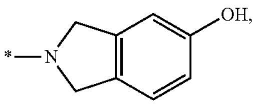
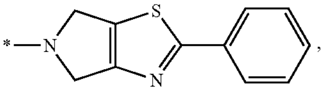
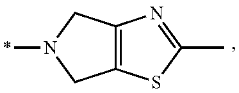
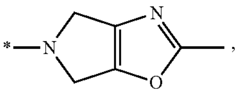
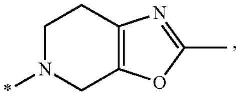
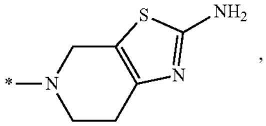
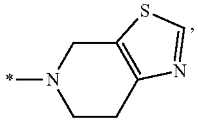
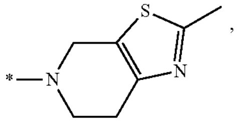
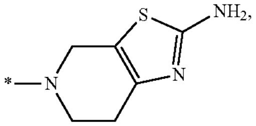
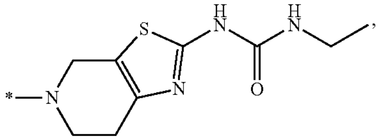
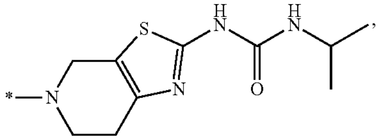
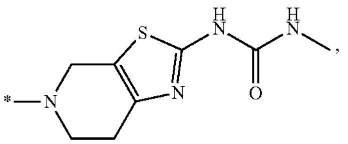
-continued
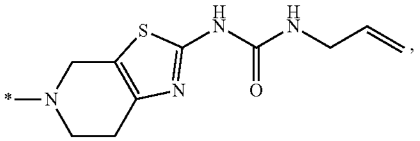
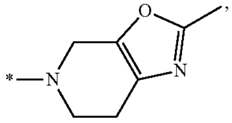
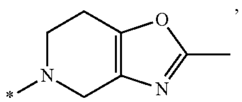
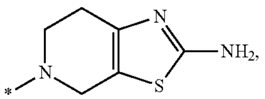
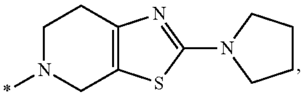
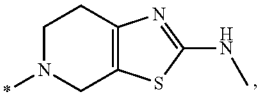
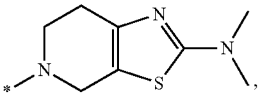
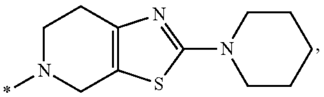
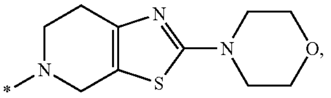
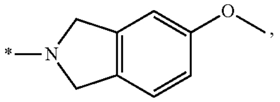
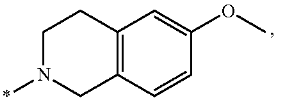
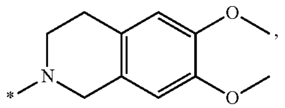
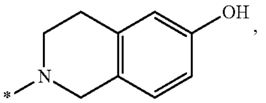
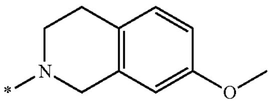
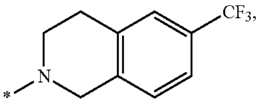
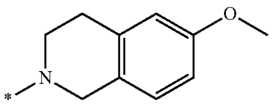
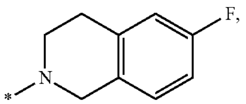
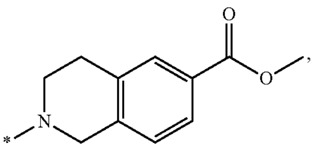
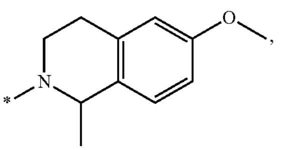
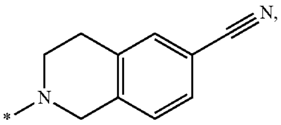
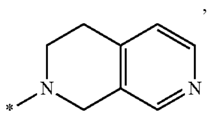

-continued
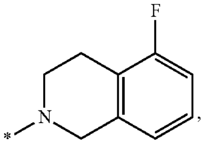
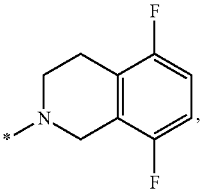
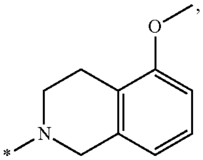
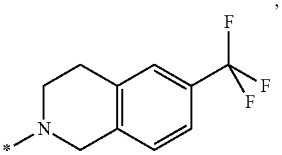
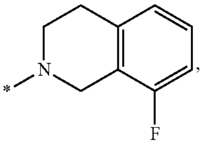
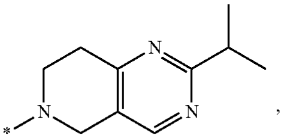
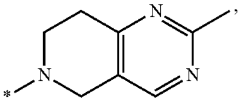
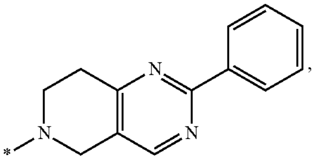
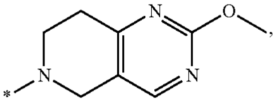
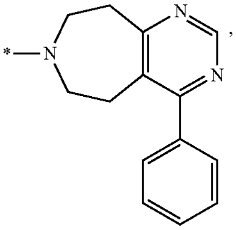
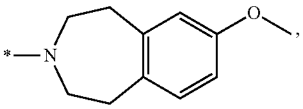
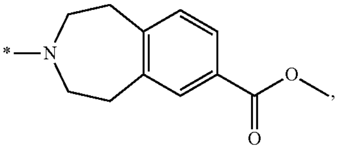
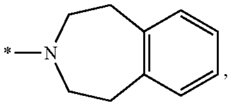
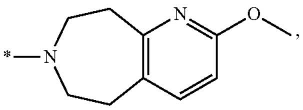
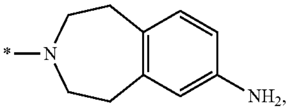
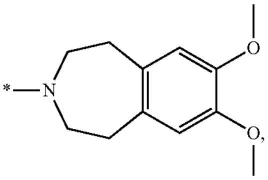
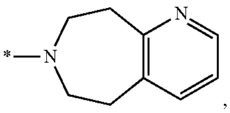
-continued
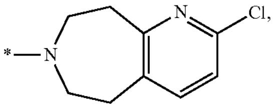
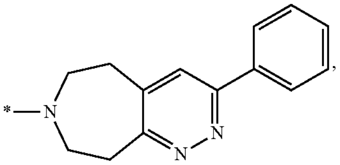
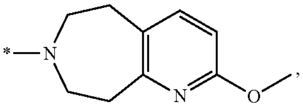
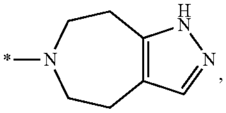
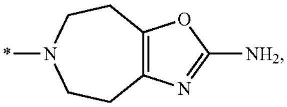
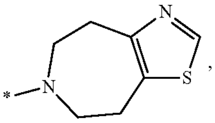
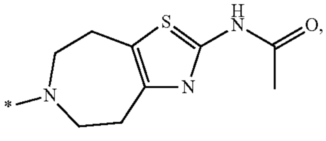
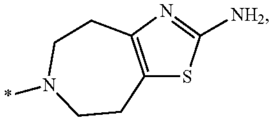
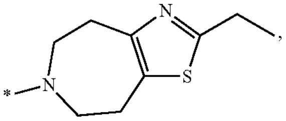
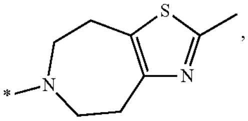
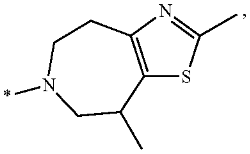
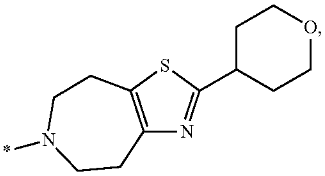
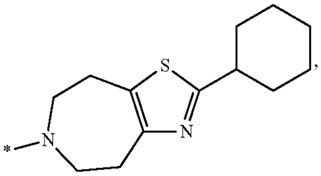
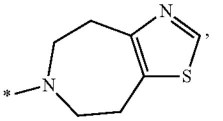
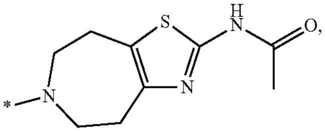

-continued

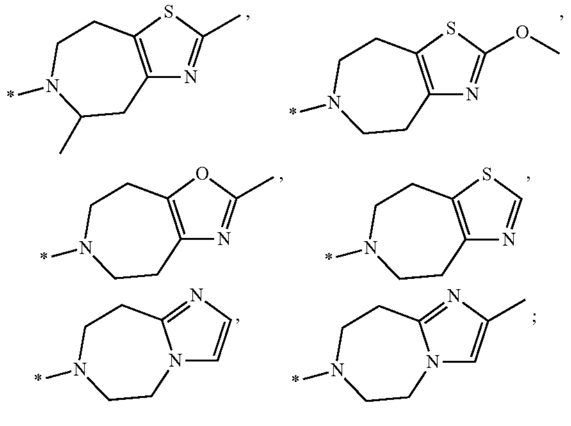

In another embodiment, in the general formula I, X, $R^1$ have the same meaning as defined in any of the preceding embodiments, and A represents N or CH;

B represents CH.

In another embodiment, in the general formula I, X, $R^1$ have the same meaning as defined in any of the preceding embodiments, and the group

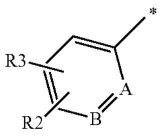

represents

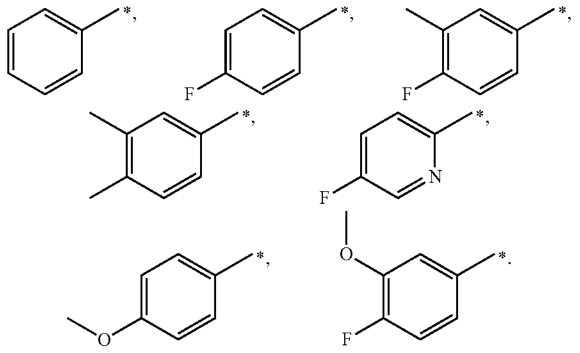

A further embodiment of the present invention comprises compounds of formula I in which A represents N or CH;

B represents CH;

$R^1$ represents phenyl, methyl, ethyl, propyl, iso-propyl, butyl, pentyl, cyclopentyl, cyclohexyl,

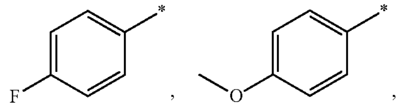

-continued

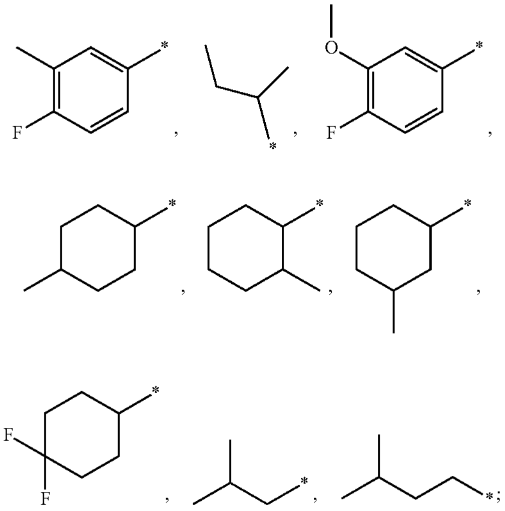

X represents

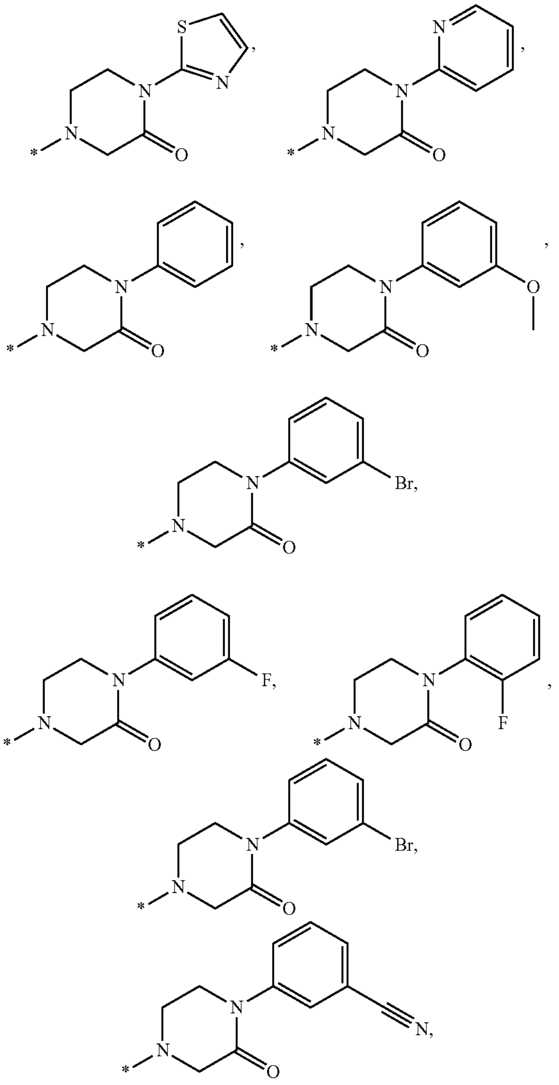

-continued
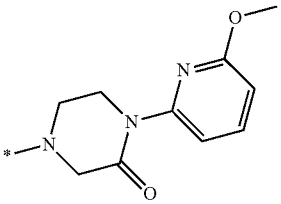
,
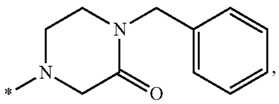
,
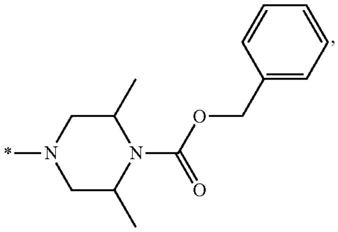
,
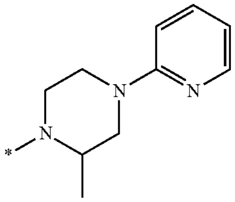
,
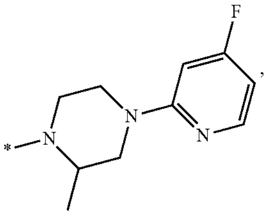
,
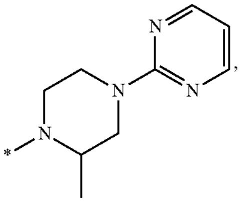
,
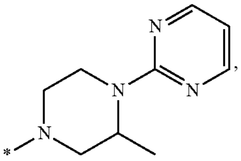
,
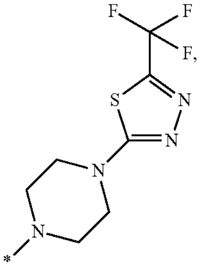
,
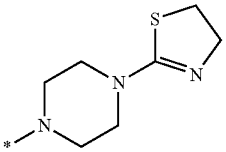
,
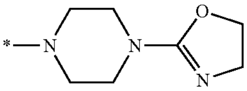
,
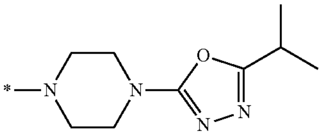
,
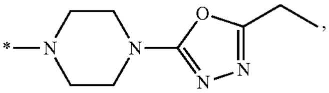
,
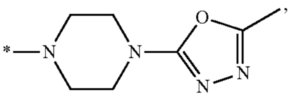
,
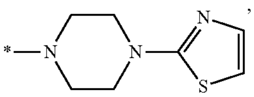
,
-continued
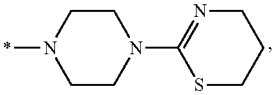
,
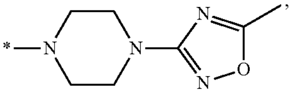
,
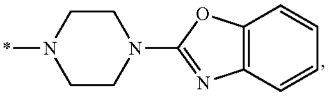
,
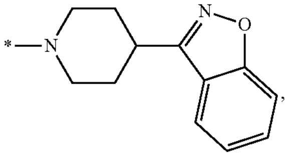
,
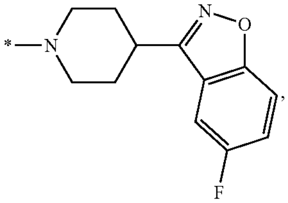
,
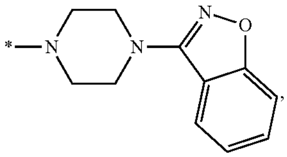
,
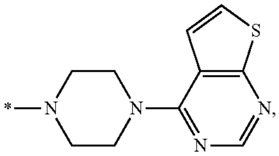
,
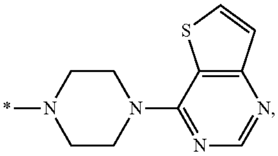
,
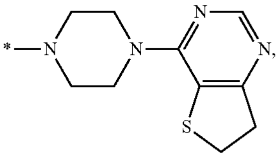
,
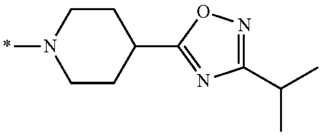
,
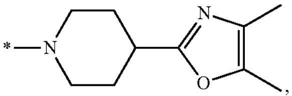
,
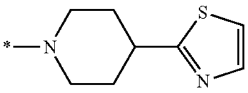
,
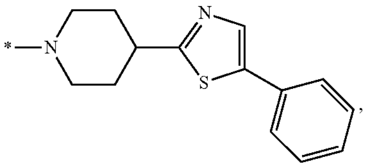
,
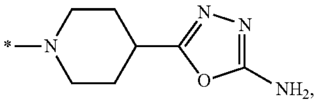
, -continued
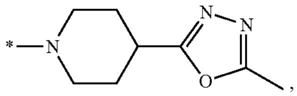,
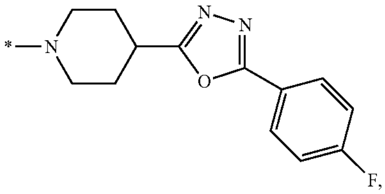
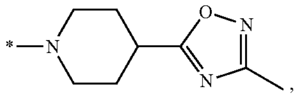,
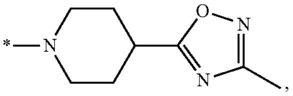, 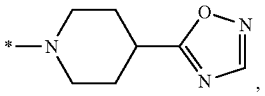,
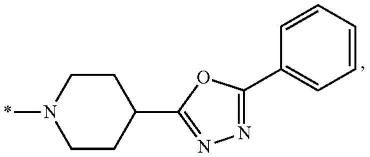,
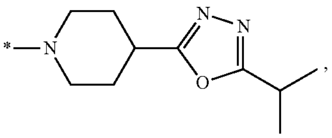,
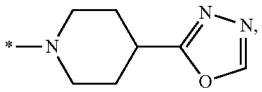 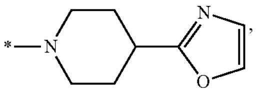
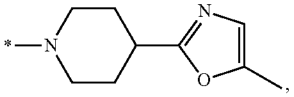,
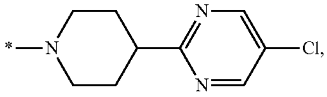
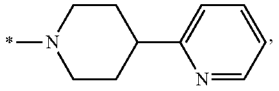,
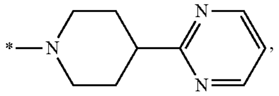,
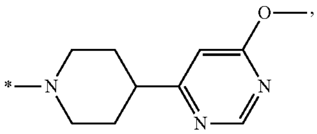
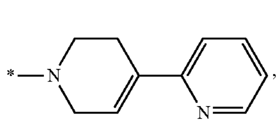, 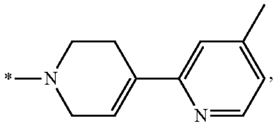,
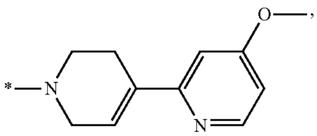
-continued
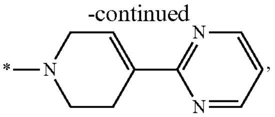,
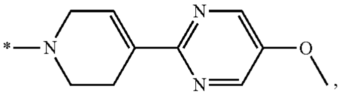,
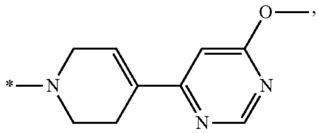
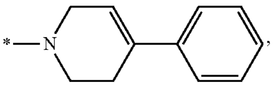,
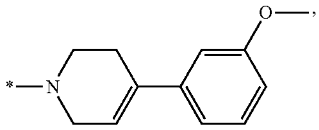
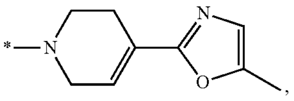,
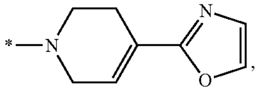,
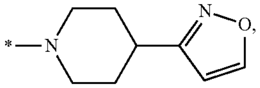 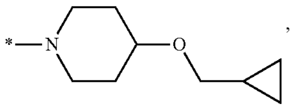,
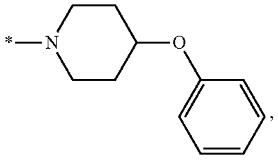, 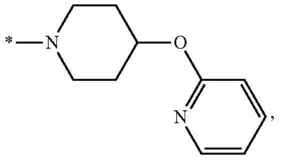,
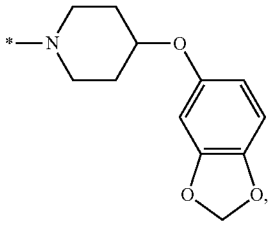
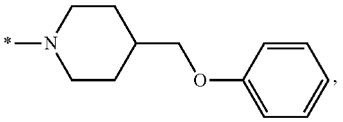,
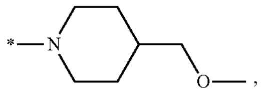, 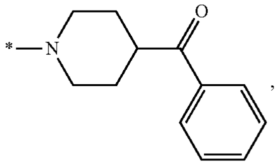,
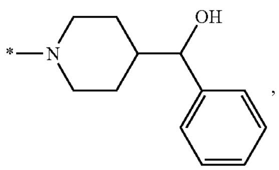, 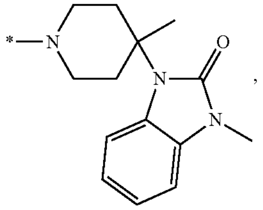, -continued
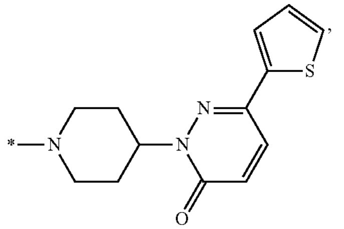
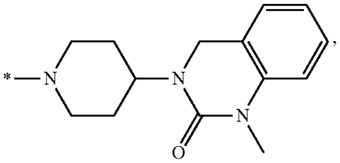
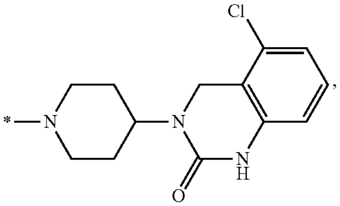
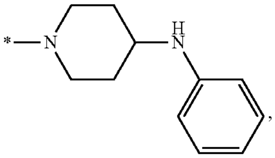
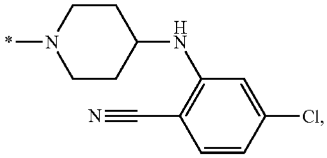
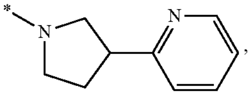
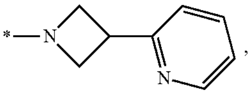
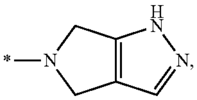
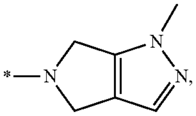
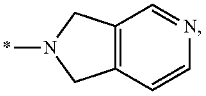
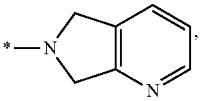
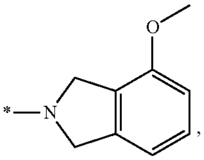
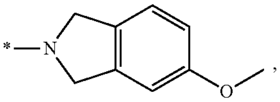
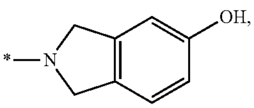
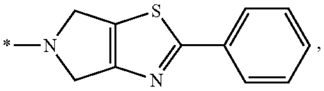
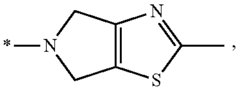
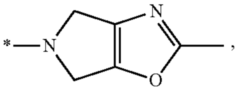
-continued
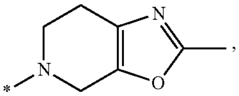
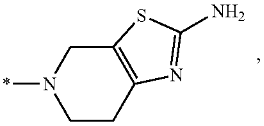
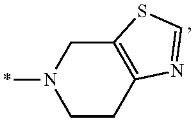
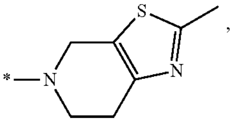
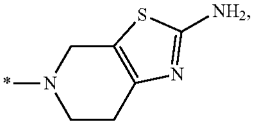
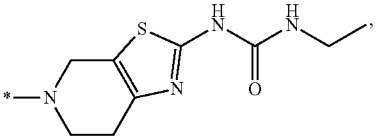
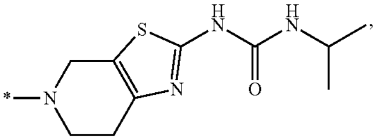
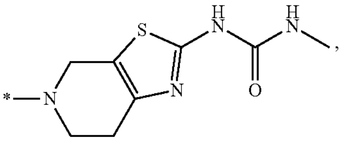
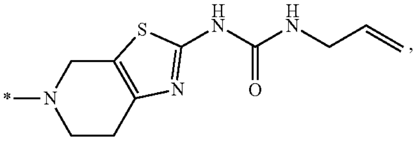
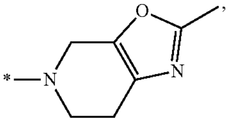
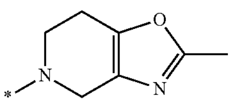
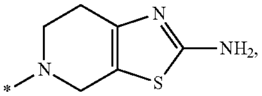
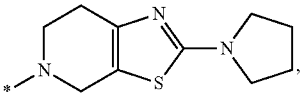
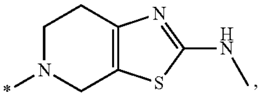
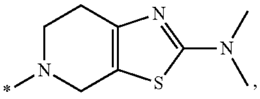
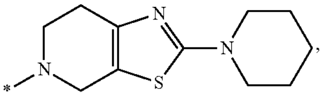
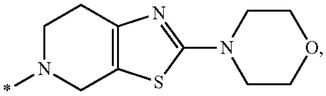
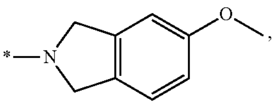
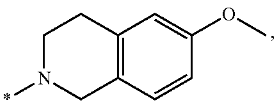

-continued
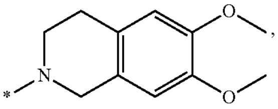
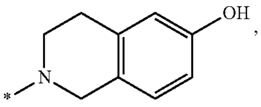
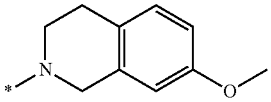
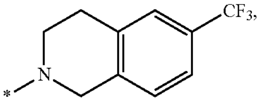
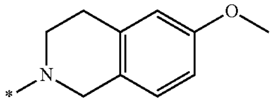
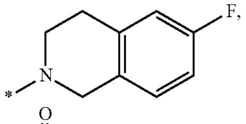
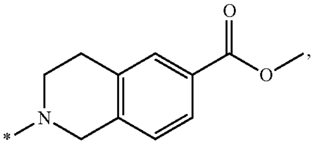
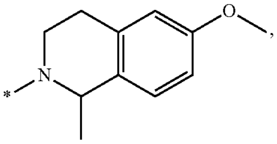
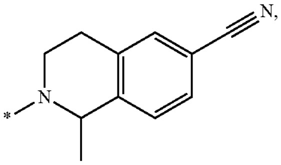
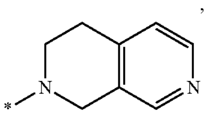
,
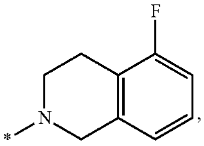
,
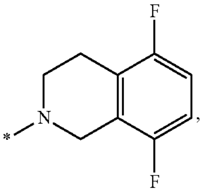
,
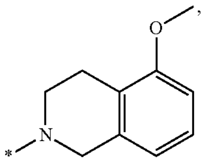
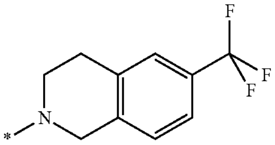
,
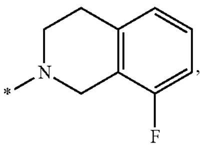
,
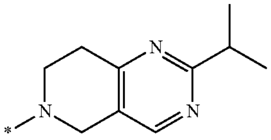
,
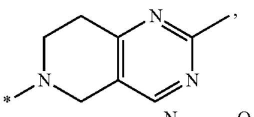
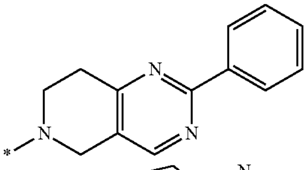
,
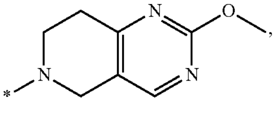
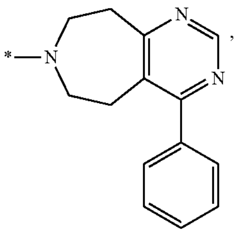
,
-continued
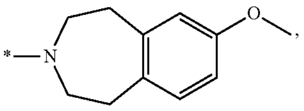
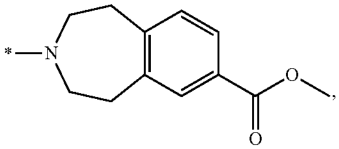
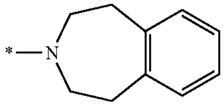
,
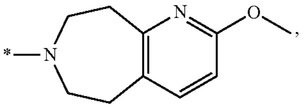
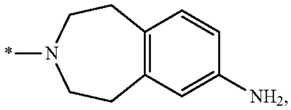
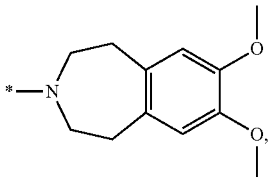
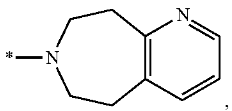
,
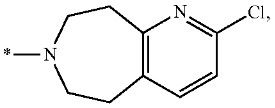
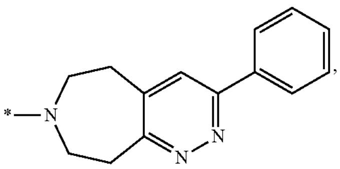
,
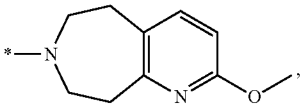
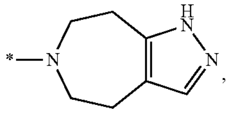
,
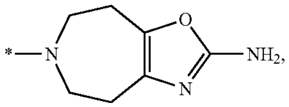
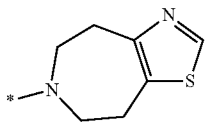
,
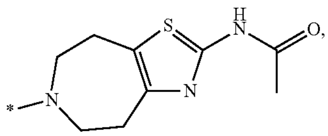
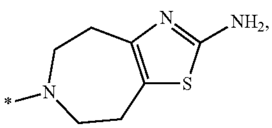
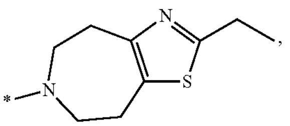
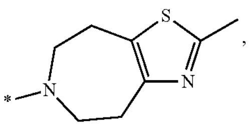
, -continued

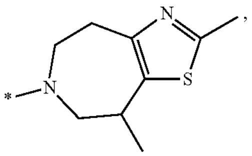

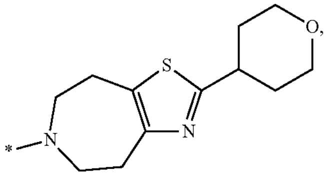

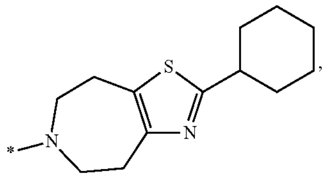

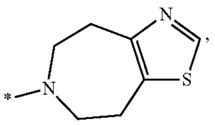

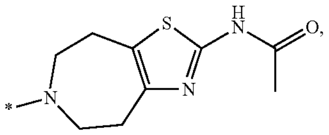

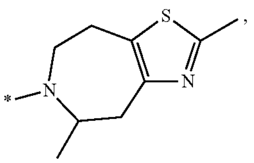

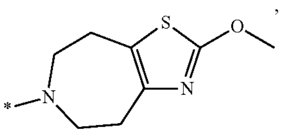

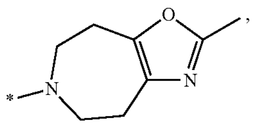

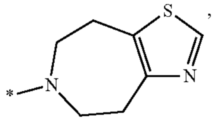

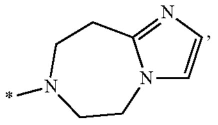

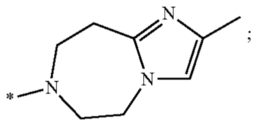

the group

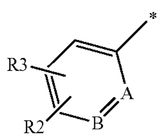

represents

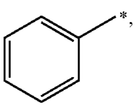

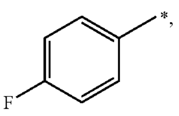

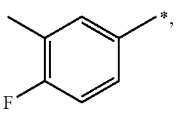

-continued

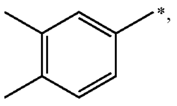

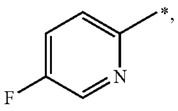

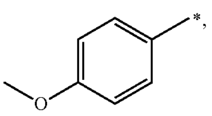

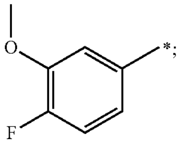

or a salt thereof, particularly a physiologically acceptable salt thereof.

TERMS AND DEFINITIONS USED

General Definitions:

Terms not specifically defined herein should be given the meanings that would be given to them by one of skill in the art in light of the disclosure and the context. As used in the specification, however, unless specified to the contrary, the following terms have the meaning indicated and the following conventions are adhered to.

In the groups, radicals, or moieties defined below, the number of carbon atoms is often specified preceding the group, for example, $C_{1-6}$-alkyl means an alkyl group or radical having 1 to 6 carbon atoms. In general, for groups comprising two or more subgroups, the last named subgroup is the radical attachment point, for example, the substituent "aryl-$C_{1-3}$-alkyl-" means an aryl group which is bound to a $C_{1-3}$-alkyl-group, the latter of which is bound to the core or to the group to which the substituent is attached.

In case a compound of the present invention is depicted in form of a chemical name and as a formula in case of any discrepancy the formula shall prevail.

An asterisk is may be used in sub-formulas to indicate the bond which is connected to the core molecule as defined.

The numeration of the atoms of a substituent starts with the atom which is closest to the core or to the group to which the substituent is attached.

For example, the term "3-carboxypropyl-group" represents the following substituent:

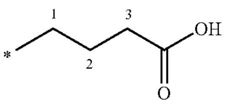

wherein the carboxy group is attached to the third carbon atom of the propyl group. The terms "1-methylpropyl-", "2,2-dimethylpropyl-" or "cyclopropylmethyl-" group represent the following groups:

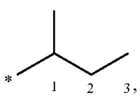

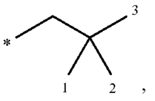

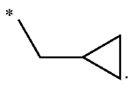

The asterisk may be used in sub-formulas to indicate the bond which is connected to the core molecule as defined.

Stereochemistry/Solvates/Hydrates:

Unless specifically indicated, throughout the specification and the appended claims, a given chemical formula or name shall encompass tautomers and all stereo, optical and geometrical isomers (e.g. enantiomers, diastereomers, E/Z isomers etc. . . . ) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

Salts:

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. For example, such salts include salts from ammonia, L-arginine, betaine, benethamine, benzathine, calcium hydroxide, choline, deanol, diethanolamine(2,2'-iminobis(ethanol)), diethylamine, 2-(diethylamino)-ethanol, 2-aminoethanol, ethylenediamine, N-ethyl-glucamine, hydrabamine, 1H-imidazole, lysine, magnesium hydroxide, 4-(2-hydroxyethyl)-morpholine, piperazine, potassium hydroxide, 1-(2-hydroxyethyl)-pyrrolidine, sodium hydroxide, triethanolamine(2,2',2"-nitrilotris(ethanol)), tromethamine, zinc hydroxide, acetic acid, 2.2-dichloro-acetic acid, adipic acid, alginic acid, ascorbic acid, L-aspartic acid, benzenesulfonic acid, benzoic acid, 2,5-dihydroxybenzoic acid, 4-acetamido-benzoic acid, (+)-camphoric acid, (+)-camphor-10-sulfonic acid, carbonic acid, cinnamic acid, citric acid, cyclamic acid, decanoic acid, dodecylsulfuric acid, ethane-1,2-disulfonic acid, ethanesulfonic acid, 2-hydroxy-ethanesulfonic acid, ethylenediaminetetraacetic acid, formic acid, fumaric acid, galactaric acid, gentisic acid, D-glucoheptonic acid, D-gluconic acid, D-glucuronic acid, glutamic acid, glutaric acid, 2-oxo-glutaric acid, glycerophosphoric acid, glycine, glycolic acid, hexanoic acid, hippuric acid, hydrobromic acid, hydrochloric acid, isobutyric acid, DL-lactic acid, lactobionic acid, lauric acid, lysine, maleic acid, (−)-L-malic acid, malonic acid, DL-mandelic acid, methanesulfonic acid, galactaric acid, naphthalene-1,5-disulfonic acid, naphthalene-2-sulfonic acid, 1-hydroxy-2-naphthoic acid, nicotinic acid, nitric acid, octanoic acid, oleic acid, orotic acid, oxalic acid, palmitic acid, pamoic acid (embonic acid), phosphoric acid, propionic acid, (−)-L-pyroglutamic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid and undecylenic acid. Further pharmaceutically acceptable salts can be formed with cations from metals like aluminium, calcium, lithium, magnesium, potassium, sodium, zinc and the like. (also see Pharmaceutical salts, Berge, S. M. et al., J. Pharm. Sci., (1977), 66, 1-19).

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention (e.g. trifluoro acetate salts,) also comprise a part of the invention.

Halogen:

The term halogen generally denotes fluorine, chlorine, bromine and iodine.

Alkyl:

The term "$C_{1-n}$-alkyl", wherein n is an integer from 2 to n, either alone or in combination with another radical denotes an acyclic, saturated, branched or linear hydrocarbon radical with 1 to n C atoms. For example the term $C_{1-5}$-alkyl embraces the radicals $H_3C—$, $H_3C—CH_2—$, $H_3C—CH_2—CH_2—$, $H_3C—CH(CH_3)—$, $H_3C—CH_2—CH_2—CH_2—$, $H_3C—CH_2—CH(CH_3)—$, $H_3C—CH(CH_3)—CH_2—$, $H_3C—C(CH_3)_2—$, $H_3C—CH_2—CH_2—CH_2—CH_2—$, $H_3C—CH_2—CH_2—CH(CH_3)—$, $H_3C—CH_2—CH(CH_3)—CH_2—$, $H_3C—CH(CH_3)—CH_2—CH_2—$, $H_3C—CH_2—C(CH_3)_2—$, $H_3C—C(CH_3)_2—CH_2—$, $H_3C—CH(CH_3)—CH(CH_3)—$ and $H_3C—CH_2—CH(CH_2CH_3)—$.

Alkenyl:

The term "$C_{2-n}$-alkenyl", is used for a group as defined in the definition for "$C_{1-n}$-alkyl" with at least two carbon atoms, if at least two of those carbon atoms of said group are bonded to each other by a double bond.

Cycloalkyl:

The term "$C_{3-n}$-cycloalkyl", wherein n is an integer from 4 to n, either alone or in combination with another radical denotes a cyclic, saturated, unbranched hydrocarbon radical with 3 to n C atoms. For example the term $C_{3-7}$-cycloalkyl includes cyclopropyl, cyclobutyl, cyclopentyl, cyclohexyl and cycloheptyl.

Aryl:

The term "aryl" as used herein, either alone or in combination with another radical, denotes a carbocyclic aromatic monocyclic group containing 6 carbon atoms which may be further fused to a second 5- or 6-membered carbocyclic group which may be aromatic, saturated or unsaturated. Aryl includes, but is not limited to, phenyl, indanyl, indenyl, naphthyl, anthracenyl, phenanthrenyl, tetrahydronaphthyl and dihydronaphthyl.

Heterocyclyl:

The term "heterocyclyl" means a saturated or unsaturated mono- or polycyclic-ring systems including aromatic ring system containing one or more heteroatoms selected from N, O or $S(O)_r$, wherein r=0, 1 or 2, consisting of 3 to 14 ring atoms wherein none of the heteroatoms is part of the aromatic ring. The term "heterocycle" is intended to include all the possible isomeric forms. Thus, the term "heterocyclyl" includes the following exemplary structures which are not depicted as radicals as each form may be attached through a covalent bond to any atom so long as appropriate valences are maintained:

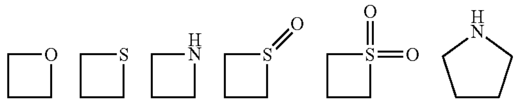

-continued
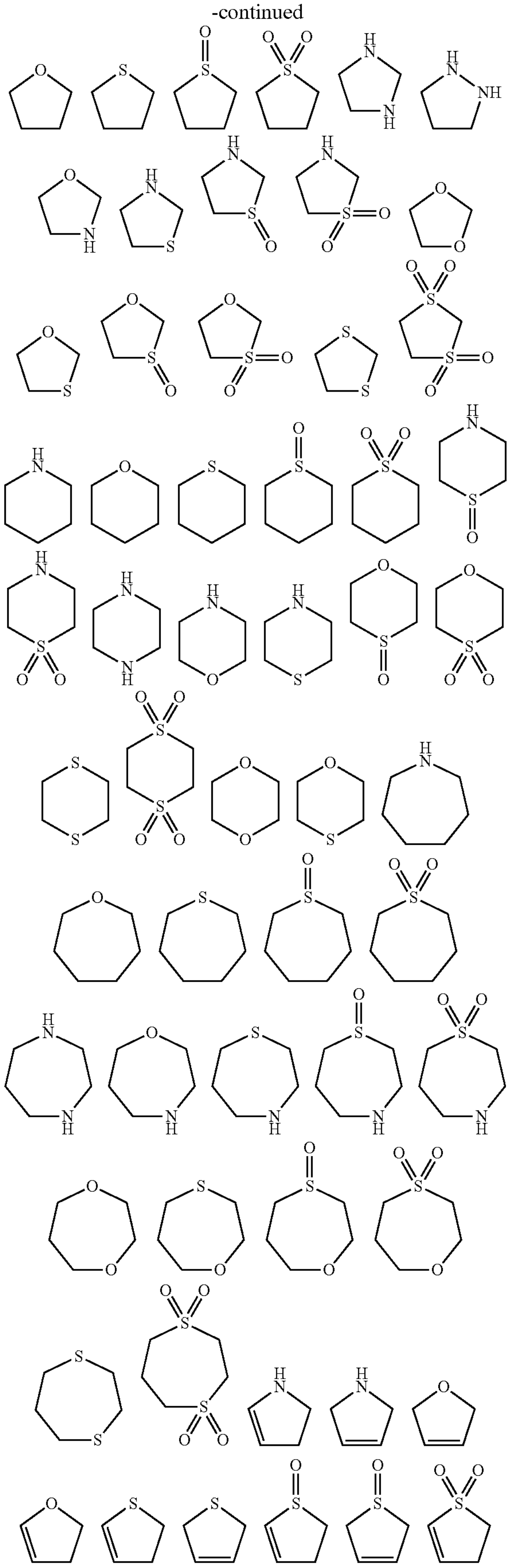
-continued
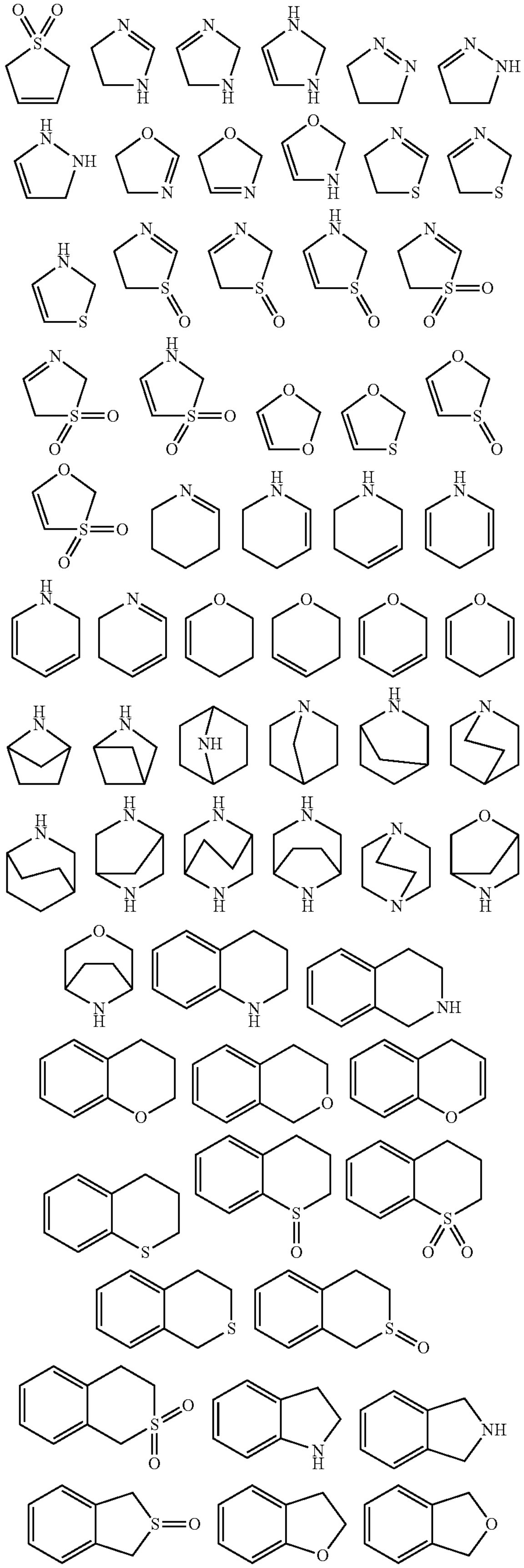

-continued

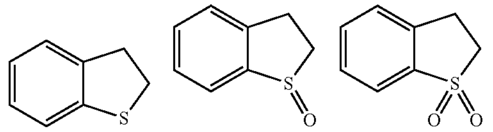
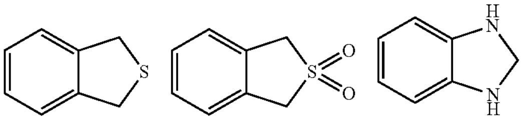
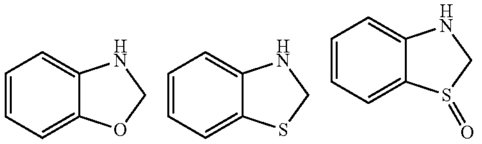
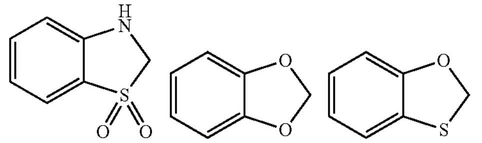
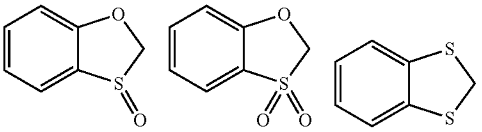
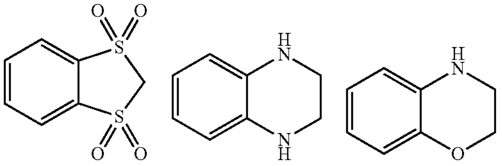
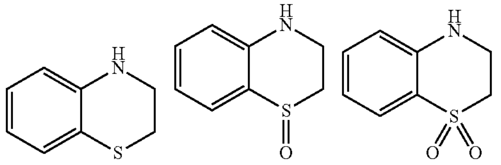
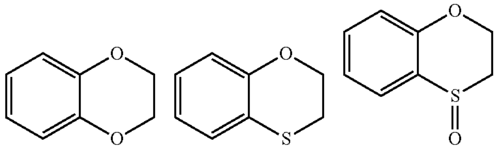
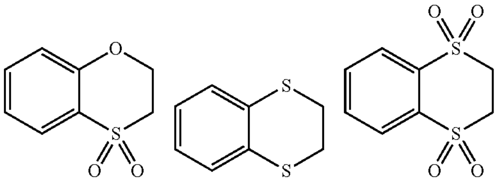

Heteroaryl:

The term "heteroaryl" means a mono- or polycyclic-ring systems containing one or more heteroatoms selected from N, O or $S(O)_r$, wherein r=0, 1 or 2, consisting of 5 to 14 ring atoms wherein at least one of the heteroatoms is part of aromatic ring. The term "heteroaryl" is intended to include all the possible isomeric forms.

Thus, the term "heteroaryl" includes the following exemplary structures which are not depicted as radicals as each form may be attached through a covalent bond to any atom so long as appropriate valences are maintained:

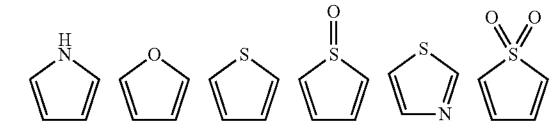
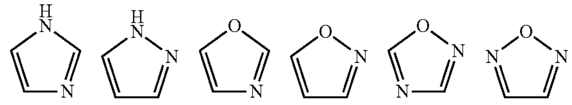
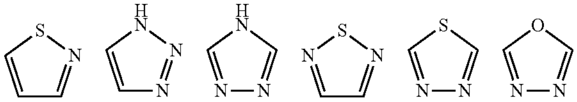
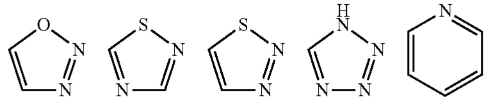
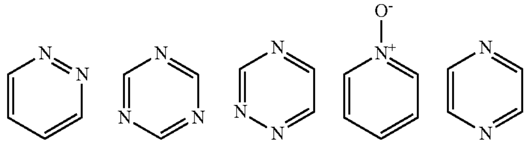
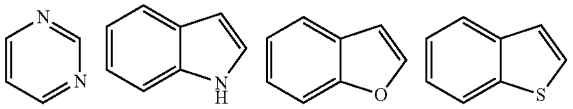
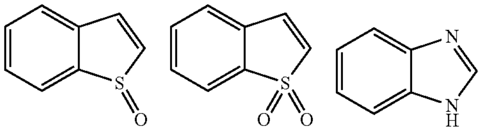
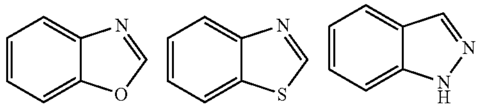
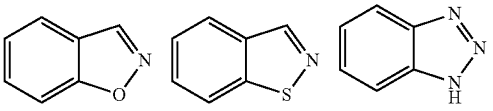
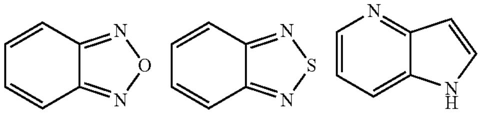
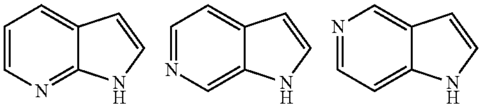
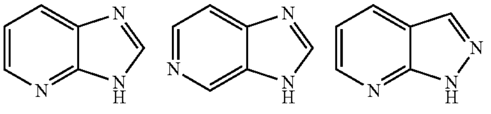
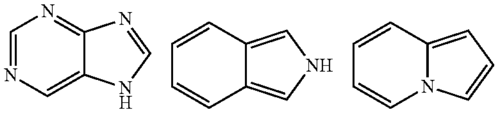
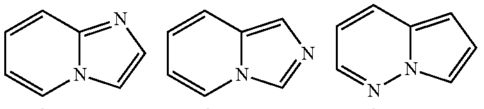
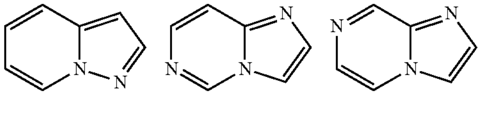

-continued

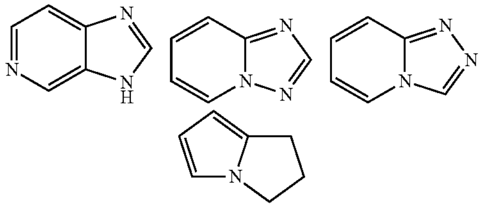

Many of the terms given above may be used repeatedly in the definition of a formula or group and in each case have one of the meanings given above, independently of one another.

GENERAL METHOD OF PREPARATION

Compounds of the present invention can be prepared in accordance with techniques that are well known to those skilled in the art.

Compounds of the present invention can be synthesized according to scheme 1

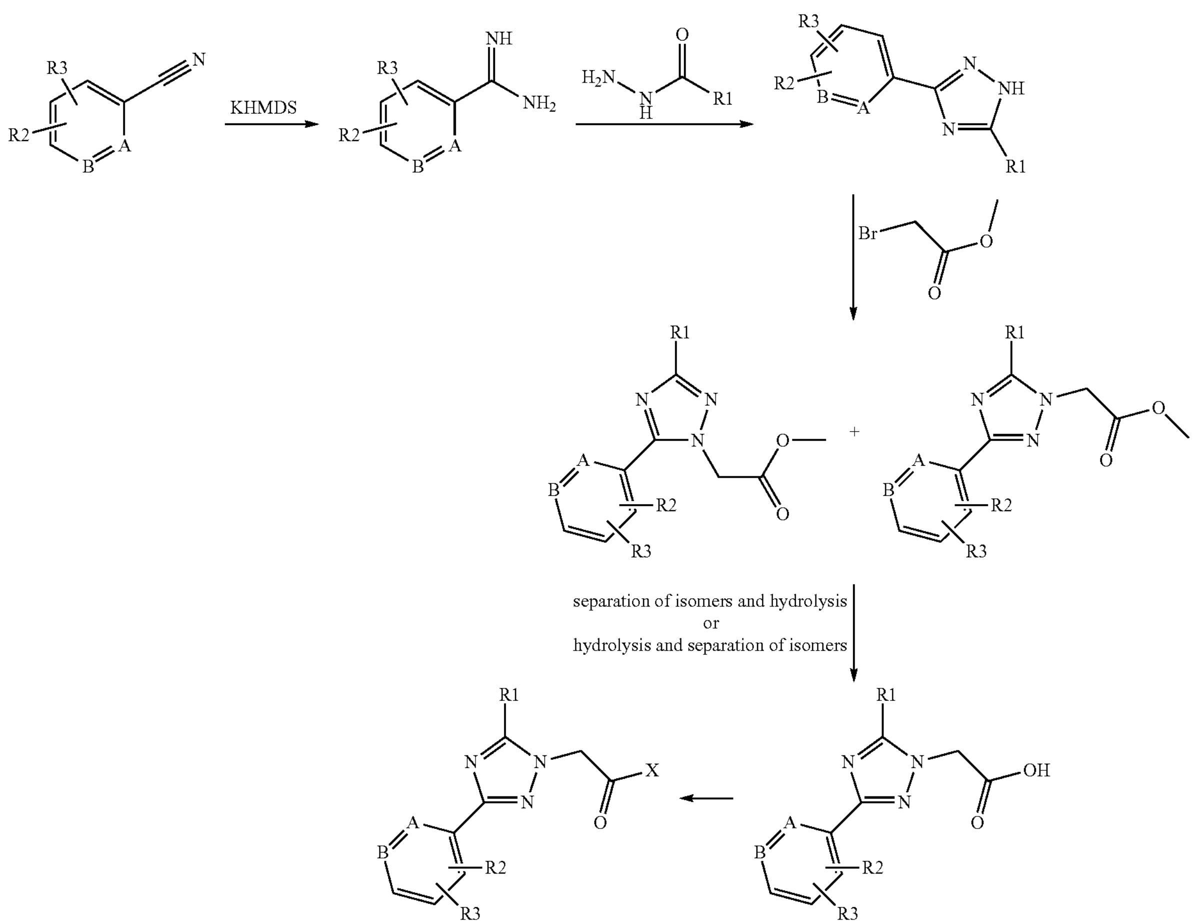

Nitriles were reacted with LiHMDS or KHMDS to benzamidines. Benzamidines were melted with acid hydrazides to yield a triazole system. The triazoles were coupled with 2-bromoacetic acid methyl ester under basic conditions to give the desired triazole-1-yl-acetic acid methyl ester together with different quantities of the isomeric systhem. The triazole-1-yl-acetic acid methyl ester was hydrolyzed with LiOH to the corresponding acid. The isomeres were either separated before or after hydrolysis of the ester. Finally, the triazole-1-yl-acetic acides were reacted in several reaction types in one or more steps to the desired triazole compounds.

Biological Assay

The positive modulation of mGluR5 is measured in a HEK 293 cell line expressing human recombinant mGluR5 and is detected with calcium based FLIPR assay. The cells are cultured with DMEM supplemented with 10% FCS, 2 μg/mL tetracycline, 100 μg/mL hygromycin and 500 μg/mL geneticin. The cell culture media is exchanged for tetracycline-free cell culture media 3-7 days before the assay. One day before the assay the cell culture medium is exchanged to DMEM without glutamine and phenol red and supplemented with 10% FCS, 100 μg/mL hygromycin and 500 μg/mL geneticin. On the assay day, the medium of the subconfluent cultures is removed and the cells are detached by addition of 2.5 ml EDTA (0.02%) per 175 cm2 culture flask for 1 minute. The cells are resuspend in Ringer solution (140 mM NaCl, 5 mM KCl, 2.5 mM CaCl2, 1.5 mM MgCl2, 5 mM Glucose, 10 mM Hepes; adjusted to pH 7.4 with NaOH), pooled and Ringer solution added to adjust the volume to 50 mL. The cell suspension is centrifuged for 5 min at 1500 U/min (425 g). The supernatant is removed and the cells washed a second time with 50 ml fresh Ringer solution and centrifuged again as before. The supernatant is again removed and the pellet resuspended in Ringer solution to 1,000,000 cells/ml (1×10^6 cells/mL). The cells are plated onto BD BioCoat Poly-D-Lysine 384 well plates (20.000 cells/well; 20 μl/well). The lid covered plates are then incubated until use at 37° C./10% CO2. For dye loading, 20 μl of Calcium-4 assay kit solution (prepared according to the manufacturer's description in Ringer solution) are added to the cells and the plates are incubated for 80 min 37° C. and then 10 min at room temperature.

Controls, Compound dilution and assay execution:

Each assay plate contained wells with "high" and "low" controls:

Low controls 1% DMSO/ringer solution+basal glutamate activation (defined as 100% CTL).

High controls 10 μM CDPPB+basal glutamate activation (defined as 200% CTL).

Test compounds are dissolved and diluted in DMSO to 100-fold the desired concentrations. In a second step, the compounds are diluted in Ringer solution such that the compounds are 4-fold more concentrated than the desired final assay concentration. The final DMSO concentration was 1%.

20 μl of each compound solution are then transferred to the assay plate and the Ca2+ kinetic is measured to determine any intrinsic compound activity. After 5 min incubation in the FLIPR device, the second stimulation with 20 μl of glutamate in Ringer solution (glutamate concentration adjusted to approximately 5% basal stimulation of the maximal possible glutamate effect) is added and the kinetic Ca2+ response of the wells was measured for the modulation effect.

Analysis:

The peak height of the Ca release related fluorescence signal (9-66) is used for the EC50. The EC50 of the modulation is calculated over a nonlinear regression with GraphPad Prism (Table 1).

TABLE 1

| Example | EC50 [nM] | Example | EC50 [nM] | Example | EC50 [nM] | Example | EC50 [nM] |
|---|---|---|---|---|---|---|---|
| 7.01.01. | 212 | 7.02.54. | 206 | 7.03.018. | 702 | 7.03.074. | 321 |
| 7.01.02. | 118 | 7.02.55. | 1196 | 7.03.019. | 439 | 7.03.075. | 1088 |
| 7.01.03. | 283 | 7.02.56. | 932 | 7.03.020. | 626 | 7.03.076. | 1709 |
| 7.02.01. | 178 | 7.02.57. | 1453 | 7.03.021. | 228 | 7.03.077. | 500 |
| 7.02.02. | 186 | 7.02.58. | 214 | 7.03.022. | 56 | 7.03.078. | 803 |
| 7.02.03. | 1221 | 7.02.59. | 450 | 7.03.023. | 186 | 7.03.079. | 545 |
| 7.02.04. | 818 | 7.02.60. | 294 | 7.03.024. | 107 | 7.03.080. | 1136 |
| 7.02.05. | 900 | 7.02.61. | 511 | 7.03.025. | 97 | 7.03.081. | 413 |
| 7.02.06. | 1399 | 7.02.62. | 311 | 7.03.026. | 987 | 7.03.082. | 1886 |
| 7.02.07. | 1199 | 7.02.63. | 1007 | 7.03.027. | 739 | 7.03.083. | 64 |
| 7.02.08. | 666 | 7.02.64. | 976 | 7.03.028. | 117 | 7.03.084. | 52 |
| 7.02.09. | 992 | 7.02.65. | 407 | 7.03.029. | 714 | 7.03.085. | 644 |
| 7.02.10. | 965 | 7.02.66. | 559 | 7.03.030. | 37 | 7.03.086. | 379 |
| 7.02.11. | 376 | 7.02.67. | 133 | 7.03.031. | 1784 | 7.03.087. | 647 |
| 7.02.12. | 1018 | 7.02.68. | 198 | 7.03.032. | 868 | 7.03.088. | 60 |
| 7.02.13. | 544 | 7.02.69. | 436 | 7.03.033. | 474 | 7.03.089. | 71 |
| 7.02.14. | 537 | 7.02.70. | 376 | 7.03.034. | 907 | 7.03.090. | 420 |
| 7.02.15. | 646 | 7.02.71. | 441 | 7.03.035. | 170 | 7.03.091. | 1682 |
| 7.02.16. | 1365 | 7.02.72. | 774 | 7.03.036. | 49 | 7.03.092. | 1156 |
| 7.02.17. | 1056 | 7.02.73. | 148 | 7.03.037. | 312 | 7.03.093. | 433 |
| 7.02.18. | 516 | 7.02.74. | 798 | 7.03.038. | 75 | 7.03.094. | 1092 |
| 7.02.19. | 1993 | 7.02.75. | 488 | 7.03.039. | 50 | 7.03.095. | 610 |
| 7.02.20. | 1530 | 7.02.76. | 242 | 7.03.040. | 54 | 7.03.096. | 355 |
| 7.02.21. | 254 | 7.02.77. | 232 | 7.03.041. | 161 | 7.03.097. | 502 |
| 7.02.22. | 746 | 7.02.78. | 274 | 7.03.042. | 885 | 7.03.098. | 226 |
| 7.02.23. | 278 | 7.02.79. | 54 | 7.03.043. | 139 | 7.03.099. | 269 |
| 7.02.24. | 560 | 7.02.80. | 323 | 7.03.044. | 96 | 7.03.100. | 302 |
| 7.02.25. | 1855 | 7.02.81. | 175 | 7.03.045. | 155 | 7.03.101. | 382 |
| 7.02.26. | 518 | 7.02.82. | 149 | 7.03.046. | 356 | 7.03.102. | 293 |
| 7.02.27. | 1827 | 7.02.83. | 105 | 7.03.047. | 140 | 7.03.103. | 113 |
| 7.02.28. | 644 | 7.02.84. | 115 | 7.03.048. | 88 | 7.03.104. | 679 |
| 7.02.29. | 504 | 7.02.85. | 33 | 7.03.049. | 1435 | 7.03.105. | 870 |
| 7.02.30. | 932 | 7.02.86. | 28 | 7.03.050. | 338 | 7.03.106. | 251 |
| 7.02.31. | 1785 | 7.02.87. | 58.8 | 7.03.051. | 282 | 7.03.107. | 63 |
| 7.02.32. | 468 | 7.02.88. | 180 | 7.03.052. | 323 | 7.03.108. | 201 |
| 7.02.33. | 309 | 7.02.89. | 194 | 7.03.053. | 242 | 7.03.109. | 422 |
| 7.02.34. | 1459 | 7.02.90. | 155 | 7.03.054. | 97 | 7.03.110. | 55 |
| 7.02.35. | 1422 | 7.02.91. | 107 | 7.03.055. | 100 | 7.03.111. | 90 |
| 7.02.36. | 1093 | 7.02.92. | 46 | 7.03.056. | 63 | 7.03.112. | 147 |
| 7.02.37. | 708 | 7.03.001. | 164 | 7.03.057. | 187 | 7.03.113. | 340 |
| 7.02.38. | 1154 | 7.03.002. | 708 | 7.03.058. | 117 | 7.03.114. | 102 |
| 7.02.39. | 279 | 7.03.003. | 851 | 7.03.059. | 540 | 7.03.115. | 231 |
| 7.02.40. | 1756 | 7.03.004. | 1064 | 7.03.060. | 255 | 7.03.116. | 392 |
| 7.02.41. | 1271 | 7.03.005. | 958 | 7.03.061. | 369 | 7.03.117. | 889 |
| 7.02.42. | 1239 | 7.03.006. | 1676 | 7.03.062. | 155 | 7.03.118. | 211 |
| 7.02.43. | 1638 | 7.03.007. | 1379 | 7.03.063. | 60 | 7.03.119. | 329 |
| 7.02.44. | 211 | 7.03.008. | 752 | 7.03.064. | 86 | | |
| 7.02.45. | 1003 | 7.03.009. | 808 | 7.03.065. | 95 | 7.03.121. | 259 |
| 7.02.46. | 381 | 7.03.010. | 734 | 7.03.066. | 71 | 7.03.122. | 57 |
| 7.02.47. | 206 | 7.03.011. | 453 | 7.03.067. | 1683 | 7.04.01. | 678 |
| 7.02.48. | 972 | 7.03.012. | 1473 | 7.03.068. | 281 | 7.04.02. | 132 |
| 7.02.49. | 1355 | 7.03.013. | 141 | 7.03.069. | 574 | 7.04.03. | 346 |
| 7.02.50. | 216 | 7.03.014. | 626 | 7.03.070. | 457 | 7.04.04. | 561 |
| 7.02.51. | 707 | 7.03.015. | 305 | 7.03.071. | 1166 | 7.04.05. | 1658 |
| 7.02.52. | 472 | 7.03.016. | 101 | 7.03.072. | 407 | 7.05.01. | 1710 |

TABLE 1-continued

| Example | EC50 [nM] | Example | EC50 [nM] | Example | EC50 [nM] | Example | EC50 [nM] |
|---|---|---|---|---|---|---|---|
| 7.02.53. | 229 | 7.03.017. | 97 | 7.03.073. | 1166 | 7.06.01. | 1131 |
| 7.03.123 | 31 | 7.03.127 | 40 | 7.03.131 | 316 | 7.03.135 | 19 |
| 7.03.124 | 61 | 7.03.128 | 85 | 7.03.132 | 95 | 07.03.136. | 498 |
| 7.03.125 | 152 | 7.03.129 | 27 | 7.03.133 | 104 | 07.03.137. | 339 |
| 7.03.126 | 201 | 7.03.130 | 481 | 7.03.134 | 129 | 07.03.138 | 61 |
| 07.03.139 | 242 | 07.03.140. | 798 | 07.03.141 | 1121 | | |

Method of Treatment

The present invention is directed to compounds of general formula I which are useful in the treatment of a disease and/or condition wherein the activity of an mGluR5 positive modulator is of therapeutic benefit, including but not limited to the treatment of psychotic disorders, cognitive disorders and dementias.

The compounds of general formula I are useful for the treatment of psychotic disorders including schizophrenia, schizoaffective disorder and substance induced psychotic disorder; cognitive disorders and dementias including age-associated learning and memory impairments or losses, post stroke dementia, deficits in concentration, mild cognitive impairment, the cognitive dysfunction in Alzheimers disease, and the cognitive dysfunction of schizophrenia. Therefore, the present invention also relates to a compound of general formula I as a medicament.

A further aspect of the present invention relates to the use of a compound of general formula I for the treatment of a disease and/or condition wherein the activity of mGluR5 positive modulator is of therapeutic benefit.

Furthermore, the present invention relates to the use of a compound of general formula I for the treatment of psychotic disorders, cognitive disorders and dementias.

Furthermore, the present invention relates to the use of a compound of general formula I for the treatment of psychotic disorders including schizophrenia, schizoaffective disorder and substance induced psychotic disorder; cognitive disorders and dementias including age-associated learning and memory impairments or losses, post stroke dementia, deficits in concentration, mild cognitive impairment, the cognitive dysfunction in Alzheimers disease, and the cognitive dysfunction of schizophrenia.

In a further aspect of the present invention the present invention relates to methods for the treatment or prevention of above mentioned diseases and conditions, which method comprises the administration of an effective amount of a compound of general formula I to a human being.

Dosage

The dose range of the compounds of general formula I applicable per day is usually from 0.1 to 5000 mg, preferably from 0.1 to 1000 mg, more preferably from 5 to 500 mg, most preferably, 10 or 100 mg. Each dosage unit may conveniently contain from 0.1 to 500 mg, preferably 10 to 100 mg.

The actual pharmaceutically effective amount or therapeutic dosage will of course depend on factors known by those skilled in the art such as age and weight of the patient, route of administration and severity of disease. In any case the combination will be administered at dosages and in a manner which allows a pharmaceutically effective amount to be delivered based upon patient's unique condition.

Pharmaceutical Compositions

Suitable preparations for administering the compounds of formula will be apparent to those with ordinary skill in the art and include for example tablets, pills, capsules, suppositories, lozenges, troches, solutions, syrups, elixirs, sachets, injectables, inhalatives and powders etc. The content of the pharmaceutically active compound(s) should be in the range from 1 to 99 wt.-%, preferably 10 to 90 wt.-%, more preferably 20 to 70 wt.-%, of the composition as a whole. Suitable tablets may be obtained, for example, by mixing one or more compounds according to formula I with known excipients, for example inert diluents, carriers, disintegrants, adjuvants, surfactants, binders and/or lubricants. The tablets may also consist of several layers. A further aspect of the invention is a pharmaceutical formulation including a compound of formula I in admixture with a pharmaceutically acceptable adjuvant, diluent or carrier.

Combination Therapy

In another aspect the present invention relates to a combination therapy in which an active compound according to the present invention is administered together with another active compound. Accordingly, the invention also refers to pharmaceutical formulations that provide such a combination of active ingredients, whereby one of which is an active compound of the present invention. Such combinations may be fixed dose combinations (the active ingredients that are to be combined are subject of the same pharmaceutical formulation) or free dose combinations (active ingredients are in separate pharmaceutical formulations). Consequently, a further aspect of the present invention refers to a combination of each of the active compounds of the present invention, preferably at least one active compound according to the present invention, with another active compound for example selected from the group of antipsychotics such as haloperidol, clozapine, risperidone, quetiapine, aripripazole, and olanzapine; antidepressants such as selective serotonin re-uptake inhibitors and dual serotonin/noradrenaline re-uptake inhibitors; mood stabilizers such as lithium valproate and lamotrigine; beta-secretase inhibitors; gamma-secretase inhibitors; gamma-secretase modulators; amyloid aggregation inhibitors such as e.g. scyllo-inositol; directly or indirectly acting neuroprotective and/or disease-modifying substances; antioxidants, such as e.g. vitamin E, ginko biloba or ginkolide; anti-inflammatory substances, such as e.g. Cox inhibitors, NSAIDs additionally or exclusively having Aβ Abeta) lowering properties; HMG-CoA reductase inhibitors, such as statins; acetylcholine esterase inhibitors, such as donepezil, rivastigmine, tacrine, galantamine; NMDA receptor antagonists such as e.g. memantine; AMPA receptor agonists; AMPA receptor positive modulators, AMPkines, glycine transporter 1 inhibitors; monoamine receptor reuptake inhibitors; substances modulating the concentration or release of neurotransmitters; substances inducing the secretion of growth hormone such as ibutamoren mesylate and capromorelin; CB-1 receptor antagonists or inverse agonists; antibiotics such as minocyclin or rifampicin; PDE1, PDE2, PDE4, PDE5, PDE9 or PDE10 inhibitors, GABAA receptor inverse agonists; GABAA alpha5 receptor inverse agonists; GABAA receptor antagonists; nicotinic receptor agonists or partial agonists or positive modulators; alpha4beta2 nicotinic receptor agonists or partial agonists or positive modulators; alpha7 nicotinic receptor agonists or partial agonists; histamine receptor H3 antagonists; 5-HT4 receptor agonists or partial agonists; 5-HT6 receptor antagonists; alpha2-adrenoreceptor antagonists, calcium antagonists; muscarinic receptor M1 agonists or partial agonists or positive modulators; muscarinic receptor M2 antagonists; muscarinic receptor M4 antagonists; muscarinic receptor M4 positive allosteric modulators; metabotropic glutamate receptor 5 positive allosteric modulators; metabotropic glutamate receptor 2 antagonists; metabotropic glutamate receptor 2/3 agonists; metabotropic glutamate receptor 2 positive allosteric modulators and other substances that modulate receptors or enzymes in a manner such that the efficacy and/or safety of the active compounds according to the invention is increased and/or unwanted side effects are reduced. The active compounds according to the invention may also be used in combination with immunotherapies such as e.g. active immunisation with Abeta or parts thereof or passive immunisation with humanised anti-Abeta antibodies, nanobodies or antibody fragments for the treatment of the above mentioned diseases and conditions.

The active compounds according to the invention also may be combined with antipsychotics like haloperidol, flupentixol, fluspirilene, chlorprothixene, prothipendyl, levomepromazine, clozapine, olanzapine, quetiapine, risperidone, paliperidone, amisulpride, ziprasidone, aripiprazol, sulpiride, zotepine, sertindole, fluphenazine, perphenazine, perazine, promazine, chlorpromazine, levomepromazine, benperidol, bromperidol, pimozid, melperone, pipamperone, iloperidone, asenapine, perospirone, blonanserin, lurasidone.

The active compounds according to the invention also may be combined with antidepressants like amitriptyline imipramine hydrochloride, imipramine maleate, lofepramine, desipramine, doxepin, trimipramine.

Or the active compounds according to the invention also may be combined with serotonin (5-HT) reuptake inhibitors such as alaproclate, citalopram escitalopram, clomipramine, duloxetine, femoxetine, fenfluramine, norfenfluramine, fluoxetine, fluvoxamine, indalpine, milnacipran, paroxetine, sertraline, trazodone, venlafaxine, zimelidine, bicifadine, desvenlafaxine, brasofensme and tesofensine.

The combinations according to the present invention may be provided simultaneously in one and the same dosage form, i.e. in form of a combination preparation, for example the two components may be incorporated in one tablet, e.g. in different layers of said tablet. The combination may be also provided separately, in form of a free combination, i.e. the active compounds of the present invention are provided in one dosage form and one or more of the above mentioned combination partners is provided in another dosage form. These two dosage forms may be equal dosage forms, for example a co-administration of two tablets, one containing a therapeutically effective amount of the active compound of the present invention and one containing a therapeutically effective amount of the above mentioned combination partner. It is also possible to combine different administration forms, if desired. Any type of suitable administration forms may be provided.

The active compound according to the invention, or a physiologically acceptable salt thereof, in combination with another active substance may be used simultaneously or at staggered times, but particularly close together in time. If administered simultaneously, the two active substances are given to the patient together; if administered at staggered times the two active substances are given to the patient successively within a period of less than or equal to 12, particularly less than or equal to 6 hours.

The dosage or administration forms are not limited, in the frame of the present invention any suitable dosage form may be used. Exemplarily the dosage forms may be selected from solid preparations such as patches, tablets, capsules, pills, pellets, dragees, powders, troches, suppositories, liquid preparations such as solutions, suspensions, emulsions, drops, syrups, elixirs, or gaseous preparations such as aerosols, sprays and the like.

The dosage forms are advantageously formulated in dosage units, each dosage unit being adapted to supply a single dose of each active component being present. Depending from the administration route and dosage form the ingredients are selected accordingly.

The dosage for the above-mentioned combination partners may be expediently 1/5 of the normally recommended lowest dose up to 1/1 of the normally recommended dose.

The dosage forms are administered to the patient for example 1, 2, 3, or 4 times daily depending on the nature of the formulation. In case of retarding or extended release formulations or other pharmaceutical formulations, the same may be applied differently (e.g. once weekly or monthly etc.). It is preferred that the active compounds of the invention be administered either three or fewer times, more preferably once or twice daily.

Preparation of Examples for Compounds of the General Formula I

Unless otherwise stated, one or more tautomeric forms of compounds of the examples described hereinafter may be prepared in situ and/or isolated. All tautomeric forms of compounds of the examples described hereinafter should be considered to be disclosed.

The invention is illustrated by way of the following examples, in which the following abbreviations may be employed:

Abbreviations

RT: room temperature
THF: tetrahydrofuran
KOtBu: kalium tert butoxide
PFTU: pentafluorphenol-tetramethyluronium hexafluorophosphat
ACN: acetonitrile
MeOH: methanol
DIPEA: diisopropylamine
DEA: diethylamine
EtOAC: ethyl acetate
DMF: dimethylformamide
TBTU: [(Benzotriazol-1-yloxy)-dimethylamino-methylene]-dimethyl-ammonium; tetrafluoro borate
HATU: (O-(7-AZOBENZOTRIAZOL-1-YL)-1,1,3,3-TETRAMETHYLURONIUM HEXAFLUOROPHOSPHATE)
conc.: concentrated
min.: minutes
DCM: dichlormethane
LiHMDS: lithium bis(trimethylsilyl)amide
HCl: hydrochlorid acid
BINAP: 2,2'-bis(diphenylphosphino)-1,1'-binaphzhyl
BYBOP: benzotriazole-1-yl-oxy-trispyrrolidinophosphonium hexafluorophospate
CDT bis-1,2,4-triazol-1-yl-methanone
DMAP: 4-dimethylaminopyridine
Dess-Martin: 1,1,1-triacetoxy-1,2-benziodoxol-3(1H)-one
CDI: carbonyl diimidazole Analytical Methods All compounds specified in the examples below gave the correct mass spectra matching the theoretical isotope pattern. For practical reasons, only one of the major isotope peaks is given as representative data for the mass spectrum.

List of Analytical HPLC-methods:

Method 1:

column: Daicel IC, 250 mm×20 mm flow: 70 ml/min, mobile phases: 75% $CO_2$, 25% ethanol with 0.2% DEA wave lengh: 254

Method A:

Waters ZMD, Alliance 2690/2695 HPLC, Waters 996/2996 diodenarraydetector eluent:

A: water with 0.10% TFA

B: acetonitril with 0.10% TFA gradient:

| time in min | % A | % B | flow in ml/min |
|---|---|---|---|
| 0.00 | 95 | 5 | 2.80 |
| 0.30 | 95 | 5 | 2.80 |
| 1.60 | 2 | 98 | 2.80 |
| 1.90 | 2 | 98 | 2.80 |
| 2.00 | 95 | 5 | 2.50 |

column: Merck Chromolith™ Flash RP-18e, 3 mm×100 mm (temperature: isocratic 25° C.)

Method B:

Waters ZQ MS, Alliance 2690/2695 HPLC, Waters 996/2996 diodenarraydetector eluent:

A: water with 0.10% TFA

D: methanol gradient:

| time in min | % A | % D | flow in ml/min |
|---|---|---|---|
| 0.00 | 95 | 5 | 4.00 |
| 0.20 | 95 | 5 | 4.00 |
| 1.60 | 0 | 100 | 4.00 |
| 2.10 | 0 | 100 | 4.00 |

column: Waters XBridge™ C18 3.5 μm, 4.6×20 mm IS™ (temperature: isocratic 40° C.).

diodenarray detection: 210-400 nm.

Method C:

Waters Alliance with DA and MS-detector eluent:

A: water with 0.10% $NH_3$

D: methanol gradient:

| time in min | % A | % D | flow in ml/min |
|---|---|---|---|
| 0.00 | 95 | 5 | 4.00 |
| 0.20 | 95 | 5 | 4.00 |
| 1.50 | 0 | 100 | 4.00 |
| 1.75 | 0 | 100 | 4.00 |

column: Waters XBridge™ C18 3.5 μm, 4.6×30 mm (temperature: isocratic 60° C.).

Method D:

Waters ZQ 2000MS, Agilent HP100, binäre pumps eluent:

A: water with 0.1% TFA

B: methanol gradient:

| time in min | % A | % B | flow in ml/min |
|---|---|---|---|
| 0.00 | 95 | 5 | 1.50 |
| 1.30 | 0 | 100 | 1.50 |
| 2.50 | 0 | 100 | 1.50 |
| 2.60 | 95 | 5 | 1.50 |

column: Sunfire C18, 4.6×50 mm, 3.5 μm (temperature: isocratic 40° C.).

diodenarray detection: 210-500 nm

Method E:

Agilent 1200 System eluent:

A: water with 0.10% formicacid

B: acetonitril 0.10% formicacid gradient:

| time in min | % A | % B | flow in ml/min |
|---|---|---|---|
| 0.00 | 95 | 5 | 1.60 |
| 0.10 | 95 | 5 | 1.60 |
| 1.75 | 5 | 95 | 1.60 |
| 1.90 | 5 | 95 | 1.60 |
| 1.95 | 95 | 5 | 1.60 |
| 2.00 | 95 | 5 | 1.60 |

column: Zorbax StableBond C18, 3.0×30 mm, 1.8 μm (temperature: isocratic 25° C.).

detection: 254 nm

Method F:

Waters ZQ MS, Waters 2690/2695 eluent:

A: water with 0.10% $NH_3$

D: acetonitrile gradient:

| time in min | % A | % D | flow in ml/min |
|---|---|---|---|
| 0.00 | 95 | 5 | 3.00 |
| 0.20 | 95 | 5 | 3.00 |
| 1.50 | 2 | 98 | 3.00 |
| 1.70 | 2 | 98 | 3.00 |
| 1.90 | 95 | 5 | 3.00 |

column: Waters XBridge™ C18 3.5 μm, 4.6×20 mm (temperature: isocratic 25° C.).

detection: 210-500 nm

Method G:

Waters ZQ 2000MS, Agilent HP100, binäre pumps eluent:

A: water with 0.032% ammonia

B: methanol gradient:

| time in min | % A | % B | flow in ml/min |
|---|---|---|---|
| 0.00 | 5 | 95 | 1.50 |
| 2.00 | 0 | 100 | 1.50 |

column: waters C18, 4.6×50 mm, 3.5 μm (temperature: isocratic 40° C.).
diodenarray detection: 210-500 nm
Method H:
Waters ZQ 2000MS, Agilent HP100, binäre pumps
eluent:
A: water with 0.1% TFA
B: methanol
gradient:

| time in min | % A | % B | flow in ml/min |
|---|---|---|---|
| 0.00 | 80 | 20 | 2.00 |
| 1.70 | 0 | 100 | 2.00 |
| 2.50 | 0 | 100 | 2.00 |
| 2.60 | 80 | 20 | 2.00 |

column: sunfire C18, 4.6×50 mm, 3.5 μm (temperature: isocratic 60° C.).
diodenarray detection: 210-500 nm
Method I:
Waters ZQ 2000MS, Agilent HP100, binäre pumps
eluent:
A: water with 0.10% TFA
B: methanol
gradient:

| time in min | % A | % B | flow in ml/min |
|---|---|---|---|
| 0.00 | 80 | 20 | 2.00 |
| 1.70 | 0 | 100 | 2.00 |
| 2.50 | 0 | 100 | 2.00 |
| 2.60 | 80 | 20 | 2.00 |

column: Sunfire C18, 4.6×50 mm, 3.5 μm (temperature: isocratic 60° C.).
diodenarray detection: 210-500 nm
Method J:
Waters ZQ 2000MS, Agilent HP100, binäre pumps
eluent:
A: water with 0.10% TFA
B: methanol
gradient:

| time in min | % A | % B | flow in ml/min |
|---|---|---|---|
| 0.00 | 95 | 5 | 1.50 |
| 2.00 | 0 | 100 | 1.50 |
| 2.50 | 0 | 100 | 1.50 |
| 2.60 | 95 | 5 | 1.50 |

column: Sunfire C18, 4.6×50 mm, 3.5 μm (temperature: isocratic 40° C.).
diodenarray detection: 210-500 nm Method K:
Waters Alliance with diodenarraydetector and massdetector
eluent:
A: water with 0.10% TFA
B: methanol with 0.10% TFA
gradient:

| time in min | % A | % B | flow in ml/min |
|---|---|---|---|
| 0.00 | 95 | 5 | 4.00 |
| 0.20 | 95 | 5 | 4.00 |
| 1.50 | 0 | 100 | 4.00 |
| 1.75 | 0 | 100 | 4.00 |
| 1.85 | 95 | 5 | 4.00 |

column: XBridge C18, 4.6×30 mm, 3.5 μm (temperature: isocratic 60° C.).
Method L:
Waters Acquity with diodenarraydetector and massdetector
eluent:
A: water with 0.13% TFA
B: methanol with 0.08% TFA
gradient:

| time in min | % A | % B | flow in ml/min |
|---|---|---|---|
| 0.00 | 99 | 1 | 1.30 |
| 0.05 | 99 | 1 | 1.30 |
| 1.05 | 0 | 100 | 1.30 |
| 1.20 | 0 | 100 | 1.30 |

column: Xbridge BEH C18, 2.1×30 mm, 1.7 μm (temperature: isocratic 60° C.).
Method M:
Waters Acquity with diodenarraydetector
eluent:
A: water with 0.13% TFA
B: methanol with 0.05% TFA
gradient:

| time in min | % A | % B | flow in ml/min |
|---|---|---|---|
| 0.00 | 99 | 1 | 1.20 |
| 0.05 | 99 | 1 | 1.20 |
| 1.05 | 0 | 100 | 1.20 |
| 1.25 | 0 | 100 | 1.20 |

column: Sunfire C18, 2.1×30 mm, 2.5 μm (temperature: isocratic 60° C.).
Method N:
Waters Alliance with diodenarraydetector and massdetector
eluent:
A: water with 0.10% $NH_3$
D: methanol with 0.10% $NH_3$
gradient:

| time in min | % A | % D | flow in ml/min |
|---|---|---|---|
| 0.00 | 95 | 5 | 4.00 |
| 0.20 | 95 | 5 | 4.00 |
| 1.50 | 0 | 100 | 4.00 |
| 1.75 | 0 | 100 | 4.00 |

column: Waters XBridge™ C18 3.5 μm, 4.6×30 mm (temperature: isocratic 60° C.).

Method O:

Waters ZQ 2000MS, Agilent HP100, binäre pumps eluent:

A: water with 0.032% ammonia

B: acetonitrile gradient:

| time in min | % A | % B | flow in ml/min |
|---|---|---|---|
| 0.00 | 95 | 0 | 1.50 |
| 2.00 | 0 | 100 | 1.50 |

column: Xbridge C18, 4.6×50 mm, 3.5 μm (temperature: isocratic 40° C.).

diodenarray detection: 210-500 nm

Method P:

Agilent 1100 with diodenarraydetector and massdetector eluent:

A: water with 0.10% TFA

D: methanol with 0.10% TFA gradient:

| time in min | % A | % D | flow in ml/min |
|---|---|---|---|
| 0.00 | 95 | 5 | 4.00 |
| 0.15 | 95 | 5 | 4.00 |
| 1.70 | 0 | 100 | 4.00 |
| 2.25 | 0 | 100 | 4.00 |

column: Waters XBridge™ C18 3.5 μm, 4.6×30 mm (temperature: isocratic 60° C.).

Method Q:

Waters Acquity with diodenarraydetector and massdetector eluent:

A: water with 0.1% TFA

B: methanol gradient:

| time in min | % A | % B | flow in ml/min |
|---|---|---|---|
| 0.00 | 99 | 1 | 1.50 |
| 0.05 | 99 | 1 | 1.50 |
| 1.05 | 0 | 100 | 1.50 |
| 1.20 | 0 | 100 | 1.50 |

column: Xbridge BEH C18, 2.1×30 mm, 1.7 μm (temperature: isocratic 60° C.).

Method R:

Waters Alliance with diodenarraydetector and massdetector eluent:

A: water with 0.10% TFA

B: methanol gradient:

| time in min | % A | % B | flow in ml/min |
|---|---|---|---|
| 0.00 | 95 | 5 | 4.90 |
| 1.60 | 0 | 100 | 4.90 |
| 2.20 | 95 | 5 | 4.90 |

column: XBridge C18, 4.6×30 mm, 3.5 μm (temperature: isocratic 60° C.).

Method S:

Waters Acquity with diodenarraydetector and massdetector eluent:

A: water with 0.1% TFA

B: methanol gradient:

| time in min | % A | % B | flow in ml/min |
|---|---|---|---|
| 0.00 | 99 | 1 | 1.40 |
| 0.05 | 99 | 1 | 1.40 |
| 1.00 | 0 | 100 | 1.40 |
| 1.10 | 0 | 100 | 1.40 |

column: Xbridge BEH C18, 2.1×30 mm, 1.7 μm (temperature: isocratic 60° C.).

diodenarray detektion: 210-400 nm.

Method T:

Waters SQD MS, Agilent UPLC eluent:

A: water with 0.1% TFA

B: acetonitrile with 0.08% TFA gradient:

| time in min | % A | % B | flow in ml/min |
|---|---|---|---|
| 0.00 | 95 | 5 | 1.50 |
| 0.70 | 0 | 100 | 1.50 |
| 0.80 | 0 | 100 | 1.50 |
| 0.81 | 95 | 5 | 1.50 |

column: Ascentis Express C18, 2.1×50 mm, 2.7 μm (temperature: isocratic 60° C.).

diodenarray detection: 210-500 nm

Method U:

Waters Acquity with diodenarraydetector and massdetector eluent:

A: water with 0.1% TFA

B: methanol with 0.08% TFA gradient:

| time in min | % A | % B | flow in ml/min |
|---|---|---|---|
| 0.00 | 99 | 1 | 1.50 |
| 0.05 | 99 | 1 | 1.50 |
| 0.35 | 0 | 100 | 1.50 |
| 0.50 | 0 | 100 | 1.50 |

column: Xbridge BEH C18, 2.1×30 mm, 1.7 μm (temperature: isocratic 60° C.).

Method V:

Waters Acquity with diodenarraydetector eluent:

A: water with 0.1% TFA

B: methanol gradient:

| time in min | % A | % B | flow in ml/min |
|---|---|---|---|
| 0.00 | 99 | 1 | 1.30 |
| 0.05 | 99 | 1 | 1.30 |
| 1.05 | 0 | 100 | 1.30 |
| 1.25 | 0 | 100 | 1.30 |

column: Sunfire C18, 2.1×20 mm, 2.5 μm (temperature: isocratic 60° C.).

Method W:

Waters Alliance with diodenarraydetector and massdetector eluent:

A: water with 0.1% ammonia

B: methanol with 0.1% ammonia gradient:

| time in min | % A | % B | flow in ml/min |
|---|---|---|---|
| 0.00 | 95 | 5 | 4.00 |
| 0.20 | 95 | 5 | 4.00 |
| 1.50 | 0 | 100 | 4.00 |
| 1.75 | 0 | 100 | 4.00 |

column: XBridge C18, 4.6×30 mm, 3.5 μm (temperature: isocratic 60° C.).

Method X:

Waters Alliance with diodenarraydetector and massdetector eluent:

A: water with 0.1% TFA

B: methanol gradient:

| time in min | % A | % B | flow in ml/min |
|---|---|---|---|
| 0.00 | 95 | 5 | 4.00 |
| 0.20 | 95 | 5 | 4.00 |
| 1.50 | 0 | 100 | 4.00 |
| 1.75 | 0 | 100 | 4.00 |
| 1.85 | 95 | 5 | 4.00 |

column: XBridge C18, 4.6×30 mm, 3.5 μm (temperature: isocratic 60° C.).

Method Y:

Waters Alliance with diodenarraydetector and massdetector eluent:

A: water with 0.1% TFA

B: methanol gradient:

| time in min | % A | % B | flow in ml/min |
|---|---|---|---|
| 0.00 | 95 | 5 | 4.80 |
| 1.60 | 95 | 5 | 4.80 |
| 1.85 | 0 | 100 | 4.80 |
| 1.90 | 95 | 5 | 4.80 |

column: XBridge C18, 4.6×30 mm, 3.5 μm (temperature: isocratic 60° C.).

Method Z:

Waters ZQ 2000MS, Agilent HP100, binäre pumps eluent:

A: water with 0.01% ammonia

B: methanol gradient:

| time in min | % A | % B | flow in ml/min |
|---|---|---|---|
| 0.00 | 5 | 95 | 1.50 |
| 2.00 | 0 | 100 | 1.50 |

column: waters C18, 4.6×50 mm, 3.5 μm (temperature: isocratic 40° C.).

diodenarray detection: 210-500 nm

Method AA:

Applied Biosystem: LCM/MS API 2000, HPLC: Shimadzu Prominence dual wavelength: 220 and 260 nm eluent:

A: water with 0.05% TFA

B: acetonitrile gradient:

| time in min | % A | % B | flow in ml/min |
|---|---|---|---|
| 0.01 | 90 | 10 | 1.20 |
| 1.50 | 70 | 30 | 1.20 |
| 3.00 | 10 | 90 | 1.20 |
| 4.00 | 10 | 90 | 1.20 |
| 5.00 | 90 | 10 | 1.20 |

column: Gemini C18, 4.6×50 mm, 2.7 μm (temperature: isocratic 20° C.).

Method AB:

Agilent 1200 with diodenarraydetector and massdetector eluent:

A: water with 0.10% TFA

D: methanol gradient:

| time in min | % A | % D | flow in ml/min |
|---|---|---|---|
| 0.00 | 95 | 5 | 1.80 |
| 0.25 | 95 | 5 | 1.80 |
| 1.70 | 0 | 100 | 1.80 |
| 1.75 | 0 | 100 | 2.50 |

column: Sunfire C18 2.5 μm, 3×30 mm (temperature: isocratic 60° C.).

Method AC:

Agilent 1200 with diodenarraydetector and massdetector eluent:

A: water with 0.10% TFA

D: methanol gradient:

| time in min | % A | % D | flow in ml/min |
|---|---|---|---|
| 0.00 | 95 | 5 | 2.20 |
| 0.30 | 95 | 5 | 2.20 |
| 1.18 | 0 | 100 | 2.20 |
| 1.23 | 0 | 100 | 2.90 |

column: XBridge C8 2.5 μm, 3×30 mm (temperature: isocratic 60° C.).

Method AD:

Waters ZQ 2000MS, Agilent HP100, binäre pumps eluent:

A: water with 0.1% TFA

B: methanol gradient:

| time in min | % A | % B | flow in ml/min |
|---|---|---|---|
| 0.00 | 95 | 5 | 4.00 |
| 0.05 | 95 | 5 | 3.00 |
| 2.05 | 0 | 100 | 3.00 |
| 2.10 | 0 | 100 | 4.50 |

column: Sunfire C18, 4.6×50 mm, 2.5 μm (temperature: isocratic 60° C.).

diodenarray detection: 210-500 nm

SYNTHESIS OF INTERMEDIATES

6.01. Synthesis of building blocks

6.01.01 5,6,7,8-Tetrahydro-4H-thiazolo[4,5-d]azepin-2-ylamine hydrobromide

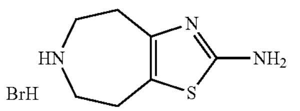

6.01.01.1 5-Bromo-azepan-4-one hydrobromide

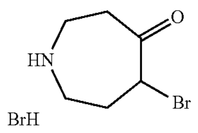

32 mL 62% HBr solution in 50 mL conc. acetic acid was added to 50 g hexahydro-azepin-4-on hydrochloride in 600 mL conc. acetic acid. Then 17.2 mL bromine in 50 mL conc. acetic acid was dropped to the reaction. The solvent was removed and the residue was crystallized from a mixture of DCM/MeOH (8/2) to give 79 g of the desired compound.

$(M+H)^+$: 192

6.01.01.2 5,6,7,8-tetrahydro-4H-thiazolo[4,5-d]azepin-2-ylamine hydrobromide

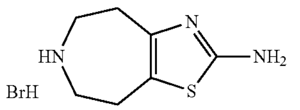 [SMILES: Br ; Nc1nc2c(s1)CCNCC2]

1.44 g thiourea was added to 4 g 5-bromo-azepan-4-one hydrobromide in 50 mL ethanol and stirred 3 h at 80° C. and over the weekend at RT. The precipitate was filtered and dried to yield 3.8 g of the product.

$R_t$: 0.61 min (method C)

$(M+H)^+$: 170

By using the same synthesis strategy as for 5,6,7,8-tetrahydro-4H-thiazolo[4,5-d]azepin-2-ylamine hydrobromide the following compounds were obtained:

| Examples | Product | MS m/z $[M+H]^+$ | HPLC Method | Rt min |
|---|---|---|---|---|
| 6.01.02 | 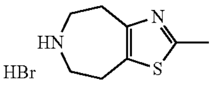 | 169 | Method E | 0.33 |
| 6.01.03 | 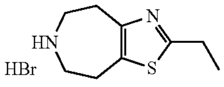 | 183 | Method L | 0.35 |
| 6.01.04 | 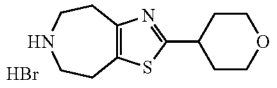 [SMILES: Br ; C1Cc2nc(C3CCOCC3)sc2CCN1] | 239 | Method P | 0.68 |
| 6.01.05 | 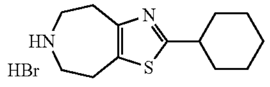 | 237 | Method P | 1.12 |

6.01.06 2-Bromo-5,6,7,8-tetrahydro-4H-thiazolo[4,5-d]azepine

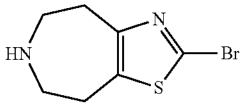

6.01.06.01 2-Amino-4,5,7,8-tetrahydro-thiazolo[4,5-d]azepine-6-carboxylic acid tert-butyl ester

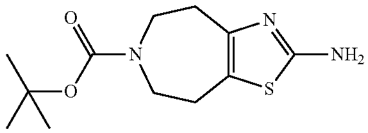 [SMILES: CC(C)(C)OC(=O)N1CCc2nc(N)sc2CC1]

5.7 g di-tert.butyl-dicarbonat in 25 mL THF was added to 4 g 5,6,7,8-Tetrahydro-4H-thiazolo[4,5-d]azepin-2-yl-amine in 75 mL THF at 0-5° C. The reaction was stirred over night at RT. The solvent was removed. The residue was dissolved in ethylacetate and washed with water. The organic layer was evaporated to give 5.9 g of the desired product.

$R_f$: 0.59 (dichlormethane 7: ethylacetate 2: methanol 1), $(M+H)^+$: 270

6.01.06.02 2-Bromo-5,6,7,8-tetrahydro-4H-thiazolo[4,5-d]azepine

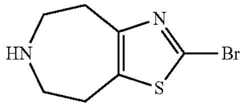 [SMILES: Brc1nc2c(s1)CCNCC2]

238 µl tert.-butyl nitrite was added to 447 mg cupper (II) bromide in 50 mL acetonitrile. The reaction was stirred 10 min. at RT and then 270 mg 2-amino-4,5,7,8-tetrahydro-thiazolo[4,5-d]-azepine-6-carboxylic acid tert-butyl ester was added. The reaction was stirred 30 min. at 60° C. The reaction was purified by HPLC. The residue was dissolved in 10 mL dichlormethane and 10 mL trifluor acetic acid and stirred at RT for 1 h. The mixture was evaporated to give 112 mg of the desired product. $R_t$: 0.92 min (method I), $(M+H)^+$: 233/235

6.01.07 N-(5,6,7,8-Tetrahydro-4H-thiazolo[4,5-d]azepin-2-yl)-acetamide

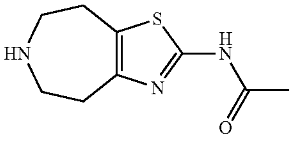

6.01.07.01 2-Acetylamino-4,5,7,8-tetrahydro-thiazolo[4,5-d]azepine-6-carboxylic acid tert-butyl ester

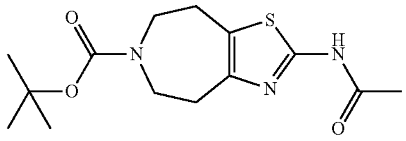 [SMILES: CC(=O)Nc1nc2c(s1)CCN(C(=O)OC(C)(C)C)CC2]

95 mg acetyl chloride was added to 312 mg 2-amino-4,5,7,8-tetrahydro-thiazolo[4,5-d]azepine-6-carboxylic acid tert-butyl ester in 5 mL pyridine at 15° C. The reaction was stirred 3 h at RT. The reaction was diluted with dichlormethane and 1 mL water was added. The solution was filtered over 40 mL Alox and 100 mL Extrelut and evaporated to give 127 mg of the desired product. (M+H)+: 312

6.01.07.02 N-(5,6,7,8-Tetrahydro-4H-thiazolo[4,5-d]azepin-2-yl)-acetamide

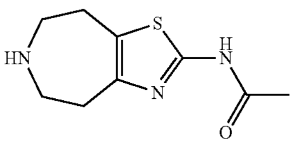

35 ml trifluoroacetic acid was added to 2.4 g 2-acetylamino-4,5,7,8-tetrahydro-thiazolo[4,5-d]-azepine-6-carboxylic acid tert-butyl ester in 80 mL chloroform. The reaction was stirred 3 h at RT and concentrated. The residue was dissolved in 75 mL chloroform and basified with 2.5 M potassiumcarbonate solution. The chloroform layer was separated and concentrated to give 1.3 g of the desired product., (M+H)+=212

6.01.08 1-Methyl-3-(4,5,6,7-tetrahydro-thiazolo[5,4-c]pyridin-2-yl)-urea

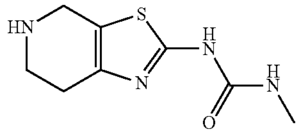

6.01.08.01 3-Bromo-piperidin-4-one hydrobromide

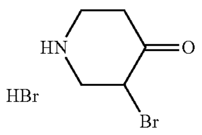

4.7 mL 33% HBr in acetic acid and 11.4 g bromine in 30 mL acetic acid were added slowly to a stirred solution of 10 g piperidin-4-one in 60 mL acetic acid at RT. The reaction mixture was stirred for additional 45 min at ambient temperature and the acetic acid was completely removed under reduced pressure. The residue was dissolved in 200 mL acetone and refluxed for 1 h, cooled, filtered and washed with acetone and dried to give 15.2 g of the desired product, (M+H)+: 180.

6.01.08.02 4,5,6,7-Tetrahydro-thiazolo[5,4-c]pyridin-2-ylamine dihydrobromide

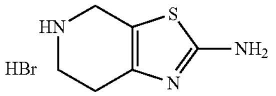

4.55 g thiourea was added to 15.2 g 3-Bromo-piperidin-4-one hydrobromide in 152 mL ethanol and refluxed for 20 h. The reaction was cooled and the solid was filtered, washed with ethanol and dried to give 15.8 g of the desired product., (M+H)+: 184

6.01.08.03 2-Amino-6,7-dihydro-4H-thiazolo[5,4-c]pyridine-5-carboxylic acid tert-butyl ester

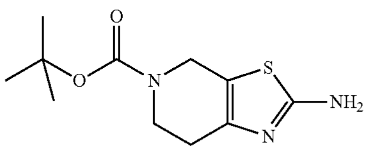 [SMILES: CC(C)(C)OC(=O)N1CCc2nc(N)sc2C1]

15.8 g 4,5,6,7-tetrahydro-thiazolo[5,4-c]pyridin-2-yl-amine and 100 mL dioxane was added to 15.2 g potassium carbonate in 158 mL water. 13.1 g di tert-butyl dicarbonate in 58 mL dioxane was added at 0° C. The reaction mixture was allowed to stir for 3 h at ambient temperature. The reaction mixture was diluted with water and the solid was filtered through silica gel, washed with water (2×50 mL) to afford the desired product. The filtrate was concentrated, diluted with water and extracted with ethyl acetat. The organic layer was dried over magnesium sulfate and concentrated to afford 11.6 g of the desired product.

1H NMR (400 MHz, DMSO-d6): δ 1.41 (s, 9H), 2.43 (t, 2H), 3.56 (t, 2H), 4.28 (s, 2H), 6.80 (s, 2H); (M+H)+: 256

6.01.08.04 2-Phenoxycarbonylamino-6,7-dihydro-4H-thiazolo[5,4-c]pyridine-5-carboxylic acid tert-butyl ester

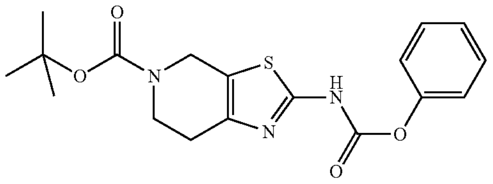 [SMILES: CC(C)(C)OC(=O)N1CCc2nc(NC(=O)Oc3ccccc3)sc2C1]

39 g calcium carbonate and 36.8 g phenyl chloroformate in 250 mL THF was added to a stirred solution of 50 g 2-amino-6,7-dihydro-4H-thiazolo[5,4-c]pyridine-5-carboxylic acid tert-butyl ester in 1 L THF. The reaction mixture was allowed to stir for 15 h at RT. The reaction mixture was filtered through silica gel and the filtrate was concentrated under reduced pressure. The residue was diluted with water and extracted with ethyl acetate and the organic layer was dried over magnesium sulfate. The organic layer was concentrated under reduced pressure. The residue was washed with 20% ethyl acetate in hexane to give 60 g of the desired product.

1H NMR (400 MHz, CDCl3): δ 1.44 (s, 9H), 2.81 (s, 2H), 3.66 (s, 2H), 4.53 (s, 2H), 7.18 (d, 2H), 7.25-7.30 (m, 1H), 7.41 (t, 2H), 11.99 (br s, 1H); (M+H)+: 376

6.01.08.05 2-(3-Methyl-ureido)-6,7-dihydro-4H-thiazolo[5,4-c]pyridine-5-carboxylic acid tert-butyl ester

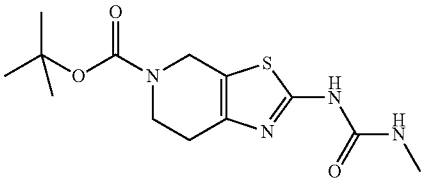 [SMILES: CNC(=O)Nc1nc2c(s1)CN(C(=O)OC(C)(C)C)CC2]

25 mg methylamine was added to 200 mg 2-phenoxycarbonylamino-6,7-dihydro-4H-thiazolo-[5,4-c]pyridine-5-carboxylic acid tert-butyl ester in 25 mL DMF. The reaction was stirred for 12 h at RT, diluted with water and extracted with ethyl acetate. The organic layer was washed with brine solution and concentrated. The residue was purified by column chromatographie (silica gel, eluent: 40% ethylacetate in hexane) to give 151 mg of desired product. (M+H)+: 313

6.01.08.06 1-Methyl-3-(4,5,6,7-tetrahydro-thiazolo[5,4-c]pyridin-2-yl)-urea

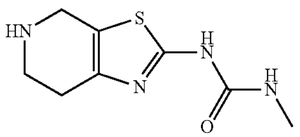

10% TFA in 60 ml chloroform was added to 2.3 g 2-(3-methyl-ureido)-6,7-dihydro-4H-thiazolo-[5,4-c]pyridine-5-carboxylic acid tert-butyl ester in 28 ml chloroform and stirred for 2 h at RT. The mixture was concentrated, the residue was diluted with chloroform and basified with 2.5 M aqueous potassium carbonate solution and extracted with chloroform. The organic layer was concentrated. The residue was washed with a mixture of 50% ethyl acetate and 50% hexane to yield 1.5 g of the desired product. (M+H)+: 213

By using the same synthesis strategy as for 1-methyl-3-(4,5,6,7-tetrahydro-thiazolo[5,4-c]-pyridin-2-yl)-urea the following compound was obtained:

| Examples | Product | MS m/z $[M + H]^+$ |
|---|---|---|
| 6.01.09 | 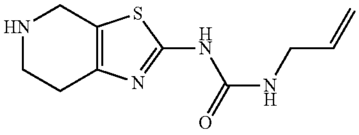 [SMILES: C=CCNC(=O)Nc1nc2c(s1)CNCC2] | 239 |

6.01.10 4-(4,5-Dimethyl-oxazol-2-yl)-piperidine

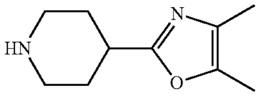

6.01.10.01 1-Benzyl-piperidine-4-carboxylic acid amide

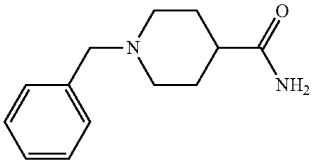 [SMILES: NC(=O)C1CCN(Cc2ccccc2)CC1]

10.2 mL benzylchloride was added to 10 g piperidine-4-carboxylic acid amide and 21.6 g potassiumcarbonate in 280 mL DMF at 5° C. The reaction was stirred over night at RT. The solvent was removed and the residue was dissolved in water and dichlormethane. The organic layer was separated and evaporated. The residue was purified by column chromatographie (silica gel, eluent: dichlormethane/methanol 95:5 to 90:10) to give 9.8 g of the desired product.

$R_t$: 0.95 min (method A), $(M+H)^+$: 219

6.01.10.02
1-Benzyl-4-(4,5-dimethyl-oxazol-2-yl)-piperidine

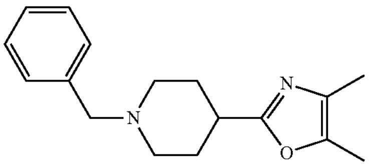 [SMILES: Cc1nc(C2CCN(Cc3ccccc3)CC2)oc1C]

7 g 1-benzyl-piperidine-4-carboxylic acid amide and 13 mL 3-chlorobutan-2-on were stirred 6 h at 180° C. under microwave conditions. The mixture was diluted in methanol and n-methylpyridinone and purified by HPLC to give 1.48 g of the desired product.

$R_t$: 1.32 min (method F), $(M+H)^+$: 271

6.01.10.03 4-(4,5-Dimethyl-oxazol-2-yl)-piperidine

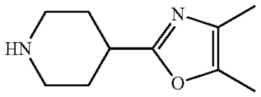

1.48 g 1-benzyl-4-(4,5-dimethyl-oxazol-2-yl)-piperidine were stirred at RT for 28 h under 50 psi hydrogen atmosphere and 150 mg palladium charcoal. The mixture was filtered and evaporated to give 1.1 g of the desired product.

$R_t$: 0.91 min (method F), $(M+H)^+$: 181

6.01.11 1-Methyl-3-piperidin-4-yl-3,4-dihydro-1H-quinazolin-2-one

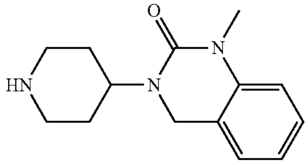 [SMILES: CN1C(=O)N(C2CCNCC2)Cc2ccccc21]

6.01.11.01 (1-Benzyl-piperidin-4-yl)-(2-nitro-benzyl)-amine

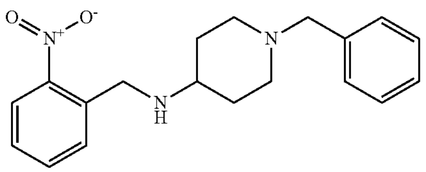 [SMILES: O=[N+]([O-])c1ccccc1CNC1CCN(Cc2ccccc2)CC1]

5955 g 2-nitrobenzaldehyde was suspended in 10 L methanol under nitrogen atmosphere and 7500 g 4-amino-1-benzyl-piperadine in 5 L methanol was added over 30 min. The reaction was stirred 1 h at RT. The reaction mixture was cooled to 0° C. and a cold solution of 1044 g sodium borohydride in 6425 mL water was added at a rate to keep the temperature below 10° C. After 1 h stirring at 0° C. and 1 h at RT the reaction was cooled again to 0° C. and aqueous 4 mol/L hydrochlorid acid was added. Then the reaction mixture was stirred at RT for 30 min and cooled again to 0-10° C. Aqueous 5 mol/L sodium hydroxide solution was added until pH=14 and the reaction was extracted with tert-butyl methylether. The organic layer was washed with water and saturated sodium chloride solution and the solvent was evaporated. The residue was dissolved in toluol, filtered and concentrated again to yield 12.8 kg of the desired product.

6.01.11.02 2-((1-Benzyl-piperidin-4-ylamino)-methyl)-phenyl-ammonium dihydrochloride

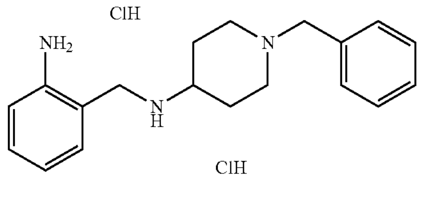 [SMILES: Cl ; Nc1ccccc1CNC1CCN(Cc2ccccc2)CC1 ; Cl]

1 g tin (II) chloride-dihydrate was added to 290 mg (1-benzyl-piperidin-4-yl)-(2-nitro-benzyl)-amine in 18 mL ethanol. The reaction was refluxed for 15 min. DMF was added until the reaction was diluted. Then, 5 mL 10 M HCl in ethanol was added, the solvent was removed, 8 mL acetone was added and the mixture was stirred at RT. The precipitate was filtered to give 550 mg of the desired product. $R_f$: 0.35 (dichlormethane 9: methanol 1: ammonia 0.1), $(M+H)^+$: 296

6.01.11.03 3-(1-Benzyl-piperidin-4-yl)-3,4-dihydro-1H-quinazolin-2-one

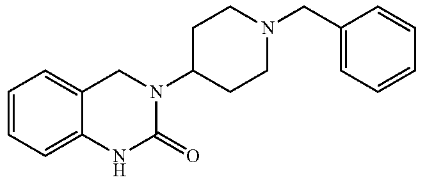 [SMILES: O=C1Nc2ccccc2CN1C1CCN(Cc2ccccc2)CC1]

110 μL diisopropylamine and 22 mg CDT were added to 50 mg 2-((1-benzyl-piperidin-4-ylamino)-methyl)-phenyl-ammonium dichloride in 2.5 mL THF and 1 mL DMF. The reaction was stirred 1 h at RT and 4 h at 85° C. Then, 55 μL diisopropylamine and 17 mg CDT were added and the reaction was stirred at 85° C. over night. The solvent was removed and the residue was purified by column chromatographie (silica gel, eluent: dichlormethane/methanole/ammonia: 9/1/0.1) to give 50 mg of the desired product.

$R_f$: 0.45 (dichlormethane 9: methanol 1: ammonia 0.1), $(M+H)^+$: 322

6.01.11.04 3-(1-Benzyl-piperidin-4-yl)-1-methyl-3,4-dihydro-1H-quinazolin-2-one

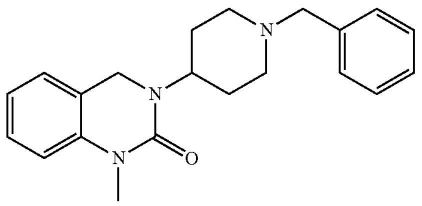 [SMILES: CN1C(=O)N(C2CCN(Cc3ccccc3)CC2)Cc2ccccc21]

1 g sodium hydride (60% oil dispersion) was added to 7 g 3-(1-benzyl-piperidin-4-yl)-3,4-dihydro-1H-quinazolin-2-one at 0° C. under nitrogen. The reaction was stirred at RT for 1 h and 1.5 mL methyliodide was added. The reaction was stirred 1 h at RT and poured into 600 mL water. The water layer was extracted with ethyl acetate. The organic layer was dried and evaporated to give 7.3 g of the desired product.

$R_f$: 0.8 (petrolether/ethylacetate: 1/1)alox, $(M+H)^+$: 336

6.01.11.05 1-Methyl-3-piperidin-4-yl-3,4-dihydro-1H-quinazolin-2-one

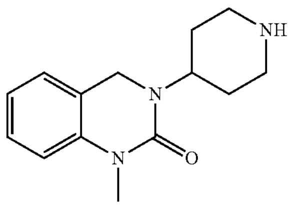 [SMILES: CN1C(=O)N(C2CCNCC2)Cc2ccccc21]

2 g palladium charcoal was added to 7.3 g 3-(1-benzyl-piperidin-4-yl)-1-methyl-3,4-dihydro-1H-quinazolin-2-one in 150 mL methanol and stirred for 5 h under 50 psi hydrogen atmosphere. The mixture was filtered and the solvent was removed. Diethylether was added and the precipate was filtered to yield 3.4 g of the desired product.

$R_f$: 0.63 (dichlormethane 9.5: methanol 0.5), $(M+H)^+$: 246

6.01.12 4-Phenyl-6,7,8,9-tetrahydro-5H-pyrimido[4,5-d]azepine hydrochloride

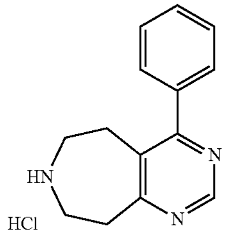 [SMILES: Cl ; c1ccc(-c2ncnc3c2CCNCC3)cc1]

6.01.12.01 (1-Benzyl-5-chloro-2,3,6,7-tetrahydro-1H-azepin-4-yl)-phenyl-methanol

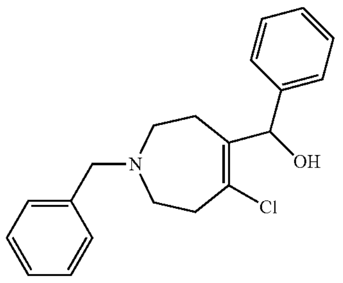 [SMILES: OC(C1=C(Cl)CCN(Cc2ccccc2)CC1)c1ccccc1]

136.6 g brombenzol in 300 mL diethylether was added to 21.2 g magnesium in 100 mL diethylether. The Grignard reaction is initiated with a small amount of iodine, kept at reflux by adding the bromebenzole and stirred additional 15 min for completion. Then, 21.2 g 1-benzyl-5-chloro-2,3,6,7-tetrahydro-1H-azepine-4-carbaldehyde in 300 mL diethylether was added. The mixture was stirred 2 h at 50° C. and quenched with 200 ml 6 M HCl solution at 0° C. The reaction was filtered and the filtrate was washed with diethylether and water. The filtrate was dissolved in sodium carbonate solution and chloroform. The layers were separated and the organic layer was washed with water and evaporated to give 89.9 g of the desired product. Fp:124° C.

6.01.12.02 (1-Benzyl-5-chloro-2,3,6,7-tetrahydro-1H-azepin-4-yl)-phenyl-methanone

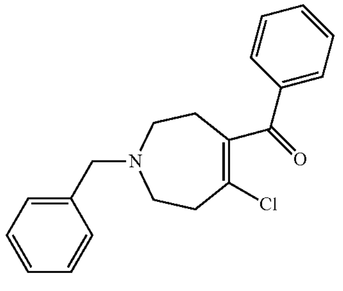 [SMILES: O=C(C1=C(Cl)CCN(Cc2ccccc2)CC1)c1ccccc1]

89 g (1-benzyl-5-chloro-2,3,6,7-tetrahydro-1H-azepin-4-yl)-phenyl-methanol in 800 mL dichlormethane was dropped to 115.4 g pyridiniumchlorchromate in 600 mL dichlormethane. The reaction was stirred 2.5 days at RT. Potassium carbonate solution was added to the reaction, the mixture was stirred 2 h at RT and filtered over celite. The layers were separated and the organic layer was washed with water. The solvent was removed and the residue was purified by chromatography to yield 64.6 g of the desired compound. $R_f$: 0.5 (toluol/EE: 8.5/1.5)

6.01.12.03 7-Benzyl-4-phenyl-6,7,8,9-tetrahydro-5H-pyrimido[4,5-d]azepine

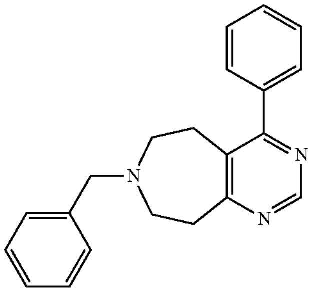 [SMILES: c1ccc(CN2CCc3ncnc(-c4ccccc4)c3CC2)cc1]

16.8 g sodium was added to 500 mL ethanol at 10° C. Then, 48.5 g formamidine hydrochloride was added and the reaction was stirred 15 min at 6° C. 28 g (1-benzyl-5-chloro-2,3,6,7-tetrahydro-1H-azepin-4-yl)-phenyl-methanone was added and the reaction was stirred 17 h at RT and 1 h at 40° C. The mixture was filtered and the solvent was removed. The residue was dissolved in ethyl acetate. The layers were separated and the organic layer was washed with water and evaporated. The residue was crystallized with diethylether to yield 10.7 g of the desired product. Fp: 81-82° C.

6.01.12.04 4-Phenyl-6,7,8,9-tetrahydro-5H-pyrimido[4,5-d]azepine hydrochloride

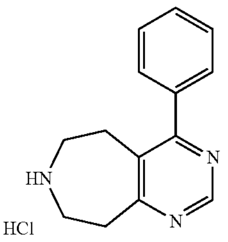 [SMILES: c1ccc(-c2ncnc3c2CCNCC3)cc1 ; Cl]

Palladium charcoal was added to 17 g 7-benzyl-4-phenyl-6,7,8,9-tetrahydro-5H-pyrimido[4,5-d]azepine in 250 mL ethanol and 54 mL 1 M HCl solution. The reaction was stirred at 80° C. and 5 bar hydrogen. The mixture was filtered and evaporated to give 13.1 g of the desired product.

$R_f$: 0.45 (dichlormethane 9: methanol 1: ammonia 0.1), $(M+H)^+$: 322

6.01.13 1-Methyl-3-(4-methyl-piperidin-4-yl)-1,3-dihydro-benzoimidazol-2-one

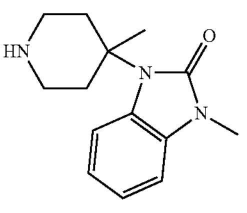 [SMILES: Cn1c(=O)n(C2(C)CCNCC2)c2ccccc21]

6.01.13.01 (1-Benzyl-4-methyl-piperidin-4-yl)-(2-nitro-phenyl)-amine

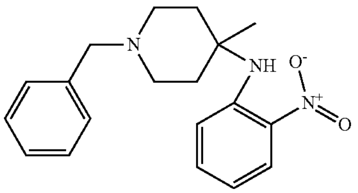 [SMILES: CC1(Nc2ccccc2[N+](=O)[O-])CCN(Cc2ccccc2)CC1]

3.6 g 1-fluor-2-nitrobenzene and 82.7 g potassiumcarbonate were added to 5.3 g 1-benzyl-4-methyl-piperidin-4-ylamine in 50 mL DMSO and the mixture was stirred at 150° C. 24 h. The reaction was diluted with water and the aqueous layer was extracted with ethylacetate. The organic layer was evaporated and the residue purified by column chromatographie on silica gel (heptane/ethylacetate:9/1) to give 5.9 g of the desired product.

$R_f$: 0.15 (heptane/ethylacetate: 8/2), $(M+H)^+$: 326

6.01.13.02 N-(1-Benzyl-4-methyl-piperidin-4-yl)-benzene-1,2-diamine

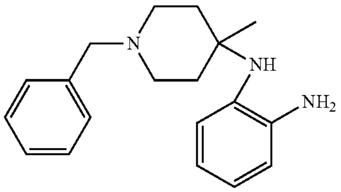 [SMILES: CC1(Nc2ccccc2N)CCN(Cc2ccccc2)CC1]

168 mg ferrum was added to 160 mL ammonium chloride in 5 mL water. A solution of 244 mg (1-benzyl-4-methyl-piperidin-4-yl)-(2-nitro-phenyl)-amine in 5 mL methanol and 5 mL tetrahydrofuran were added and the mixture was stirred at 70° C. under nitrogen. The mixture was filtered over Celite and water was added to the filtrate. The solution was extracted with ethylacetate. The organic layer was evaporated to yield 121 mg of the desired product.

$(M+H)^+$: 296

6.01.13.03 1-(1-Benzyl-4-methyl-piperidin-4-yl)-1,3-dihydro-benzoimidazol-2-one

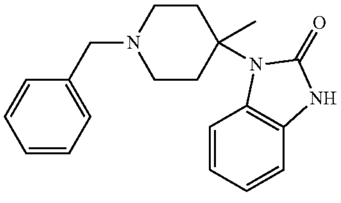 [SMILES: CC1(n2c(=O)[nH]c3ccccc32)CCN(Cc2ccccc2)CC1]

A mixture of 121 mg N-(1-benzyl-4-methyl-piperidin-4-yl)-benzene-1,2-diamine and 79 mg CDI in 5 mL dichlormethane was stirred 24 h at RT. Water was added and the mixture was extracted with ethylacetate. The organic layer was concentrated to give 119 mg of the desired product. $(M+H)^+$:322

6.01.13.04 1-(1-Benzyl-4-methyl-piperidin-4-yl)-3-methyl-1,3-dihydro-benzoimidazol-2-one

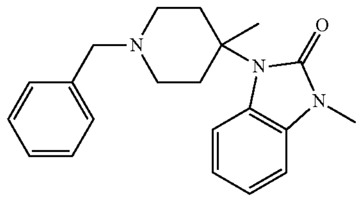 [SMILES: Cn1c(=O)n(C2(C)CCN(Cc3ccccc3)CC2)c2ccccc21]

170 mg methyliodide was added to 320 mg 1-(1-benzyl-4-methyl-piperidin-4-yl)-1,3-dihydro-benzoimidazol-2-one and 50 mg sodium hydride (60% oil dispersion). The reaction was stirred 1 h at RT. The reaction was diluted with water and extracted with ethylacetate. The organic layer was evaporated and the residue was purified by column chromatographie on silica gel (heptane/ethylacetate/triethylamine: 1/1/0.01) to give 155 mg of the desired product.

$R_f$: 0.36 (heptane/ethylacetate/triethylamine: 1/1/0.01), $(M+H)^+$: 336

6.01.13.05 1-Methyl-3-(4-methyl-piperidin-4-yl)-1,3-dihydro-benzoimidazol-2-one

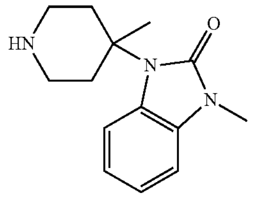 [SMILES: Cn1c(=O)n(C2(C)CCNCC2)c2ccccc21]

2.5 g palladium charcoal was added to 4.6 g 1-(1-benzyl-4-methyl-piperidin-4-yl)-3-methyl-1,3-dihydro-benzoimidazol-2-one in 100 mL methanol. The reaction was stirred 3 h at 50° C. and 30 bar under hydrogen. The reaction was filtered and evaporated to yields 3 g of the desired product. $(M+H)^+$: 246

6.01.14 5,6,7,8-Tetrahydro-4H-oxazolo[4,5-d]azepin-2-ylamine

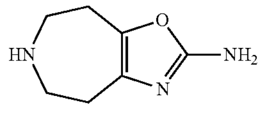 [SMILES: Nc1nc2c(o1)CCNCC2]

6.6 g urea was added to 6 g 5-bromo-azepan-4-one hydrobromide. The mixture was stirred 24 h at 70° C. The reaction was basified with 4 N NaOH and extracted with chloroform and ethylacetate. The combined organic layers were evaporated to yield 800 mg of the desired product.

1H NMR (400 MHz, DMSO-d6): 2.82 (m, 8H, 4/CH2), 2.30 (t, 3H, CH3); $(M+H)^+$: 154

6.01.15 2-(1,2,3,6-Tetrahydro-pyridin-4-yl)-pyrimidine hydrochloride

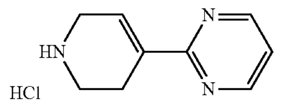 [SMILES: C1=C(c2ncccn2)CCNC1 ; Cl]

6.01.15.01 4-Hydroxy-4-pyrimidin-2-yl-piperidine-1-carboxylic acid tert-butyl ester

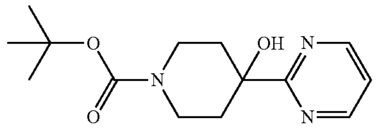 [SMILES: CC(C)(C)OC(=O)N1CCC(O)(c2ncccn2)CC1]

9.9 mL 1.6 mol/L n-butyllithium solution in hexane was added to 3.85 g 2-tributyl stannanyl-pyrimidine at −78° C. The reaction was stirred 30 min. at −78° C. and 2.1 g 1-carboxylic acid tert-butyl ester-4-piperidone in 10 mL THF was added. The reaction mixture was warmed up and stirred at RT over night. Then, the reaction was cooled to 0° C., water and subsequently EtOAc were added and the layers were separated. The organic layer was washed with water and with a saturated ammonia chloride solution. Then, the organic layer was dried and evaporated. The residue was purified by HPLC to yield 448 mg of the desired product.

$R_t$: 1.21 min (method B), $(M+H)^+$: 280

6.01.15.02 4-Pyrimidin-2-yl-3,6-dihydro-2H-pyridine-1-carboxylic acid tert-butyl ester

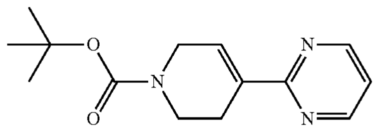 [SMILES: CC(C)(C)OC(=O)N1CC=C(c2ncccn2)CC1]

110 mg 4-hydroxy-4-pyrimidin-2-yl-piperidine-1-carboxylic acid tert-butyl ester was dissolved in 2.5 mL pyridine and 0.18 ml phosphoroxychloride was added. The reaction mixture was stirred at RT for one day. The reaction was decomposed with water and extracted with DCM. The organic layer was dried and the solvent was removed to yield 84 mg of the desired compound. $R_t$: 1.31 min (method B), $(M+H)^+$: 262

6.01.16.01 3',6'-Dihydro-2'H-[2,4']bipyridinyl-1'-carboxylic acid tert-butyl ester

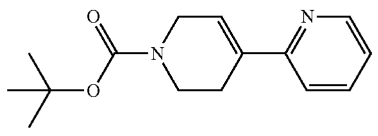 [SMILES: CC(C)(C)OC(=O)N1CC=C(c2ccccn2)CC1]

52 mg tetrakis(triphenylphosphine) palladium was added to 100 mg 2-chloropyridine, 327 mg 4-(4,4,5,5-tetramethyl-(1,3,2)dioxaborolan-2-yl)-3,6-dihydro-2H-pyridine-1-carboxylic acid tert-butyl ester and 0.88 mL 2 mol/L sodiumcarbonate in 2 mL dioxane. The reaction was stirred for 15 min. at 140° C. in a microwave. Water was added and the reaction was extracted with DCM. The organic layer was dried and evaporated. The residue was purified by HPLC to yield 116 mg of the desired product. $R_t$: 1.03 min (method L), $(M+H)^+$: 261

By using the same synthesis strategy as for 4-(6-methoxy-pyrimidin-4-yl)-3,6-dihydro-2H-pyridine-1-carboxylic acid tert-butyl ester the following compounds were obtained:

| Examples | Product | MS m/z $[M+H]^+$ | HPLC Method | Rt min |
|---|---|---|---|---|
| 6.01.17.01 | 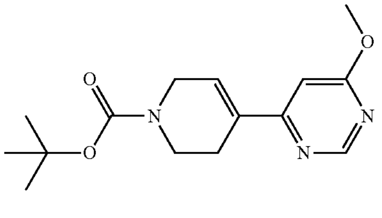 [SMILES: COc1cc(C2=CCN(C(=O)OC(C)(C)C)CC2)ncn1] | 292 | method K | 1.38 |
| 6.01.20.01 | 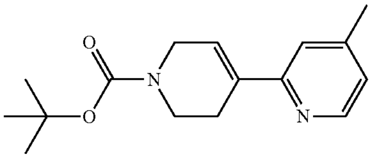 [SMILES: Cc1ccnc(C2=CCN(C(=O)OC(C)(C)C)CC2)c1] | 275 | method V | 0.61 |
| 6.01.21.01 | 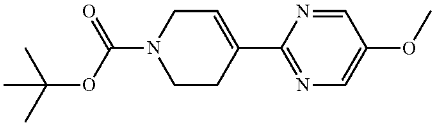 [SMILES: COc1cnc(C2=CCN(C(=O)OC(C)(C)C)CC2)nc1] | 292 | method V | 0.96 |

6.01.17.02 4-(6-Methoxy-pyrimidin-4-yl)-piperidine-1-carboxylic acid tert-butyl ester

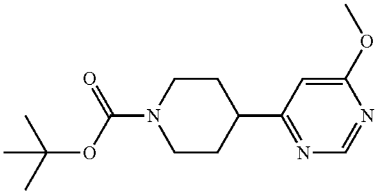 [SMILES: COc1cc(C2CCN(C(=O)OC(C)(C)C)CC2)ncn1]

150 mg palladium on charcoal was added to 765 mg 4-(6-methoxy-pyrimidin-4-yl)-3,6-dihydro-2H-pyridine-1-carboxylic acid tert-butyl ester in 90 mL methanol. The reaction was stirred 3.5 h at RT and 3 bar hydrogen. Then, the reaction was filtered and evaporated to yield 769 mg of the desired product. $R_t$: 1.31 min (method K), $(M+H)^+$: 294

By using the same synthesis strategy as for 4-(6-methoxy-pyrimidin-4-yl)-piperidine-1-carboxylic acid tert-butyl ester the following compounds were obtained:

| Examples | Product | MS m/z $[M+H]^+$ | HPLC Method | Rt min |
|---|---|---|---|---|
| 6.01.19.02 | 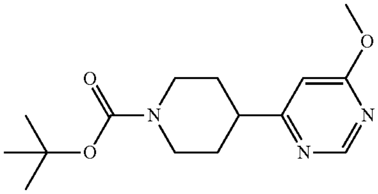 | 263 | method B | 1.04 |

6.01.15.03
2-(1,2,3,6-Tetrahydro-pyridin-4-yl)-pyrimidine hydrochloride

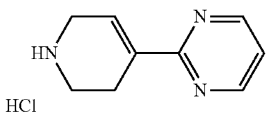

429m g 4-(6-Methoxy-pyrimidin-4-yl)-piperidine-1-carboxylic acid tert-butyl ester was stirred in 10 mL 4 mol/L HCl solution in dioxane for 5 h. The mixture was evaporated. The residue was crystallized from isopropanol and diethylether to yield 245 mg of the desired product.

$R_t$: 1.31 min (method B), $(M+H)^+$: 162

By using the same synthesis strategy as for 2-(1,2,3,6-tetrahydro-pyridin-4-yl)-pyrimidine hydrochloride the following compounds were obtained:

| Examples | Product | MS m/z $[M+H]^+$ | HPLC Method | Rt min |
|---|---|---|---|---|
| 6.01.16 | 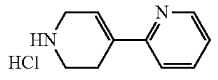 [SMILES: Cl ; C1=C(c2ccccn2)CCNC1] | 161 | method B | 1.02 |
| 6.01.17 | 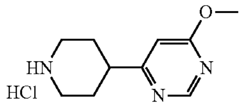 | 162 | method K | 1.31 |
| 6.01.18 | 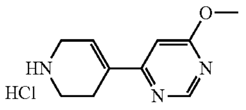 | 192 | method B | 1.40 |
| 6.01.19 | 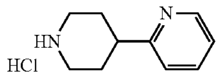 | 163 | method B | 1.04 |
| 6.01.20 | 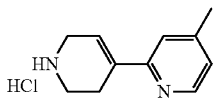 | 175 | method C | 0.19 |
| 6.01.21 | 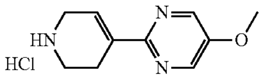 | 192 | method C | 0.16 |

6.01.22 2-Methyl-6,7,8,9-tetrahydro-5H-imidazo[1,2-a]diazepine dihydrochloride

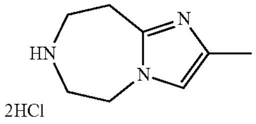

6.01.22.01
Benzyl-(2,2-dimethoxy-1-methyl-ethylidene)-amine

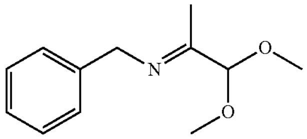

12.9 mL 1,1-dimethoxyacetone was added to 10 mL benzylamine in 100 mL petrolether. Magnesiumsulfate was added and the reaction was stirred over night at RT. The mixture was filtered and evaporated to give 18.9 g of the desired product. $(M+H)^+$: 209

6.01.22.02
Benzyl-(2,2-dimethoxy-1-methyl-ethyl)-amine

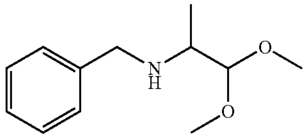

3.95 g sodium borohydride was added to 18.9 g benzyl-(2,2-dimethoxy-1-methyl-ethylidene)-amine in 100 mL methanol at 0-5° C. The reaction was stirred over night at RT. The solvent was removed, dissolved in toluol and washed with water and saturated ammoniumchloride solution. The organic layer was evaporated and the residue was purified by column chromatographie on silica gel (cyclohexane/ethylacetate) to give 10.7 g of the desired product.

$R_t$: 1.26 min (method N), $(M+H)^+$: 210

6.01.22.03 2,2-Dimethoxy-1-methyl-ethylamine

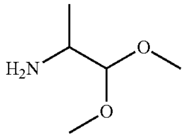

10.7 g benzyl-(2,2-dimethoxy-1-methyl-ethyl)-amine and 1.1 g 10% palladium charcoal in 100 mL methanol were stirred under 3 bar hydrogen 9 h at RT. The reaction was filtered and evaporated to yield 6.1 g of the desired product. $(M+H)^+$: 120

6.01.22.04 5-Oxo-1,4-diazepane-1-carboxylic acid tert-butyl ester

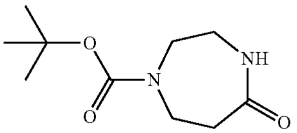

3.26 g di-tert-butyl dicarbonate 160.5 mg DMAP were added to 2,3,6,7-tetrahydro-(1H)-1,4-diazepin-5(4H)-one in 50 mL dichlormethane. The reaction was stirred 4 h at RT and washed with 10% citric acid, saturated sodium hydrogencarbonate and saturated sodium chloride solution and evaporated. The residue was purified by column chromatographie on silica gel (cyclohexane/ethylacetate: 1/1) and crystallized from diethylether/petrolether:3/1 to yield 795 mg of the desired product. $R_t$: 0.98 min (method B), $(M+H)^+$: 215

6.01.22.05 5-Methoxy-2,3,6,7-tetrahydro-(1,4)-diazepine-1-carboxylic acid tert-butyl ester

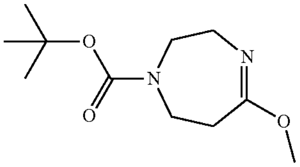 [SMILES: COC1=NCCN(C(=O)OC(C)(C)C)CC1]

77.5 mg trimethyloxonium tetrafluoroborate was added to 100 mg 5-oxo-[1,4]diazepane-1-carboxylic acid tert-butyl ester in 2 mL dichlormethane at 0-5° C. The reaction mixture was stirred over night at RT. The reaction was washed with saturated sodium hydrogencarbonate solution and water and evaporated to yield 100 mg of the desired product. $R_t$: 0.79 min (method B), $(M+H)^+$: 229

6.01.22.06 2-Methyl-6,7,8,9-tetrahydro-5H-imidazo[1,2-a](1,4)diazepine dihydrochloride

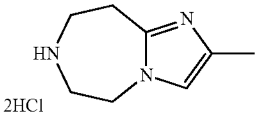

2HCl 6.1 g 2,2-dimethoxy-1-methyl-ethylamine was added to 4.1 g 5-methoxy-2,3,6,7-tetrahydro-(1,4)diazepine-1-carboxylic acid tert-butyl ester in 30 mL methanol. The reaction was refluxed over night and evaporated. 40 mL 2M HCL was added to the residue and stirred 2 h at 80° C. The solvent was removed and the residue was crystallized from methanol to yield 750 mg of the desired product. $R_t$: 0.60 min (method N), $(M+H)^+$: 152

6.01.23 4-(5-Isopropyl-(1,3,4) oxadiazol-2-yl)-piperidine

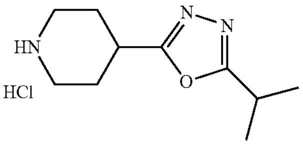

HCl 6.0.1.23.01 4-Hydrazinocarbonyl-piperidine-1-carboxylic acid tert-butyl ester

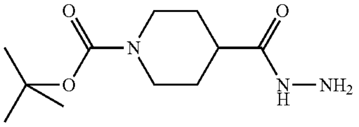 [SMILES: CC(C)(C)OC(=O)N1CCC(C(=O)NN)CC1]

100 g piperidine-1,4-dicarboxylic acid 1-tert-butyl ester was dissolved in 100 mL methanol and 100 mL hydrazine monohydrate was added. The mixture was reflux overnight. The reaction was cooled to RT and then the solvent was removed under vacuum to give 95 g of the desired product. $R_f$: 0.2 (DCM/MeOH=20/1)

1H NMR: (400 MHz, MeOD): δ 4.08 (d, J=13.2 Hz, 2H, CH2), 2.27 (br, 2H, NH2), 2.38-2.29 (m, 1H, CH), 1.72-1.68 (m, 2H, CH2), 1.63-1.56 (m, 2H, CH2), 1.45 (s, 9H, 3CH3).

6.01.23.02 4-(5-Isopropyl-(1,3,4) oxadiazol-2-yl)-piperidine-1-carboxylic acid tert-butyl ester

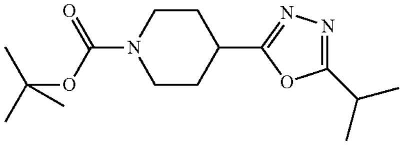 [SMILES: CC(C)c1nnc(C2CCN(C(=O)OC(C)(C)C)CC2)o1]

25 g 4-hydrazinocarbonyl-piperidine-1-carboxylic acid tert-butyl ester was refluxed with 125 mL 1,1,1-trimethoxy-2-methyl-propane overnight. The excess of reagent was removed under vacuum and the residue was purified by chromatography on silica gel to give 16 g of the desired product. 1H NMR (400 MHz, MeOD): δ 4.08-4.04 (m, 2H, $CH_2$), 3.20-3.13 (m, 2H, 2CH), 3.01 (br, 2H, $CH_2$), 2.07-2.03 (m, 2H, $CH_2$), 1.75-1.68 (m, 2H, $CH_2$), 1.46 (s, 9H, $3CH_3$), 1.36 (d, J=6.8 Hz, 6H, $2CH_3$).

By using the same synthesis strategy as for 4-(5-Isopropyl-(1,3,4) oxadiazol-2-yl)-piperidine-1-carboxylic acid tert-butyl ester the following compound was obtained:

| Examples | Product | NMR |
|---|---|---|
| 6.01.24.02 | 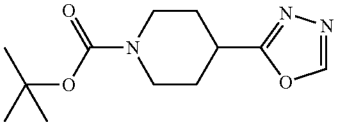 [SMILES: CC(C)(C)OC(=O)N1CCC(c2nnco2)CC1] | $^1$H NMR (TH03335-014-1, 400 MHz, MeOD): δ 8.86 (s, 1H, ArH) 4.08-4.05 (m, 2H, $CH_2$), 3.31-3.29 (m, 1H, CH), 3.23 (br, 2H, $CH_2$), 2.11-2.09 (m, 2H, $CH_2$), 1.75-1.74 (m, 2H, $CH_2$), 1.47-1.16 (m, 9H, $3CH_3$). |

6.01.23.03 4-(5-Isopropyl-(1,3,4) oxadiazol-2-yl)-piperidine

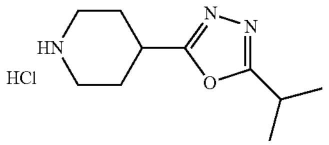

100 mL saturated dioxane-HCl was added to 16 g 4-(5-isopropyl-(1,3,4) oxadiazol-2-yl)-piperidine-1-carboxylic acid tert-butyl ester in 100 mL dioxane at 0° C. The mixture was stirred at RT for 2 h. The precipitate was filtered and washed with ethyl acetate to give 12.3 g of the desired product.

1H NMR (400 MHz, MeOD): δ 3.49-3.44 (m, 2H, $CH_2$), 3.38-3.34 (m, 1H, CH), 3.22-3.16 (m, 3H, $CH_2$/CH), 2.36-2.32 (m, 2H, $CH_2$), 2.09-2.02 (m, 2H, $CH_2$), 1.37 (d, J=7.2 Hz, 6H, $CH_3$).

By using the same synthesis strategy as for 4-(5-isopropyl-(1,3,4) oxadiazol-2-yl)-piperidine-1-carboxylic acid tert-butyl ester the following compound was obtained:

| Examples | Product | MS m/z $[M + H]^+$ |
|---|---|---|
| 6.01.24 | 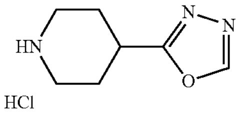 [SMILES: c1nnc(C2CCNCC2)o1 ; Cl] | 1H NMR (400 MHz, MeOD): δ 8.93 (s, 1H, ArH), 3.50-3.42 (m, 3H, $CH_2$/CH), 3.24-3.17 (m, 2H, $CH_2$), 2.39-2.34 (m, 2H, $CH_2$), 2.12-2.05 (m, 2H, $CH_2$). |

6.01.25 4-(5-Methyl-oxazol-2-yl)-piperidine

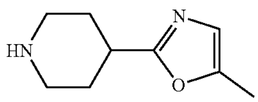

6.01.25.01 N-(2-Hydroxy-propyl)-isonicotinamide

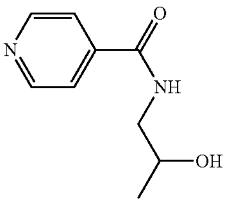

289 g isonicotinoyl chloride hydrochloride was added to 128 g 1-amino-propan-2-ol and 549 mL triethylamine in 2 L dichlormethane at 0° C. The reaction was stirred for 30 min. at 0° C. and then the solvent was removed. The residue was suspended in ethyl acetate and the precipitate was filtered. The filtrate was recrystallized from ethyl acetate to give 154 g of the desired product. $R_f$: 0.4 (DCM/MeOH=20/1), $(M+H)^+$: 181

6.01.25.02 N-(2-Oxo-propyl)-isonicotinamide

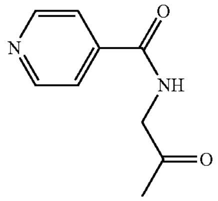

154 g N-(2-hydroxy-propyl)-isonicotinamide in 500 mL dichlormethane was added to a solution of Dess-Martin reagenz in 1.5 L dichlormethane at 0° C. under nitrogen. The reaction was stirred for 30 min. at 0° C. and 4 h at RT. The mixture was concentrated and the crude product was purified by chromatographie on silica to give 91 g of the desired product.

$R_f$: 0.55 (DCM/MeOH=20/1), $(M+H)^+$: 179

6.01.25.03 4-(5-Methyl-oxazol-2-yl)-pyridine

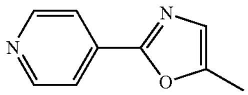

20 g N-(2-oxo-propyl)-isonicotinamide was dissolved in 200 mL phosphoroxychloride at 0° C. and the mixture was heated at 120° C. over night. The reaction was quenched with water and extracted with ethyl acetate. The organic layer was washed with brine and concentrated. The residue was purified by chromatographie on silica to yield 10.5 g of the desired product.

$R_f$: 0.35 (petrolether/ethyl acetate=1/1), $(M+H)^+$: 161

6.01.25.04 1-Benzyl-4-(5-methyl-oxazol-2-yl)-pyridinium bromide

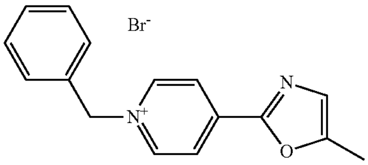 [SMILES: Cc1cnc(-c2cc[n+](Cc3ccccc3)cc2)o1 ; [Br-]]

141 g benzylbromide was added to 66 g 4-(5-methyl-oxazol-2-yl)-pyridine in 1.5 L acetone. The mixture was refluxed over night. The precipitate was filtered to give 126 g of the desired product. $R_f$: 0.00 (petrolether/ethyl acetate=1/1), $(M+H)^+$: 252

By using the same synthesis strategy as for 1-benzyl-4-(5-methyl-oxazol-2-yl)-1,2,3,6-tetrahydro-pyridine the following compounds was obtained:

| Examples | Product | MS m/z [M + H]$^+$ | $R_f$ |
|---|---|---|---|
| 6.01.26.03 | 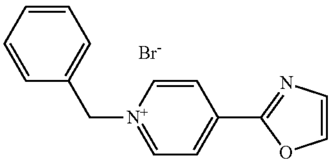 [SMILES: c1ccc(C[n+]2ccc(-c3ncco3)cc2)cc1 ; [Br-]] | 238 | 0.00 (petrolether 1/ethyl acetate 1) |

6.01.25.05 1-Benzyl-4-(5-methyl-oxazol-2-yl)-1,2,3,6-tetrahydro-pyridine

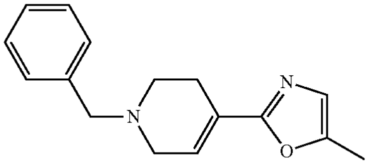 [SMILES: Cc1cnc(C2=CCN(Cc3ccccc3)CC2)o1]

21.6 g sodium borohydride was added to 130 g 1-benzyl-4-(5-methyl-oxazol-2-yl)-pyridinium in 1.5 L ethanol at 0° C. under nitrogen. The reaction was stirred 30 min at 0° C. and 2 h at RT. The mixture was concentrated and treated with water and ethyl acetate. The organic layer was separated and washed with brine and evaporated. The residue was purified by chromatographie on silica to give 81.2 g of the desired product.

$R_f$: 0.30 (petrolether/ethyl acetate=1/1), (M+H)$^+$: 255

By using the same synthesis strategy as for 1-benzyl-4-(5-methyl-oxazol-2-yl)-1,2,3,6-tetrahydro-pyridine the following compounds was obtained:

| Examples | Product | MS m/z [M + H]$^+$ | $R_f$ |
|---|---|---|---|
| 6.01.26.05 | 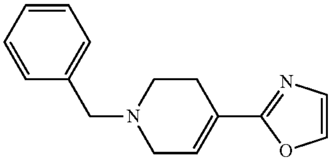 [SMILES: C1=C(c2ncco2)CCN(Cc2ccccc2)C1] | 241 | 0.35 (petrolether 1/ethyl acetate 1) |

6.01.25.06 4-(5-Methyl-oxazol-2-yl)-piperidine

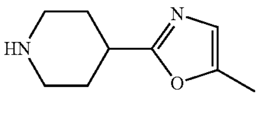

25 g 1-benzyl-4-(5-methyl-oxazol-2-yl)-1,2,3,6-tetrahydro-pyridine and 6 g palladium charcoal in 200 mL tetrahydrofuran and 200 mL ethanol were stirred at RT for 12 h under hydrogen atmosphere (30 psi). The mixture was filtered and the filtrate concentrated to yield 15 g of the desired product.

$R_f$: 0.05 (petrolether/ethyl acetate=1/1), (M+H)$^+$: 167

By using the same synthesis strategy as for 4-(5-methyl-oxazol-2-yl)-piperidine the following compounds was obtained:

| Examples | Product | MS m/z [M + H]$^+$ | $R_f$ |
|---|---|---|---|
| 6.01.26 | 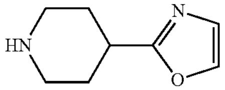 | 153 | 0.02 (petrolether 1/ ethyl acetate 1) |

6.01.26.01 (2,2-Diethoxy-ethyl)-pyridin-4-ylmethylene-amine

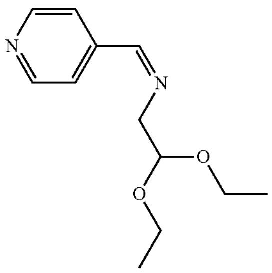 [SMILES: CCOC(C/N=C\c1ccncc1)OCC]

300 g pyridine-4-carbaldehyde and 372 g 2,2-diethoxy-ethylamine were refluxed in 2 L toluol over night. The mixture was evaporated to give 621 g of the desired product. The residue was purified by chromatographie on silica to give 100 g desired product.

$R_f$: 0.50 (petrolether/ethyl acetate=5/1), $(M+H)^+$: 223

6.01.26.02 4-(5-Methyl-oxazol-2-yl)-pyridine

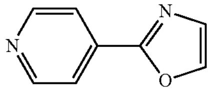 [SMILES: c1cc(-c2ncco2)ccn1]

300 g (2,2-diethoxy-ethyl)-pyridin-4-ylmethylene-amine was added to 1400 L concentrated sulfuric acid at 0° C. and added to a mixture of 600 g phosphorus pentoxide in 600 mL sulfuric acid. The mixture was heated for 2 h at 100° C. Then, the reaction mixture was cooled and poured on crushed ice, neutralized and extracted with ethyl acetate. The organic layer was washed with brine and concentrated. $R_f$: 0.40 (petrolether/ethyl acetate=1/1), $(M+H)^+$: 147

6.01.27 4-(5-Methyl-oxazol-2-yl)-1,2,3,6-tetrahydro-pyridine hydrochloride

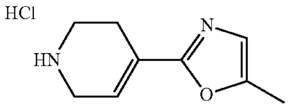

20 g 1-chloroethyl chloroformate was added to 24 g 1-benzyl-4-(5-methyl-oxazol-2-yl)-1,2,3,6-tetrahydro-pyridine in 200 mL dichlormethane at 0° C. under nitrogen. After 2 h the solution was concentrated and 200 mL methanol was added. The mixture was refluxed 4 h and concentrated. The residue was crystallized from dichlormethane to give 16 g of the desired product. $R_f$: 0.02 (petrolether/ethyl acetate=1/1), $(M+H)^+$: 165

By using the same synthesis strategy as for 4-(5-methyl-oxazol-2-yl)-piperidine the following compounds was obtained:

| Examples | Product | MS m/z $[M + H]^+$ | $R_f$ |
|---|---|---|---|
| 6.01.28 | 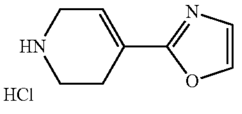 [SMILES: C1=C(c2ncco2)CCNC1 ; Cl] | 151 | 0.01 (petrolether 1/ethyl acetate 1) |

6.01.29 1-(4,5-Dihydro-oxazol-2-yl)-piperazine dihydrochloride

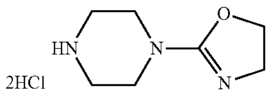 [SMILES: "2HCl" ; C1COC(N2CCNCC2)=N1]

6.01.29.01 4-(4,5-Dihydro-oxazol-2-yl)-piperazine-1-carboxylic acid tert-butyl esterhydrobromide

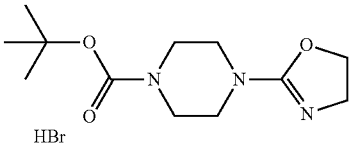 [SMILES: CC(C)(C)OC(=O)N1CCN(C2=NCCO2)CC1 ; Br]

1.94 g 3-brom-methyl isocyanate was added to 2 g piperazine-1-carboxylic acid tert-butyl ester in 20 mL tetrahydrofuran. The reaction was stirred for 6 h at RT. 25 mL n-hexane was added to the mixture and the precipitate was filtered to give 3.4 g of the desired product.

$R_t$: 0.89 min (method B), $(M+H)^+$: 256

6.01.29.02 1-(4,5-Dihydro-oxazol-2-yl)-piperazine dihydrochloride

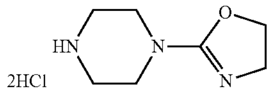 [SMILES: "2HCl" ; C1COC(N2CCNCC2)=N1]

430 mg 4-(4,5-dihydro-oxazol-2-yl)-piperazine-1-carboxylic acid tert-butyl esterhydrobromide was stirred in 5 mL 4 M HCl solution in dioxane for 20 min. The mixture was filtered to give 165 mg of the desired product. $R_t$: 0.88 min (method B), $(M+H)^+$: 156

By using the same synthesis strategy as for 1-(4,5-dihydro-oxazol-2-yl)-piperazine dihydrochloride the following compounds was obtained:

| Examples | Product | MS m/z $[M + H]^+$ | HPLC Method | Rt min |
|---|---|---|---|---|
| 6.01.30 | 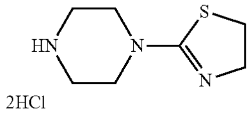 [SMILES: C1CSC(N2CCNCC2)=N1] | 172 | method B | 0.89 |

6.01.30.01 4-(4,5-Dihydro-thiazol-2-yl)-piperazine-1-carboxylic acid tert-butyl ester dihydrochloride

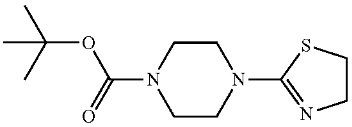

HCl 3.3 g 2-chlor ethyl isothiocyanate and 12.5 g sodiumcarbonate were added to 2 g piperazine-1-carboxylic acid tert-butyl ester in 100 mL chloroform. The reaction was stirred over night at 60° C. The reaction was filtered over silicagel and evaporated. $R_t$: 0.89 min (method B), $(M+H)^+$: 272

6.01.31 2,8-Dimethyl-5,6,7,8-tetrahydro-4H-thiazolo[4,5-d]azepine hydrobromide

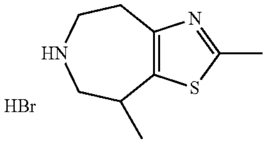

6.01.31.01 6-Methylazepane-2,4-dione

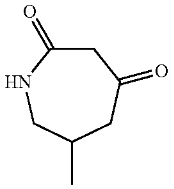

150 g 5-methylcyclohexane-1,3-dione was dissolved in 1.4 L methanol and 82.5 g hydroxylamine hydrochloride was added. The mixture was stirred for 1.5 h under reflux. The solvent was removed in vacuo and the residue was dissolved in 1 L acetonitrile and was cooled to 0° C. Triethylamine was added followed by addition of a solution of 4-toluenesulfonyl chloride in 1.1 L acetonitrile. The mixture was stirred for 1 h at RT, 6.7 mL of water was added and the mixture was stirred for additional 1 h while gently warming the mixture to 55° C. The volatiles were removed in vacuo. 250 mL water was added to the residue and the pH was adjusted to 5 with 5 N aq. NaOH and the volatiles were removed in vacuo. The solids were extracted with acetone and after concentration in vacuo the residue was purified by column chromatography on silica gel with ethyl acetate to yield 82.6 g of the desired compound.

$(M+H)^+$: 142

6.01.31.02 6-Methylazepan-4-ol

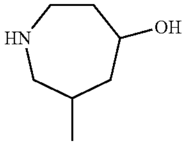

57.2 g lithium aluminium chloride was suspended in 700 mL THF and cooled to 0° C. A solution of 82.6 g 6-methylazepane-2,4-dionein 1.4 L THF was added and the mixture was stirred for 1 h at RT and for 1 h under reflux. The mixture was cooled to 0° C. and 57 mL water was added followed by addition of 57 mL 10% aq. Sodiumhydroxde solution. After 1 h the mixture was filtered over Celite and the filtrate was concentrated in vacuo. The residue was extracted with ethylacetate and the extract was concentrated to give 31.8 g of the desired compound. $(M+H)^+$: 130

6.01.31.03 tert-Butyl 5-hydroxy-3-methylazepane-1-carboxylate

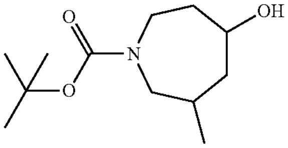 [SMILES: CC1CC(O)CCN(C(=O)OC(C)(C)C)C1]

31.3 g 6-methylazepan-4-ol was dissolved in 1 L acetonitrile. 53.2 g di tert-butyl dicarbonate and 1.7 g DMAP were added and the mixture was stirred at RT for 2 h. The volatiles were removed in vacuo to yield 50.6 g of the desired compound. $(M+H)^+$: 230

6.01.31.04 tert-Butyl 3-methyl-5-oxoazepane-1-carboxylate

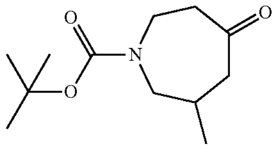 [SMILES: CC1CC(=O)CCN(C(=O)OC(C)(C)C)C1]

A mixture of 46 mL DMSO and 500 mL dichlormethane was cooled to −78° C. and a solution of 68 mL, trifluoroacetic anhydride in 200 mL dichlormethane was added. Then, a solution of 50.6 g tert-butyl 5-hydroxy-3-methylazepane-1-carboxylat in 500 mL dichlormethane was added. The mixture was stirred at −78° C. for 1 h, 128 mL triethylamine was added and the mixture was warmed to RT. 1 L water was added and the layers were separated. The aqueous fraction was extracted two times with 500 mL dichlormethane. The combined organic fractions were dried, filtered and concentrated. Column chromatography on silica with ethyl acetate/heptane (1:4) yielded 13.7 g of the desired product. $(M+H)^+$: 228

6.01.31.05 6-Methylazepan-4-one hydrobromic acid

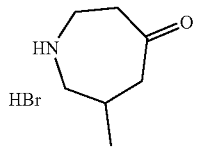

13.7 g tert-butyl 3-methyl-5-oxoazepane-1-carboxylat was dissolved in 350 mL acetic acid and 99 mL hydro bromide solution (33%) in acetic acid was added. The mixture was stirred for 1.5 h at RT. The volatiles were removed in vacuo and the residue was used in the next step without further purification. $(M+H)^+$: 128

6.01.31.06 5-Bromo-6-methylazepan-4-one hydrobromic acid

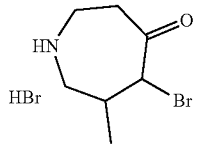

6-methylazepan-4-one hydrobromic acid was dissolved in 100 mL acetic acid. A solution of 3.2 mL bromine in 10 mL acetic acid was added. The mixture was stirred for 1.5 h at RT. The volatiles were removed in vacuo and the residue was crystallized with acetonitrile to yield 18.5 g of the desired product. $(M+H)^+$: 228

6.01.31.07 2,8-Dimethyl-5,6,7,8-tetrahydro-4H-thiazolo[4,5-d]azepine hydrobromic acid

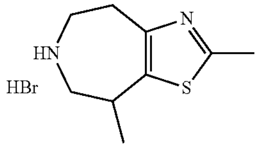

18.5 g 5-bromo-6-methylazepan-4-one hydrobromic acid salt and 5.0 g thioacetamide were dissolved in 125 mL ethanol. The mixture was heated for 3 h under reflux. The solids were removed by filtration and the filtrate was concentrated in vacuo. 100 mL acetonitrile was added and the precipitate formed was isolated by filtration to yield 15.7 g of the desired product.

1H NMR (400 MHz, DMSO-d6): 1.4 (d, 3H, CH3), 2.7 (s, 3H, CH3), 2.9-3.5 (m, 6H, 3/CH2), 3.65 (t, 1H, CH3). $(M+H)^+$: 185

6.01.32 5-Chloro-3-piperidin-4-yl-3,4-dihydro-1H-quinazolin-2-one

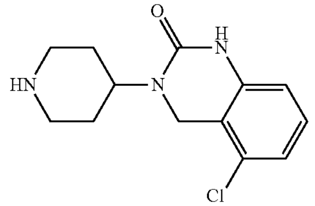 [SMILES: O=C1Nc2cccc(Cl)c2CN1C1CCNCC1]

6.01.32.01 (1-Benzyl-piperidin-4-yl)-(2-chloro-6-nitro-benzyl)-amine

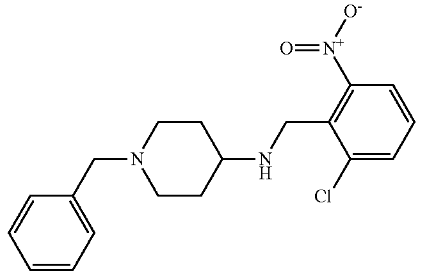 [SMILES: O=[N+]([O-])c1cccc(Cl)c1CNC1CCN(Cc2ccccc2)CC1]

15 g 2-chloro-6-nitro-benzaldehyde and 4-amino-1-benzylpiperidine in 150 mL toluol were refluxed for 3 h. The toluol was removed and the residue was dissolved in 300 mL methanol. 6.6 g sodium borohydride was added and the reaction was refluxed over night. The solvent was removed, water and dichlormethane were added and the layers were separated. The organic layer was washed with water, dried and filtered to yield 29 g of the desired product.

$R_f$: 0.45 min (dichlormethane: methanol: ammonia=9:1: 0.1), $(M+H)^+$: 360

6.01.32.02 2-((1-Benzyl-piperidin-4-ylamino)-methyl)-3-chloro-phenyl-ammonium

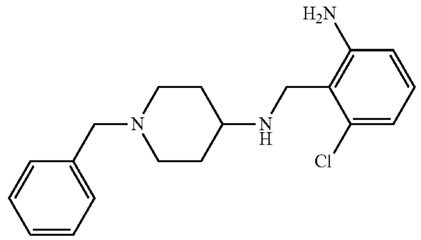 [SMILES: Nc1cccc(Cl)c1CNC1CCN(Cc2ccccc2)CC1]

17 g (1-benzyl-piperidin-4-yl)-(2-chloro-6-nitro-benzyl)-amine and 3.4 g rhodium on charcoal were stirred for 3.5 h at RT in a hydrogen atmosphere (50 psi). The reaction was filtered and the filtrate was evaporated. The residue was used in the next step without further purification.

$R_f$: 0.33 min (dichlormethane:methanol:ammonia=9:1: 0.1)), $(M+H)^+$: 331

6.01.32.03 3-(1-Benzyl-piperidin-4-yl)-5-chloro-3,4-dihydro-1H-quinazolin-2-one

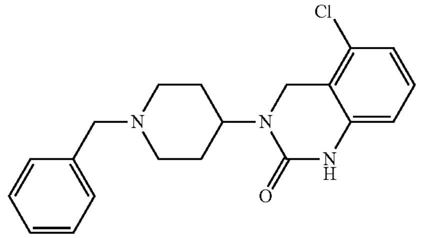 [SMILES: O=C1Nc2cccc(Cl)c2CN1C1CCN(Cc2ccccc2)CC1]

16 g 2-((1-benzyl-piperidin-4-ylamino)-methyl)-3-chloro-phenyl-ammonium and 8.2 g CDI in 150 mL DMF were stirred for 3 h at 60° C. Water and tert.-butyl-methyl-ether were added. The precipitate was filtered to give 6.3 g of the desired product. $(M+H)^+$: 356

6.01.32.04 5-Chloro-3-piperidin-4-yl-3,4-dihydro-1H-quinazolin-2-one

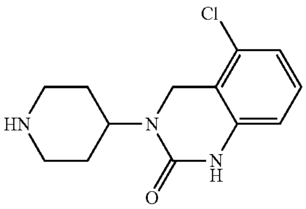 [SMILES: O=C1Nc2cccc(Cl)c2CN1C1CCNCC1]

100 mg (3-(1-benzyl-piperidin-4-yl)-5-chloro-3,4-dihydro-1H-quinazolin-2-one and 15 mg Raney nickel were stirred for 12 h at RT in a hydrogen atmosphere (30 psi). The reaction was filtered and the filtrate was evaporated to give 67 mg of the desired product. $(M+H)^+$: 266

6.01.33 2-(3-Methyl-piperazin-1-yl)-pyrimidine

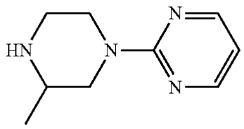

6.01.33.01 2-Methyl-4-pyrimidin-2-yl-piperazine-1-carboxylic acid tert-butyl ester

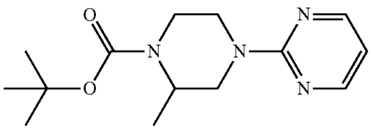

100 mg 2-chloro-pyrimidine was added to 175 mg 2-Methyl-piperazine-1-carboxylic acid tert-butyl ester and this mixture was stirred for 2 h at 120° C. to give 240 mg of the desired compound. $R_t$: 1.31 min (method B), $(M+H)^+$: 279

By using the same synthesis strategy as for 2-methyl-4-pyrimidin-2-yl-piperazine-1-carboxylic acid tert-butyl ester the following compound was obtained:

| Examples | Product | MS m/z $[M + H]^+$ | HPLC Method | Rt min |
|---|---|---|---|---|
| 6.01.34.01 | 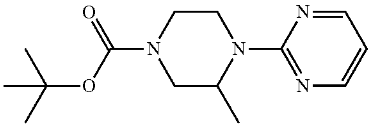 | 279 | method B | 1.32 |

6.01.33.02 2-(3-Methyl-piperazin-1-yl)-pyrimidine

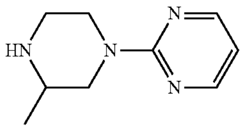

5 mL trifluoro acetic acid was added to 240 mg of 2-methyl-4-pyrimidin-2-yl-piperazine-1-carboxylic acid tert-butyl ester in 10 mL dichlormethane. The mixture was stirred for 24 h at RT. The solvent of the mixture was evaporated and the residue was dissolved in dichlormethane and extracted with 10% aqueous potassium hydrogencarbonate. The organic layer was evaporated to yield 150 mg of the desired product. $R_t$: 0.50 min (method B), $(M+H)^+$: 179

By using the same synthesis strategy as for 2-(1,2,3,6-tetrahydro-pyridin-4-yl)-pyrimidine hydrochloride the following compounds were obtained:

| Examples | Product | MS m/z $[M + H]^+$ | HPLC Method | Rt min |
|---|---|---|---|---|
| 6.01.34 | 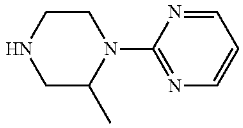 | 179 | method B | 0.51 |

6.01.35 1-(6-Methoxypyridin-2-yl)-piperazin-2-on

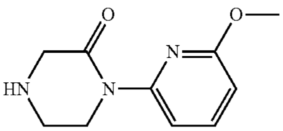

6.01.35.01 tert-Butyl-4-(6-methoxypyridin-2-yl)-3-oxopiperazine-1-carboxylat

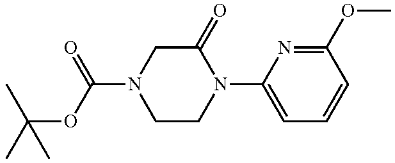 [SMILES: COc1cccc(N2CCN(C(=O)OC(C)(C)C)CC2=O)n1]

106 g potassium phosphate, 25 g 1-tert-butyl-oxocarbonyl-3-oxopiperazine, 8.8 g N,N'-dimethylethylenediamine and 9.5 g cupper(I) iodide were added to 23.5 g 2-brom-6-methoxypyridine in 1.2 L dioxane under argon. The reaction was refluxed for 10 h, filtered and the solvent was removed. The residue was purified by chromatographie on silica gel (cyclohexane/ethylacetate:3/2). The residue was crystallized from hexane to yield 25.1 g of the desired product. $(M+H)^+$: 308, $R_f$: 0.69 (cyclohexane/ethylacetate:1/1)

6.01.35.02
1-(6-Methoxypyridin-2-yl)-piperazin-2-on

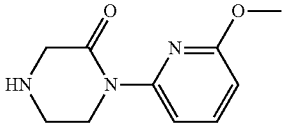

35 mL trifluoro acetic acid was added to 5.8 g tert-butyl-4-(6-methoxypyridin-2-yl)-3-oxopiperazine-1-carboxylat in 35 mL dichlormethane under argon. The mixture was stirred for 1 h and evaporated. The residue was purified by chromatographie on silica gel (100% MeOH) to yield 4.5 g of the desired product.

1H-NMR (400 MHz, MeOD): δ 7.71 (t, 1H, ar); 7.52 (d, 1H, ar); 6.65 (d, 1H, ar); 4.32 (t, 2H, CH2CH2); 4.09 (s, 2H, CH2); 3.93 (s, 3H, CH3); 3.68 (t, 2H, CH2CH2) ppm;

$(M+H)^+$: 208, $R_f$: 0.48 (methanol)

6.01.36 4-Fluoro-3-methyl-benzoyl chloride

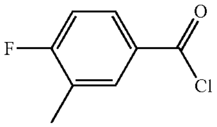

10 g 4-fluoro-3-methyl-benzoic acid in 150 g thionylchloride was refluxed 1 h. The reaction was evaporated to give 11.2 g desired product.

By using the same synthesis strategy as for 4-fluoro-3-methyl-benzoyl chloride the following compounds were obtained:

| Examples | Product |
|---|---|
| 6.01.37 | 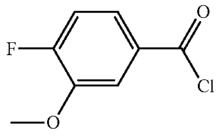 |
| 6.01.38 | 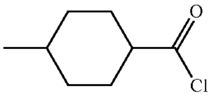 |
| 6.01.39 | 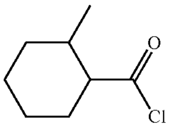 |
| 6.01.40 | 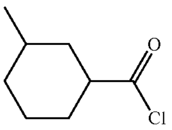 |
| 6.01.41 | 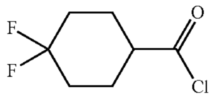 |

6.01.42 4-piperazin-1-yl-6,7-dihydro-thieno[3,2-d]pyrimidine hydrochloride

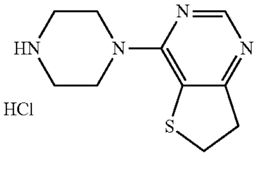 [SMILES: Cl ; c1nc2c(c(N3CCNCC3)n1)SCC2]

6.01.42.01
2,4-dichloro-6,7-dihydro-thieno[3,2-d]pyrimidine

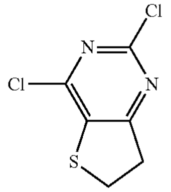 [SMILES: Clc1nc(Cl)c2c(n1)CCS2]

500 mg 6,7-Dihydro-thieno[3,2-d]pyrimidine-2,4-diol and 10 mL phosphoroxychloride was stirred 30 min at 140° C. under microwave conditions. The reaction was added to water and then dichlormethane was added. The mixture was stirred for 20 min. The layers were separated and the dichlormethane layer was evaporated to give 586 mg of the desired product.

$R_t$: 1.23 min (method P)

$(M+H)^+$: 208/09

6.01.42.02 4-(2-Chloro-6,7-dihydro-thieno[3,2-d]pyrimidin-4-yl)-piperazine-1-carboxylic acid tert-butyl ester

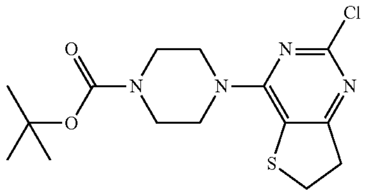 [SMILES: CC(C)(C)OC(=O)N1CCN(c2nc(Cl)nc3c2SCC3)CC1]

454 mg piperazine-1-carboxylic acid tert-butyl ester in 5 mL ethanol was added to 0.5 g 2,4-dichloro-6,7-dihydro-thieno[3,2-d]pyrimidine in 5 mL dichlormethane. The reaction was stirred 2 h at RT, 3 h at 60° C. and over night at RT. The solvents were removed and water was added to the residue. The precipitate was filtered and dried to give 0.83 g of the desired product.

$R_t$: 2.33 min (method I), $(M+H)^+$: 357/359

6.01.42.03 4-(6,7-Dihydro-thieno[3,2-d]pyrimidin-4-yl)-piperazine-1-carboxylic acid tert-butyl ester

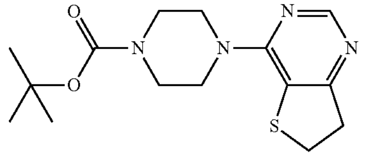 [SMILES: CC(C)(C)OC(=O)N1CCN(c2ncnc3c2SCC3)CC1]

200 mg 4-(2-Chloro-6,7-dihydro-thieno[3,2-d]pyrimidin-4-yl)-piperazine-1-carboxylic acid tert-butyl ester and 200 mg Raney-nickel in 20 mL methanol was stirred at 65° C. for 10 h under 4 bar hydrogen atmosphere. The reaction was filtered and the filtrate was evaporated. The residue was purified by HPLC to give 69 mg of the desired product. $(M+H)^+$: 323/324, Rt: 1.58 min (method AD)

6.01.42.04 4-piperazin-1-yl-6,7-dihydro-thieno[3,2-d]pyrimidine hydrochloride

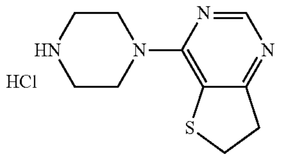 [SMILES: Cl ; c1nc2c(c(N3CCNCC3)n1)SCC2]

69 mg 4-(6,7-Dihydro-thieno[3,2-d]pyrimidin-4-yl)-piperazine-1-carboxylic acid tert-butyl ester was stirred in 2 mL 4 mol/L HCl solution in dioxane for 5 h. The mixture was evaporated. The residue was crystallized from isopropanol and diethylether to yield 48 mg of the desired product. $(M+H)^+$: 223

6.01.43 2,7-dimethyl-5,6,7,8-tetrahydro-4H-thiazolo[4,5-d]azepine dihydrobromide

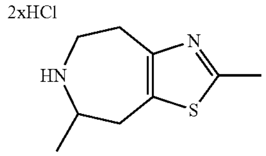

6.01.43.01 5-bromo-7-methyl-azepan-4-one hydrobromide/3-bromo-7-methyl-azepan-4-one hydrobromide (mixture of isomeres)

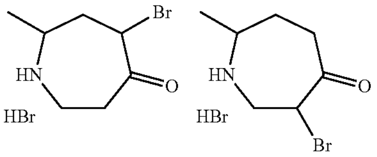

9.8 mL bromine was added to 30 g 7-methyl-azepan-4-one hydrobromide in 180 mL acetic acid. The reaction was stirred over night at RT. The reaction was evaporated to yield 33 g of the desired product as isomere mixture. $R_f$: 0.4 (DCM/MeOH=20/1), $(M+H)^+$=206

6.01.43.02 2,7-dimethyl-5,6,7,8-tetrahydro-4H-thiazolo[4,5-d]azepine hydrobromide 2,6-dimethyl-5,6,7,8-tetrahydro-4H-thiazolo[5,4-c]azepine hydrobromide isomere mixture

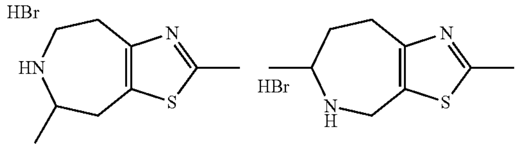

A mixture of 33 g 5-bromo-7-methyl-azepan-4-one hydrobromide and 3-bromo-7-methyl-azepan-4-one hydrobromide and 8.6 g thioacetamide in 400 mL dry EtOH was refluxed overnight. The reaction mixture was concentrated to give 30 g of the desired product, which was used for the next step without further purification. $R_f$: 0.2 (DCM/MeOH=20/1), $(M+H)^+$=183

6.01.43.03 2,7-Dimethyl-4,5,7,8-tetrahydro-thiazolo[4,5-d]azepine-6-carboxylic acid tert-butyl ester

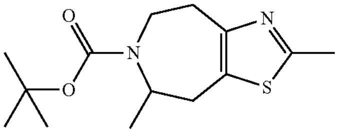 [SMILES: Cc1nc2c(s1)CC(C)N(C(=O)OC(C)(C)C)CC2]

A mixture of 30 g 2,7-dimethyl-5,6,7,8-tetrahydro-4H-thiazolo[4,5-d]azepine hydrobromide and 2,6-dimethyl-5,6,7,8-tetrahydro-4H-thiazolo[5,4-c]azepine hydrobromide, 38.5 g di-tert.butyl-dicarbonate and 9.1 g sodium hydroxide in 300 mL water and 500 mL tetrahydrofuran was stirred at RT for 3 h. The reaction mixture was extracted with ethyl acetate. The organic layer was washed with brine, dried over sodium sulfate and evaporated to dryness. The residue was purified by pre-HPLC to give 7.7 g of the desired product.

$R_f$ 0.6 (DCM/MeOH=20/1), $(M+H)^+$=283

6.01.43.04 2,7-dimethyl-5,6,7,8-tetrahydro-4H-thiazolo[4,5-d]azepine dihydrobromide

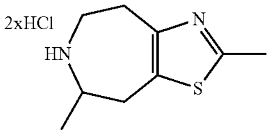

54 ml 4 mol/L HCL in ethyl acetate was added to 7.7 g 2,7-Dimethyl-4,5,7,8-tetrahydro-thiazolo[4,5-d]azepine-6-carboxylic acid tert-butyl ester in 100 mL ethyl acetate. The reaction was stirred 2 h at RT and evaporated to give 6.2 g of the desired product.

$R_f$ 0.2 (DCM/MeOH=20/1), $(M+H)^+$=183

6.01.44 N-(5,6,7,8-tetrahydro-4H-thiazolo[4,5-d]azepin-2-yl)-acetamide

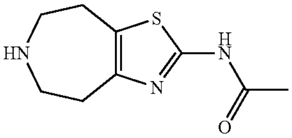

6.01.44.01 2-amino-4,5,7,8-tetrahydro-thiazolo[4,5-d]azepine-6-carboxylic acid tert-butyl ester

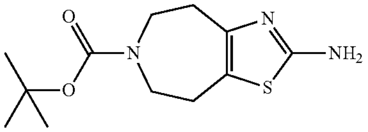 [SMILES: CC(C)(C)OC(=O)N1CCc2nc(N)sc2CC1]

5.7 g di-tert.butyl-dicarbonate in 25 mL THF was added to 4 g 5,6,7,8-Tetrahydro-4H-thiazolo-[4,5-d]-azepin-2-ylamine in 75 mL THF at 0-5° C. The reaction was stirred over night at RT. The solvent was removed. The residue was dissolved methylacetate and washed with water. The organic layer was evaporated to give 5.9 g of the desired product.

$R_f$: 0.59 (dichlormethane 7: ethylacetate 2: methanol 1); $(M+H)^+$: 270

6.01.44.02 2-acetylamino-4,5,7,8-tetrahydro-thiazolo[4,5-d]azepine-6-carboxylic acid tert-butyl ester

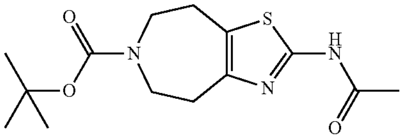 [SMILES: CC(=O)Nc1nc2c(s1)CCN(C(=O)OC(C)(C)C)CC2]

95 mg acetyl chloride was added to 312 mg 2-amino-4,5,7,8-tetrahydro-thiazolo[4,5-d]azepine-6-carboxylic acid tert-butyl ester in 5 mL pyridine at 15° C. The reaction was stirred 3 h at RT. The reaction was diluted with dichlormethane and 1 mL water was added. The solution was filtered over 40 mL Alox and 100 mL Extrelut and evaporated to give 127 mg of the desired product. $(M+H)^+$: 312

6.01.44.03 N-(5,6,7,8-tetrahydro-4H-thiazolo[4,5-d]azepin-2-yl)-acetamide

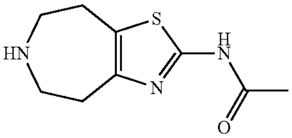

35 mL trifluoroacetic acid was added to 2.4 g 2-acetylamino-4,5,7,8-tetrahydro-thiazolo[4,5-d]azepine-6-carboxylic acid tert-butyl ester in 80 mL chloroform. The reaction was stirred 3 h at RT and concentrated. The residue was dissolved in 75 mL chloroform and basified with 2.5 M potassiumcarbonate solution. The chloroform layer was separated and concentrated to give 1.3 g of the desired product. $(M+H)^+$ =212

6.01.45 3-phenyl-6,7,8,9-tetrahydro-5H-1,2,7-triaza-benzocycloheptene dihydrochloride

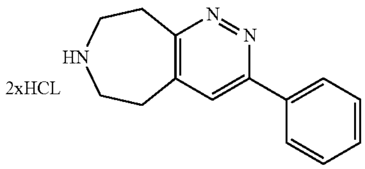 [SMILES: c1ccc(-c2cc3c(nn2)CCNCC3)cc1]

6.01.45.01 4-ethoxycarbonylmethyl-5-oxo-azepane-1,4-dicarboxylic acid 1-tert-butyl ester 4-ethyl ester

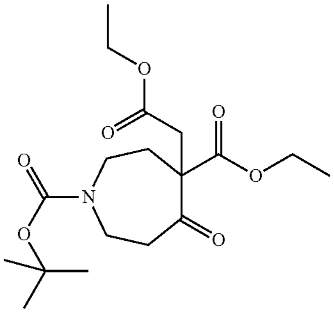 [SMILES: CCOC(=O)CC1(C(=O)OCC)CCN(C(=O)OC(C)(C)C)CCC1=O]

6.7 g potassium carbonate was added to 7 g 5-oxo-azepane-1,4-dicarboxylic acid 1-tert-butyl ester 4-ethyl ester in 50 mL DMF and stirred at RT. After 30 min 6.1 g ethyl bromoacetate was added and the reaction was stirred at RT over night. The reaction was diluted with water and extracted with ethyl acetate/hexane (1/1). The organic phase was washed with brine, dried and concentrated. The residue was purified by column chromatography on silica gel (15% ethyl acetate in hexane) to give 5.6 g of the desired product. $(M+H)^+=372$ 6.01.45.02
4-carboxymethyl-5-oxo-azepane-1-carboxylic acid tert-butyl ester

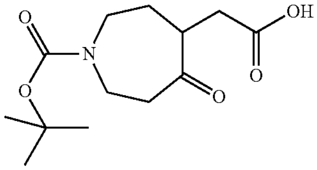 [SMILES: CC(C)(C)OC(=O)N1CCC(=O)C(CC(=O)O)CC1]

23.3 g sodium hydroxide in 218 mL water was added to 38 g 4-ethoxycarbonylmethyl-5-oxo-azepane-1,4-dicarboxylic acid 1-tert-butyl ester 4-ethyl ester in 155 mL THF. The reaction was stirred over night at RT, THF was removed and the mixture was extracted with dichlormethane. The aqueous part was acidified with 3M HCl to pH 3 at 0° C. The aqueous solution was extracted with dichloromethane, dried over magnesium sulfate, concentrated under reduced pressure to give 18.2 g of the desired product. $(M+H)^+=272$ 6.01.45.03 3-oxo-2,3,4,4a, 5,6,8,9-octahydro-1,2,7-triaza-benzocycloheptene-7-carboxylic acid tert-butyl ester

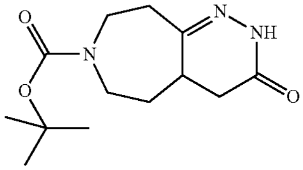 [SMILES: CC(C)(C)OC(=O)N1CCC2=NNC(=O)CC2CC1]

60 mL acetic acid was added to 16 g 4-carboxymethyl-5-oxo-azepane-1-carboxylic acid tert-butyl ester in 120 mL THF at 5° C. 14 mL hydrazine hydrate was added to the reaction and the mixture was refluxed over night. After completion of the reaction, volatiles were removed and the residue was basified with sodium carbonate and extracted with chloroform. The organic layer was dried and concentrated under reduced pressure to afford 11 g of the desired product $(M+H)^+=268$ 6.01.45.04 3-oxo-2,3,5,6,8,9-hexahydro-1,2,7-triaza-benzocycloheptene-7-carboxylic acid tert-butyl ester

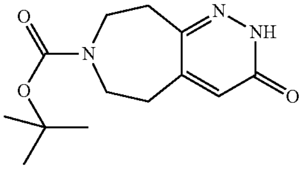 [SMILES: CC(C)(C)OC(=O)N1CCc2cc(=O)[nH]nc2CC1]

7 g 3-oxo-2,3,4,4a, 5,6,8,9-octahydro-1,2,7-triaza-benzocycloheptene-7-carboxylic acid tert-butyl ester was dissolved in 70 mL toluene and 6.7 g manganese dioxide was added to the reaction mixture. It was heated at reflux for 48 h. After completion of the reaction, the reaction mixture was diluted with chloroform and filtered through celite. The filtrate was concentrated and purified by column chromatography to afford 5.5 g of the desired product. $(M+H)^+=266$ 6.01.45.05 3-chloro-5,6,8,9-tetrahydro-1,2,7-triaza-benzocycloheptene-7-carboxylic acid tert-butyl ester

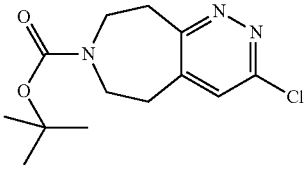 [SMILES: CC(C)(C)OC(=O)N1CCc2cc(Cl)nnc2CC1]

11 g 3-oxo-2,3,5,6,8,9-hexahydro-1,2,7-triaza-benzocycloheptene-7-carboxylic acid tert-butyl ester in 90 ml phosphor oxychloride was refluxed overnight. The phosphor oxychloride was quenched with 8.7 g sodium carbonate to pH 8 and 100 mL water was added to the reaction mixture. Di-tert.butyl-dicarbonate was added to the reaction mixture and stirred over night. The solution was extracted with 50% ethyl acetate in hexane. The extracted organic layer was dried, concentrated under reduced pressure and purified by column chromatography to afford 8.0 g of the desired product. $(M+H)^+=284$ 6.01.45.06 3-phenyl-5,6,8,9-tetrahydro-1,2,7-triaza-benzocycloheptene-7-carboxylic acid tert-butyl ester

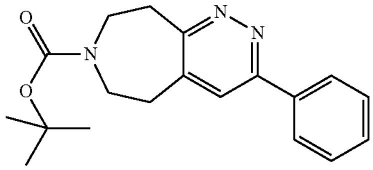 [SMILES: CC(C)(C)OC(=O)N1CCc2cc(-c3ccccc3)nnc2CC1]

5 g phenylboronic acid in 30 mL dioxane was added to 3.2 g 3-chloro-5,6,8,9-tetrahydro-1,2,7-triaza-benzocycloheptene-7-carboxylic acid tert-butyl ester and 388 mg (1,1'-bis (diphenyl-phosphinoferrocene)palladium(II)dichloride in 50 mL dioxane under argon. The reaction was stirred at 90° C. over night. The mixture was cooled to RT diluted with water and extracted with ethyl acetate. The organic layer was washed with aqueous sodium hydroxide and brine. The solvent was removed and the precipitate was purified by column chromatographie to yielded 5.5 g of the desired product. $(M+H)^{+}=325$ 6.01.45.07 3-phenyl-6,7,8,9-tetrahydro-5H-1,2,7-triaza-benzocycloheptene dihydrochloride

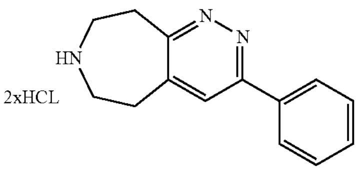 [SMILES: c1ccc(-c2cc3c(nn2)CCNCC3)cc1]

40 mL hydrogen chloride in dioxane was added to 5.5 g 3-phenyl-5,6,8,9-tetrahydro-1,2,7-triaza-benzocyclohep-tene-7-carboxylic acid tert-butyl ester in 40 mL dioxane at 5° C. The reaction was stirred over night. The solvent was removed and co-evaporated with ethyl acetate to yield 3.7 g of the desired product. $R_t$: 4.09 min (method AE), $(M+H)^{+}$: 226

6.01.46 2-Methoxy-5,6,7,8-tetrahydro-thiazolo[4,5-d]azepine

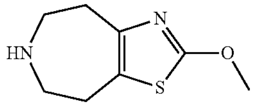

6.01.46.01 Diazo-acetic acid ethyl ester

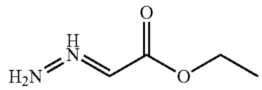

11.4 g sodium nitrite in water was added to 20 g Amino-acetic acid ethyl ester hydrochloride and 5.88 g sodium acetate in 50 mL water at 0° C. The reaction was stirred 10 min. at RT. 3 mL of 10% sulfuric acid was added and the mixture was extracted with ethyl acetate. The organic layer was washed with 10% sodium carbonate, dried and evaporated to give 9 g of the desired product.

$R_f$: 0.40 (petrol ether/ethyl acetate=6/4); $(M+H)^{+}=116$ 6.01.46.02 5-Oxo-azepane-1,4-dicarboxylic acid 1-tert-butyl ester 4-ethyl ester

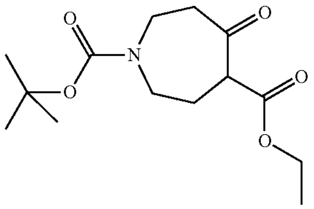 [SMILES: CCOC(=O)C1CCN(C(=O)OC(C)(C)C)CCC1=O]

3 mL boron trifluoride etherate was added to 4 g 4-oxo-piperidine-1-carboxylic acid tert-butyl ester in 30 mL diethyl ether at −30° C. Then 3.5 g diazo-acetic acid ethyl ester in diethyl ether was added at the same temperature and stirred for 30 min. The reaction was poured in to ice water and the organic layer was separated, washed with aqueous sodium-carbonate solution, dried and evaporated to give 3 g of the desired product.

$R_f$: 0.20 (petrol ether/ethyl acetate=6/4), $(M+H)^{+}=286$ 6.01.46.03 Azepan-4-one hydrochloride

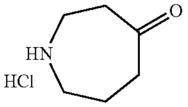

20 g 5-Oxo-azepane-1,4-dicarboxylic acid 1-tert-butyl ester 4-ethyl ester was stirred over night at 110° C. in 200 mL 6 M hydrochloric acid. The reaction was concentrated to yield 11 g of the desired product. $R_f$: 0.20 (dichlormethane/methanol=9/1), $(M+H)^{+}=114$ 6.01.46.04 1-Benzyl-azepan-4-one

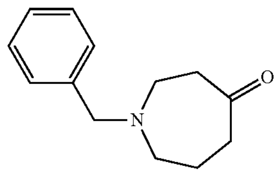 [SMILES: O=C1CCCN(Cc2ccccc2)CC1]

6 mL benzyl bromide was added to 5 g azepane-4-one hydrochloride and 18.5 g potassium carbonate in 50 mL THF and 25 mL water. The mixture was stirred 5 h at 50° C., evaporated, diluted with water and extracted with ethyl acetate. The organic layer was evaporated. The residue was purified by chromatographie on silica gel (petrolether/ethyl acetate:8/2) to give 5 g of the desired product. $R_f$: 0.40 (hexane/ethyl acetate=1/1), $(M+H)^{+}=204$ 6.01.46.05 1-Benzyl-5-bromo-azepan-4-one

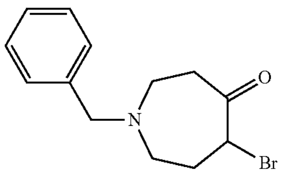 [SMILES: O=C1CCN(Cc2ccccc2)CCC1Br]

33% hydrobromic acid in conc. acetic acid and 1.97 g bromine was added to 5 g 1-benzyl-azepane-4-one in 15 mL conc. acetic acid. The reaction was stirred 2 h at RT and completely concentrated under reduced pressure. The residue was diluted with ethyl acetate and refluxed for 1 h and crystallized with ethyl acetate to give 4 g of the desired product.

$R_f$: 0.40 (hexane/ethyl acetate=1/1), $(M+H)^{+}=282/84$ 6.01.46.06 6-Benzyl-5,6,7,8-tetrahydro-thiazolo[4,5-d]azepine-2-ylamine

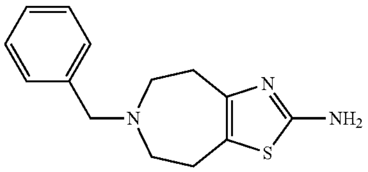 [SMILES: Nc1nc2c(s1)CCN(Cc1ccccc1)CC2]

2.7 g thiourea was added to 5 g 1-benzyl-5-bromo-azepan-4-one in 50 ml ethanol. The reaction was refluxed 5 h and concentrated. The residue was diluted with water and extracted with ethyl acetate. The organic layer was concentrated to give 4 g of the desired product.

$R_f$: 0.4 (hexane/ethyl acetate=1/1), $(M+H)^+=262$ 6.01.46.07 6-Benzyl-2-chloro-5,6,7,8-tetrahydro-thiazolo[4,5-d]azepine

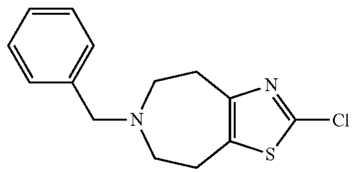 [SMILES: Clc1nc2c(s1)CCN(Cc1ccccc1)CC2]

6 mL hydrochloric acid was added at 0° C. to 6 g 6-benzyl-5,6,7,8-tetrahydro-thiazolo[4,5-d]azepine-2-ylamine in 80 mL acetonitrile. The reaction was stirred for 15 min. and 1.9 g sodium nitrite was added. After 30 min. 2.75 g copper(I) chloride was added and the mixture was stirred 2 h at RT. The reaction was evaporated, water was added and the mixture was extracted with ethyl acetate. The organic layer was evaporated. The residue was purified by chromatographie on silica gel (hexane/ethyl acetate:9/1) to give 4 g of the desired product.

$R_f$: 0.6 (hexane/ethyl acetate=1/1), $M+H)^+=281$ 6.01.46.08 6-Benzyl-2-methoxy-5,6,7,8-tetrahydro-thiazolo[4,5-d]azepine

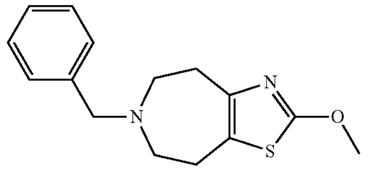 [SMILES: COc1nc2c(s1)CCN(Cc1ccccc1)CC2]

3.87 g sodium methoxide was added to 4 g 6-Benzyl-2-chloro-5,6,7,8-tetrahydro-thiazolo[4,5-d]azepine in 40 mL methanol. The reaction was heated to 80° C. in a sealed tube. After completion of the reaction the solvent was removed, water was added and extracted with ethyl acetate. The organic layer was evaporated and the residue was purified by chromatographie on silica gel (petrolether/ethyl acetate:8/2) to give 3 g of the desired product.

$R_f$: 0.4 (hexane/ethyl acetate=1/1), $(M+H)^+=277$ 6.01.46.09 2-Methoxy-5,6,7,8-tetrahydro-thiazolo[4,5-d]azepine-6-carboxylic acid 1-chloro-ethyl ester

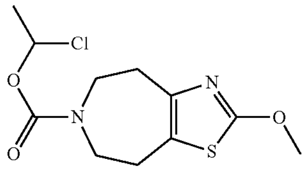 [SMILES: COc1nc2c(s1)CCN(C(=O)OC(C)Cl)CC2]

12.5 g 1-chloroethylchloroformic acid was added to 8 g 6-benzyl-2-methoxy-5,6,7,8-tetrahydro-thiazolo[4,5-d]azepine and 24 mL DIPEA in 80 mL ethyl acetate at 0° C. The reaction was stirred 3 h at RT and evaporated to give 7 g of the desired product.

$R_f$: 0.6 (hexane/ethyl acetate=1/1), $(M+H)^+=293$ 6.01.46.10 2-Methoxy-5,6,7,8-tetrahydro-thiazolo[4,5-d]azepine

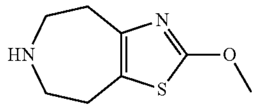

7 g 2-Methoxy-5,6,7,8-tetrahydro-thiazolo[4,5-d]azepine-6-carboxylic acid 1-chloro-ethyl ester in 70 mL methanol was heated 15 min. at 40° C. and concentrated. The residue was purified by chromatography (dichlormethane/methanol:6/4) to give 4 g of the desired product.

$R_f$: 0.2 (DCM/MeOH=1/1), $(M+H)^+=187$ 6.01.47. 5,6,7,8-Tetrahydro-4H-oxazolo[4,5-d]azepin-2-ylamine

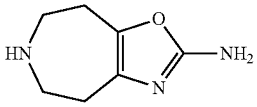 [SMILES: Nc1nc2c(o1)CCNCC2]

6.6 g urea was added to 6 g 5-bromo-azepan-4-one hydrobromide and heated 24 h at 70° C. 4 M aqueous sodium hydroxide was added and the mixture was extracted with chloroform and ethyl acetate. The combined organic layers were evaporated to give 800 mg of the desired product.

$R_t$: 0.39 min (method B), $(M+H)^+$: 154

6.01.48. 2-Methyl-5,6,7,8-tetrahydro-4H-oxazolo[4,5-d]azepine hydrochloride

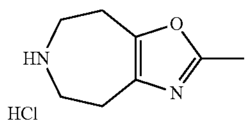

6.01.48.01 N-benzyl-N-(but-3-enyl)-but-3-en-1-amine

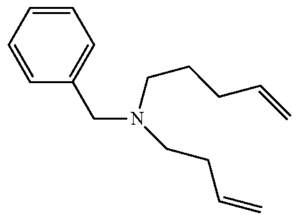 [SMILES: C=CCCCN(CCC=C)Cc1ccccc1]

12 g Benzylamine and 25 g 4-bromo-1-buten were added to a suspension of 46 g potassium carbonate in 150 mL DMF and the mixture was heated at 50° C. for 16 h. The reaction mixture was cooled to RT, diluted with ethyl acetate, washed with water and brine, dried, concentrated, and purified by chromatographie on silica gel (hexane/ethyl acetate 50:1) to yield 18.3 g of the desired product. $(M+H)^+$: 230

6.01.48.02 benzyl dibut-3-enylcarbamate

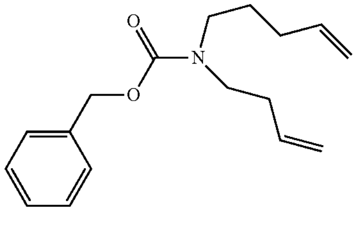 [SMILES: C=CCCCN(CCC=C)C(=O)OCc1ccccc1]

11.2 mL benzylchloroformate was added to 14 g N-benzyl-N-(but-3-enyl)-but-3-en-1-amine in 100 mL toluene at 0° C. After being heated at 70° C. for 3 h, the reaction mixture was cooled to RT, basified with saturated aqueous sodium hydrogencarbonate solution, extracted with ethyl acetate, washed with brine, dried, concentrated, and purified by chromatographie on silica gel (hexane/ethyl acetate 20:1) to yield 16.8 g of the desired product. $(M+H)^+$: 274

6.01.48.03 benzyl 2,3,6,7-tetrahydro-1H-azepine-1-carboxylate

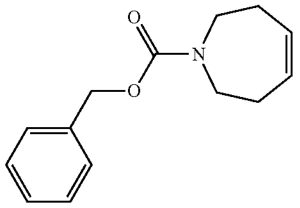 [SMILES: O=C(OCc1ccccc1)N1CCC=CCC1]

0.15 g Grubb's 2 catalyst was added to a solution of 8 g benzyl dibut-3-enylcarbamate in 680 mL toluene and heated at 50° C. for 5 h. The solvent was removed and the residue was purified by chromatographie on silica gel (ethyl acetate/hexane 1:5) to yield 6.6 g of the desired product. $(M+H)^+$: 232

6.01.48.04 benzyl 8-oxa-4-azabicyclo[5.1.0]octane-4-carboxylate

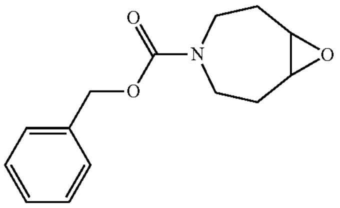 [SMILES: O=C(OCc1ccccc1)N1CCC2OC2CC1]

18 g m-chloroperbenzoic acid was added to 10 g benzyl 2,3,6,7-tetrahydro-1H-azepine-1-carboxylate in 250 ml dichloromethane at 0° C. in several portions. The mixture was allowed to warm to RT over 2 h. 1 L ethyl acetate was added and the solution was extracted with aqueous sodium bicarbonate, 1N aqueous sodium hydroxide and brine. The organic layer was evaporated and the residue was purified by chromatographie on silica gel (ethyl acetate/hexanes 1:5) to yield 10.4 g of the desired product.

6.01.48.05 4-Amino-5-hydroxy-azepane-1-carboxylic acid benzyl ester

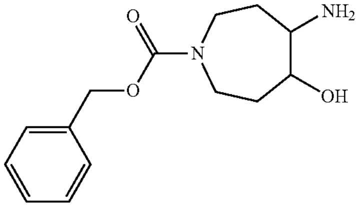 [SMILES: NC1CCN(C(=O)OCc2ccccc2)CCC1O]

3 g benzyl 8-oxa-4-azabicyclo[5.1.0]octane-4-carboxylate in 70 mL 30% aqueous ammonia was stirred at 65° C. in a sealed vessel overnight. The reaction was extracted with dichloromethane. The organic layer was washed with brine, dried over sodium sulfate filtered and concentrated to yield 3.1 g of the desired product. $(M+H)^+$: 265

6.01.48.06 4-Acetylamino-5-hydroxy-azepane-1-carboxylic acid benzyl ester

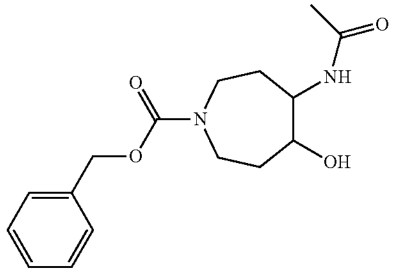 [SMILES: CC(=O)NC1CCN(C(=O)OCc2ccccc2)CCC1O]

3 mL acetic anhydride was added to 8.4 g benzyl 4-amino-5-hydroxy-azepane-1-carboxylic acid benzyl ester in 115 ml dichloromethane at 0° C. After 1 h at RT, saturated sodium bicarbonate was added. The phases were separated and the aqueous phase was extracted with dichloromethane. The combined organic phase was washed with brine, dried over sodium sulphate, filtered and concentrated. The residue was purified by chromatographie on silica gel (ethyl acetate/hexane 2:1) to yield 4.5 g of the desired product. $(M+H)^+$: 307

6.01.48.07 4-Acetylamino-5-oxo-azepane-1-carboxylic acid benzyl ester

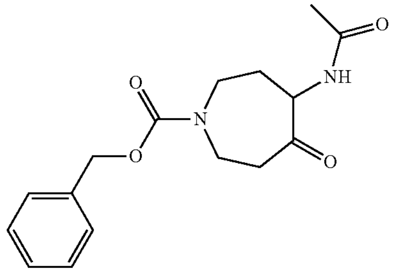 [SMILES: CC(=O)NC1CCN(C(=O)OCc2ccccc2)CCC1=O]

11 g Dess Martin Periodane was added to 6.2 g 4-acetylamino-5-hydroxy-azepane-1-carboxylic acid benzyl ester in 100 mL dichloromethane and stirred for 1 h at RT. The mixture was diluted with dichloromethane and washed with 2 mol/L sodium hydroxide solution. The organic layer was washed with brine, dried and concentrated. The residue was purified by chromatographie on silica gel (EtOAc) to yield 5.5 g of the desired product. $(M+H)^+$: 305

6.01.48.08 Benzyl 2-methyl-4,5,7,8-tetrahydrooxazolo[4,5-d]azepine-6-carboxylate

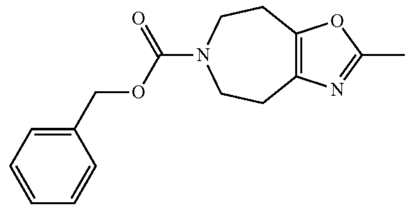 [SMILES: Cc1nc2c(o1)CCN(C(=O)OCc1ccccc1)CC2]

3 g 4-acetylamino-5-oxo-azepane-1-carboxylic acid benzyl ester in 100 mL tetrahydrofuran and 3.8 g (methoxycarbonylsulfamoyl)triethylammonium hydroxide were heated in a sealed tube at 75° C. for 1 h. The solvent was evaporated and the residue was purified by chromatographie on silica gel (ethyl acetate/hexane 1:2) to yield 23 g of the desired product. $(M+H)^+$: 287

6.01.48.09 2-Methyl-5,6,7,8-tetrahydro-4H-oxazolo[4,5-d]azepine hydrochloride

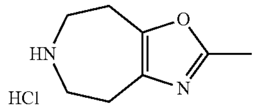

A solution of 25 g of benzyl 2-methyl-4,5,7,8-tetrahydrooxazolo[4,5-d]azepine-6-carboxylate in 500 ml 2-propanol was stirred under hydrogen atmosphere (1 atm) in the presence of 450 mg of 5% palladium/charcoal (50% water) at RT overnight. After filtration over celite the filtrate was concentrated. The residue was diluted in a mixture of dichloromethane and diethylether and 2 mol/L hydrochloric acid in diethylether was added. The precipitate was filtered and dried to yield 15.5 g of the desired product. $R_t$: 0.86 min (method C), $(M+H)^+$: 153

6.02. Synthesis of triazole-1yl-acids 6.02.01.01 N'-(4-Fluoro-3-methyl-benzoyl)-hydrazinecarboxylic acid tert-butyl ester

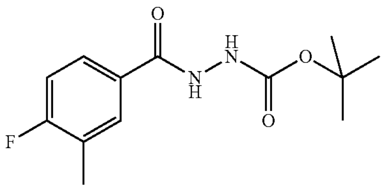 [SMILES: Cc1cc(C(=O)NNC(=O)OC(C)(C)C)ccc1F]

11.2 g 4-fluoro-3-methyl-benzoyl chloride was added to 6.1 g triethylamine and 8 g hydrazinecarboxylic acid tert-butyl ester in 150 mL dichlormethane. The reaction was stirred for 1 h at RT and extracted with water. The organic layer was evaporated and the residue was crystallized from diisopropylether to yield 13 g of the desired product. $R_t$: 1.22 min (method B) $(M+H)^+$: 269

By using the same synthesis strategy as for N'-(4-bromo-3-methyl-benzoyl)-hydrazinecarboxylic acid tert-butyl ester the following compounds were obtained:

| Examples | Product | MS m/z [M + H]+ | HPLC Method | Rt min |
|---|---|---|---|---|
| 6.02.01.02 | 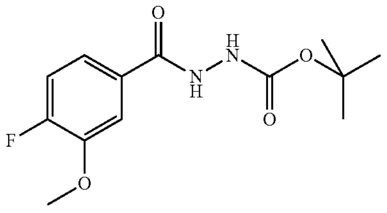 [SMILES: COc1cc(C(=O)NNC(=O)OC(C)(C)C)ccc1F] | 285 | method B | 1.14 |
| 6.02.01.03 | 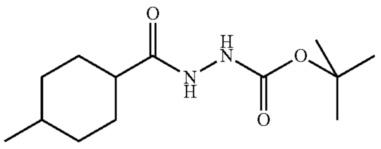 [SMILES: CC1CCC(C(=O)NNC(=O)OC(C)(C)C)CC1] | 257 | method L | 0.88 |
| 6.02.01.04 | 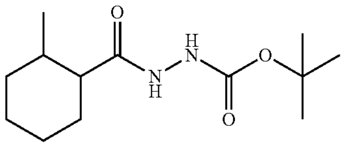 [SMILES: CC1CCCCC1C(=O)NNC(=O)OC(C)(C)C] | 257 | method L | 0.86 |
| 6.02.01.05 | 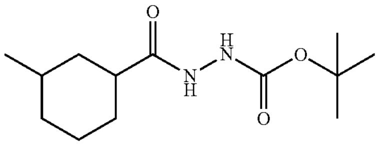 [SMILES: CC1CCCC(C(=O)NNC(=O)OC(C)(C)C)C1] | 257 | method L | 0.87 |
| 6.02.01.06 | 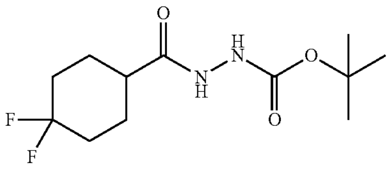 [SMILES: CC(C)(C)OC(=O)NNC(=O)C1CCC(F)(F)CC1] | 279 | method L | 0.75 |

6.02.02.01 4-Fluoro-3-methyl-benzoic acid hydrazide

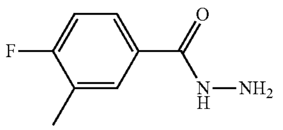

50 mL trifluor acetic acid was added to 13 g N'-(4-fluoro-3-methyl-benzoyl)-hydrazinecarboxylic acid tert-butyl ester in 150 mL dichlormethane. The reaction was stirred for 1 h at RT and the solvent was evaporated. The residue was basicfied with 1 N sodium hydroxide and extracted with saturated sodium chloride solution and tetrahydrofuran. The organic layer was evaporated and the residue crystallized from ethyl acetate to yield 6.8 g of the desired product.

$R_t$: 0.80 min (method B), $(M+H)^+$: 169

By using the same synthesis strategy as for N'-(4-bromo-3-methyl-benzoyl)-hydrazinecarboxylic acid tert-butyl ester the following compounds were obtained:

| Examples | Product | MS m/z [M + H]+ | HPLC Method | Rt min |
|---|---|---|---|---|
| 6.02.02.02 | 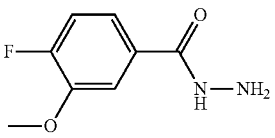 | 185 | method B | 0.67 |
| 6.02.02.03 | 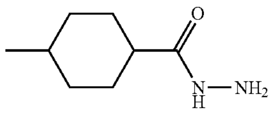 | 157 | method L | 0.63 |

-continued

| Examples | Product | MS m/z [M + H]$^+$ | HPLC Method | Rt min |
|---|---|---|---|---|
| 6.02.02.04 | 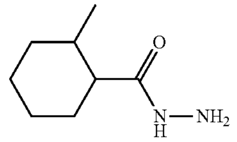 | 157 | method L | 0.61 |
| 6.02.02.05 | 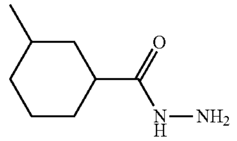 | 157 | method L | 0.63 |
| 6.02.02.06 | 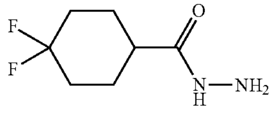 [SMILES: NNC(=O)C1CCC(F)(F)CC1] | 179 | method L | 0.51 |

6.02.03.01 4-Fluoro-benzamidine

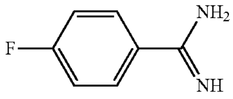

380 mL 1N LiHMDS-solution in n-hexane was added to 20 g 4-fluoro-benzonitrile in 1 L diethylether. The reaction was stirred for 2 h at RT and decomposed with 1 L 4 NHCL-solution at 0° C. 4 N sodium hydroxide was added until pH 12 was reached and the water layer was extracted with chloroform. The organic layer was dried and evaporated to give 6.6 g of the desired product. $R_t$: 0.30 min (method B), $(M+H)^+$: 139

By using the same synthesis strategy as for 4-fluoro-benzamidine the following compounds were obtained:

| Examples | Product | MS m/z [M + H]$^+$ | HPLC Method | Rt min |
|---|---|---|---|---|
| 6.02.03.02 | 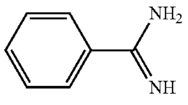 | 121 | method B | 0.24 |
| 6.02.03.03 | 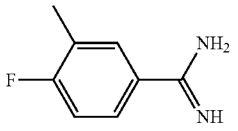 | 153 | method K | 0.75 |
| 6.02.03.04 | 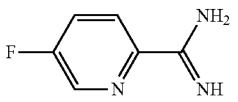 | 140 | $R_f$ = 0.05 (dichloromethane) | |

6.02.03.05 4-Fluoro-3-methyl-benzimidic acid ethyl ester

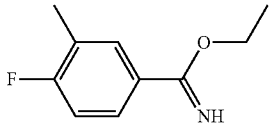

Hydrogen chloride gas was passed through a solution of 40 g 4-fluoro-3-methylbenzonitrile in 250 mL ethanol. The reaction was stirred for 1 h at RT and for 30 min. at 40° C. Then, the solvent was evaporated, diethyl ether was added and the precipitate was filtered and dried under nitrogen.

The hydrochloride was dissolved in ethanol and ammonia gas was passed through the solution. The solvent was removed and the residue was suspended in n-hexane. The suspension was filtered through silica gel and the filtrate was concentrated to yield 3.7 g of the desired product.

$R_t$: 0.99 min (method K), $(M+H)^+$: 182

6.02.04.01 3,5-bis-(4-Fluoro-phenyl)-1H-(1,2,4)triazole

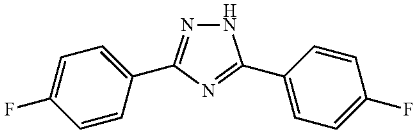 [SMILES: Fc1ccc(-c2n[nH]c(-c3ccc(F)cc3)n2)cc1]

4 g 4-fluoro-benzamidine was mixed with 4.5 g 4-fluoro-benzoic acid hydrazide and the mixture was melted. Then the mixture was crystallized from ethyl acetate to yield 5.3 g of the desired compound. $R_t$: 1.55 min (method A), $(M+H)^+$: 258

By using the same synthesis strategy as for 3,5-bis-(4-fluoro-phenyl)-1H-(1,2,4)triazole the following compounds were obtained

| Examples | Product | MS m/z [M + H]+ | HPLC Method | Rt min |
|---|---|---|---|---|
| 6.02.04.02 | 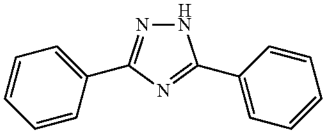 [SMILES: c1ccc(-c2n[nH]c(-c3ccccc3)n2)cc1] | 222 | method B | 1.30 |
| 6.02.04.03 | 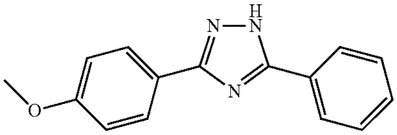 [SMILES: COc1ccc(-c2n[nH]c(-c3ccccc3)n2)cc1] | 252 | method B | 1.29 |
| 6.02.04.04 | 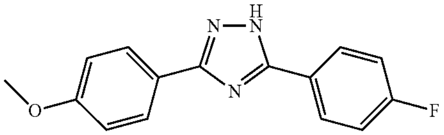 [SMILES: COc1ccc(-c2n[nH]c(-c3ccc(F)cc3)n2)cc1] | 270 | method A | 1.34 |
| 6.02.04.05 | 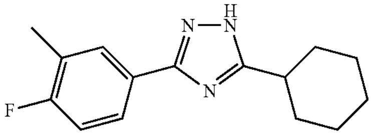 [SMILES: Cc1cc(-c2n[nH]c(C3CCCCC3)n2)ccc1F] | 260 | method B | 1.40 |
| 6.02.04.06 | 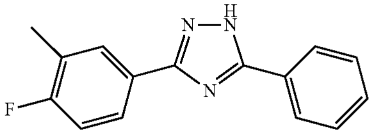 [SMILES: Cc1cc(-c2n[nH]c(-c3ccccc3)n2)ccc1F] | 254 | method B | 1.45 |
| 6.02.04.07 | 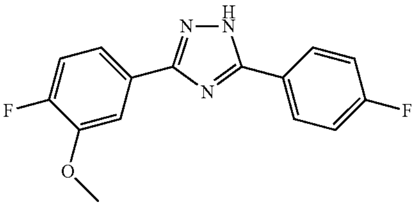 [SMILES: COc1cc(-c2n[nH]c(-c3ccc(F)cc3)n2)ccc1F] | 288 | method B | 1.42 |
| 6.02.04.08 | 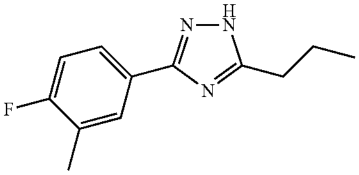 [SMILES: CCCc1nc(-c2ccc(F)c(C)c2)n[nH]1] | 220 | method K | 1.25 |
| 6.02.04.09 | 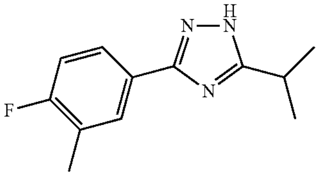 [SMILES: Cc1cc(-c2n[nH]c(C(C)C)n2)ccc1F] | 220 | method K | 1.23 |
| 6.02.04.10 | 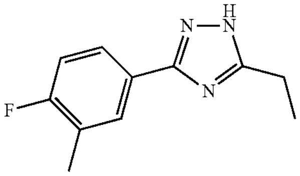 | 206 | method L | 0.66 |

-continued
| Examples | Product | MS m/z [M + H]+ | HPLC Method | Rt min |
| --- | --- | --- | --- | --- |
| 6.02.04.11 | 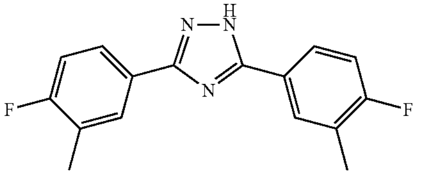 [SMILES: Cc1cc(-c2n[nH]c(-c3ccc(F)c(C)c3)n2)ccc1F] | 286 | method L | 0.94 |
| 6.02.04.12 | 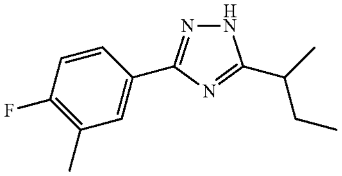 [SMILES: CCC(C)c1nc(-c2ccc(F)c(C)c2)n[nH]1] | 234 | method L | 0.79 |
| 6.02.04.13 | 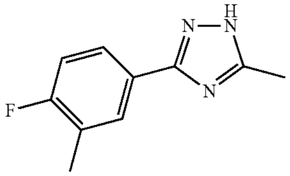 | 192 | method W | 1.16 |
| 6.02.04.14 | 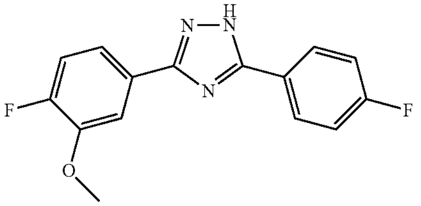 [SMILES: COc1cc(-c2n[nH]c(-c3ccc(F)cc3)n2)ccc1F] | 288 | method B | 1.42 |
| 6.02.04.15 | 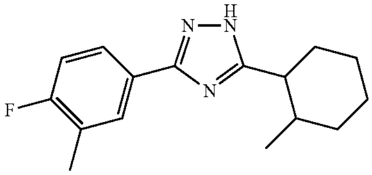 [SMILES: Cc1cc(-c2n[nH]c(C3CCCCC3C)n2)ccc1F] | 274 | method L | 1.00 |
| 6.02.04.16 | 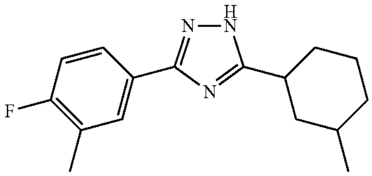 [SMILES: Cc1cc(-c2n[nH]c(C3CCCC(C)C3)n2)ccc1F] | 274 | method Q | 0.91 |
| 6.02.04.17 | 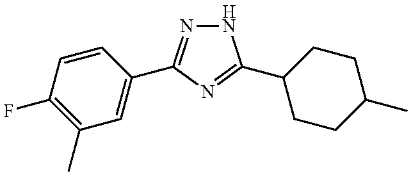 [SMILES: Cc1cc(-c2n[nH]c(C3CCC(C)CC3)n2)ccc1F] | 274 | method L | 0.98 |
| 6.02.04.18 | 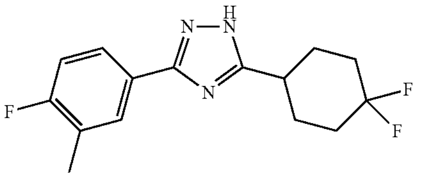 [SMILES: Cc1cc(-c2n[nH]c(C3CCC(F)(F)CC3)n2)ccc1F] | 296 | method Q | 0.86 |

-continued
| Examples | Product | MS m/z [M + H]+ | HPLC Method | Rt min |
|---|---|---|---|---|
| 6.02.04.19 | 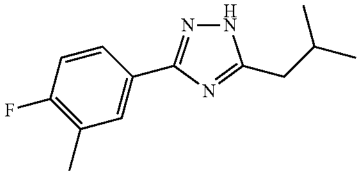 [SMILES: Cc1cc(-c2n[nH]c(CC(C)C)n2)ccc1F] | 234 | method K | 1.35 |
| 6.02.04.20 | 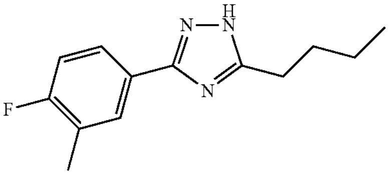 [SMILES: CCCCc1nc(-c2ccc(F)c(C)c2)n[nH]1] | 234 | method K | 1.23 |
| 6.02.04.21 | 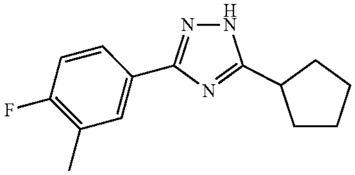 [SMILES: Cc1cc(-c2n[nH]c(C3CCCC3)n2)ccc1F] | 246 | method L | 0.81 |
| 6.02.04.22 | 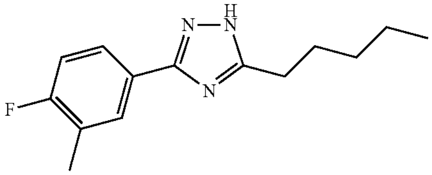 [SMILES: CCCCCc1nc(-c2ccc(F)c(C)c2)n[nH]1] | 248 | method L | 0.83 |
| 6.02.04.23 | 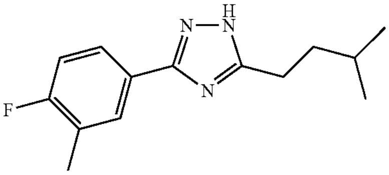 [SMILES: Cc1cc(-c2n[nH]c(CCC(C)C)n2)ccc1F] | 248 | method L | 0.87 |
| 6.02.04.24 | 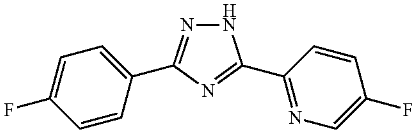 | 259 | method Y | 1.19 |
| 6.02.04.26 | 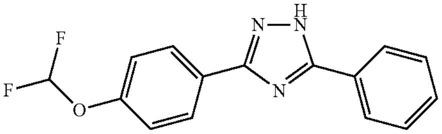 [SMILES: FC(F)Oc1ccc(-c2n[nH]c(-c3ccccc3)n2)cc1] | 288 | method L | 0.87 |
| 6.02.04.27 | 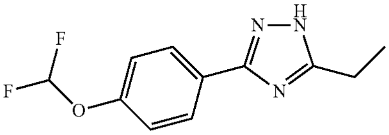 [SMILES: CCc1nc(-c2ccc(OC(F)F)cc2)n[nH]1] | 240 | method L | 0.69 |
| 6.02.04.28 | 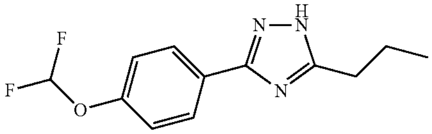 [SMILES: CCCc1nc(-c2ccc(OC(F)F)cc2)n[nH]1] | 254 | method L | 0.76 |

6.02.05.01 (3,5-bis-(4-Fluoro-phenyl)-(1,2,4)triazol-1-yl)-acetic acid methyl ester

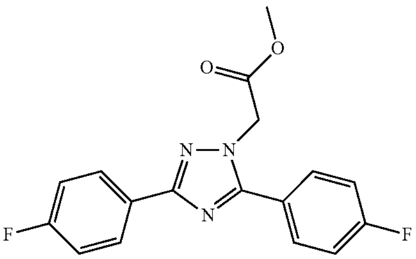 [SMILES: COC(=O)Cn1nc(-c2ccc(F)cc2)nc1-c1ccc(F)cc1]

26.5 g 3,5-bis-(4-fluoro-phenyl)-1H-(1,2,4)triazole, 62.6 g $K_2CO_3$ and 15.7 g 2-bromoacetic acid methyl ester were mixed in 1 L acetone and stirred for 24 h under reflux. $K_2CO_3$ was filtered and the solvent was removed to yield 30.8 g of the desired product.

$R_t$: 1.35 min (method B), $(M+H)^+$: 330

By using the same synthesis strategy as for (3,5-bis-(4-fluoro-phenyl)-(1,2,4)triazol-1-yl)-acetic acid methyl ester the following compounds were obtained:

| Examples | Product | MS m/z $[M + H]^+$ | HPLC Method | Rt min |
|---|---|---|---|---|
| 6.02.05.02 | 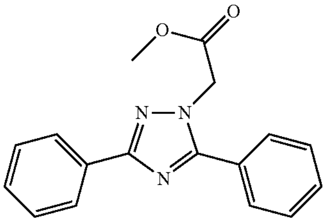 [SMILES: COC(=O)Cn1nc(-c2ccccc2)nc1-c1ccccc1] | 294 | method B | 1.31 |
| 6.02.05.03 | 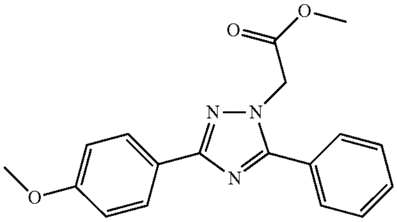 [SMILES: COC(=O)Cn1nc(-c2ccc(OC)cc2)nc1-c1ccccc1] | 324 | method B | 1.37 |
| 6.02.05.04 | 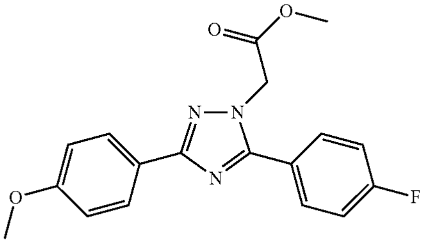 [SMILES: COC(=O)Cn1nc(-c2ccc(OC)cc2)nc1-c1ccc(F)cc1] | 342 | method A | 1.32 |
| 6.02.05.05 | 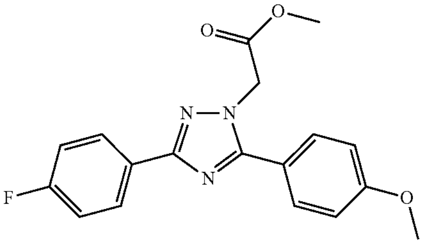 [SMILES: COC(=O)Cn1nc(-c2ccc(F)cc2)nc1-c1ccc(OC)cc1] | 342 | method A | 1.36 |
| 6.02.05.06 | 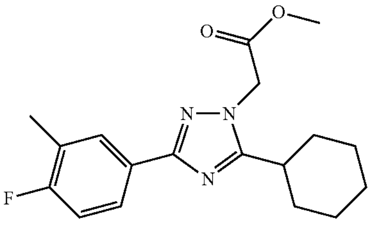 [SMILES: COC(=O)Cn1nc(-c2ccc(F)c(C)c2)nc1C1CCCCC1] | 332 | method B | 1.50 |

-continued
| Examples | Product | MS m/z $[M + H]^+$ | HPLC Method | Rt min |
|---|---|---|---|---|
| 6.02.05.07 | 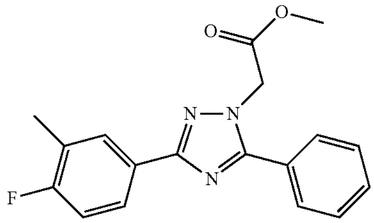 [SMILES: COC(=O)Cn1nc(-c2ccc(F)c(C)c2)nc1-c1ccccc1] | 326 | method B | 1.43 |
| 6.02.05.08 | 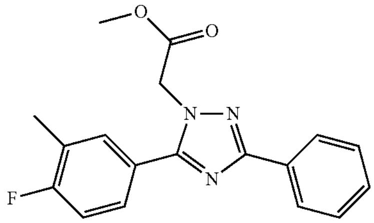 [SMILES: COC(=O)Cn1nc(-c2ccccc2)nc1-c1ccc(F)c(C)c1] | 326 | method B | 1.43 |
| 6.02.05.09 | 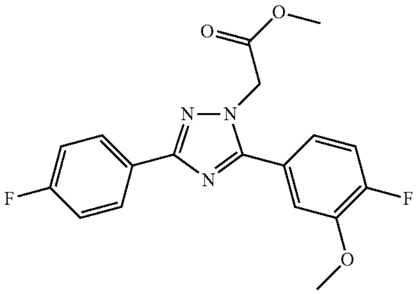 [SMILES: COC(=O)Cn1nc(-c2ccc(F)cc2)nc1-c1ccc(F)c(OC)c1] | 360 | method B | 1.37 |
| 6.02.05.10 | 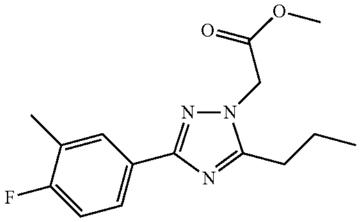 [SMILES: CCCc1nc(-c2ccc(F)c(C)c2)nn1CC(=O)OC] | 292 | method K | 1.38 |
| 6.02.05.11 | 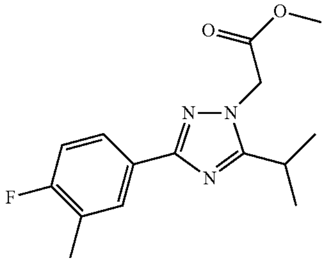 [SMILES: COC(=O)Cn1nc(-c2ccc(F)c(C)c2)nc1C(C)C] | 292 | method K | 1.36 |
| 6.02.05.12 | 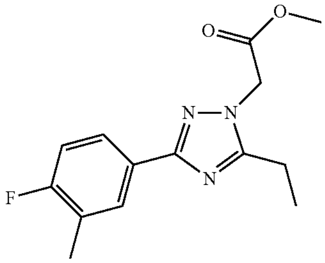 [SMILES: CCc1nc(-c2ccc(F)c(C)c2)nn1CC(=O)OC] | 278 | method L | 0.78 |

-continued
| Examples | Product | MS m/z [M + H]+ | HPLC Method | Rt min |
|---|---|---|---|---|
| 6.02.05.13 | 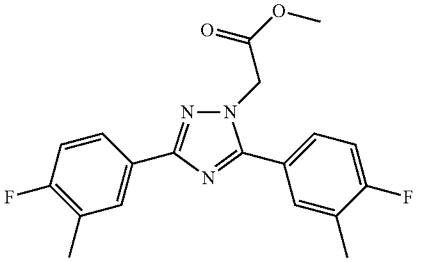 [SMILES: COC(=O)Cn1nc(-c2ccc(F)c(C)c2)nc1-c1ccc(F)c(C)c1] | 358 | method L | 0.94 |
| 6.02.05.14 | 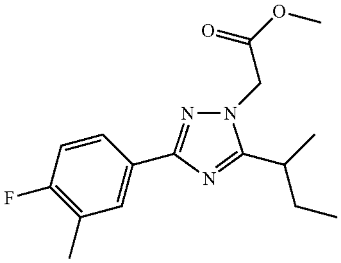 [SMILES: CCC(C)c1nc(-c2ccc(F)c(C)c2)nn1CC(=O)OC] | 306 | method L | 0.88 |
| 6.02.05.15 | 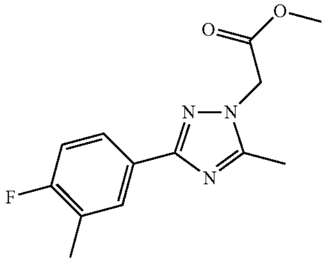 [SMILES: COC(=O)Cn1nc(-c2ccc(F)c(C)c2)nc1C] | 264 | method W | 1.26 |
| 6.02.05.16 | 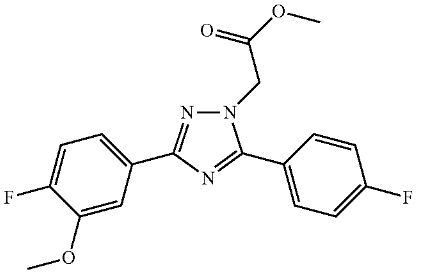 [SMILES: COC(=O)Cn1nc(-c2ccc(F)c(OC)c2)nc1-c1ccc(F)cc1] | 360 | method B | 1.39 |
| 6.02.05.17 | 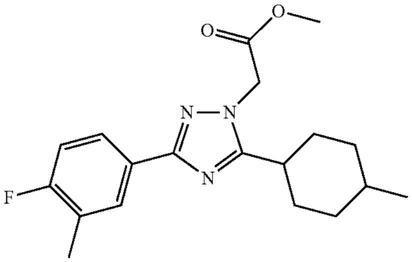 [SMILES: COC(=O)Cn1nc(-c2ccc(F)c(C)c2)nc1C1CCC(C)CC1] | 346 | method L | 1.05 |

-continued
| Examples | Product | MS m/z [M + H]+ | HPLC Method | Rt min |
|---|---|---|---|---|
| 6.02.05.18 | 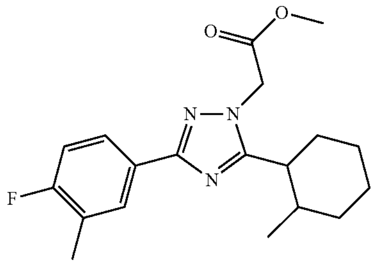 [SMILES: COC(=O)Cn1nc(-c2ccc(F)c(C)c2)nc1C1CCCCC1C] | 346 | method L | 1.06 |
| 6.02.05.19 | 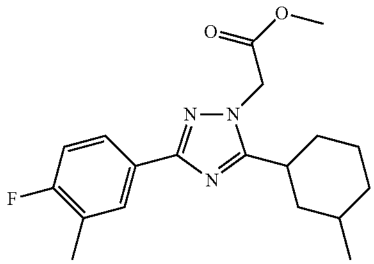 [SMILES: COC(=O)Cn1nc(-c2ccc(F)c(C)c2)nc1C1CCCC(C)C1] | 346 | method R | 0.95 |
| 6.02.05.20 | 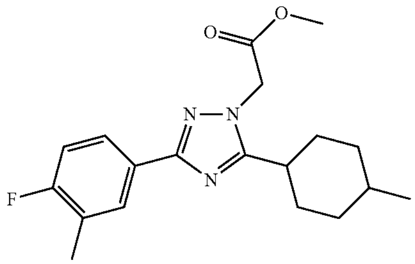 [SMILES: COC(=O)Cn1nc(-c2ccc(F)c(C)c2)nc1C1CCC(C)CC1] | 346 | method L | 1.05 |
| 6.02.05.21 | 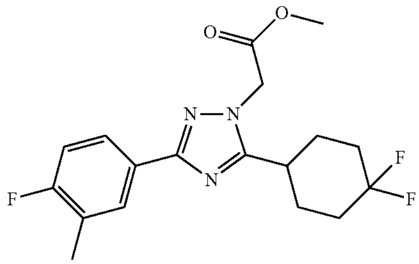 [SMILES: COC(=O)Cn1nc(-c2ccc(F)c(C)c2)nc1C1CCC(F)(F)CC1] | 368 | method X | 1.47 |
| 6.02.05.22 | 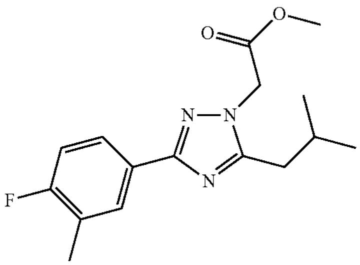 [SMILES: COC(=O)Cn1nc(-c2ccc(F)c(C)c2)nc1CC(C)C] | 306 | method K | 1.43 |

-continued
| Examples | Product | MS m/z [M + H]+ | HPLC Method | Rt min |
|---|---|---|---|---|
| 6.02.05.23 | 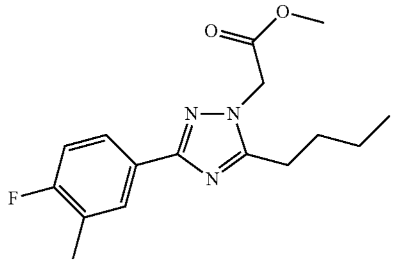 | 306 | method K | 1.33 |
| 6.02.05.24 | 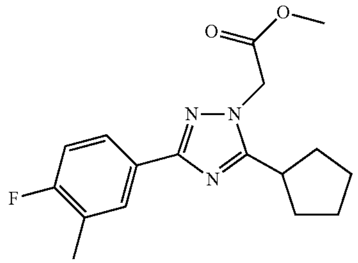 [SMILES: COC(=O)Cn1nc(-c2ccc(F)c(C)c2)nc1C1CCCC1] | 304 | method L | 0.85 |
| 6.02.05.25 | 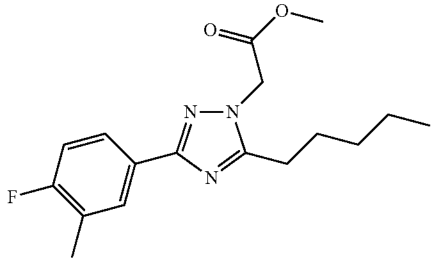 [SMILES: CCCCCc1nc(-c2ccc(F)c(C)c2)nn1CC(=O)OC] | 320 | method L | 0.88 |
| 6.02.05.26 | 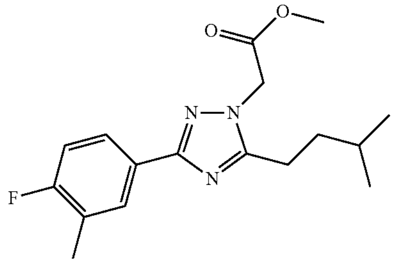 [SMILES: COC(=O)Cn1nc(-c2ccc(F)c(C)c2)nc1CCC(C)C] | 320 | method L | 0.92 |
| 6.02.05.27 | 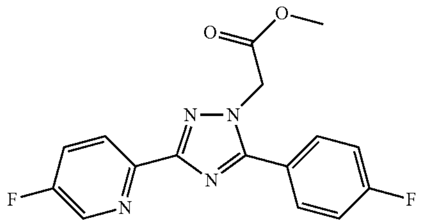 [SMILES: COC(=O)Cn1nc(-c2ccc(F)cn2)nc1-c1ccc(F)cc1] | 331 | method S | 0.71 |
| 6.02.05.28 | 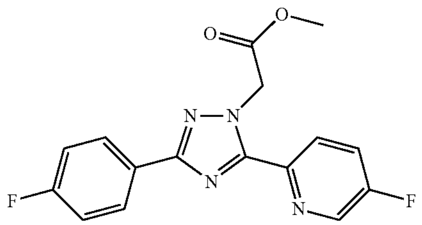 [SMILES: COC(=O)Cn1nc(-c2ccc(F)cc2)nc1-c1ccc(F)cn1] | 331 | method S | 0.83 |

-continued

| Examples | Product | MS m/z $[M + H]^+$ | HPLC Method | Rt min |
|---|---|---|---|---|
| 6.02.05.29 | 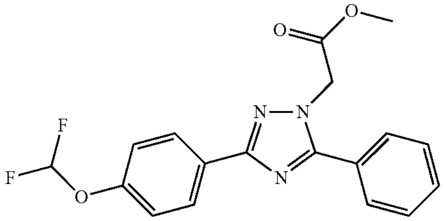 [SMILES: COC(=O)Cn1nc(-c2ccc(OC(F)F)cc2)nc1-c1ccccc1] | 360 | | |
| 6.02.05.30 | 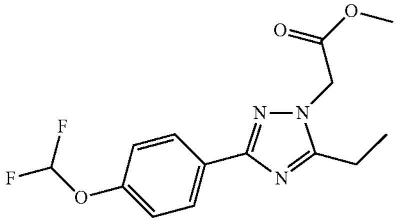 [SMILES: CCc1nc(-c2ccc(OC(F)F)cc2)nn1CC(=O)OC] | 312 | method L | 0.79 |
| 6.02.05.31 | 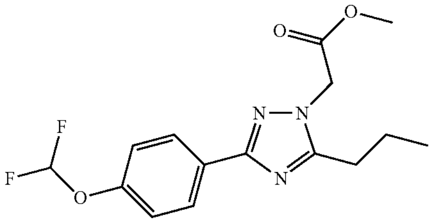 [SMILES: CCCc1nc(-c2ccc(OC(F)F)cc2)nn1CC(=O)OC] | 326 | method L | 0.83 |

6.02.06.01 (3,5-bis-(4-Fluoro-phenyl)-(1,2,4)triazol-1-yl)-acetic acid

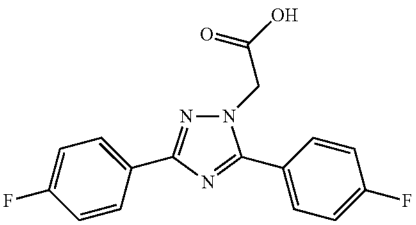 [SMILES: O=C(O)Cn1nc(-c2ccc(F)cc2)nc1-c1ccc(F)cc1]

30.8 g of (3,5-bis-(4-fluoro-phenyl)-(1,2,4)triazol-1-yl)-acetic acid methyl ester was dissolved in 250 mL dioxane and a solution of 2.4 g LiOH in 250 mL of water was added. The mixture was stirred for 24 h at RT. Then, HCl-solution was added and the precipitate was filtered to give 29 g of the desired product. $R_t$: 1.28 min (method B), $(M+H)^+$: 316

6.02.06.02 (3-(4-methoxy-phenyl)-5-phenyl-(1,2,4)triazol-1-yl)-acetic acid

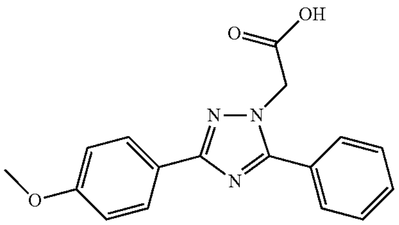 [SMILES: COc1ccc(-c2nc(-c3ccccc3)n(CC(=O)O)n2)cc1]

30.8 g of (3-(4-methoxy-phenyl)-5-phenyl-(1,2,4)triazol-1-yl)-acetic acid methyl ester was dissolved in 140 mL dioxane and a solution of 0.8 g LiOH in 140 mL of water was added. The mixture was stirred for 4 h at RT. The mixture was acidified with HCl-solution and the precipitate was filtered to give 9.0 g of the desired product as mixture of isomers. These isomers were separated by HPLC chiral (method 1; solvent MeOH: DCM=1:1, concentration: 90 mg/mL). $R_t$: 1.26 min (method A) and 1.24 min., $(M+H)^+$: 310

By using the same synthesis strategy the following compounds were obtained:

| Examples | Product | MS m/z [M + H]+ | HPLC Method | Rt min |
|---|---|---|---|---|
| 6.02.06.03 | 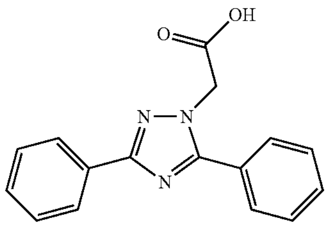 [SMILES: O=C(O)Cn1nc(-c2ccccc2)nc1-c1ccccc1] | 280 | method B | 1.23 |
| 6.02.06.04 | 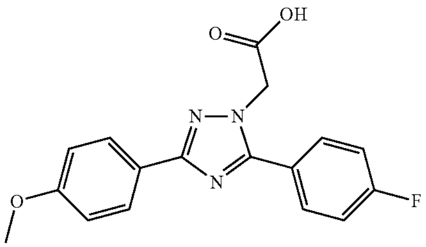 [SMILES: COc1ccc(-c2nc(-c3ccc(F)cc3)n(CC(=O)O)n2)cc1] | 328 | method B | 1.26 |
| 6.02.06.05 | 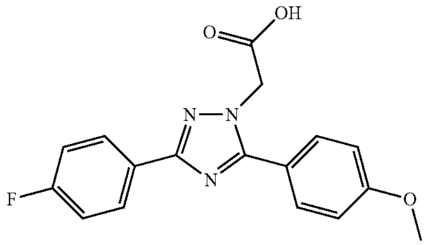 [SMILES: COc1ccc(-c2nc(-c3ccc(F)cc3)nn2CC(=O)O)cc1] | 328 | method B | 1.31 |
| 6.02.06.06 | 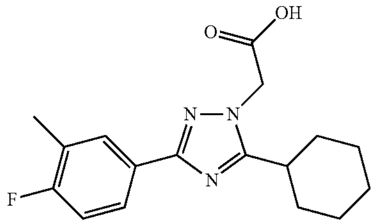 [SMILES: Cc1cc(-c2nc(C3CCCCC3)n(CC(=O)O)n2)ccc1F] | 318 | method B | 1.45 |
| 6.02.06.07 | 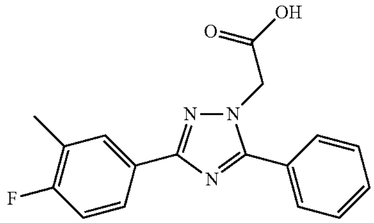 [SMILES: Cc1cc(-c2nc(-c3ccccc3)n(CC(=O)O)n2)ccc1F] | 312 | method B | 1.38 |
| 6.02.06.08 | 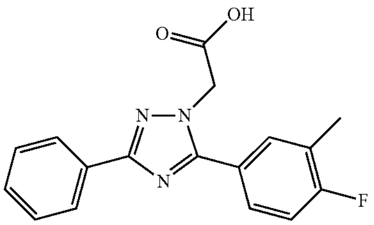 [SMILES: Cc1cc(-c2nc(-c3ccccc3)nn2CC(=O)O)ccc1F] | 312 | method B | 1.35 |

-continued
| Examples | Product | MS m/z [M + H]+ | HPLC Method | Rt min |
|---|---|---|---|---|
| 6.02.06.09 | 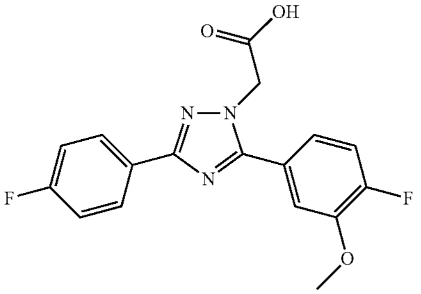 [SMILES: COc1cc(-c2nc(-c3ccc(F)cc3)nn2CC(=O)O)ccc1F] | 346 | method K | 1.31 |
| 6.02.06.10 | 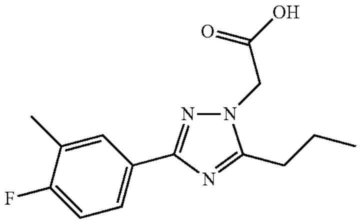 [SMILES: CCCc1nc(-c2ccc(F)c(C)c2)nn1CC(=O)O] | 278 | method K | 1.31 |
| 6.02.06.11 | 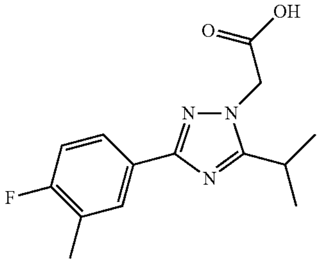 [SMILES: Cc1cc(-c2nc(C(C)C)n(CC(=O)O)n2)ccc1F] | 278 | method K | 1.29 |
| 6.02.06.12 | 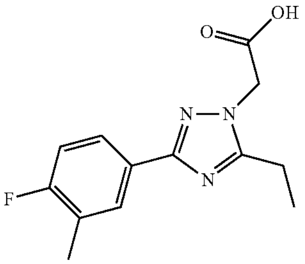 [SMILES: CCc1nc(-c2ccc(F)c(C)c2)nn1CC(=O)O] | 264 | method W | 0.93 |
| 6.02.06.13 | 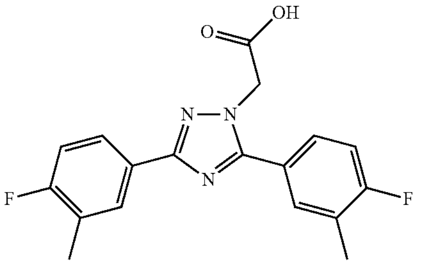 [SMILES: Cc1cc(-c2nc(-c3ccc(F)c(C)c3)n(CC(=O)O)n2)ccc1F] | 344 | method L | 0.90 |

-continued
| Examples | Product | MS m/z [M + H]+ | HPLC Method | Rt min |
|---|---|---|---|---|
| 6.02.06.14 | 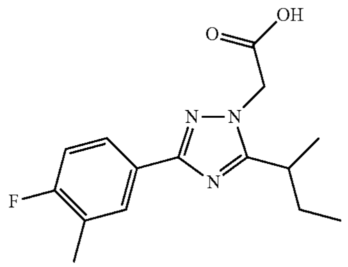 [SMILES: CCC(C)c1nc(-c2ccc(F)c(C)c2)nn1CC(=O)O] | 292 | method L | 0.85 |
| 6.02.06.15 | 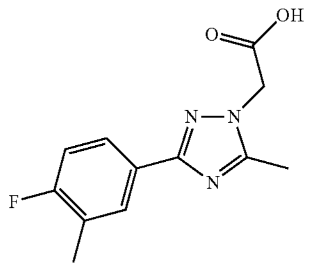 [SMILES: Cc1cc(-c2nc(C)n(CC(=O)O)n2)ccc1F] | 250 | method W | 0.87 |
| 6.02.06.16 | 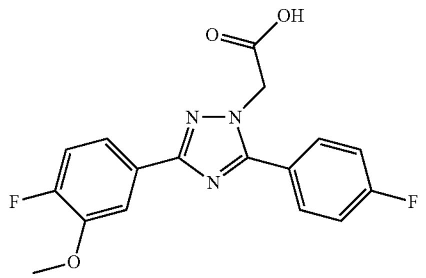 [SMILES: COc1cc(-c2nc(-c3ccc(F)cc3)n(CC(=O)O)n2)ccc1F] | 346 | method L | 0.87 |
| 6.02.06.17 | 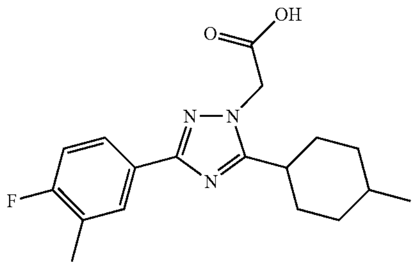 [SMILES: Cc1cc(-c2nc(C3CCC(C)CC3)n(CC(=O)O)n2)ccc1F] | 332 | method L | 0.98 |
| 6.02.06.18 | 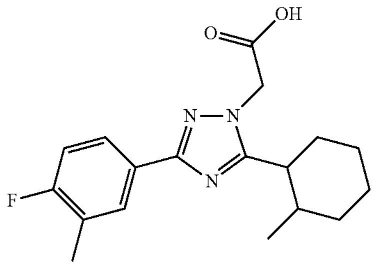 [SMILES: Cc1cc(-c2nc(C3CCCCC3C)n(CC(=O)O)n2)ccc1F] | 332 | method L | 0.98 |

-continued
| Examples | Product | MS m/z [M + H]+ | HPLC Method | Rt min |
|---|---|---|---|---|
| 6.02.06.19 | 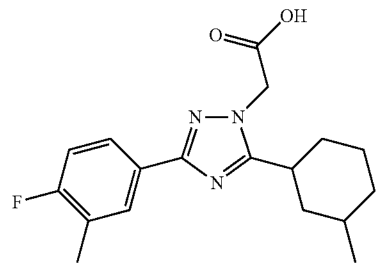 [SMILES: Cc1cc(-c2nc(C3CCCC(C)C3)n(CC(=O)O)n2)ccc1F] | 332 | method F | 1.42 |
| 6.02.06.20 | 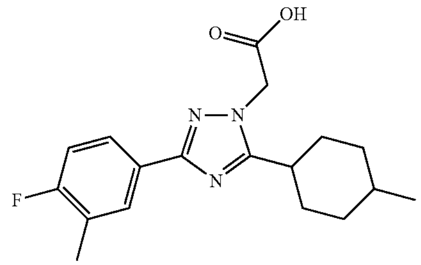 [SMILES: Cc1cc(-c2nc(C3CCC(C)CC3)n(CC(=O)O)n2)ccc1F] | 332 | method L | 0.98 |
| 6.02.06.21 | 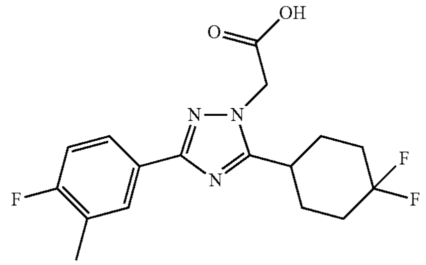 [SMILES: Cc1cc(-c2nc(C3CCC(F)(F)CC3)n(CC(=O)O)n2)ccc1F] | 354 | method Q | 0.87 |
| 6.02.06.22 | 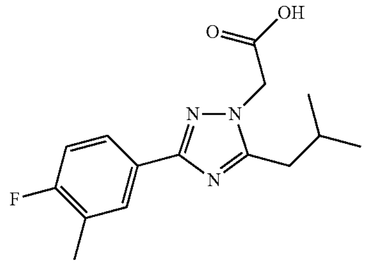 [SMILES: Cc1cc(-c2nc(CC(C)C)n(CC(=O)O)n2)ccc1F] | 292 | method K | 1.39 |
| 6.02.06.23 | 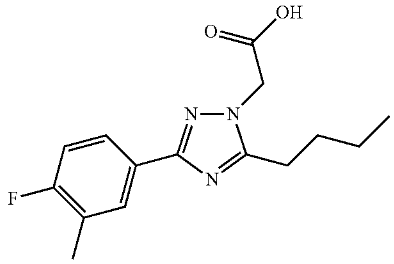 [SMILES: CCCCc1nc(-c2ccc(F)c(C)c2)nn1CC(=O)O] | 292 | method U | 1.24 |

-continued
| Examples | Product | MS m/z $[M + H]^+$ | HPLC Method | Rt min |
|---|---|---|---|---|
| 6.02.06.24 | 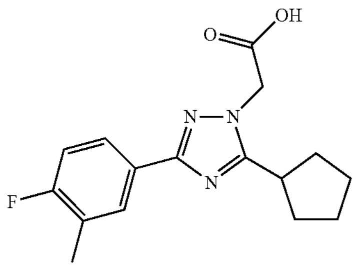 [SMILES: Cc1cc(-c2nc(C3CCCC3)n(CC(=O)O)n2)ccc1F] | 304 | method R | 1.29 |
| 6.02.06.25 | 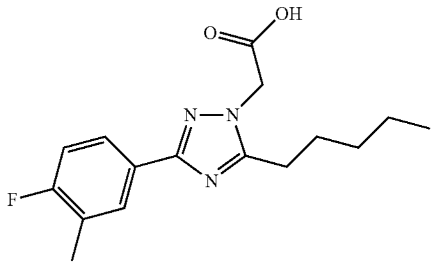 [SMILES: CCCCCc1nc(-c2ccc(F)c(C)c2)nn1CC(=O)O] | 306 | method L | 0.84 |
| 6.02.06.26 | 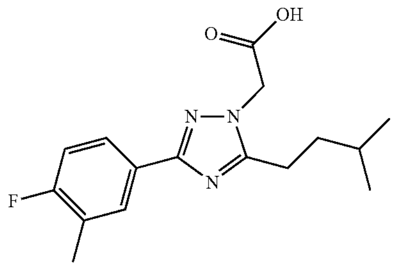 [SMILES: Cc1cc(-c2nc(CCC(C)C)n(CC(=O)O)n2)ccc1F] | 306 | method L | 0.88 |
| 6.02.06.27 | 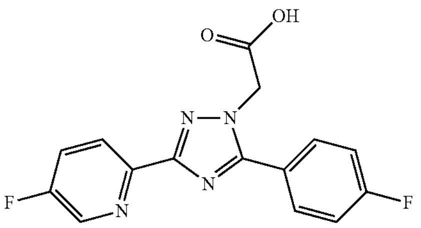 [SMILES: O=C(O)Cn1nc(-c2ccc(F)cn2)nc1-c1ccc(F)cc1] | 317 | method S | 0.65 |

-continued

| Examples | Product | MS m/z [M + H]+ | HPLC Method | Rt min |
|---|---|---|---|---|
| 6.02.06.28 | 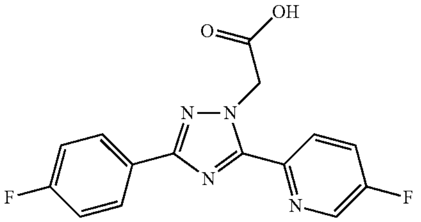 | 317 | method S | 0.79 |
| 6.02.06.29 | 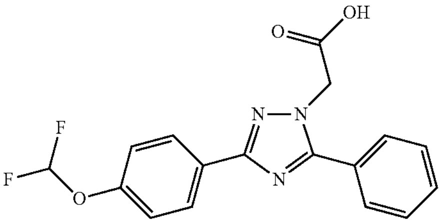 [SMILES: O=C(O)Cn1nc(-c2ccc(OC(F)F)cc2)nc1-c1ccccc1] | 346 | method L | 0.80 |
| 6.02.06.30 | 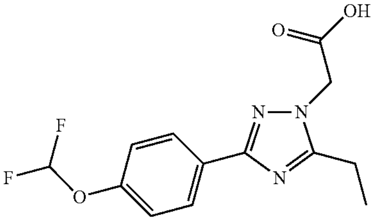 [SMILES: CCc1nc(-c2ccc(OC(F)F)cc2)nn1CC(=O)O] | 298 | method L | 0.72 |
| 6.02.06.31 | 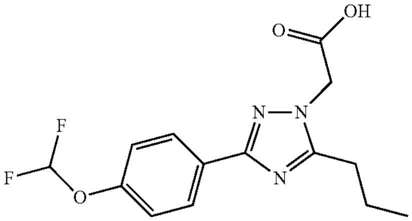 [SMILES: CCCc1nc(-c2ccc(OC(F)F)cc2)nn1CC(=O)O] | 312 | method L | 0.79 |

6.02.07.01 (3,5-bis-(4-Fluoro-phenyl)-(1,2,4)triazol-1-yl)-acetyl chloride

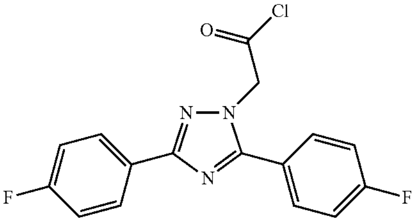 [SMILES: O=C(Cl)Cn1nc(-c2ccc(F)cc2)nc1-c1ccc(F)cc1]

1.2 g of ((3,5-bis-(4-fluoro-phenyl)-(1,2,4)triazol-1-yl)-acetic acid in 15 mL thionylchloride was stirred 30 min. at 60° C. The solvent was removed to give 1.3 g desired product. $(M+H)^+$: 334

By using the same synthesis strategy as for (3,5-bis-(4-fluoro-phenyl)-(1,2,4)triazol-1-yl)-acetyl chloride the following compounds was obtained:

| Examples | Product | MS m/z [M + H]+ |
|---|---|---|
| 6.02.07.02 | 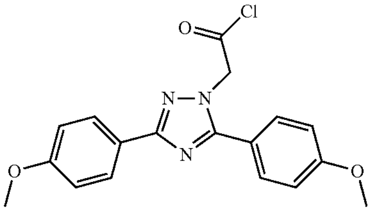 | 358 |

6.02.08 1-(2-Bromo-4,5,7,8-tetrahydro-thiazolo[4,5-d]azepin-6-yl)-2-(5-(4-fluoro-phenyl)-3-p-tolyl-(1,2,4)triazol-1-yl)-ethanone

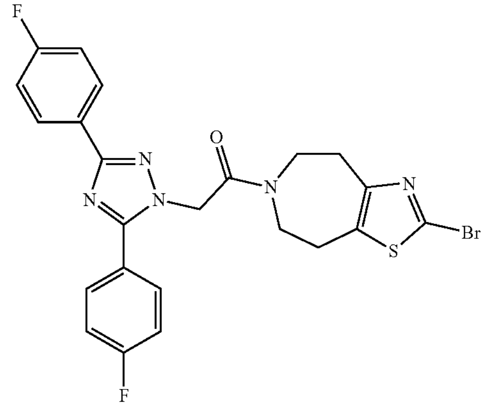 [SMILES: O=C(Cn1nc(-c2ccc(F)cc2)nc1-c1ccc(F)cc1)N1CCc2nc(Br)sc2CC1]

151 mg (3,5-bis-(4-fluoro-phenyl)-(1,2,4)triazol-1-yl)-acetic acid and 84 μL DIPEA were dissolved in 2.5 mL DMF. 154 mg TBTU was added to this solution and the mixture was stirred for 10 min. at RT. Then, 112 mg 2-bromo-5,6,7,8-tetrahydro-4H-thiazolo[4,5-d]azepine in 2.5 mL DMF was added. The mixture was stirred for 2 h at RT. The reaction-solution was purified by HPLC to yield 19.8 mg of the desired compound. $R_t$: 2.21 (method I), $(M+H)^+$: 530/32

6.02.09 2-(3,5-bis-(4-Fluoro-phenyl)-(1,2,4)triazol-1-yl)-1-piperazin-1-yl-ethanone

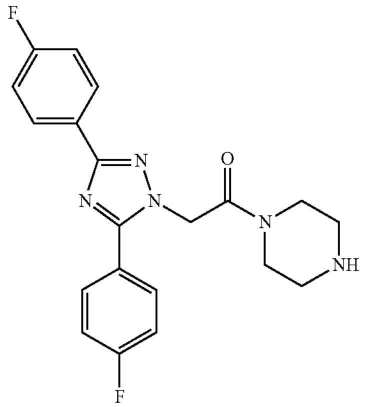 [SMILES: O=C(Cn1nc(-c2ccc(F)cc2)nc1-c1ccc(F)cc1)N1CCNCC1]

6.02.09.01 4-(2-(3,5-bis-(4-Fluoro-phenyl)-(1,2,4)triazol-1-yl)-acetyl)-piperazine-1-carboxylic acid tert-butyl ester

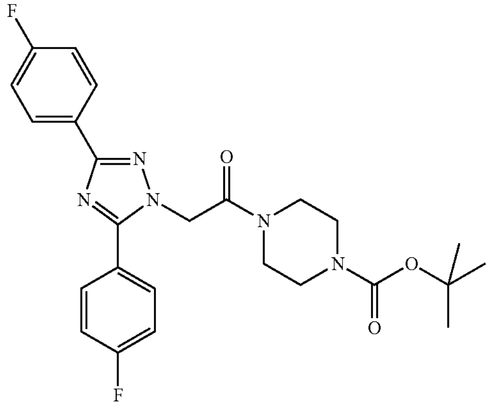 [SMILES: CC(C)(C)OC(=O)N1CCN(C(=O)Cn2nc(-c3ccc(F)cc3)nc2-c2ccc(F)cc2)CC1]

1.8 g piperazine-1-carboxylic acid tert-butyl ester was added to 3.2 g (3,5-bis-(4-fluoro-phenyl)-(1,2,4)triazol-1-yl)-acetyl chloride and 1 g triethylamine in 50 mL dichlormethane. The reaction was stirred for 1 day at RT, the solvent was evaporated and the residue was purified by chromatography on silica gel (petrolether/diethylether: 1/1) to yield 3.1 g of the desired compound. $R_t$: 1.42 min (method B), $(M+H)^+$: 484

6.02.09.02 2-(3,5-bis-(4-Fluoro-phenyl)-(1,2,4)triazol-1-yl)-1-piperazin-1-yl-ethanone

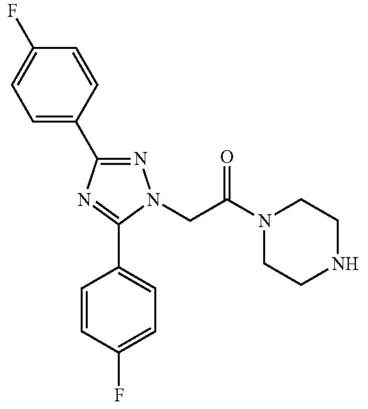 [SMILES: O=C(Cn1nc(-c2ccc(F)cc2)nc1-c1ccc(F)cc1)N1CCNCC1]

3.1 g 4-(2-(3,5-bis-(4-fluoro-phenyl)-(1,2,4)triazol-1-yl)-acetyl)-piperazine-1-carboxylic acid tert-butyl ester was dissolved in 20 mL dichlormethane and 20 mL trifluoracetic acid was added. The reaction was stirred for 24 h at RT and the solvent was evaporated. Potassium carbonate solution (10%) was added to the residue, the precipate was filtered and crystallized from a mixture of acetonitrile and isopropylether to yield 2.3 g of the desired compound. $(M+H)^+$: 384

7. Synthesis of Target Compounds 7.01.01. 4-(2-(3,5-bis-(4-Fluoro-phenyl)-(1,2,4)triazol-1-yl)-acetyl)-1-pyridin-2-yl-piperazin-2-one

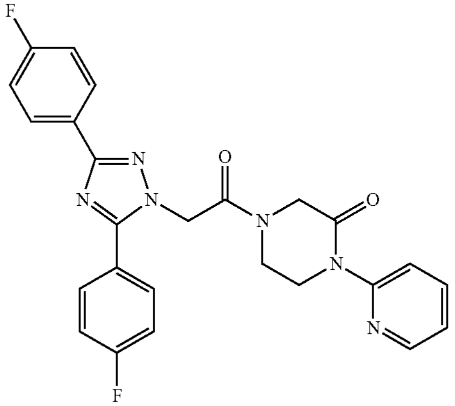 [SMILES: O=C(Cn1nc(-c2ccc(F)cc2)nc1-c1ccc(F)cc1)N1CCN(c2ccccn2)C(=O)C1]

160 mg 1-pyridin-2-yl-piperazin-2-one dihydrochloride was added to 216 mg (3,5-bis-(4-fluoro-phenyl)-(1,2,4)triazol-1-yl)-acetyl chloride and 300 μL triethylamine in 10 mL dichlormethane. The reaction was stirred for 1 day at RT, the solvent was evaporated and the residue was purified by HPLC to yield 93 mg of the desired product.

$R_t$: 1.27 (method B), $(M+H)^+$: 475

By using the same synthesis strategy as for 4-(2-(3,5-bis-(4-fluoro-phenyl)-(1,2,4)triazol-1-yl)-acetyl)-1-pyridin-2-yl-piperazin-2-one the following compounds were obtained:

| Examples | Product | MS m/z [M + H]+ | HPLC Method | Rt min |
|---|---|---|---|---|
| 7.01.02 | 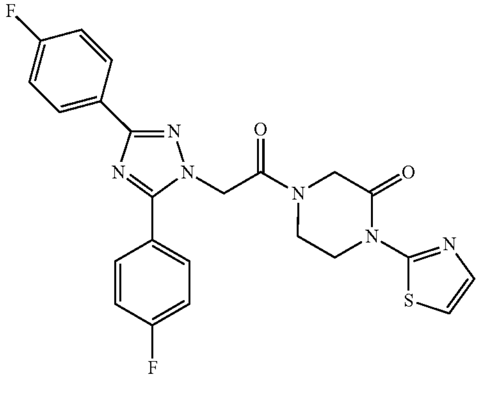 [SMILES: O=C(Cn1nc(-c2ccc(F)cc2)nc1-c1ccc(F)cc1)N1CCN(c2nccs2)C(=O)C1] | 481 | method B | 1.32 |
| 7.01.03 | 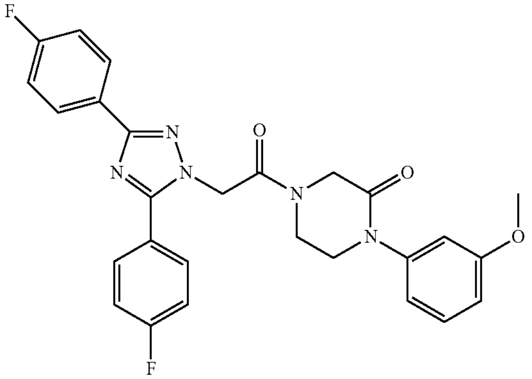 [SMILES: COc1cccc(N2CCN(C(=O)Cn3nc(-c4ccc(F)cc4)nc3-c3ccc(F)cc3)CC2=O)c1] | 504 | method B | 1.32 |

7.02.01. 1-(4-Benzo[d]isoxazol-3-yl-piperidin-1-yl)-2-(3,5-bis-(4-fluoro-phenyl)-(1,2,4)triazol-1-yl)-ethanone

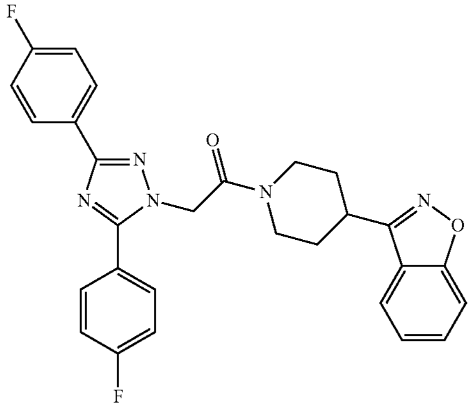 [SMILES: O=C(Cn1nc(-c2ccc(F)cc2)nc1-c1ccc(F)cc1)N1CCC(c2noc3ccccc23)CC1]

32 mg (3,5-bis-(4-fluoro-phenyl)-(1,2,4)triazol-1-yl)-acetic acid was dissolved in 2 mL DMF. 32 mg TBTU and 26 μL DIPEA were added to this solution and the mixture was stirred for 5 minutes at RT. Then, 24 mg 3-piperidin-4-yl-benzo[d]isoxazolehydrochloride was added. The mixture was stirred for 2 h at RT. The reaction solution was purified by HPLC to yield 19.8 mg of the desired compound. $R_t$: 2.24 (method D), $(M+H)^+$: 500

By using the same synthesis strategy as for 1-(4-benzo[d]isoxazol-3-yl-piperidin-1-yl)-2-(3,5-bis-(4-fluoro-phenyl)-(1,2,4)triazol-1-yl)-ethanone the following compounds were obtained:

| Examples | Product | MS m/z $[M + H]^+$ | HPLC Method | Rt min |
|---|---|---|---|---|
| 7.02.02 | 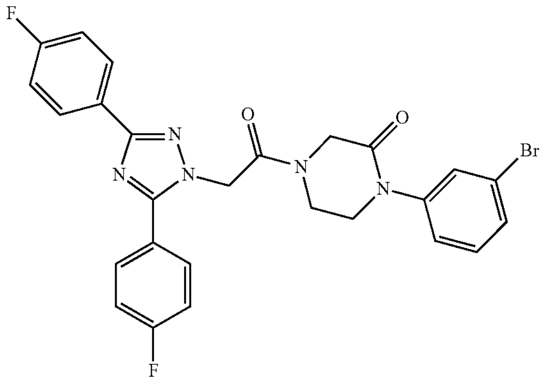 [SMILES: O=C(Cn1nc(-c2ccc(F)cc2)nc1-c1ccc(F)cc1)N1CCN(c2cccc(Br)c2)C(=O)C1] | 552/554 | method E | 1.54 |
| 7.02.03 | 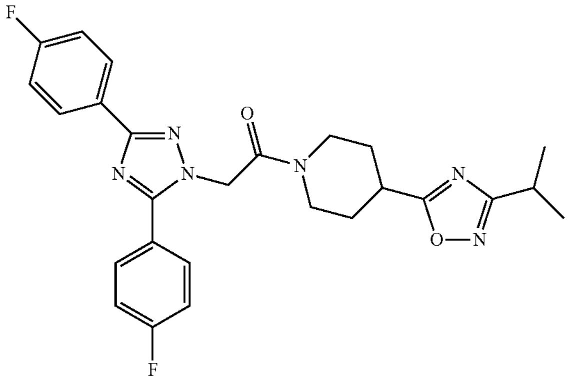 [SMILES: CC(C)c1noc(C2CCN(C(=O)Cn3nc(-c4ccc(F)cc4)nc3-c3ccc(F)cc3)CC2)n1] | 493 | method D | 2.39 |
| 7.02.04 | 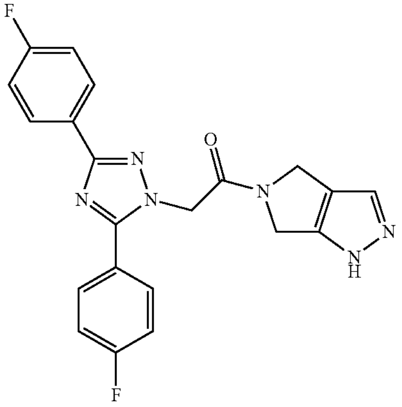 [SMILES: O=C(Cn1nc(-c2ccc(F)cc2)nc1-c1ccc(F)cc1)N1Cc2cn[nH]c2C1] | 407 | method D | 2.26 |
| 7.02.05 | 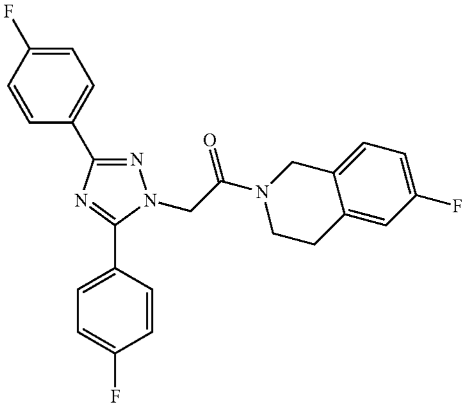 [SMILES: O=C(Cn1nc(-c2ccc(F)cc2)nc1-c1ccc(F)cc1)N1CCc2cc(F)ccc2C1] | 449 | method D | 2.39 |

-continued
| Examples | Product | MS m/z [M + H]+ | HPLC Method | Rt min |
|---|---|---|---|---|
| 7.02.06 | 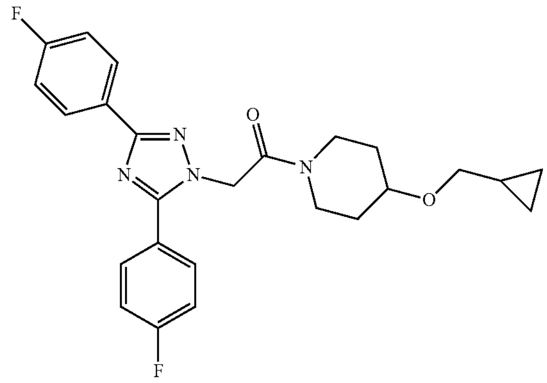 [SMILES: O=C(Cn1nc(-c2ccc(F)cc2)nc1-c1ccc(F)cc1)N1CCC(OCC2CC2)CC1] | 453 | method D | 2.37 |
| 7.02.07 | 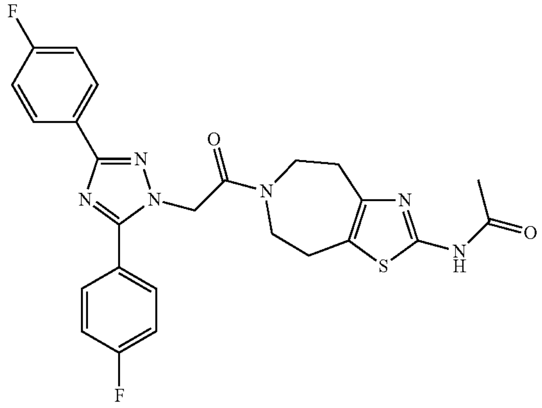 [SMILES: CC(=O)Nc1nc2c(s1)CCN(C(=O)Cn1nc(-c3ccc(F)cc3)nc1-c1ccc(F)cc1)CC2] | 509 | method D | 2.25 |
| 7.02.08 | 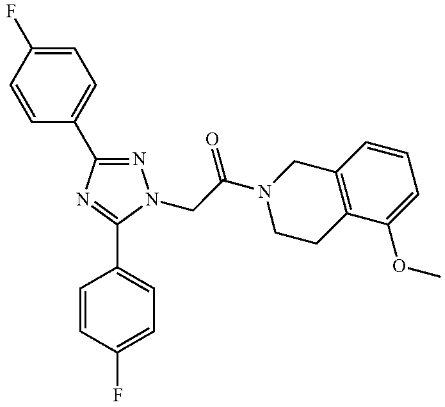 [SMILES: COc1cccc2c1CCN(C(=O)Cn1nc(-c3ccc(F)cc3)nc1-c1ccc(F)cc1)C2] | 461 | method D | 2.38 |

-continued
| Examples | Product | MS m/z [M + H]+ | HPLC Method | Rt min |
|---|---|---|---|---|
| 7.02.09 | 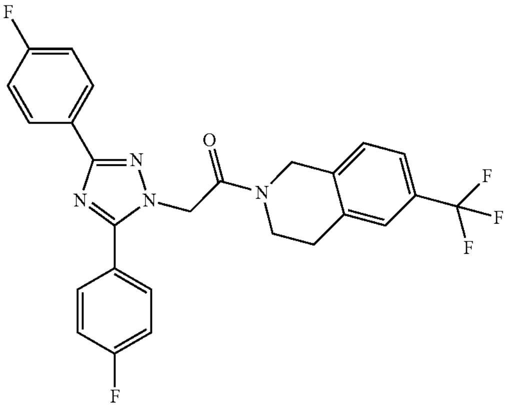 [SMILES: O=C(Cn1nc(-c2ccc(F)cc2)nc1-c1ccc(F)cc1)N1CCc2cc(C(F)(F)F)ccc2C1] | 499 | method D | 2.42 |
| 7.02.10 | 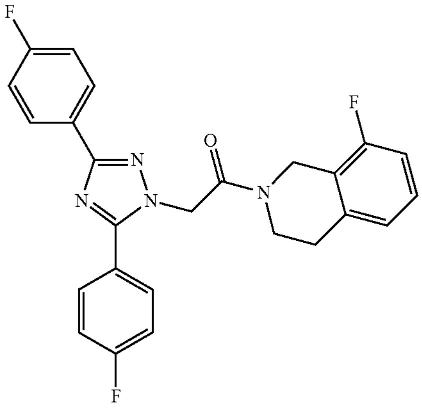 [SMILES: O=C(Cn1nc(-c2ccc(F)cc2)nc1-c1ccc(F)cc1)N1CCc2cccc(F)c2C1] | 449 | method D | 2.37 |
| 7.02.11 | 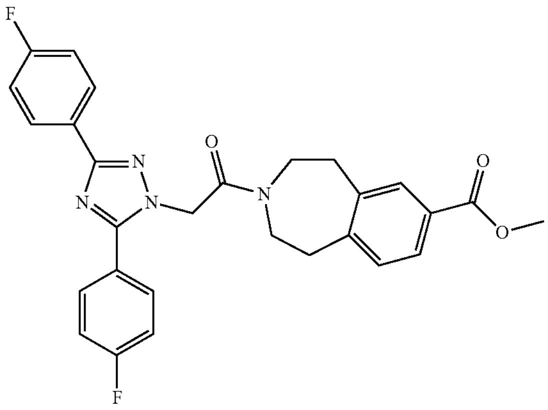 [SMILES: COC(=O)c1ccc2c(c1)CCN(C(=O)Cn1nc(-c3ccc(F)cc3)nc1-c1ccc(F)cc1)CC2] | 503 | method D | 2.34 |

-continued
| Examples | Product | MS m/z [M + H]+ | HPLC Method | Rt min |
|---|---|---|---|---|
| 7.02.12 | 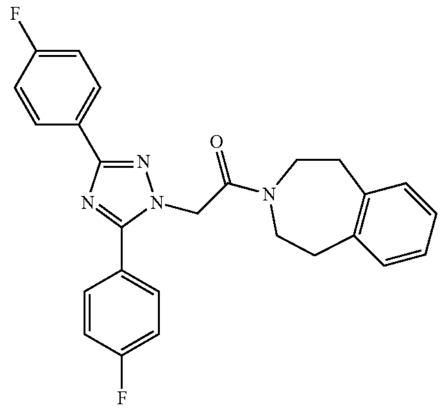 [SMILES: O=C(Cn1nc(-c2ccc(F)cc2)nc1-c1ccc(F)cc1)N1CCc2ccccc2CC1] | 445 | method D | 2.37 |
| 7.02.13 | 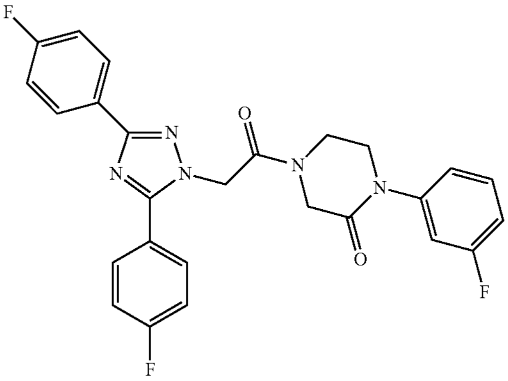 [SMILES: O=C(Cn1nc(-c2ccc(F)cc2)nc1-c1ccc(F)cc1)N1CCN(c2cccc(F)c2)C(=O)C1] | 492 | method D | 2.26 |
| 7.02.14 | 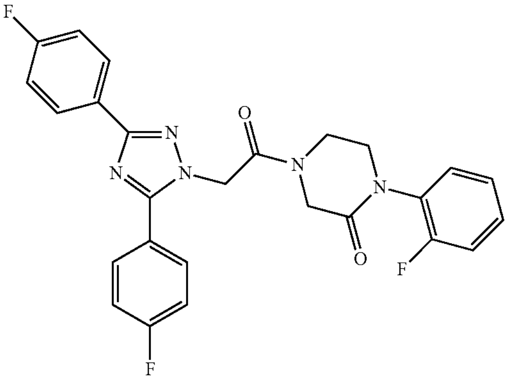 [SMILES: O=C(Cn1nc(-c2ccc(F)cc2)nc1-c1ccc(F)cc1)N1CCN(c2ccccc2F)C(=O)C1] | 492 | method D | 2.28 |
| 7.02.15 | 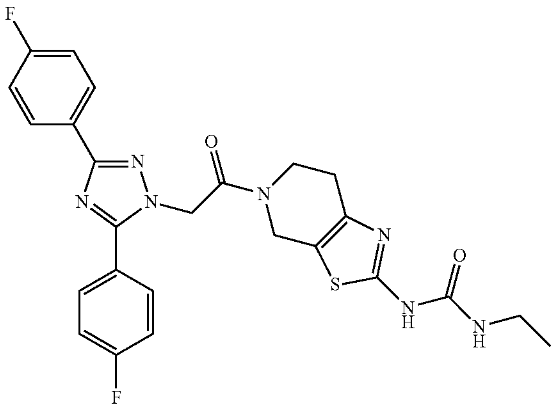 [SMILES: CCNC(=O)Nc1nc2c(s1)CN(C(=O)Cn1nc(-c3ccc(F)cc3)nc1-c1ccc(F)cc1)CC2] | 524 | method D | 2.29 |

-continued
| Examples | Product | MS m/z [M + H]+ | HPLC Method | Rt min |
|---|---|---|---|---|
| 7.02.16 | 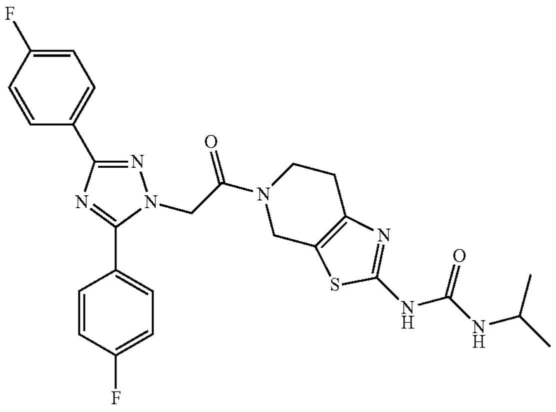 [SMILES: CC(C)NC(=O)Nc1nc2c(s1)CN(C(=O)Cn1nc(-c3ccc(F)cc3)nc1-c1ccc(F)cc1)CC2] | 538 | method D | 2.32 |
| 7.02.17 | 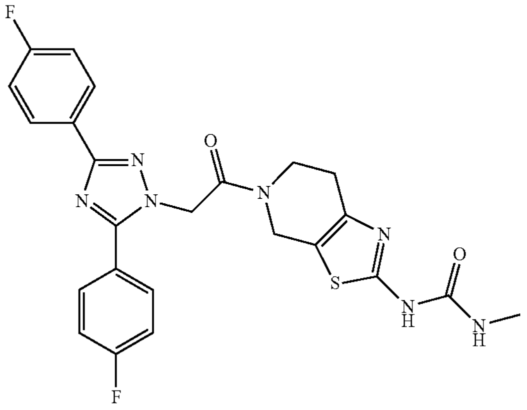 [SMILES: CNC(=O)Nc1nc2c(s1)CN(C(=O)Cn1nc(-c3ccc(F)cc3)nc1-c1ccc(F)cc1)CC2] | 510 | method D | 2.25 |
| 7.02.18 | 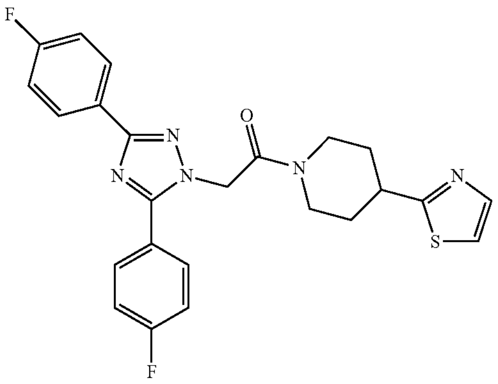 [SMILES: O=C(Cn1nc(-c2ccc(F)cc2)nc1-c1ccc(F)cc1)N1CCC(c2nccs2)CC1] | 466 | method D | 2.30 |

-continued
| Examples | Product | MS m/z [M + H]+ | HPLC Method | Rt min |
|---|---|---|---|---|
| 7.02.19 | 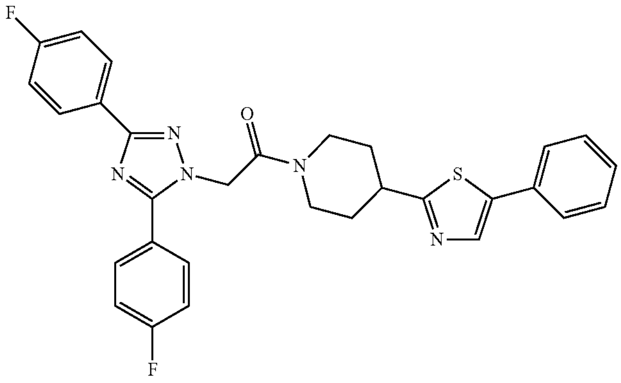 [SMILES: O=C(Cn1nc(-c2ccc(F)cc2)nc1-c1ccc(F)cc1)N1CCC(c2ncc(-c3ccccc3)s2)CC1] | 542 | method D | 2.42 |
| 7.02.20 | 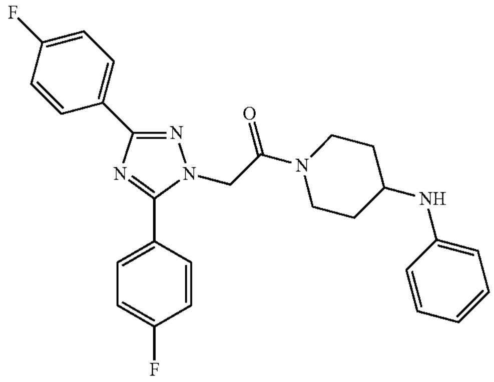 [SMILES: O=C(Cn1nc(-c2ccc(F)cc2)nc1-c1ccc(F)cc1)N1CCC(Nc2ccccc2)CC1] | 474 | method D | 2.10 |
| 7.02.21 | 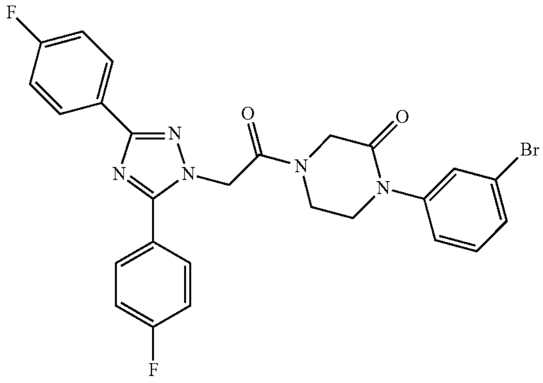 [SMILES: O=C(Cn1nc(-c2ccc(F)cc2)nc1-c1ccc(F)cc1)N1CCN(c2cccc(Br)c2)C(=O)C1] | 552 | method D | 2.35 |
| 7.02.22 | 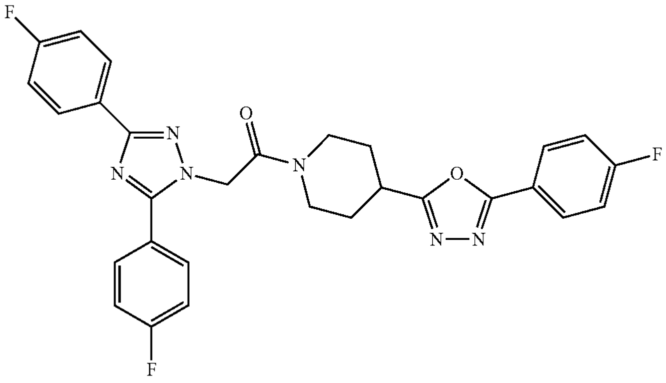 [SMILES: O=C(Cn1nc(-c2ccc(F)cc2)nc1-c1ccc(F)cc1)N1CCC(c2nnc(-c3ccc(F)cc3)o2)CC1] | 545 | method D | 2.35 |

-continued
| Examples | Product | MS m/z [M + H]$^+$ | HPLC Method | Rt min |
|---|---|---|---|---|
| 7.02.23 | 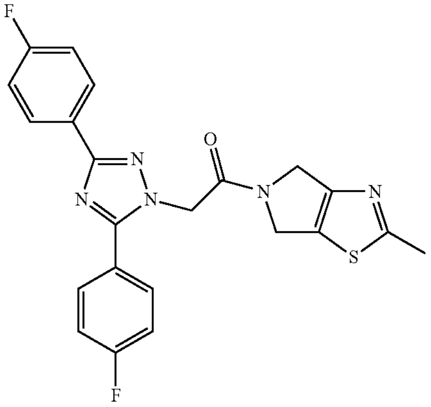 [SMILES: Cc1nc2c(s1)CN(C(=O)Cn1nc(-c3ccc(F)cc3)nc1-c1ccc(F)cc1)C2] | 438 | method D | 2.31 |
| 7.02.24 | 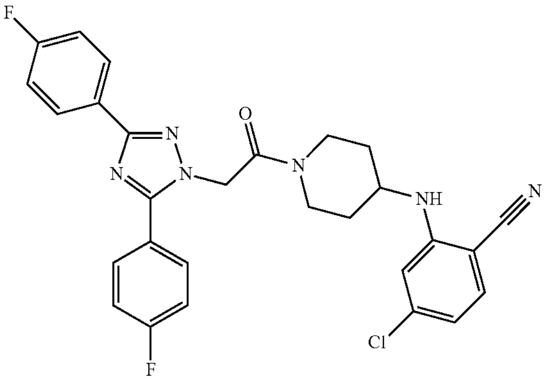 [SMILES: N#Cc1ccc(Cl)cc1NC1CCN(C(=O)Cn2nc(-c3ccc(F)cc3)nc2-c2ccc(F)cc2)CC1] | 533 | method D | 2.40 |
| 7.02.25 | 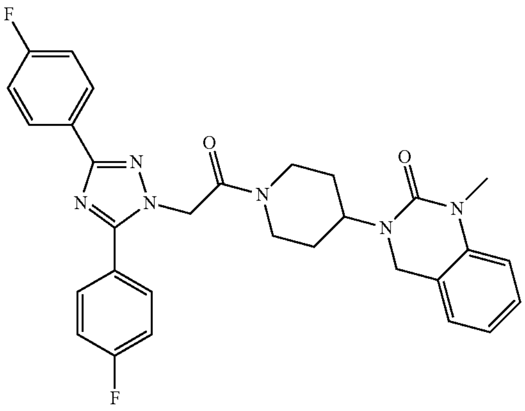 [SMILES: CN1C(=O)N(C2CCN(C(=O)Cn3nc(-c4ccc(F)cc4)nc3-c3ccc(F)cc3)CC2)Cc2ccccc21] | 543 | method D | 2.36 |

-continued
| Examples | Product | MS m/z $[M + H]^+$ | HPLC Method | Rt min |
|---|---|---|---|---|
| 7.02.26 | 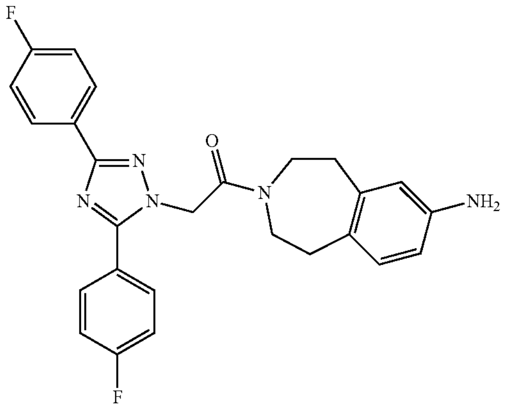 [SMILES: Nc1ccc2c(c1)CCN(C(=O)Cn1nc(-c3ccc(F)cc3)nc1-c1ccc(F)cc1)CC2] | 460 | method D | 1.96 |
| 7.02.27 | 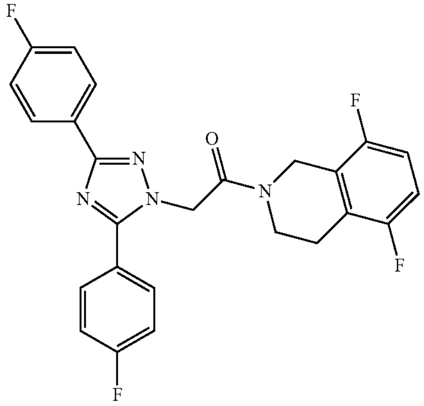 [SMILES: O=C(Cn1nc(-c2ccc(F)cc2)nc1-c1ccc(F)cc1)N1CCc2c(F)ccc(F)c2C1] | 467 | method D | 2.40 |
| 7.02.28 | 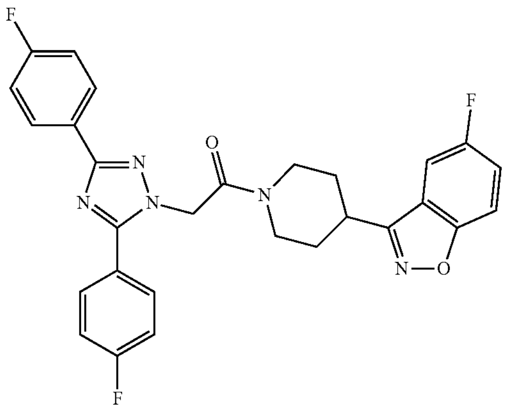 [SMILES: O=C(Cn1nc(-c2ccc(F)cc2)nc1-c1ccc(F)cc1)N1CCC(c2noc3ccc(F)cc23)CC1] | 518 | method D | 2.39 |

-continued
| Examples | Product | MS m/z [M + H]+ | HPLC Method | Rt min |
|---|---|---|---|---|
| 7.02.29 | 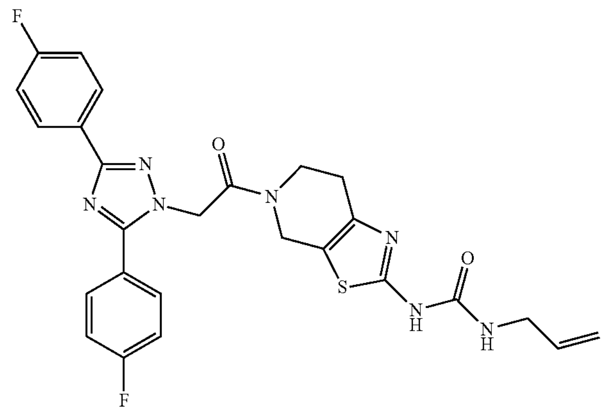 [SMILES: C=CCNC(=O)Nc1nc2c(s1)CN(C(=O)Cn1nc(-c3ccc(F)cc3)nc1-c1ccc(F)cc1)CC2] | 536 | method D | 2.29 |
| 7.02.30 | 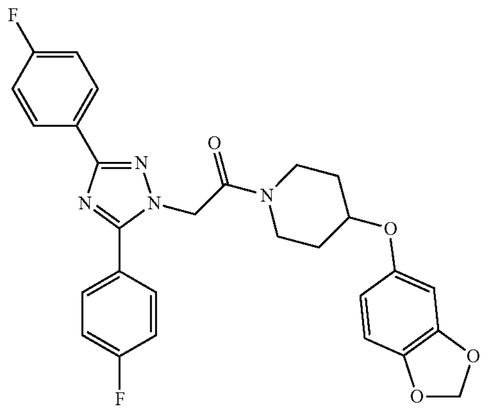 [SMILES: O=C(Cn1nc(-c2ccc(F)cc2)nc1-c1ccc(F)cc1)N1CCC(Oc2ccc3c(c2)OCO3)CC1] | 519 | method D | 2.38 |
| 7.02.31 | 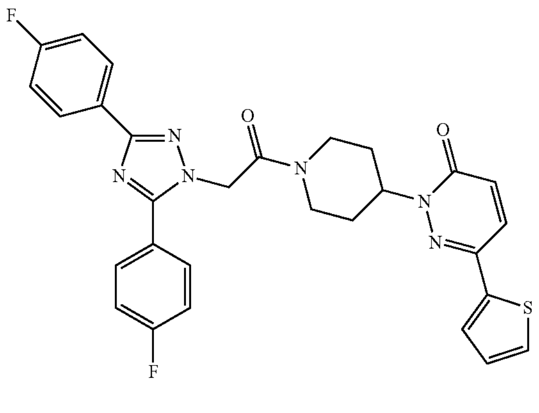 [SMILES: O=C(Cn1nc(-c2ccc(F)cc2)nc1-c1ccc(F)cc1)N1CCC(n2nc(-c3cccs3)ccc2=O)CC1] | 559 | method D | 2.33 |

-continued
| Examples | Product | MS m/z $[M + H]^+$ | HPLC Method | Rt min |
|---|---|---|---|---|
| 7.02.32 | 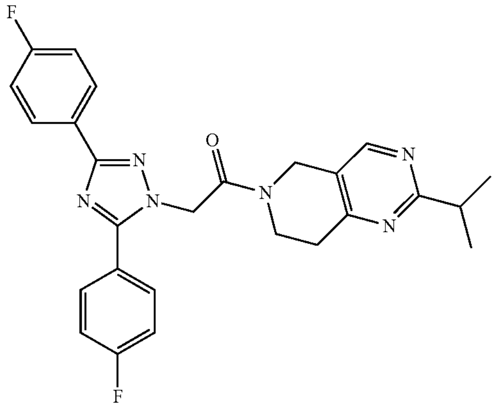 [SMILES: CC(C)c1ncc2c(n1)CCN(C(=O)Cn1nc(-c3ccc(F)cc3)nc1-c1ccc(F)cc1)C2] | 475 | method D | 2.31 |
| 7.02.33 | 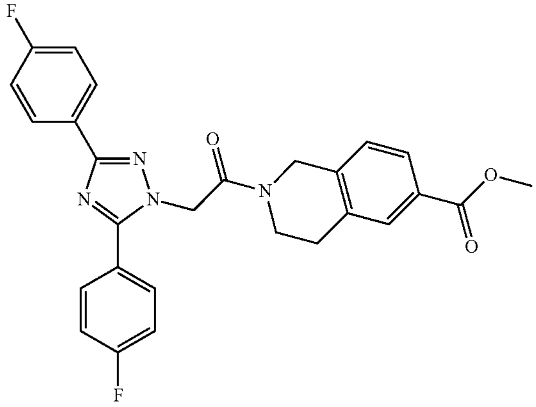 [SMILES: COC(=O)c1ccc2c(c1)CCN(C(=O)Cn1nc(-c3ccc(F)cc3)nc1-c1ccc(F)cc1)C2] | 489 | method D | 2.39 |
| 7.02.34 | 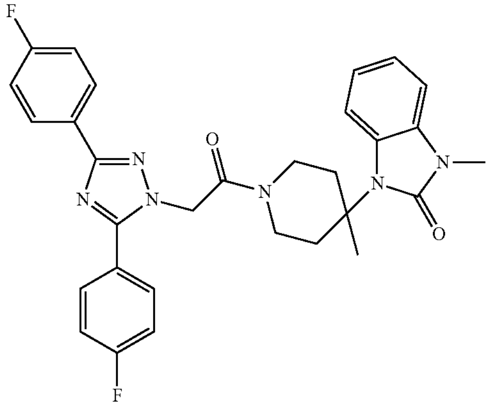 [SMILES: Cn1c(=O)n(C2(C)CCN(C(=O)Cn3nc(-c4ccc(F)cc4)nc3-c3ccc(F)cc3)CC2)c2ccccc21] | 543 | method D | 2.39 |

-continued
| Examples | Product | MS m/z [M + H]+ | HPLC Method | Rt min |
| --- | --- | --- | --- | --- |
| 7.02.35 | 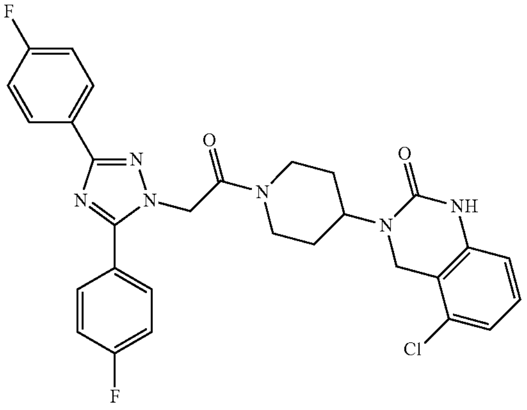 [SMILES: O=C(Cn1nc(-c2ccc(F)cc2)nc1-c1ccc(F)cc1)N1CCC(N2Cc3c(Cl)cccc3NC2=O)CC1] | 564 | method D | 2.39 |
| 7.02.36 | 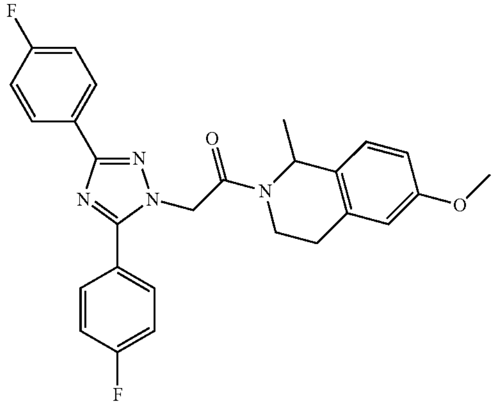 [SMILES: COc1ccc2c(c1)CCN(C(=O)Cn1nc(-c3ccc(F)cc3)nc1-c1ccc(F)cc1)C2C] | 475 | method D | 2.37 |
| 7.02.37 | 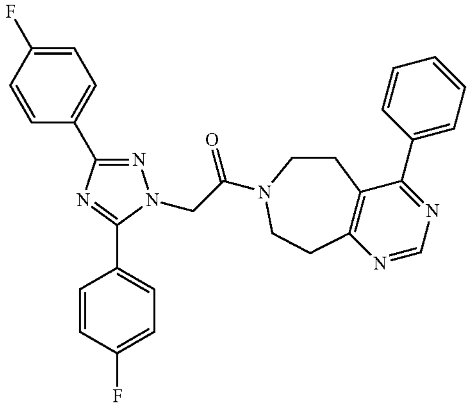 [SMILES: O=C(Cn1nc(-c2ccc(F)cc2)nc1-c1ccc(F)cc1)N1CCc2ncnc(-c3ccccc3)c2CC1] | 523 | method D | 2.34 |

-continued
| Examples | Product | MS m/z [M + H]$^+$ | HPLC Method | Rt min |
|---|---|---|---|---|
| 7.02.38 | 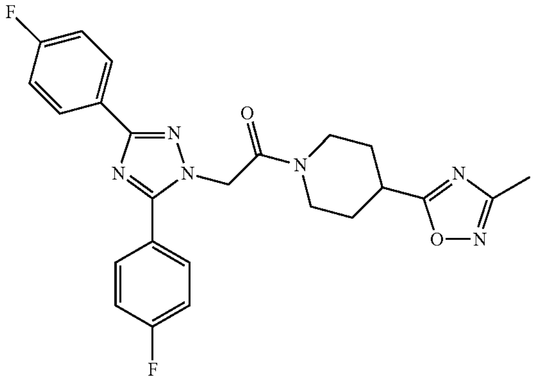 [SMILES: Cc1noc(C2CCN(C(=O)Cn3nc(-c4ccc(F)cc4)nc3-c3ccc(F)cc3)CC2)n1] | 465 | method D | 2.29 |
| 7.02.39 | 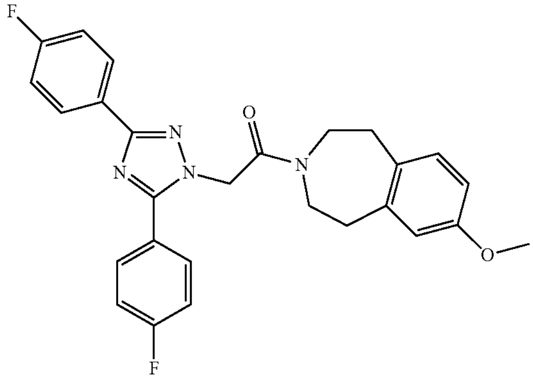 [SMILES: COc1ccc2c(c1)CCN(C(=O)Cn1nc(-c3ccc(F)cc3)nc1-c1ccc(F)cc1)CC2] | 475 | method D | 2.28 |
| 7.02.40 | 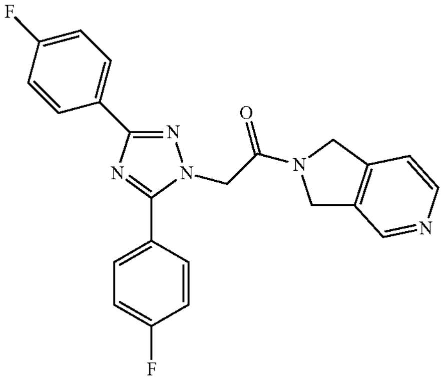 [SMILES: O=C(Cn1nc(-c2ccc(F)cc2)nc1-c1ccc(F)cc1)N1Cc2ccncc2C1] | 418 | method D | 1.93 |
| 7.02.41 | 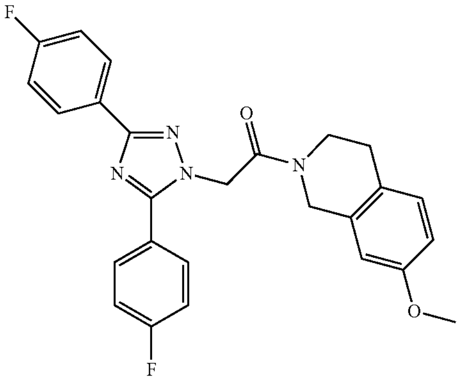 [SMILES: COc1ccc2c(c1)CN(C(=O)Cn1nc(-c3ccc(F)cc3)nc1-c1ccc(F)cc1)CC2] | 461 | method D | 2.25 |

-continued
| Examples | Product | MS m/z [M + H]+ | HPLC Method | Rt min |
|---|---|---|---|---|
| 7.02.42 | 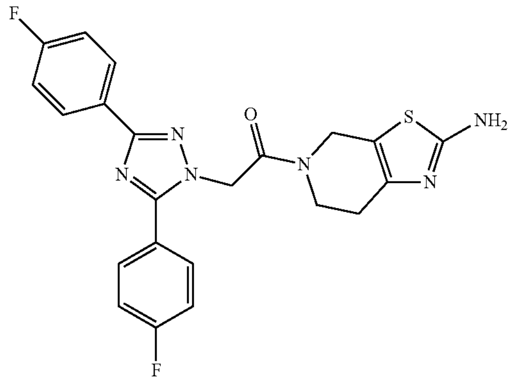 [SMILES: Nc1nc2c(s1)CN(C(=O)Cn1nc(-c3ccc(F)cc3)nc1-c1ccc(F)cc1)CC2] | 453 | method D | 1.90 |
| 7.02.43 | 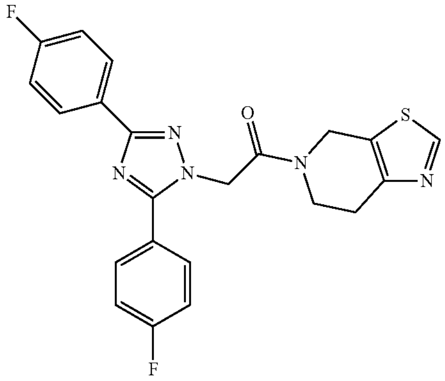 [SMILES: O=C(Cn1nc(-c2ccc(F)cc2)nc1-c1ccc(F)cc1)N1CCc2ncsc2C1] | 438 | method D | 2.17 |
| 7.02.44 | 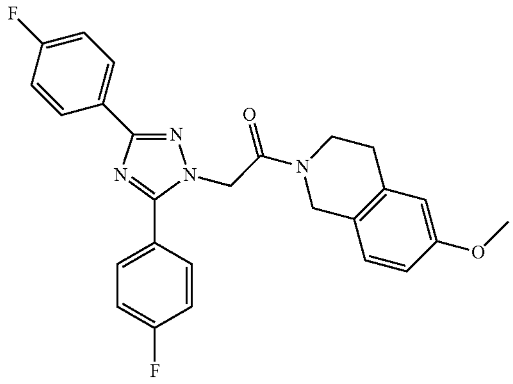 [SMILES: COc1ccc2c(c1)CCN(C(=O)Cn1nc(-c3ccc(F)cc3)nc1-c1ccc(F)cc1)C2] | 461 | method D | 2.26 |
| 7.02.45 | 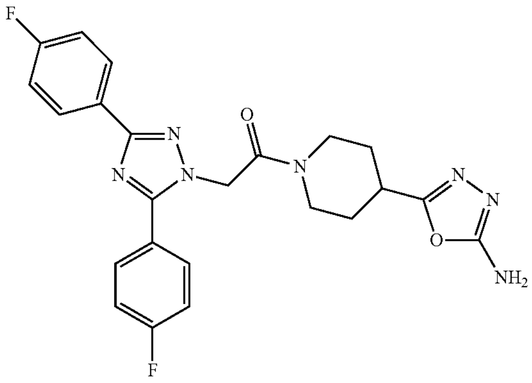 [SMILES: Nc1nnc(C2CCN(C(=O)Cn3nc(-c4ccc(F)cc4)nc3-c3ccc(F)cc3)CC2)o1] | 466 | method D | 2.06 |

-continued
| Examples | Product | MS m/z [M + H]+ | HPLC Method | Rt min |
|---|---|---|---|---|
| 7.02.46 | 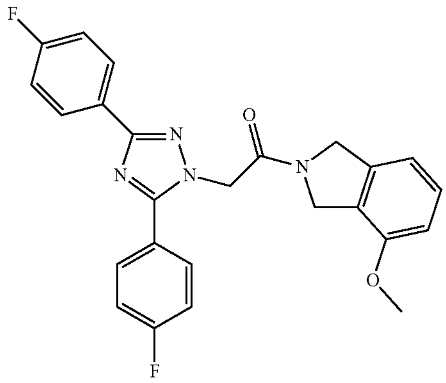 [SMILES: COc1cccc2c1CN(C(=O)Cn1nc(-c3ccc(F)cc3)nc1-c1ccc(F)cc1)C2] | 447 | method D | 2.27 |
| 7.02.47 | 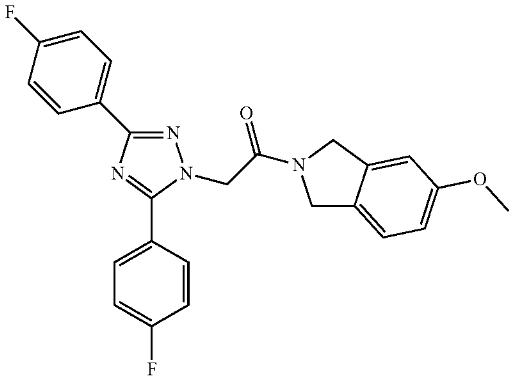 [SMILES: COc1ccc2c(c1)CN(C(=O)Cn1nc(-c3ccc(F)cc3)nc1-c1ccc(F)cc1)C2] | 447 | method D | 2.27 |
| 7.02.48 | 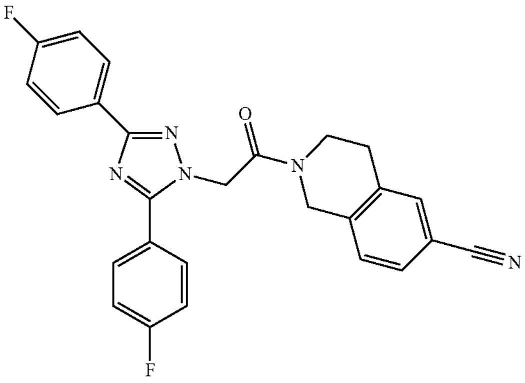 [SMILES: N#Cc1ccc2c(c1)CCN(C(=O)Cn1nc(-c3ccc(F)cc3)nc1-c1ccc(F)cc1)C2] | 456 | method D | 2.18 |
| 7.02.49 | 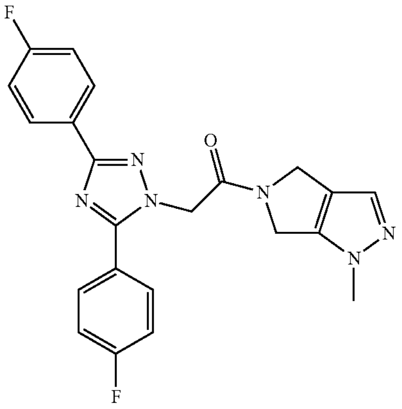 [SMILES: Cn1ncc2c1CN(C(=O)Cn1nc(-c3ccc(F)cc3)nc1-c1ccc(F)cc1)C2] | 421 | method D | 2.22 |

-continued
| Examples | Product | MS m/z $[M + H]^+$ | HPLC Method | Rt min |
|---|---|---|---|---|
| 7.02.50 | 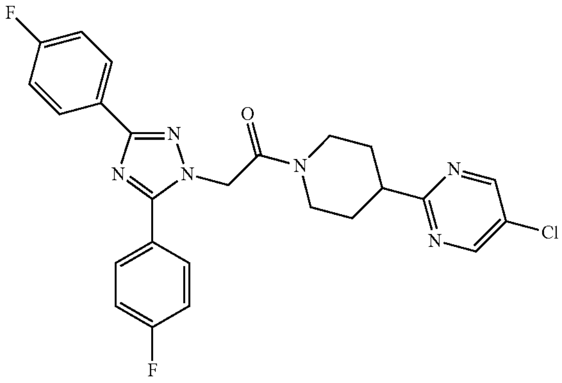 [SMILES: O=C(Cn1nc(-c2ccc(F)cc2)nc1-c1ccc(F)cc1)N1CCC(c2ncc(Cl)cn2)CC1] | 495 | method D | 2.33 |
| 7.02.51 | 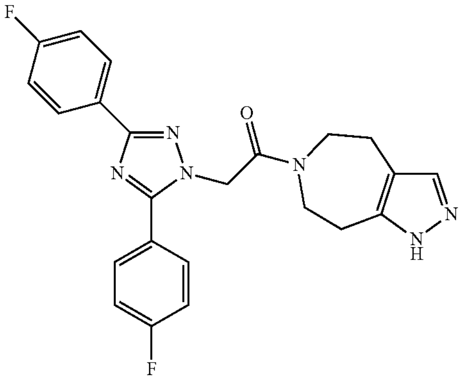 [SMILES: O=C(Cn1nc(-c2ccc(F)cc2)nc1-c1ccc(F)cc1)N1CCc2cn[nH]c2CC1] | 435 | method D | 2.15 |
| 7.02.52 | 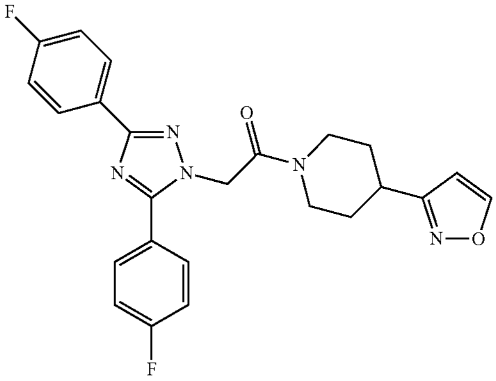 [SMILES: O=C(Cn1nc(-c2ccc(F)cc2)nc1-c1ccc(F)cc1)N1CCC(c2ccon2)CC1] | 450 | method G | 2.43 |
| 7.02.53 | 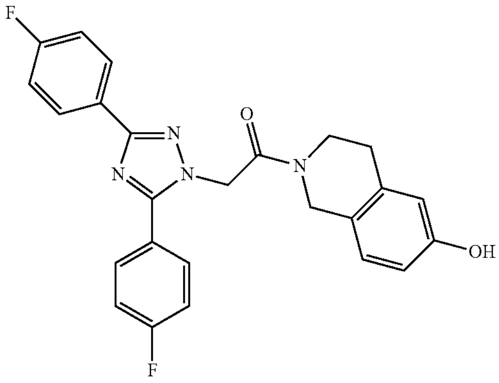 [SMILES: O=C(Cn1nc(-c2ccc(F)cc2)nc1-c1ccc(F)cc1)N1CCc2cc(O)ccc2C1] | 447 | method G | 2.41 |

-continued
| Examples | Product | MS m/z [M + H]$^+$ | HPLC Method | Rt min |
|---|---|---|---|---|
| 7.02.54 | 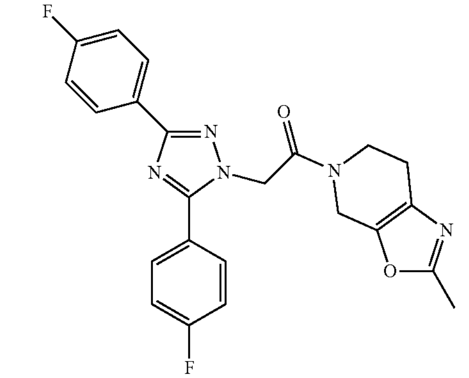 [SMILES: Cc1nc2c(o1)CN(C(=O)Cn1nc(-c3ccc(F)cc3)nc1-c1ccc(F)cc1)CC2] | 436 | method G | 2.45 |
| 7.02.55 | 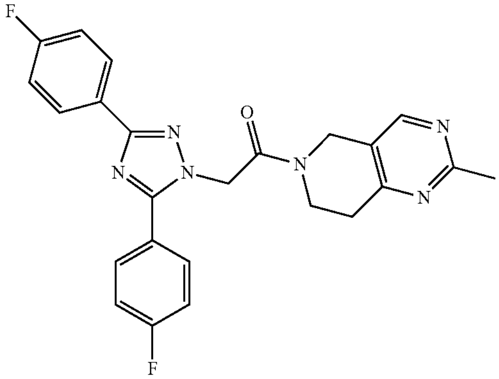 [SMILES: Cc1ncc2c(n1)CCN(C(=O)Cn1nc(-c3ccc(F)cc3)nc1-c1ccc(F)cc1)C2] | 447 | method D | 2.14 |
| 7.02.56 | 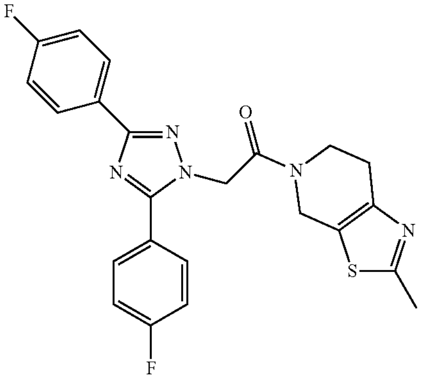 | 452 | method D | 2.18 |
| 7.02.57 | 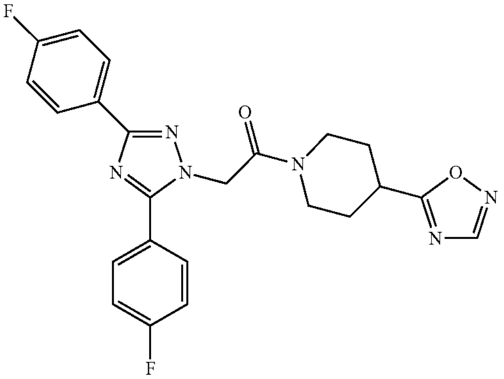 [SMILES: O=C(Cn1nc(-c2ccc(F)cc2)nc1-c1ccc(F)cc1)N1CCC(c2ncno2)CC1] | 451 | method H | 1.92 |

-continued
| Examples | Product | MS m/z [M + H]+ | HPLC Method | Rt min |
|---|---|---|---|---|
| 7.02.58 | 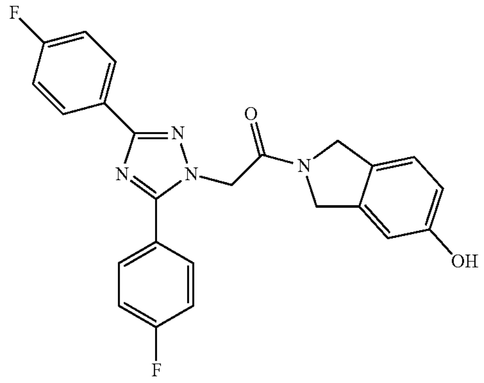 [SMILES: O=C(Cn1nc(-c2ccc(F)cc2)nc1-c1ccc(F)cc1)N1Cc2ccc(O)cc2C1] | 433 | method I | 2.10 |
| 7.02.59 | 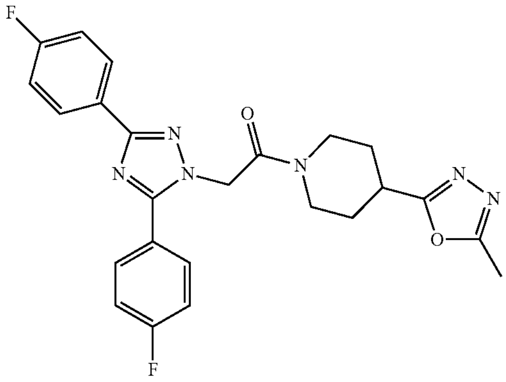 [SMILES: Cc1nnc(C2CCN(C(=O)Cn3nc(-c4ccc(F)cc4)nc3-c3ccc(F)cc3)CC2)o1] | 465 | method I | 2.00 |
| 7.02.60 | 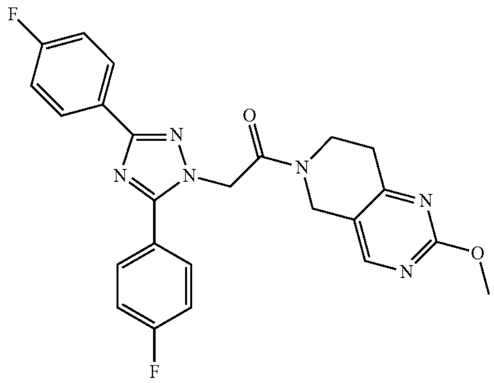 [SMILES: COc1ncc2c(n1)CCN(C(=O)Cn1nc(-c3ccc(F)cc3)nc1-c1ccc(F)cc1)C2] | 463 | method D | 2.08 |
| 7.02.61 | 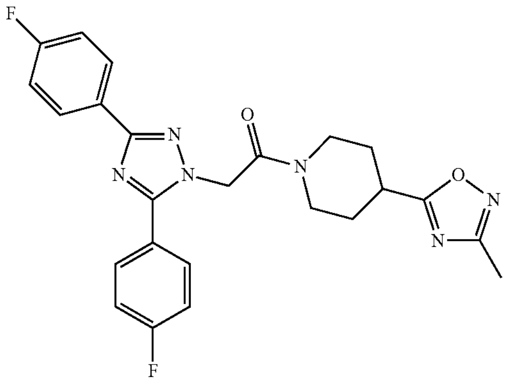 [SMILES: Cc1noc(C2CCN(C(=O)Cn3nc(-c4ccc(F)cc4)nc3-c3ccc(F)cc3)CC2)n1] | 465 | method I | 2.00 |

-continued
| Examples | Product | MS m/z [M + H]+ | HPLC Method | Rt min |
|---|---|---|---|---|
| 7.02.62 | 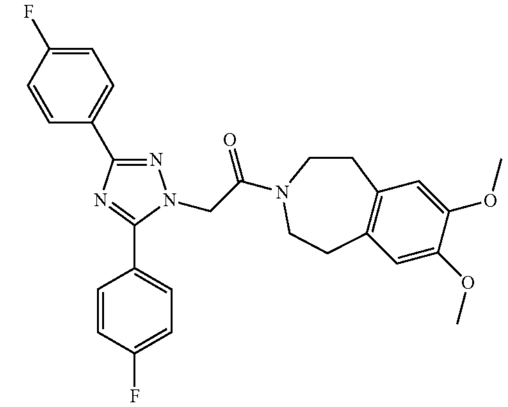 [SMILES: COc1cc2c(cc1OC)CCN(C(=O)Cn1nc(-c3ccc(F)cc3)nc1-c1ccc(F)cc1)CC2] | 505 | method J | 2.22 |
| 7.02.63 | 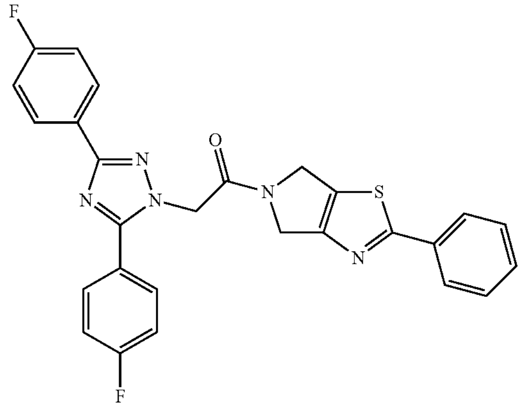 [SMILES: O=C(Cn1nc(-c2ccc(F)cc2)nc1-c1ccc(F)cc1)N1Cc2nc(-c3ccccc3)sc2C1] | 499 | method J | 2.38 |
| 7.02.64 | 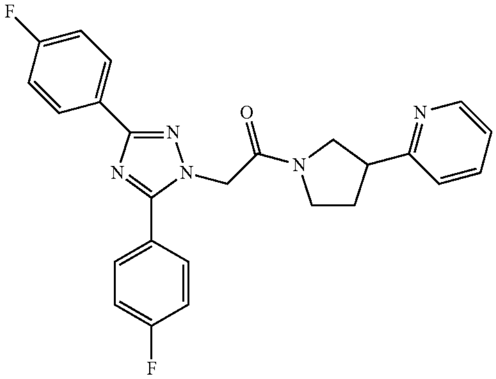 [SMILES: O=C(Cn1nc(-c2ccc(F)cc2)nc1-c1ccc(F)cc1)N1CCC(c2ccccn2)C1] | 445 | method J | 1.66 |

-continued
| Examples | Product | MS m/z [M + H]+ | HPLC Method | Rt min |
|---|---|---|---|---|
| 7.02.65 | 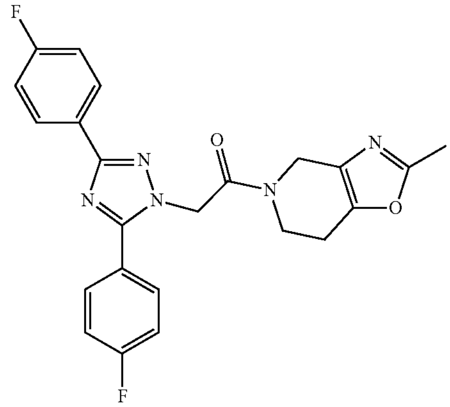 [SMILES: Cc1nc2c(o1)CCN(C(=O)Cn1nc(-c3ccc(F)cc3)nc1-c1ccc(F)cc1)C2] | 436 | method O | 1.76 |
| 7.02.66 | 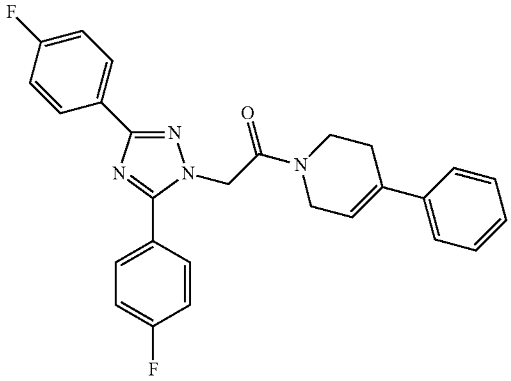 [SMILES: O=C(Cn1nc(-c2ccc(F)cc2)nc1-c1ccc(F)cc1)N1CC=C(c2ccccc2)CC1] | 457 | method O | 1.99 |
| 7.02.67 | 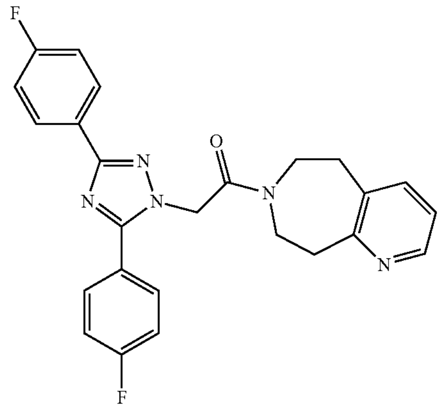 [SMILES: O=C(Cn1nc(-c2ccc(F)cc2)nc1-c1ccc(F)cc1)N1CCc2cccnc2CC1] | 446 | method O | 1.75 |
| 7.02.68 | 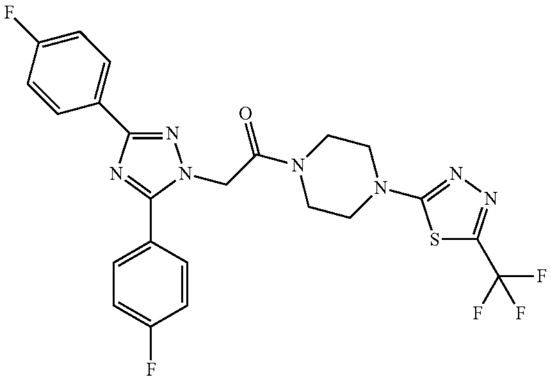 [SMILES: O=C(Cn1nc(-c2ccc(F)cc2)nc1-c1ccc(F)cc1)N1CCN(c2nnc(C(F)(F)F)s2)CC1] | 536 | method D | 2.30 |

-continued
| Examples | Product | MS m/z [M + H]+ | HPLC Method | Rt min |
|---|---|---|---|---|
| 7.02.69 | 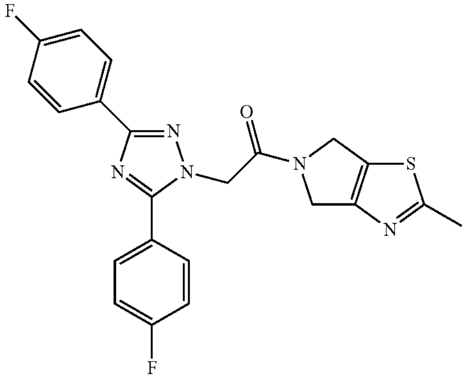 [SMILES: Cc1nc2c(s1)CN(C(=O)Cn1nc(-c3ccc(F)cc3)nc1-c1ccc(F)cc1)C2] | 437 | method D | 2.22 |
| 7.02.70 | 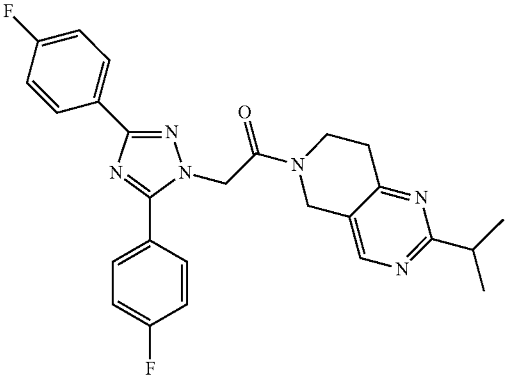 [SMILES: CC(C)c1ncc2c(n1)CCN(C(=O)Cn1nc(-c3ccc(F)cc3)nc1-c1ccc(F)cc1)C2] | 475 | method D | 2.18 |
| 7.02.71 | 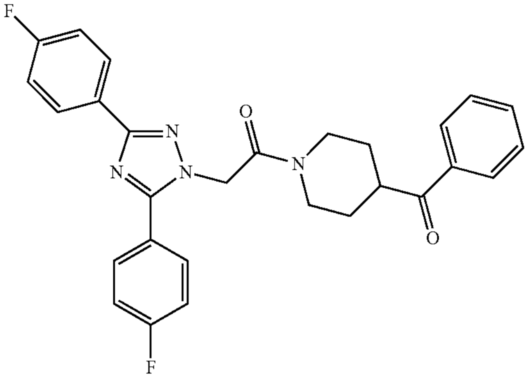 [SMILES: O=C(c1ccccc1)C1CCN(C(=O)Cn2nc(-c3ccc(F)cc3)nc2-c2ccc(F)cc2)CC1] | 487 | method D | 2.25 |
| 7.02.72 | 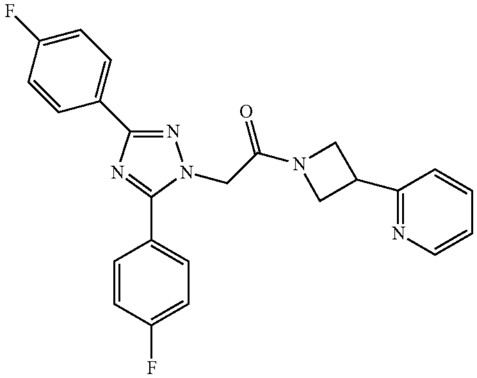 [SMILES: O=C(Cn1nc(-c2ccc(F)cc2)nc1-c1ccc(F)cc1)N1CC(c2ccccn2)C1] | 432 | method J | 1.66 |

-continued
| Examples | Product | MS m/z [M + H]+ | HPLC Method | Rt min |
|---|---|---|---|---|
| 7.02.73 | 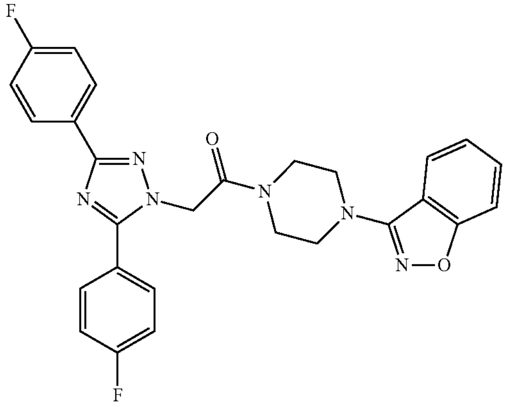 [SMILES: O=C(Cn1nc(-c2ccc(F)cc2)nc1-c1ccc(F)cc1)N1CCN(c2noc3ccccc23)CC1] | 501 | method D | 2.30 |
| 7.02.74 | 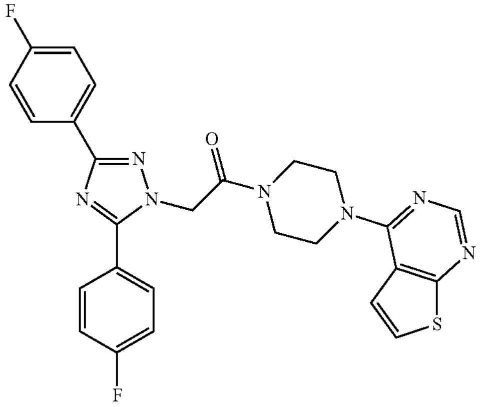 [SMILES: O=C(Cn1nc(-c2ccc(F)cc2)nc1-c1ccc(F)cc1)N1CCN(c2ncnc3sccc23)CC1] | 518 | method O | 1.83 |
| 7.02.75 | 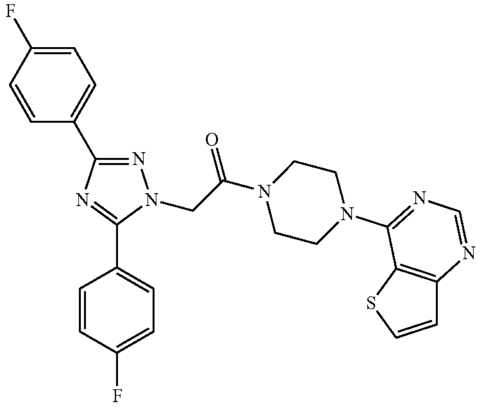 [SMILES: O=C(Cn1nc(-c2ccc(F)cc2)nc1-c1ccc(F)cc1)N1CCN(c2ncnc3ccsc23)CC1] | 518 | method O | 1.83 |

-continued
| Examples | Product | MS m/z [M + H]+ | HPLC Method | Rt min |
|---|---|---|---|---|
| 7.02.76 | 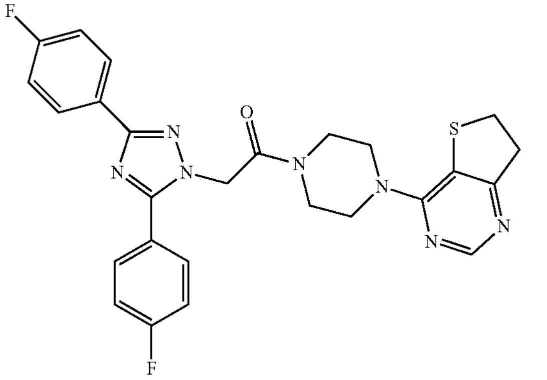 [SMILES: O=C(Cn1nc(-c2ccc(F)cc2)nc1-c1ccc(F)cc1)N1CCN(c2ncnc3c2SCC3)CC1] | 520 | method Z | 2.54 |
| 7.02.77 | 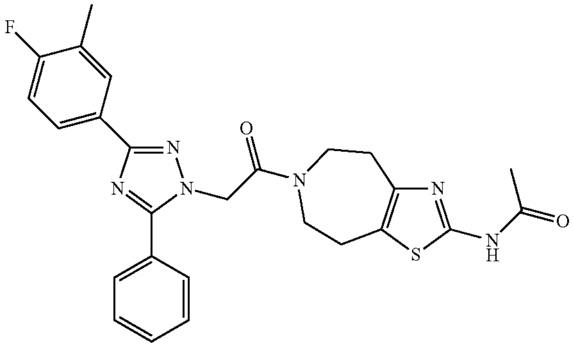 [SMILES: CC(=O)Nc1nc2c(s1)CCN(C(=O)Cn1nc(-c3ccc(F)c(C)c3)nc1-c1ccccc1)CC2] | 505 | method T | 0.69 |
| 7.02.78 | 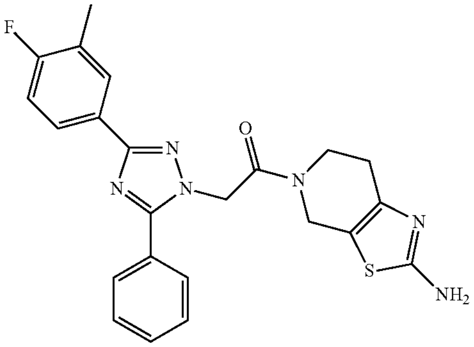 [SMILES: Cc1cc(-c2nc(-c3ccccc3)n(CC(=O)N3CCc4nc(N)sc4C3)n2)ccc1F] | 449 | method T | 0.68 |
| 7.02.79 | 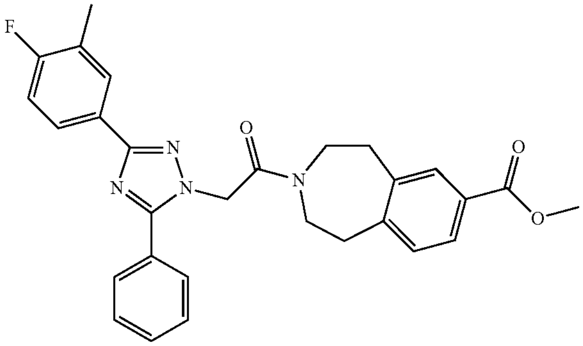 [SMILES: COC(=O)c1ccc2c(c1)CCN(C(=O)Cn1nc(-c3ccc(F)c(C)c3)nc1-c1ccccc1)CC2] | 499 | method T | 0.71 |

-continued
| Examples | Product | MS m/z [M + H]+ | HPLC Method | Rt min |
|---|---|---|---|---|
| 7.02.80 | 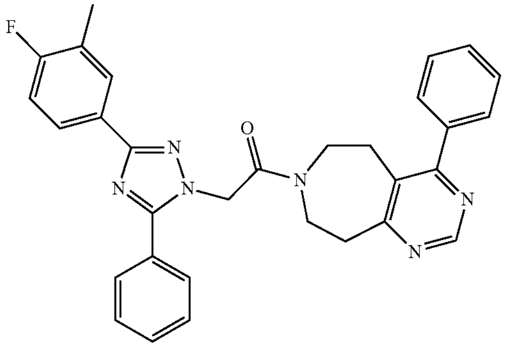 [SMILES: Cc1cc(-c2nc(-c3ccccc3)n(CC(=O)N3CCc4ncnc(-c5ccccc5)c4CC3)n2)ccc1F] | 519 | method T | 0.70 |
| 7.02.81 | 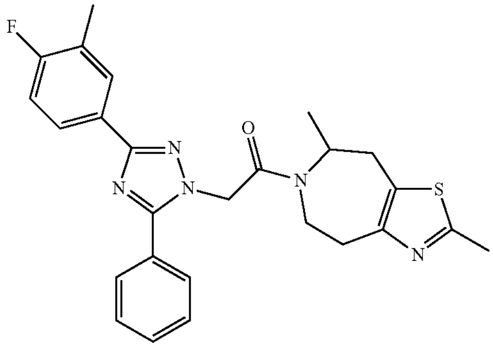 [SMILES: Cc1nc2c(s1)CC(C)N(C(=O)Cn1nc(-c3ccc(F)c(C)c3)nc1-c1ccccc1)CC2] | 476 | method T | 0.74 |
| 7.02.82 | 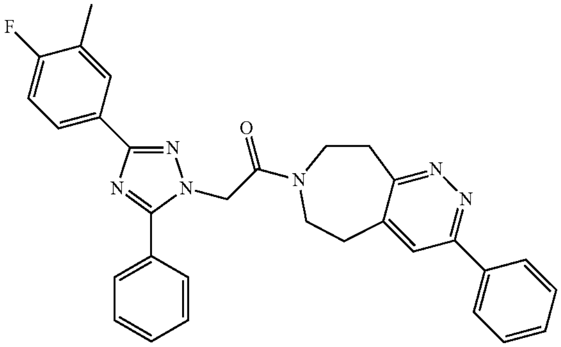 [SMILES: Cc1cc(-c2nc(-c3ccccc3)n(CC(=O)N3CCc4cc(-c5ccccc5)nnc4CC3)n2)ccc1F] | 519 | method T | 0.70 |
| 7.02.83 | 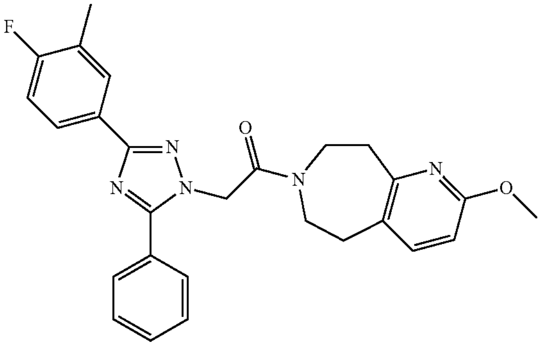 [SMILES: COc1ccc2c(n1)CCN(C(=O)Cn1nc(-c3ccc(F)c(C)c3)nc1-c1ccccc1)CC2] | 472 | method T | 0.70 |

-continued
| Examples | Product | MS m/z [M + H]+ | HPLC Method | Rt min |
|---|---|---|---|---|
| 7.02.84 | 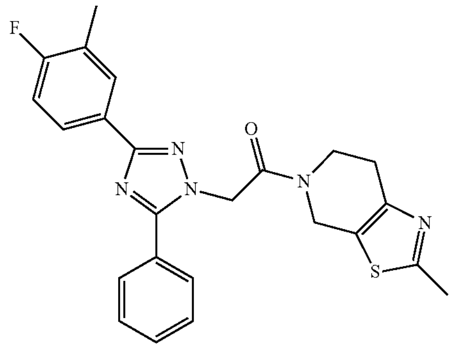 [SMILES: Cc1nc2c(s1)CN(C(=O)Cn1nc(-c3ccc(F)c(C)c3)nc1-c1ccccc1)CC2] | 448 | method T | 0.70 |
| 7.02.85 | 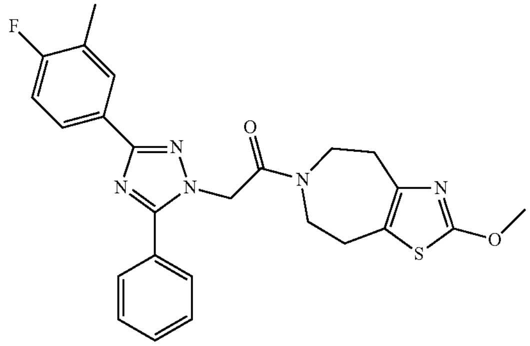 [SMILES: COc1nc2c(s1)CCN(C(=O)Cn1nc(-c3ccc(F)c(C)c3)nc1-c1ccccc1)CC2] | 478 | method T | 0.76 |
| 7.02.86 | 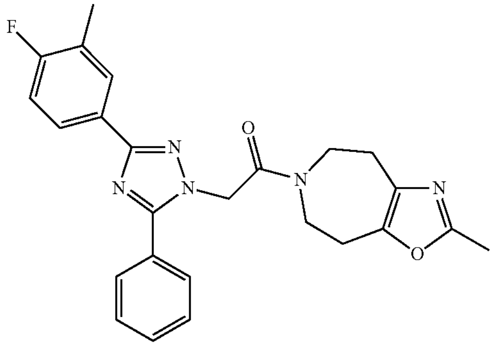 [SMILES: Cc1nc2c(o1)CCN(C(=O)Cn1nc(-c3ccc(F)c(C)c3)nc1-c1ccccc1)CC2] | 446 | method AB | 1.42 |
| 7.02.87 | 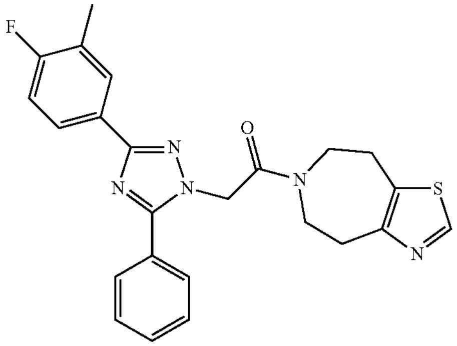 [SMILES: Cc1cc(-c2nc(-c3ccccc3)n(CC(=O)N3CCc4ncsc4CC3)n2)ccc1F] | 448 | method T | 0.74 |

-continued
| Examples | Product | MS m/z [M + H]+ | HPLC Method | Rt min |
|---|---|---|---|---|
| 7.02.88 | 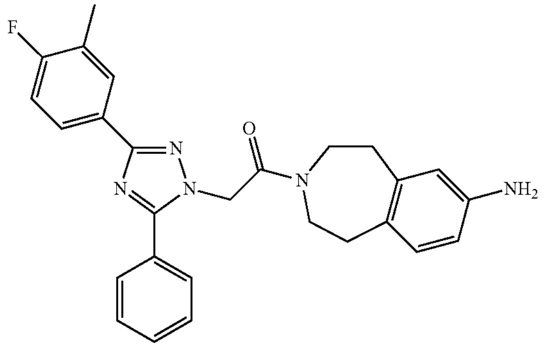 [SMILES: Cc1cc(-c2nc(-c3ccccc3)n(CC(=O)N3CCc4ccc(N)cc4CC3)n2)ccc1F] | 456 | method T | 0.66 |
| 7.02.89 | 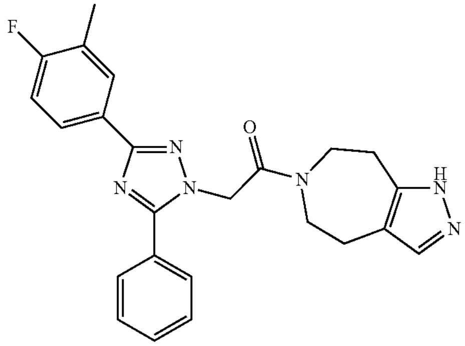 [SMILES: Cc1cc(-c2nc(-c3ccccc3)n(CC(=O)N3CCc4cn[nH]c4CC3)n2)ccc1F] | 431 | method T | 0.67 |
| 7.02.90 | 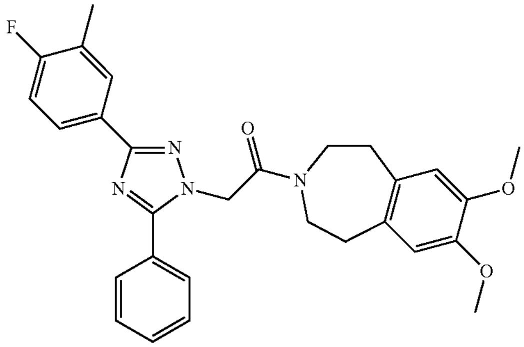 [SMILES: COc1cc2c(cc1OC)CCN(C(=O)Cn1nc(-c3ccc(F)c(C)c3)nc1-c1ccccc1)CC2] | 501 | method T | 0.72 |
| 7.02.91 | 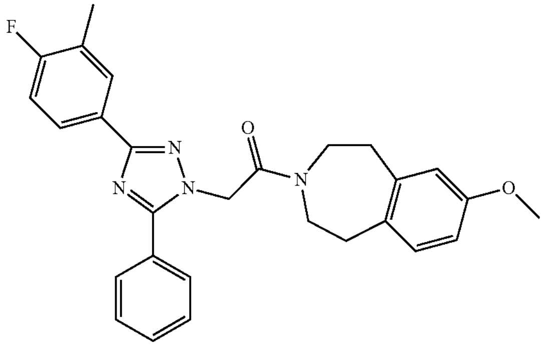 [SMILES: COc1ccc2c(c1)CCN(C(=O)Cn1nc(-c3ccc(F)c(C)c3)nc1-c1ccccc1)CC2] | 471 | method T | 0.73 |

-continued

| Examples | Product | MS m/z [M + H]+ | HPLC Method | Rt min |
|---|---|---|---|---|
| 7.02.92 | 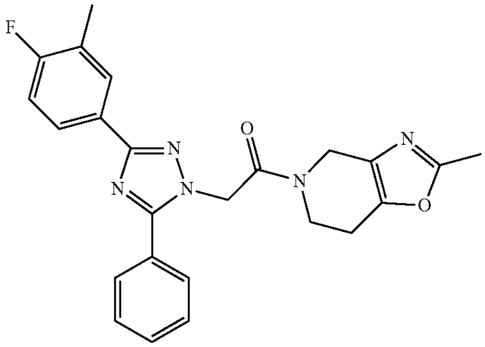 [SMILES: Cc1nc2c(o1)CCN(C(=O)Cn1nc(-c3ccc(F)c(C)c3)nc1-c1ccccc1)C2] | 432 | method AC | 0.82 |

7.03.001 1-(2-Amino-4,5,7,8-tetrahydro-thiazolo[4,5-d]azepin-6-yl)-2-(3,5-bis-(4-fluoro-phenyl)-(1,2,4)triazol-1-yl)-ethanone

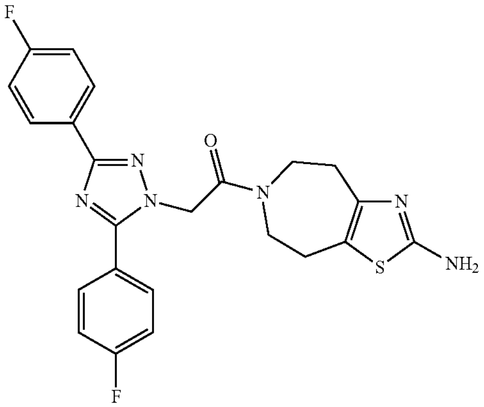 [SMILES: Nc1nc2c(s1)CCN(C(=O)Cn1nc(-c3ccc(F)cc3)nc1-c1ccc(F)cc1)CC2]

350 mg (3,5-bis-(4-fluoro-phenyl)-(1,2,4)triazol-1-yl)-acetic acid and 0.2 mL DIPEA were dissolved in 4.5 mL DMF. 570 mg PFTU was added to this solution and the mixture was stirred for 7 min at RT. Then, 333 mg 5,6,7,8-tetrahydro-4H-thiazolo[4,5-d]azepin-2-ylamine dihydrobromide and 0.4 mL DIPEA were added and the reaction was stirred over night at RT. Then, sodium hydrogencarbonate solution (10%) and $CH_2Cl_2$ were added, the organic phase was separated and the solvent was removed. The residue was purified by HPLC to yield 252 mg of the desired compound.

$R_t$: 1.16 min (method B)

$(M+H)^+$: 467

By using the same synthesis strategy as for 1-(2-amino-4,5,7,8-tetrahydro-thiazolol-[4,5-d]azepin-6-yl)-2-(3,5-bis-(4-fluoro-phenyl)-(1,2,4)triazol-1-yl)-ethanone the following compounds were obtained:

| Examples | Product | MS m/z [M + H]+ | HPLC Method | Rt min |
|---|---|---|---|---|
| 7.03.002 | 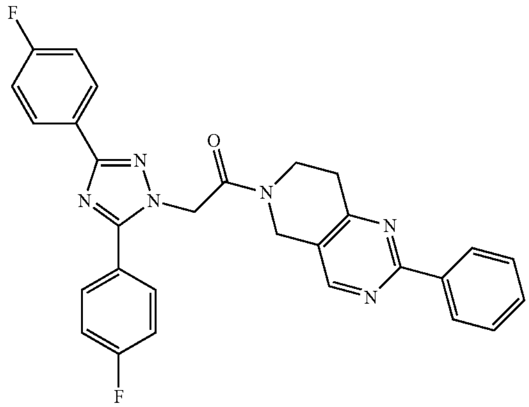 [SMILES: O=C(Cn1nc(-c2ccc(F)cc2)nc1-c1ccc(F)cc1)N1CCc2nc(-c3ccccc3)ncc2C1] | 509 | method D | 2.12 |

-continued
| Examples | Product | MS m/z [M + H]+ | HPLC Method | Rt min |
|---|---|---|---|---|
| 7.03.003 | 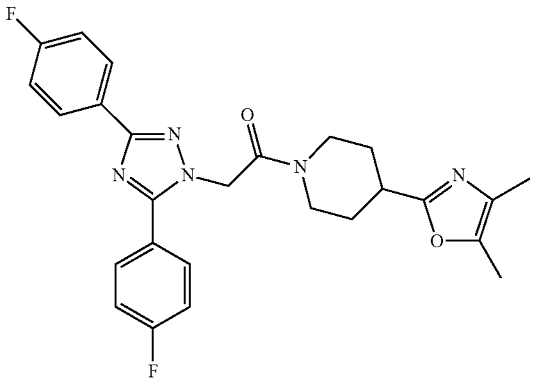 [SMILES: Cc1nc(C2CCN(C(=O)Cn3nc(-c4ccc(F)cc4)nc3-c3ccc(F)cc3)CC2)oc1C] | 478 | method D | 2.06 |
| 7.03.004 | 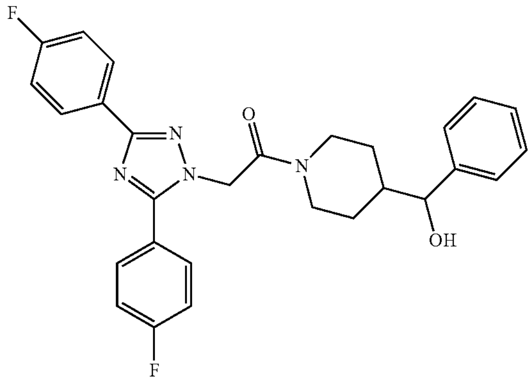 [SMILES: O=C(Cn1nc(-c2ccc(F)cc2)nc1-c1ccc(F)cc1)N1CCC(C(O)c2ccccc2)CC1] | 489 | method D | 2.05 |
| 7.03.005 | 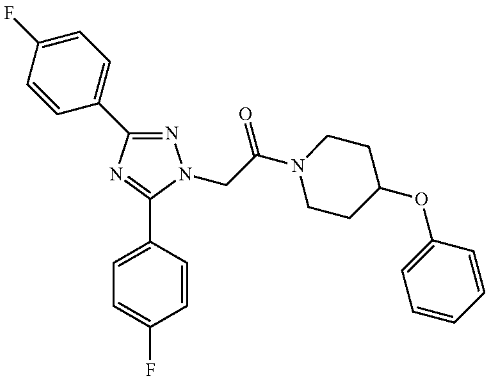 [SMILES: O=C(Cn1nc(-c2ccc(F)cc2)nc1-c1ccc(F)cc1)N1CCC(Oc2ccccc2)CC1] | 475 | method D | 2.12 |
| 7.03.006 | 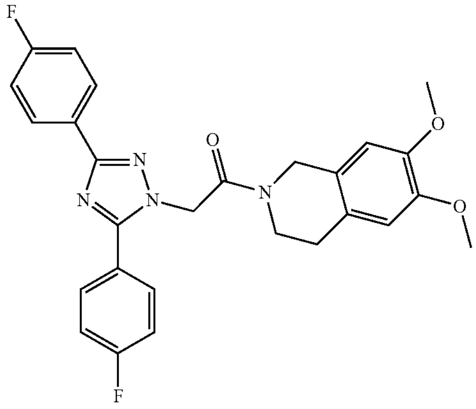 [SMILES: COc1cc2c(cc1OC)CN(C(=O)Cn1nc(-c3ccc(F)cc3)nc1-c1ccc(F)cc1)CC2] | 491 | method D | 2.04 |

-continued
| Examples | Product | MS m/z [M + H]$^+$ | HPLC Method | Rt min |
|---|---|---|---|---|
| 7.03.007 | 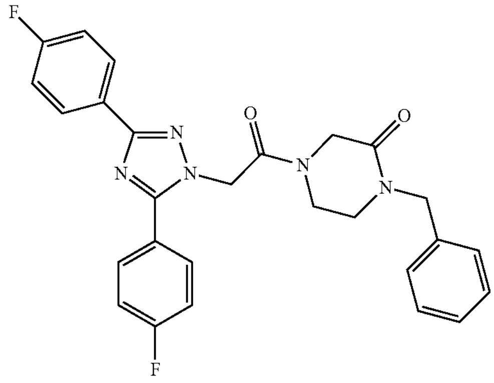 [SMILES: O=C(Cn1nc(-c2ccc(F)cc2)nc1-c1ccc(F)cc1)N1CCN(Cc2ccccc2)C(=O)C1] | 488 | method D | 2.05 |
| 7.03.008 | 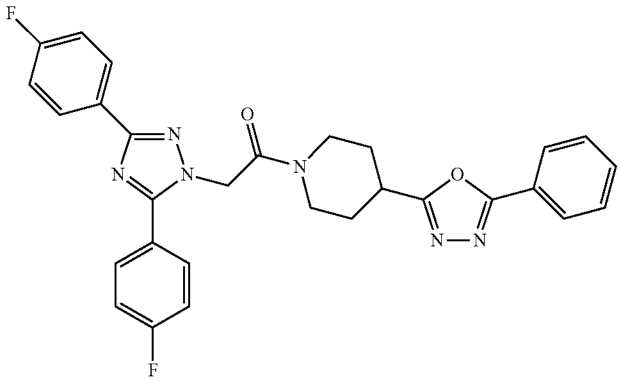 [SMILES: O=C(Cn1nc(-c2ccc(F)cc2)nc1-c1ccc(F)cc1)N1CCC(c2nnc(-c3ccccc3)o2)CC1] | 527 | method D | 2.07 |
| 7.03.009 | 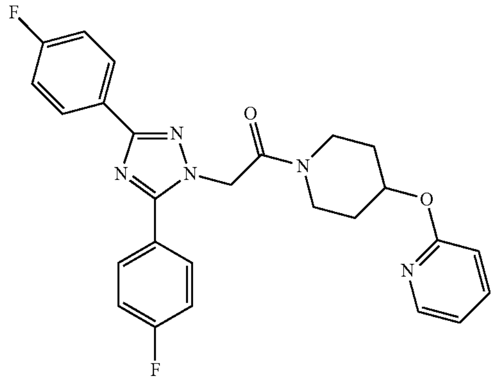 | 476 | method D | 2.06 |
| 7.03.010 | 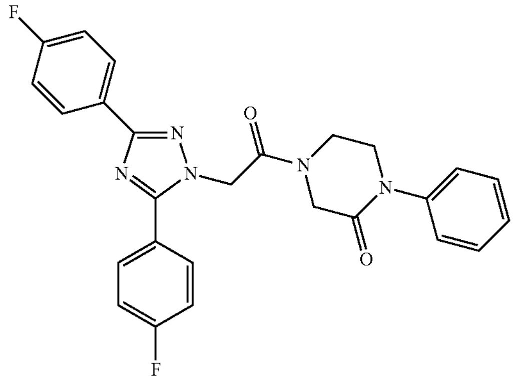 [SMILES: O=C(Cn1nc(-c2ccc(F)cc2)nc1-c1ccc(F)cc1)N1CCN(c2ccccc2)C(=O)C1] | 474 | method D | 2.00 |

-continued
| Examples | Product | MS m/z [M + H]+ | HPLC Method | Rt min |
|---|---|---|---|---|
| 7.03.011 | 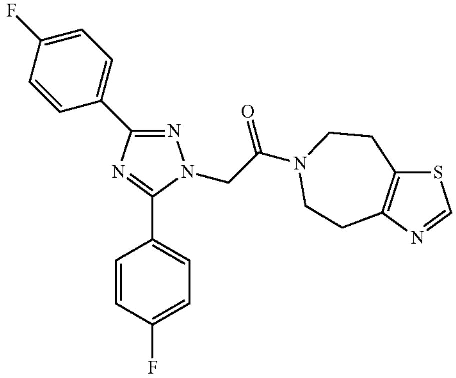 [SMILES: O=C(Cn1nc(-c2ccc(F)cc2)nc1-c1ccc(F)cc1)N1CCc2ncsc2CC1] | 452 | method D | 1.99 |
| 7.03.012 | 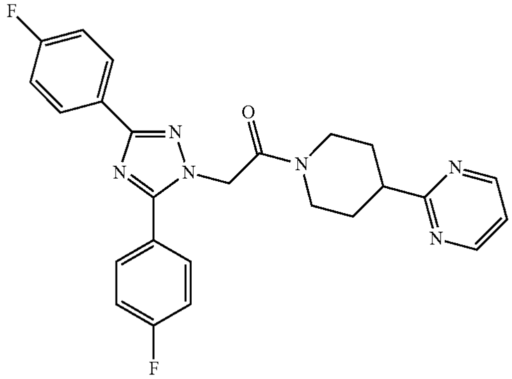 [SMILES: O=C(Cn1nc(-c2ccc(F)cc2)nc1-c1ccc(F)cc1)N1CCC(c2ncccn2)CC1] | 461 | method D | 2.01 |
| 7.03.013 | 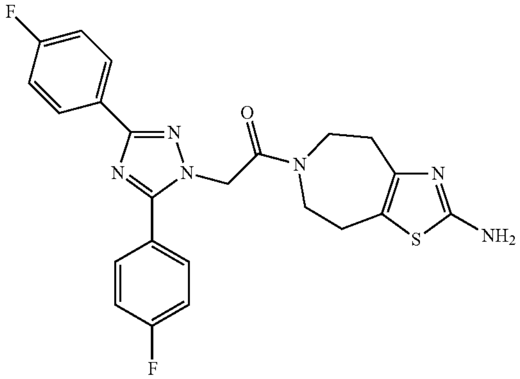 [SMILES: Nc1nc2c(s1)CCN(C(=O)Cn1nc(-c3ccc(F)cc3)nc1-c1ccc(F)cc1)CC2] | 467 | method D | 1.74 |
| 7.03.014 | 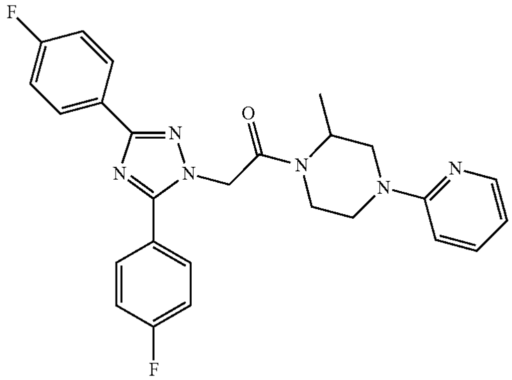 | 475 | method B | 1.17 |

-continued
| Examples | Product | MS m/z $[M + H]^+$ | HPLC Method | Rt min |
|---|---|---|---|---|
| 7.03.015 | 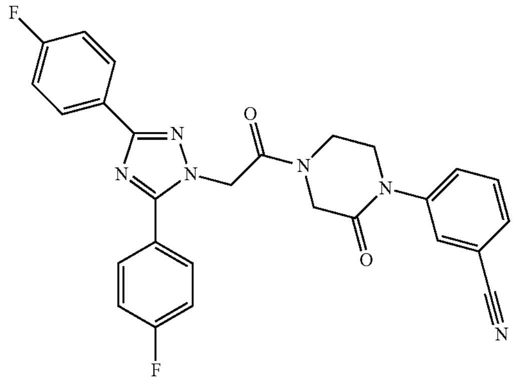 [SMILES: N#Cc1cccc(N2CCN(C(=O)Cn3nc(-c4ccc(F)cc4)nc3-c3ccc(F)cc3)CC2=O)c1] | 499 | method B | 1.29 |
| 7.03.016 | 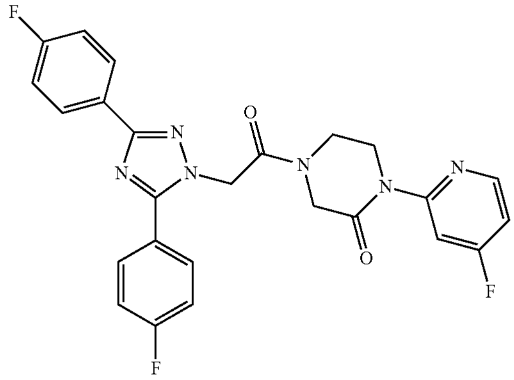 [SMILES: O=C(Cn1nc(-c2ccc(F)cc2)nc1-c1ccc(F)cc1)N1CCN(c2cc(F)ccn2)C(=O)C1] | 493 | method B | 1.36 |
| 7.03.017 | 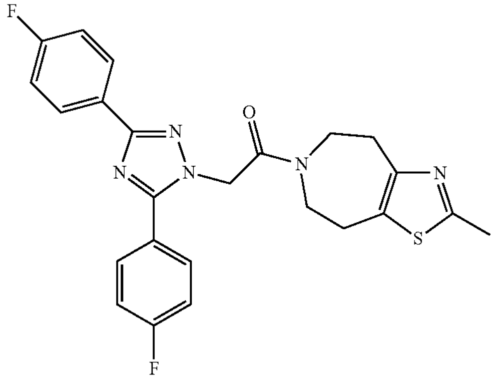 | 465 | method B | 1.29 |
| 7.03.018 | 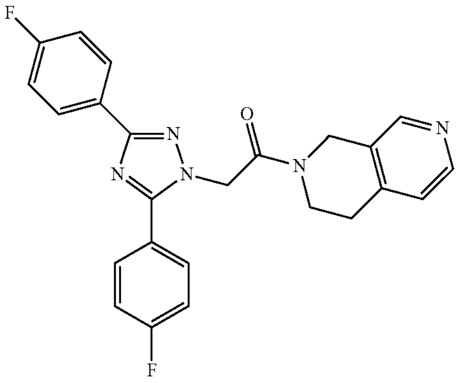 [SMILES: O=C(Cn1nc(-c2ccc(F)cc2)nc1-c1ccc(F)cc1)N1CCc2ccncc2C1] | 431 | method B | 1.17 |

-continued
| Examples | Product | MS m/z $[M + H]^+$ | HPLC Method | Rt min |
|---|---|---|---|---|
| 7.03.019 | 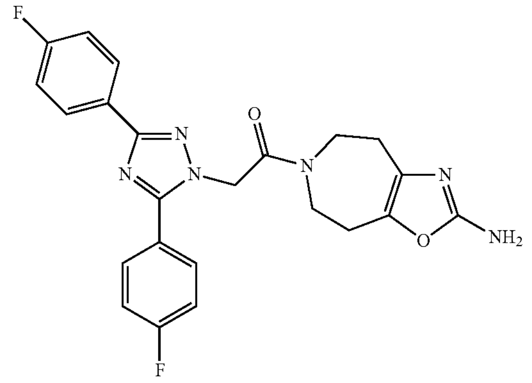 [SMILES: Nc1nc2c(o1)CCN(C(=O)Cn1nc(-c3ccc(F)cc3)nc1-c1ccc(F)cc1)CC2] | 451 | method B | 1.15 |
| 7.03.020 | 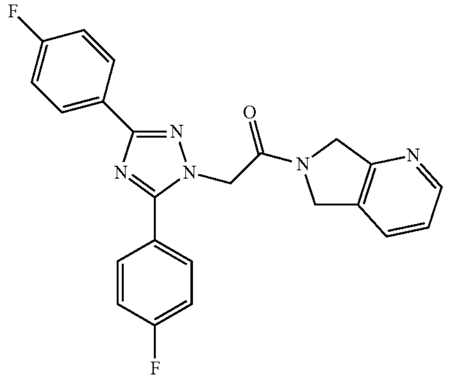 [SMILES: O=C(Cn1nc(-c2ccc(F)cc2)nc1-c1ccc(F)cc1)N1Cc2cccnc2C1] | 418 | method B | 1.28 |
| 7.03.021 | 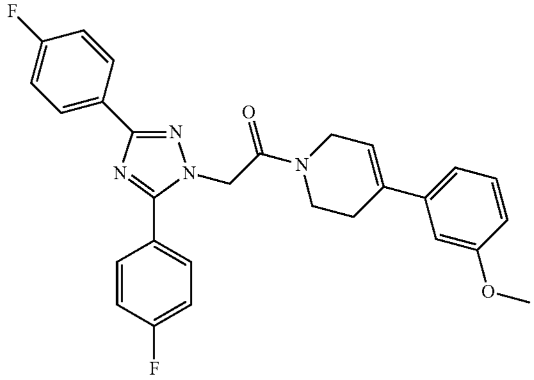 [SMILES: COc1cccc(C2=CCN(C(=O)Cn3nc(-c4ccc(F)cc4)nc3-c3ccc(F)cc3)CC2)c1] | 487 | method B | 1.51 |
| 7.03.022 | 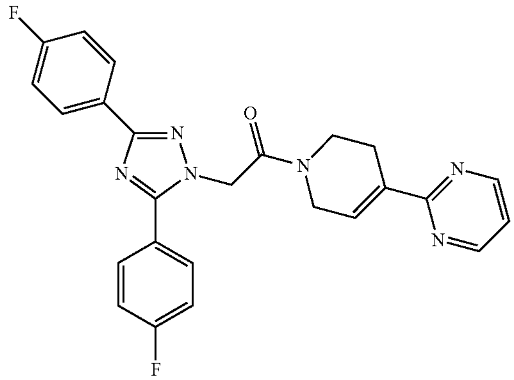 | 459 | method B | 1.35 |

-continued
| Examples | Product | MS m/z [M + H]+ | HPLC Method | Rt min |
|---|---|---|---|---|
| 7.03.023 | 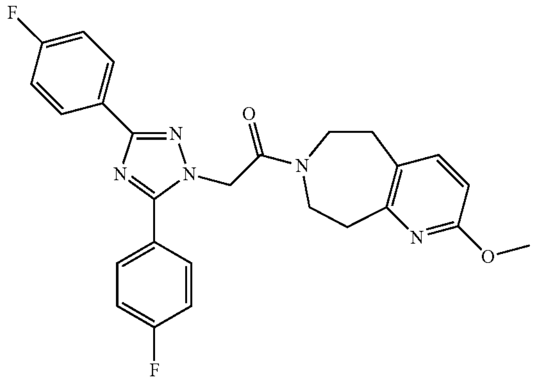 [SMILES: COc1ccc2c(n1)CCN(C(=O)Cn1nc(-c3ccc(F)cc3)nc1-c1ccc(F)cc1)CC2] | 476 | method B | 1.32 |
| 7.03.024 | 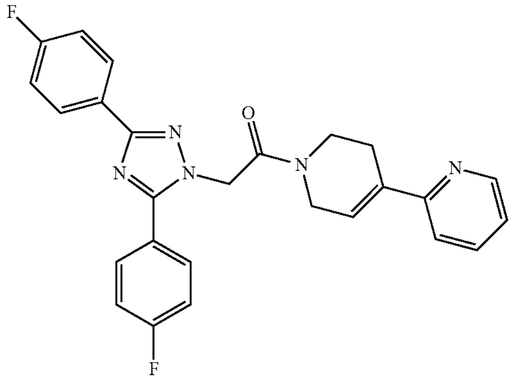 [SMILES: O=C(Cn1nc(-c2ccc(F)cc2)nc1-c1ccc(F)cc1)N1CC=C(c2ccccn2)CC1] | 458 | method B | 1.19 |
| 7.03.025 | 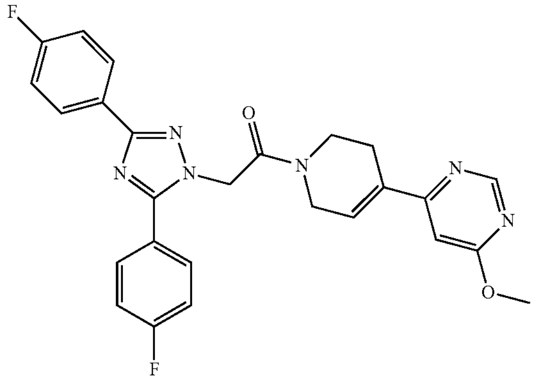 [SMILES: COc1cc(C2=CCN(C(=O)Cn3nc(-c4ccc(F)cc4)nc3-c3ccc(F)cc3)CC2)ncn1] | 489 | method B | 1.41 |
| 7.03.026 | 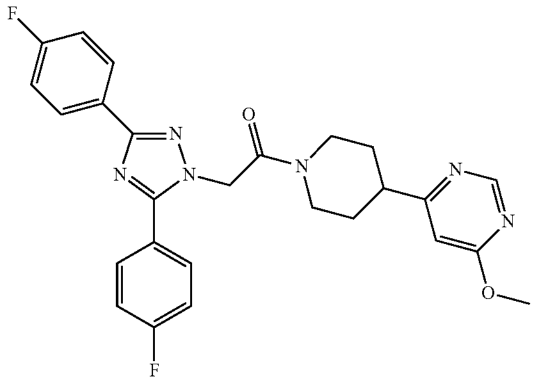 [SMILES: COc1cc(C2CCN(C(=O)Cn3nc(-c4ccc(F)cc4)nc3-c3ccc(F)cc3)CC2)ncn1] | 491 | method K | 1.35 |

-continued
| Examples | Product | MS m/z [M + H]+ | HPLC Method | Rt min |
|---|---|---|---|---|
| 7.03.027 | 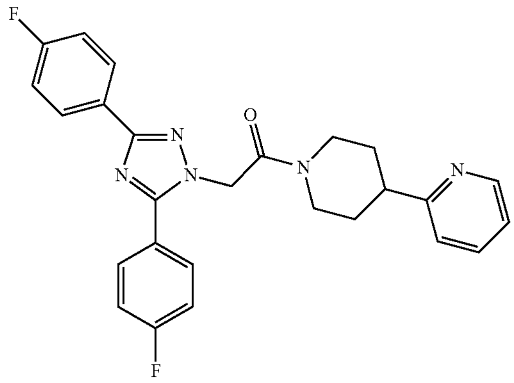 [SMILES: O=C(Cn1nc(-c2ccc(F)cc2)nc1-c1ccc(F)cc1)N1CCC(c2ccccn2)CC1] | 460 | method B | 1.18 |
| 7.03.028 | 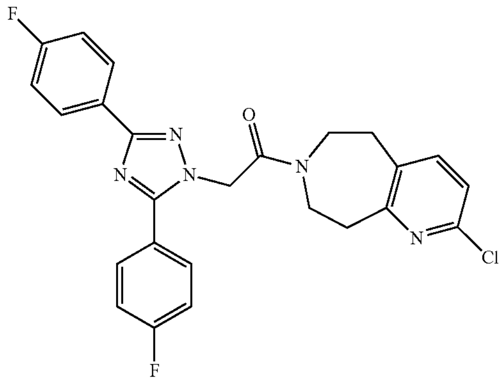 [SMILES: O=C(Cn1nc(-c2ccc(F)cc2)nc1-c1ccc(F)cc1)N1CCc2ccc(Cl)nc2CC1] | 480 | method L | 0.85 |
| 7.03.029 | 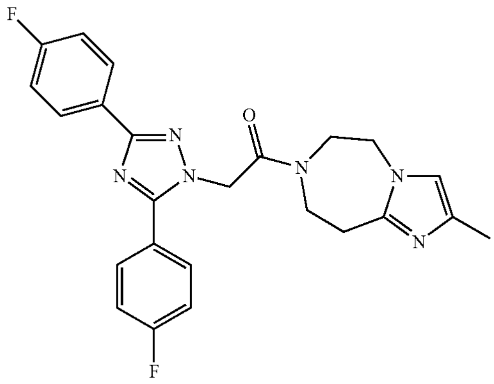 [SMILES: Cc1cn2c(n1)CCN(C(=O)Cn1nc(-c3ccc(F)cc3)nc1-c1ccc(F)cc1)CC2] | 480 | method M | 0.73 |
| 7.03.030 | 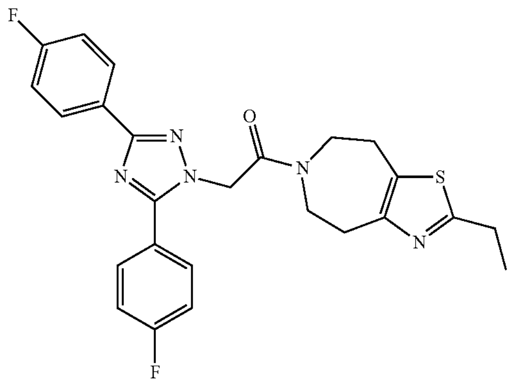 [SMILES: CCc1nc2c(s1)CCN(C(=O)Cn1nc(-c3ccc(F)cc3)nc1-c1ccc(F)cc1)CC2] | 480 | method M | 0.87 |

-continued
| Examples | Product | MS m/z $[M + H]^+$ | HPLC Method | Rt min |
| --- | --- | --- | --- | --- |
| 7.03.031 | 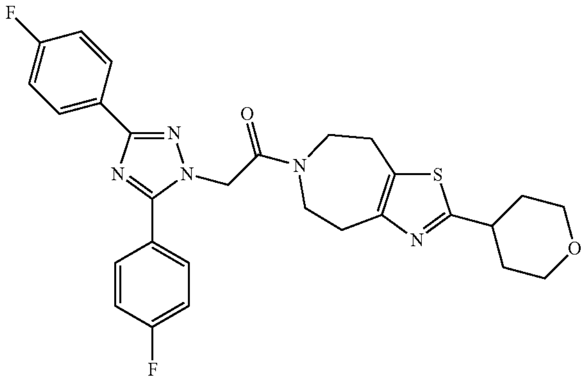 [SMILES: O=C(Cn1nc(-c2ccc(F)cc2)nc1-c1ccc(F)cc1)N1CCc2nc(C3CCOCC3)sc2CC1] | 536 | method M | 0.95 |
| 7.03.032 | 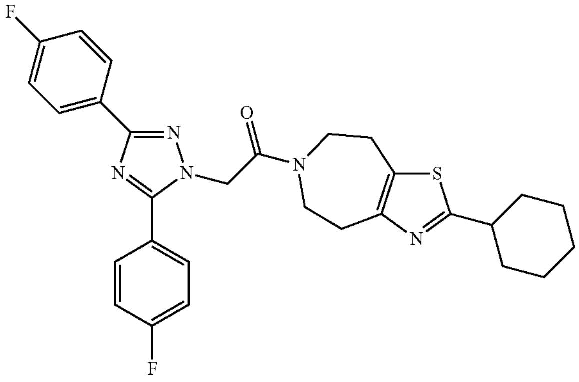 [SMILES: O=C(Cn1nc(-c2ccc(F)cc2)nc1-c1ccc(F)cc1)N1CCc2nc(C3CCCCC3)sc2CC1] | 534 | method M | 1.07 |
| 7.03.033 | 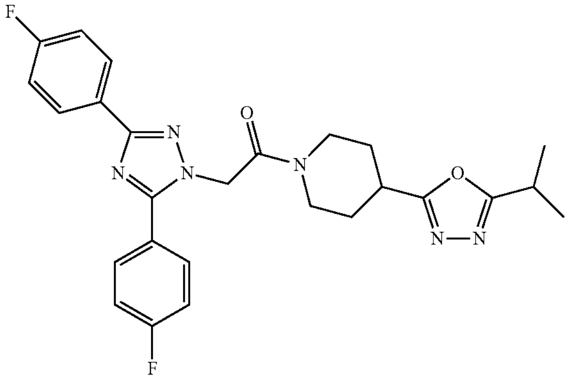 [SMILES: CC(C)c1nnc(C2CCN(C(=O)Cn3nc(-c4ccc(F)cc4)nc3-c3ccc(F)cc3)CC2)o1] | 493 | method Q | 0.82 |
| 7.03.034 | 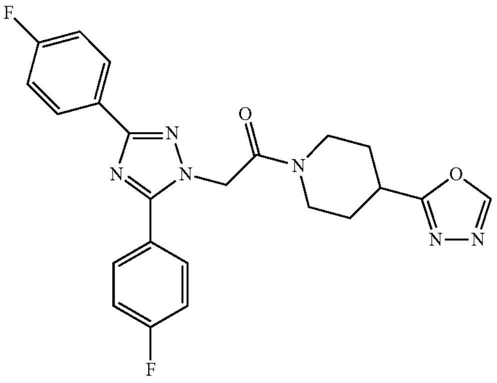 [SMILES: O=C(Cn1nc(-c2ccc(F)cc2)nc1-c1ccc(F)cc1)N1CCC(c2nnco2)CC1] | 451 | method R | 1.12 |

-continued
| Examples | Product | MS m/z [M + H]+ | HPLC Method | Rt min |
|---|---|---|---|---|
| 7.03.035 | 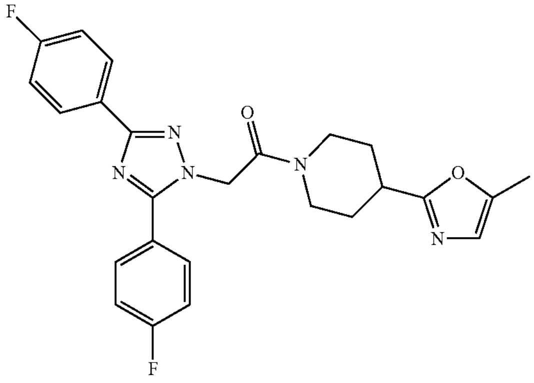 [SMILES: Cc1cnc(C2CCN(C(=O)Cn3nc(-c4ccc(F)cc4)nc3-c3ccc(F)cc3)CC2)o1] | 464 | method L | 0.84 |
| 7.03.036 | 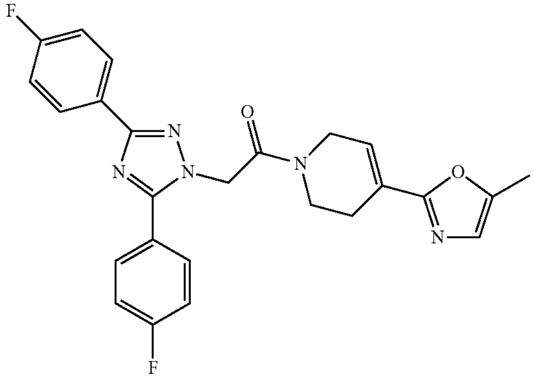 [SMILES: Cc1cnc(C2=CCN(C(=O)Cn3nc(-c4ccc(F)cc4)nc3-c3ccc(F)cc3)CC2)o1] | 462 | method L | 0.85 |
| 7.03.037 | 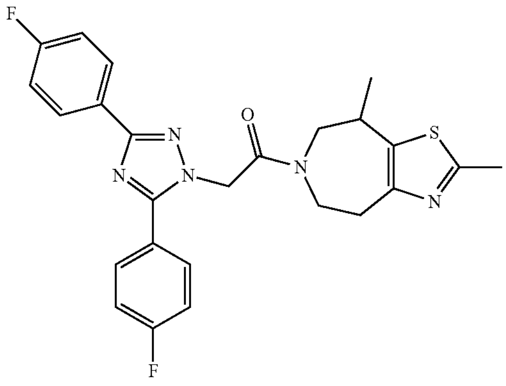 [SMILES: Cc1nc2c(s1)C(C)CN(C(=O)Cn1nc(-c3ccc(F)cc3)nc1-c1ccc(F)cc1)CC2] | 481 | method L | 0.85 |
| 7.03.038 | 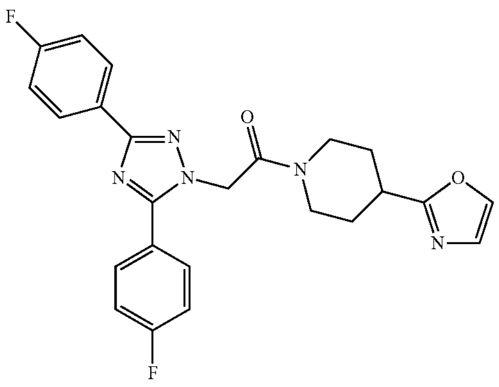 [SMILES: O=C(Cn1nc(-c2ccc(F)cc2)nc1-c1ccc(F)cc1)N1CCC(c2ncco2)CC1] | 450 | method S | 0.71 |

-continued
| Examples | Product | MS m/z [M + H]+ | HPLC Method | Rt min |
|---|---|---|---|---|
| 7.03.039 | 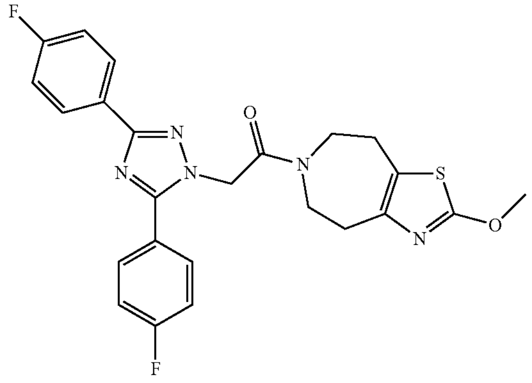 [SMILES: COc1nc2c(s1)CCN(C(=O)Cn1nc(-c3ccc(F)cc3)nc1-c1ccc(F)cc1)CC2] | 482 | method S | 0.76 |
| 7.03.040 | 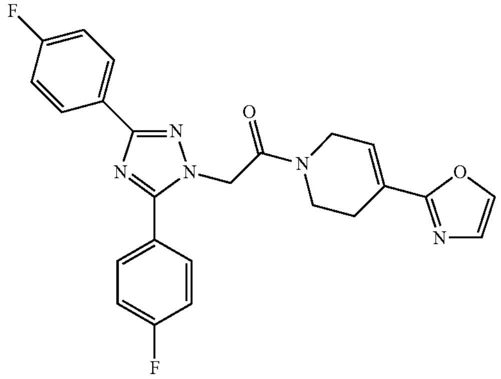 [SMILES: O=C(Cn1nc(-c2ccc(F)cc2)nc1-c1ccc(F)cc1)N1CC=C(c2ncco2)CC1] | 448 | method S | 0.72 |
| 7.03.041 | 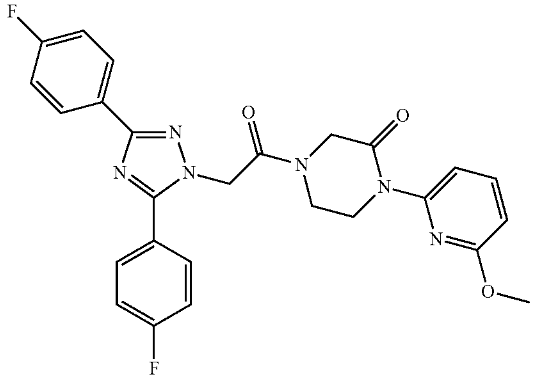 [SMILES: COc1cccc(N2CCN(C(=O)Cn3nc(-c4ccc(F)cc4)nc3-c3ccc(F)cc3)CC2=O)n1] | 505 | method S | 0.81 |
| 7.03.042 | 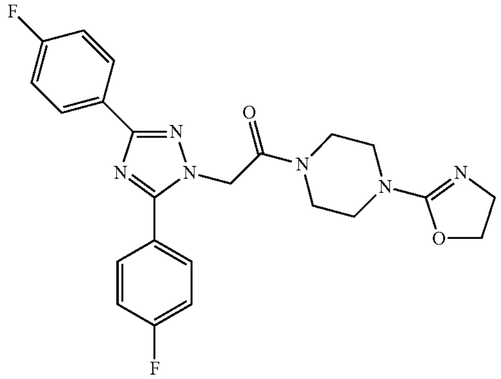 [SMILES: O=C(Cn1nc(-c2ccc(F)cc2)nc1-c1ccc(F)cc1)N1CCN(C2=NCCO2)CC1] | 453 | method B | 1.16 |

-continued
| Examples | Product | MS m/z $[M + H]^+$ | HPLC Method | Rt min |
|---|---|---|---|---|
| 7.03.043 | 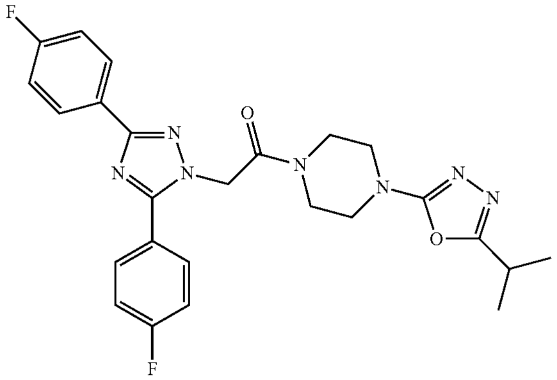 [SMILES: CC(C)c1nnc(N2CCN(C(=O)Cn3nc(-c4ccc(F)cc4)nc3-c3ccc(F)cc3)CC2)o1] | 494 | method L | 0.80 |
| 7.03.044 | 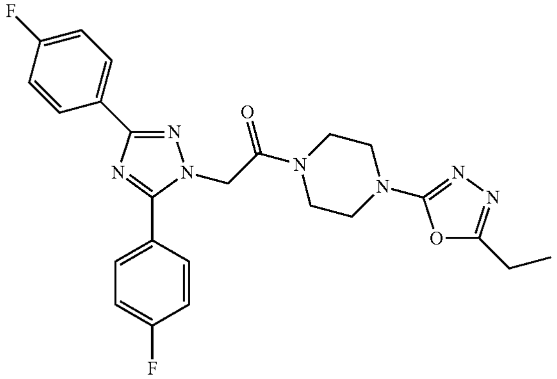 [SMILES: CCc1nnc(N2CCN(C(=O)Cn3nc(-c4ccc(F)cc4)nc3-c3ccc(F)cc3)CC2)o1] | 480 | method L | 0.77 |
| 7.03.045 | 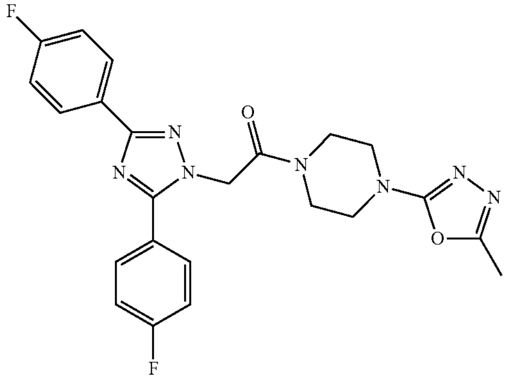 | 466 | method L | 0.73 |
| 7.03.046 | 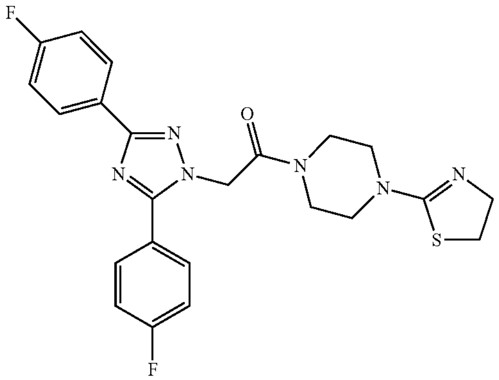 | 469 | method B | 1.16 |

-continued
| Examples | Product | MS m/z [M + H]+ | HPLC Method | Rt min |
|---|---|---|---|---|
| 7.03.047 | 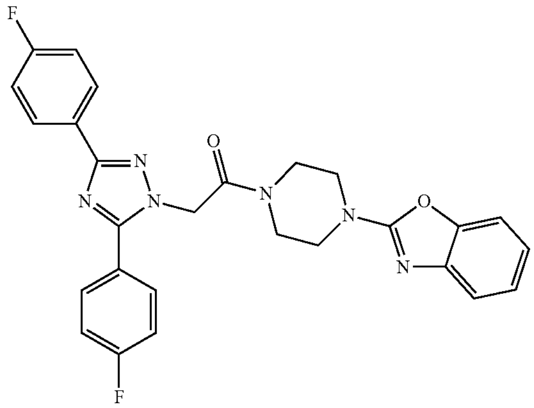 [SMILES: O=C(Cn1nc(-c2ccc(F)cc2)nc1-c1ccc(F)cc1)N1CCN(c2nc3ccccc3o2)CC1] | 501 | method D | 2.10 |
| 7.03.048 | 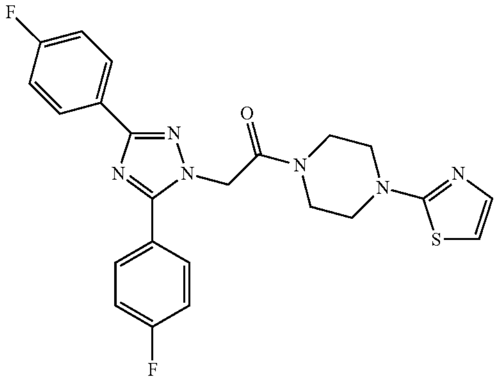 [SMILES: O=C(Cn1nc(-c2ccc(F)cc2)nc1-c1ccc(F)cc1)N1CCN(c2nccs2)CC1] | 467 | method D | 1.92 |
| 7.03.049 | 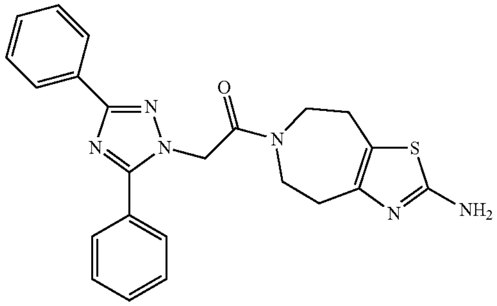 [SMILES: Nc1nc2c(s1)CCN(C(=O)Cn1nc(-c3ccccc3)nc1-c1ccccc1)CC2] | 431 | method B | 1.07 |
| 7.03.050 | 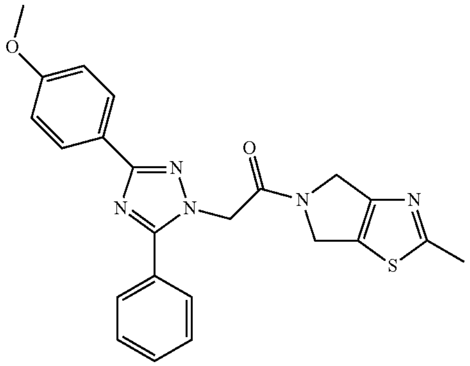 [SMILES: COc1ccc(-c2nc(-c3ccccc3)n(CC(=O)N3Cc4nc(C)sc4C3)n2)cc1] | 432 | method B | 1.27 |

-continued
| Examples | Product | MS m/z [M + H]+ | HPLC Method | Rt min |
|---|---|---|---|---|
| 7.03.051 | 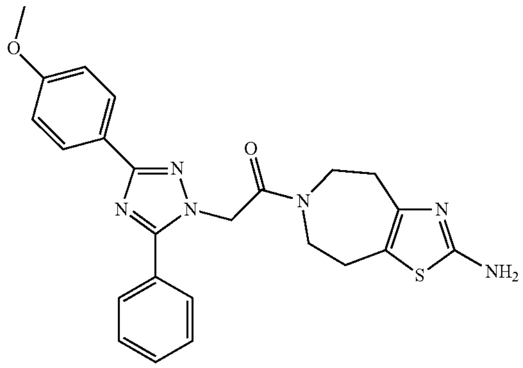 [SMILES: COc1ccc(-c2nc(-c3ccccc3)n(CC(=O)N3CCc4nc(N)sc4CC3)n2)cc1] | 461 | method B | 1.07 |
| 7.03.052 | 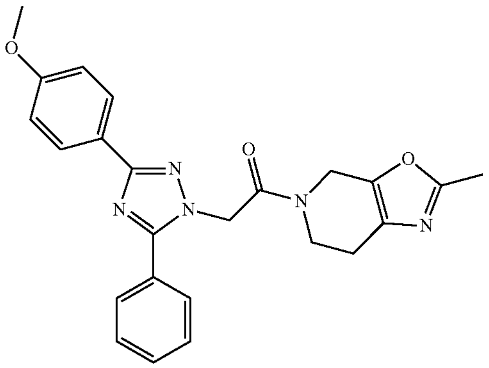 [SMILES: COc1ccc(-c2nc(-c3ccccc3)n(CC(=O)N3CCc4nc(C)oc4C3)n2)cc1] | 430 | method B | 1.25 |
| 7.03.053 | 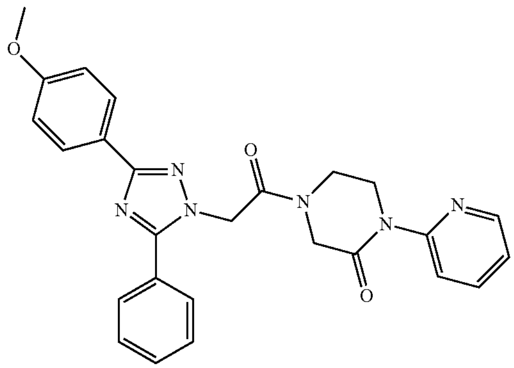 [SMILES: COc1ccc(-c2nc(-c3ccccc3)n(CC(=O)N3CCN(c4ccccn4)C(=O)C3)n2)cc1] | 469 | method B | 1.22 |
| 7.03.054 | 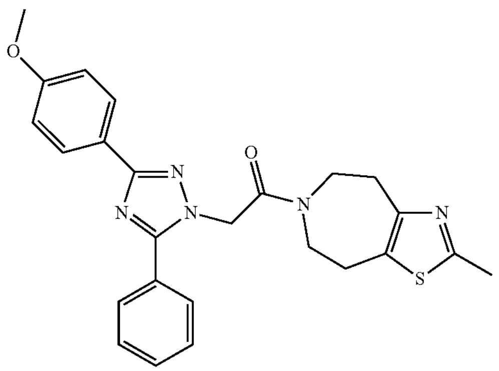 [SMILES: COc1ccc(-c2nc(-c3ccccc3)n(CC(=O)N3CCc4nc(C)sc4CC3)n2)cc1] | 460 | method B | 1.18 |

-continued
| Examples | Product | MS m/z [M + H]+ | HPLC Method | Rt min |
|---|---|---|---|---|
| 7.03.055 | 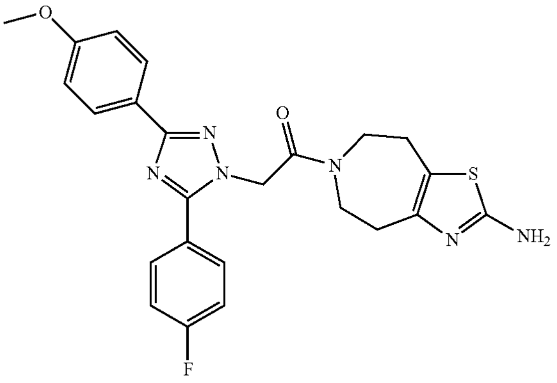 [SMILES: COc1ccc(-c2nc(-c3ccc(F)cc3)n(CC(=O)N3CCc4nc(N)sc4CC3)n2)cc1] | 479 | method B | 1.12 |
| 7.03.056 | 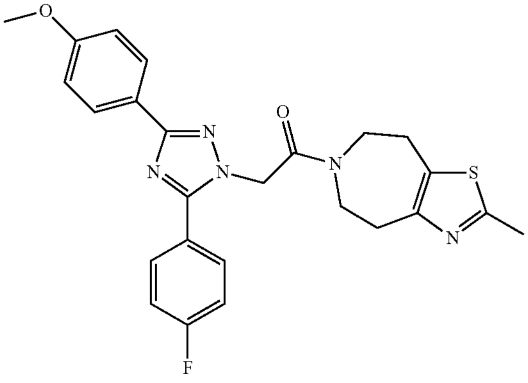 | 478 | method B | 1.23 |
| 7.03.057 | 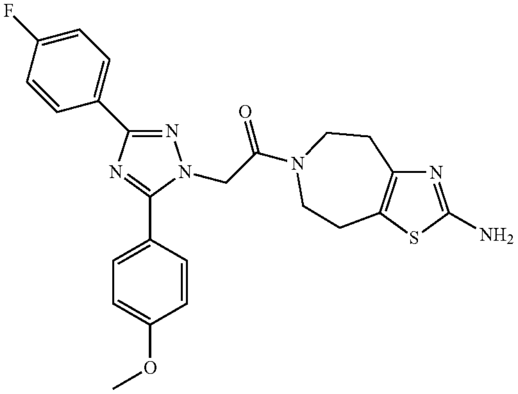 [SMILES: COc1ccc(-c2nc(-c3ccc(F)cc3)nn2CC(=O)N2CCc3nc(N)sc3CC2)cc1] | 479 | method B | 1.15 |
| 7.03.058 | 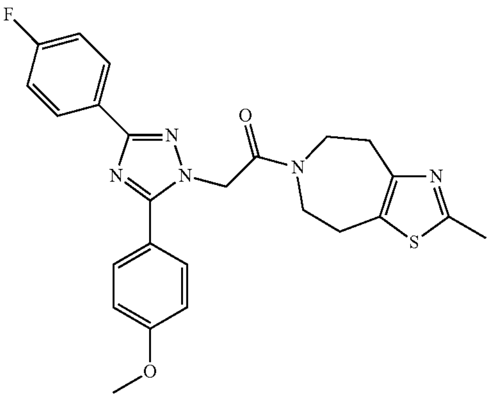 [SMILES: COc1ccc(-c2nc(-c3ccc(F)cc3)nn2CC(=O)N2CCc3nc(C)sc3CC2)cc1] | 478 | method B | 1.26 |

-continued
| Examples | Product | MS m/z [M + H]$^+$ | HPLC Method | Rt min |
|---|---|---|---|---|
| 7.03.059 | 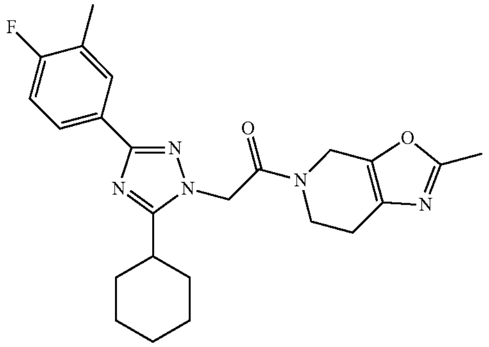 [SMILES: Cc1nc2c(o1)CN(C(=O)Cn1nc(-c3ccc(F)c(C)c3)nc1C1CCCCC1)CC2] | 438 | method B | 1.45 |
| 7.03.060 | 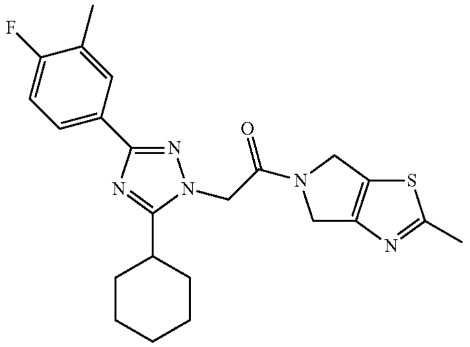 [SMILES: Cc1nc2c(s1)CN(C(=O)Cn1nc(-c3ccc(F)c(C)c3)nc1C1CCCCC1)C2] | 440 | method B | 1.46 |
| 7.03.061 | 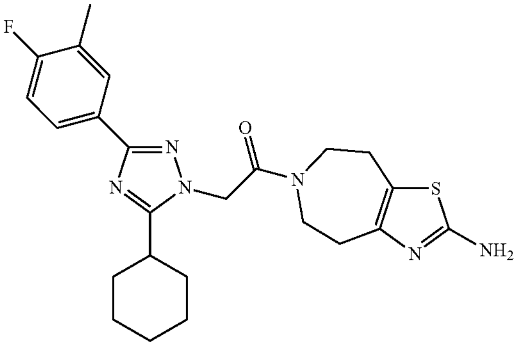 [SMILES: Cc1cc(-c2nc(C3CCCCC3)n(CC(=O)N3CCc4nc(N)sc4CC3)n2)ccc1F] | 469 | method B | 1.32 |
| 7.03.062 | 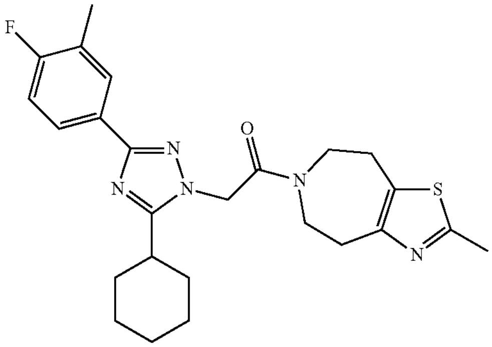 [SMILES: Cc1nc2c(s1)CCN(C(=O)Cn1nc(-c3ccc(F)c(C)c3)nc1C1CCCCC1)CC2] | 468 | method B | 1.43 |

-continued
| Examples | Product | MS m/z [M + H]+ | HPLC Method | Rt min |
|---|---|---|---|---|
| 7.03.063 | 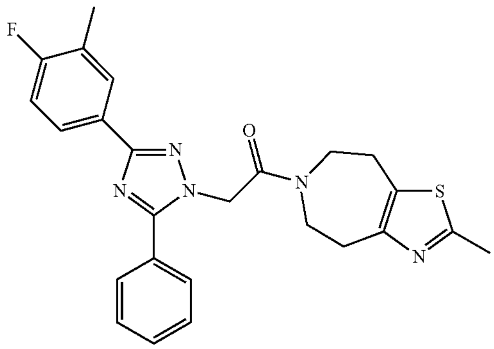 [SMILES: Cc1nc2c(s1)CCN(C(=O)Cn1nc(-c3ccc(F)c(C)c3)nc1-c1ccccc1)CC2] | 462 | method B | 1.33 |
| 7.03.064 | 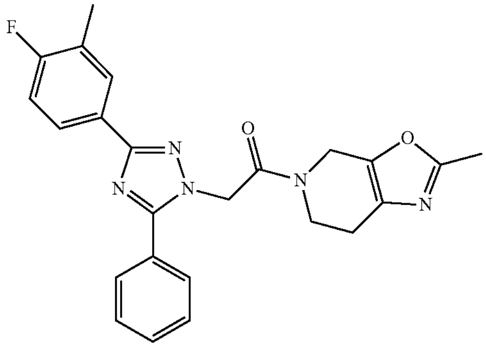 [SMILES: Cc1nc2c(o1)CN(C(=O)Cn1nc(-c3ccc(F)c(C)c3)nc1-c1ccccc1)CC2] | 432 | method B | 1.36 |
| 7.03.065 | 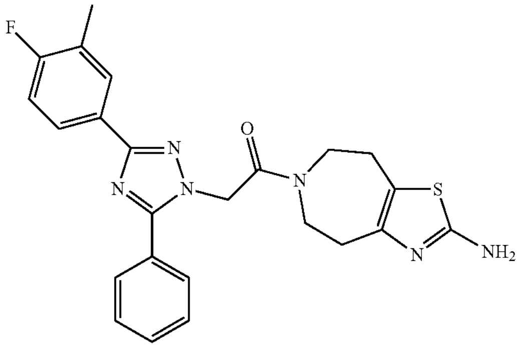 [SMILES: Cc1cc(-c2nc(-c3ccccc3)n(CC(=O)N3CCc4nc(N)sc4CC3)n2)ccc1F] | 463 | method B | 1.21 |
| 7.03.066 | 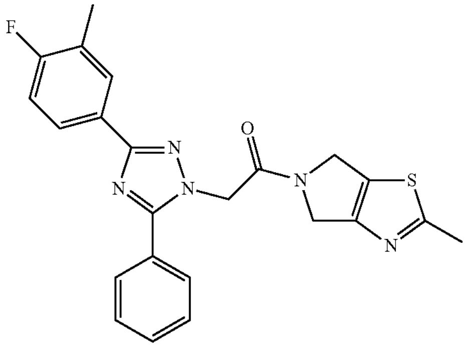 [SMILES: Cc1nc2c(s1)CN(C(=O)Cn1nc(-c3ccc(F)c(C)c3)nc1-c1ccccc1)C2] | 434 | method B | 1.38 |

-continued
| Examples | Product | MS m/z [M + H]+ | HPLC Method | Rt min |
|---|---|---|---|---|
| 7.03.067 | 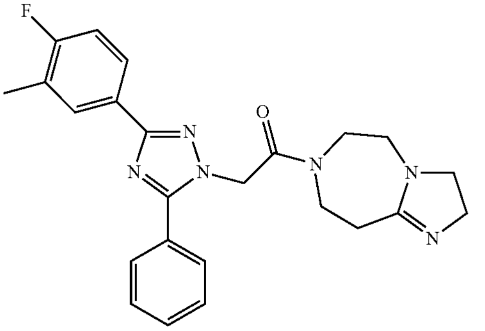 [SMILES: Cc1cc(-c2nc(-c3ccccc3)n(CC(=O)N3CCC4=NCCN4CC3)n2)ccc1F] | 431 | method U | 0.47 |
| 7.03.068 | 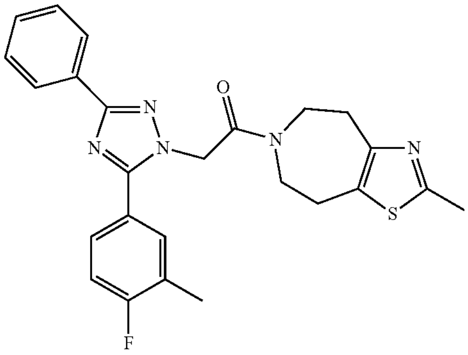 [SMILES: Cc1nc2c(s1)CCN(C(=O)Cn1nc(-c3ccccc3)nc1-c1ccc(F)c(C)c1)CC2] | 431 | method U | 0.47 |
| 7.03.069 | 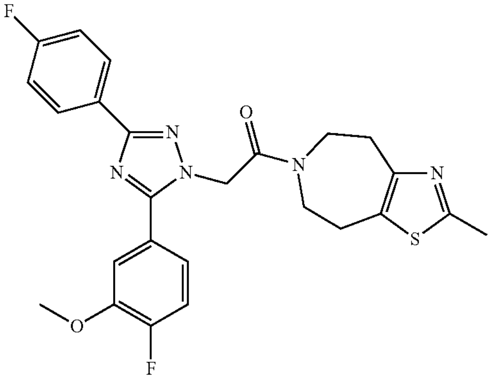 [SMILES: COc1cc(-c2nc(-c3ccc(F)cc3)nn2CC(=O)N2CCc3nc(C)sc3CC2)ccc1F] | 496 | method L | 0.76 |
| 7.03.070 | 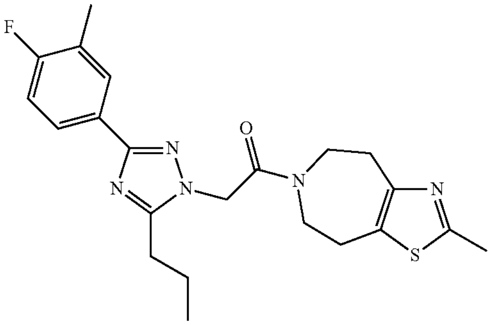 [SMILES: CCCc1nc(-c2ccc(F)c(C)c2)nn1CC(=O)N1CCc2nc(C)sc2CC1] | 428 | method B | 1.26 |

-continued
| Examples | Product | MS m/z [M + H]+ | HPLC Method | Rt min |
|---|---|---|---|---|
| 7.03.071 | 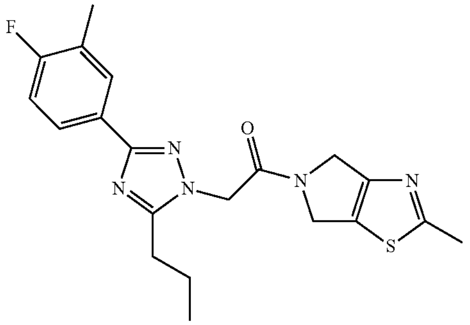 [SMILES: CCCc1nc(-c2ccc(F)c(C)c2)nn1CC(=O)N1Cc2nc(C)sc2C1] | 400 | method B | 1.34 |
| 7.03.072 | 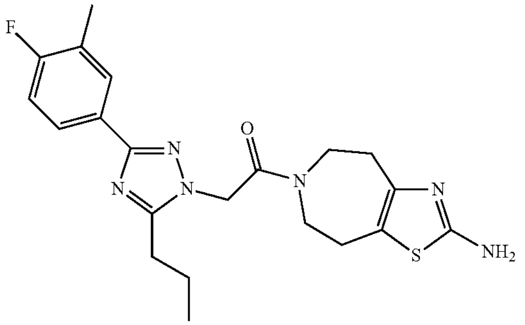 [SMILES: CCCc1nc(-c2ccc(F)c(C)c2)nn1CC(=O)N1CCc2nc(N)sc2CC1] | 429 | method B | 1.19 |
| 7.03.073 | 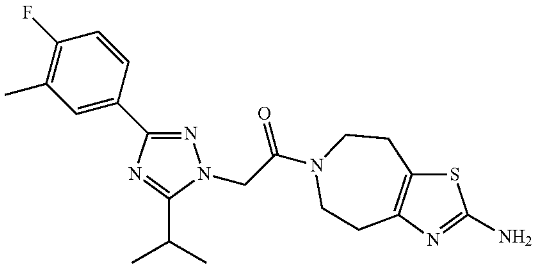 [SMILES: Cc1cc(-c2nc(C(C)C)n(CC(=O)N3CCc4nc(N)sc4CC3)n2)ccc1F] | 429 | method L | 0.69 |
| 7.03.024 | 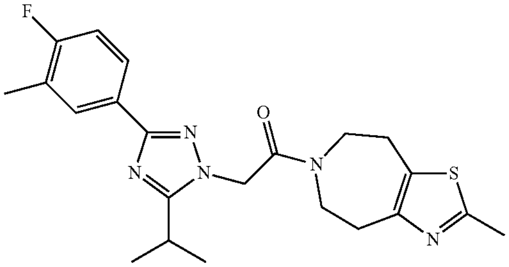 | 428 | method L | 0.76 |
| 7.03.075 | 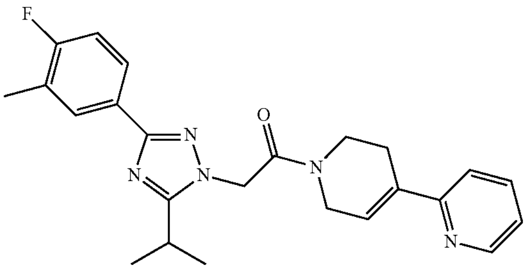 [SMILES: Cc1cc(-c2nc(C(C)C)n(CC(=O)N3CC=C(c4ccccn4)CC3)n2)ccc1F] | 420 | method V | 0.73 |

-continued
| Examples | Product | MS m/z [M + H]$^+$ | HPLC Method | Rt min |
|---|---|---|---|---|
| 7.03.076 | 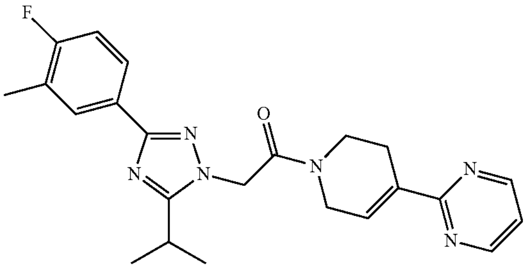 [SMILES: Cc1cc(-c2nc(C(C)C)n(CC(=O)N3CC=C(c4ncccn4)CC3)n2)ccc1F] | 421 | method V | 0.88 |
| 7.03.077 | 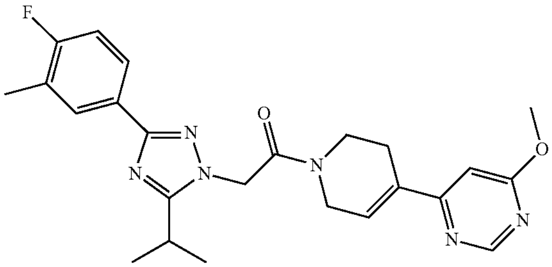 [SMILES: COc1cc(C2=CCN(C(=O)Cn3nc(-c4ccc(F)c(C)c4)nc3C(C)C)CC2)ncn1] | 451 | method V | 0.91 |
| 7.03.078 | 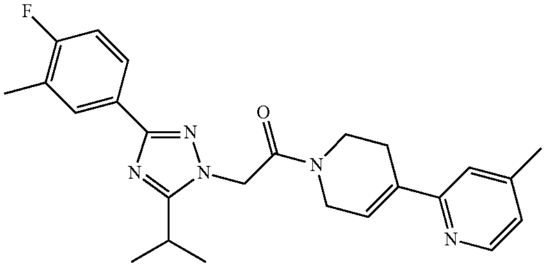 | 434 | method V | 0.72 |
| 7.03.079 | 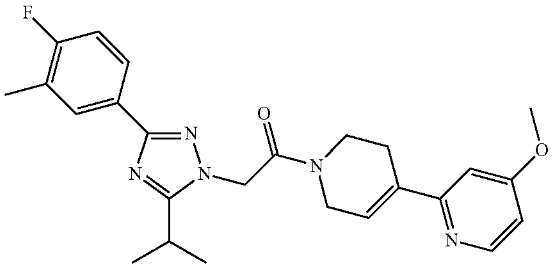 [SMILES: COc1ccnc(C2=CCN(C(=O)Cn3nc(-c4ccc(F)c(C)c4)nc3C(C)C)CC2)c1] | 450 | method V | 0.71 |
| 7.03.080 | 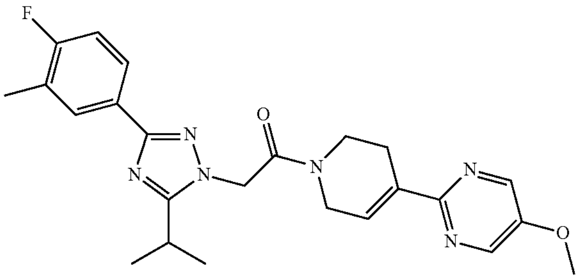 | 451 | method V | 0.75 |

-continued
| Examples | Product | MS m/z [M + H]+ | HPLC Method | Rt min |
|---|---|---|---|---|
| 7.03.081 | 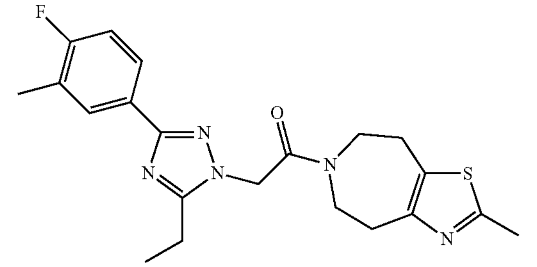 | 414 | method L | 0.74 |
| 7.03.082 | 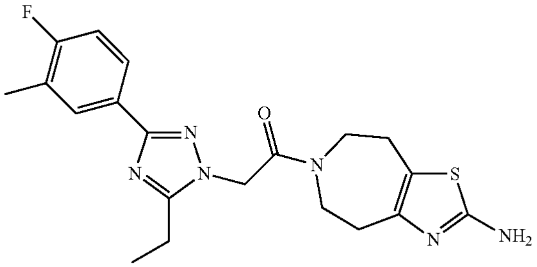 [SMILES: CCc1nc(-c2ccc(F)c(C)c2)nn1CC(=O)N1CCc2nc(N)sc2CC1] | 415 | method L | 0.65 |
| 7.03.083 | 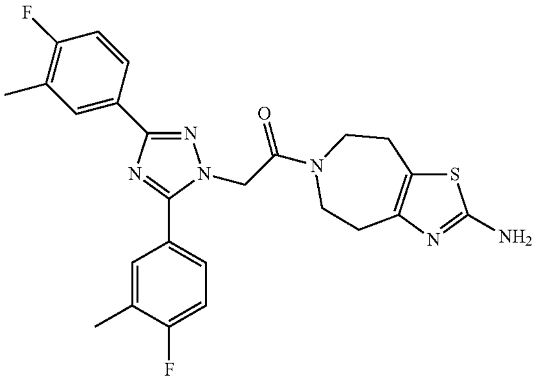 [SMILES: Cc1cc(-c2nc(-c3ccc(F)c(C)c3)n(CC(=O)N3CCc4nc(N)sc4CC3)n2)ccc1F] | 495 | method L | 0.85 |
| 7.03.084 | 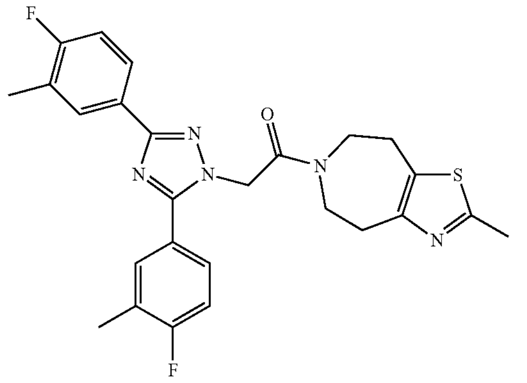 | 494 | method L | 0.94 |

-continued
| Examples | Product | MS m/z $[M + H]^+$ | HPLC Method | Rt min |
|---|---|---|---|---|
| 7.03.085 | 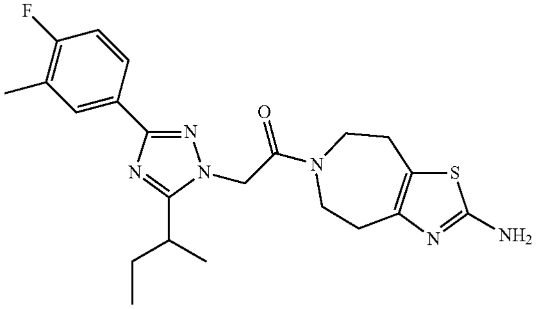 [SMILES: CCC(C)c1nc(-c2ccc(F)c(C)c2)nn1CC(=O)N1CCc2nc(N)sc2CC1] | 443 | method L | 0.84 |
| 7.03.086 | 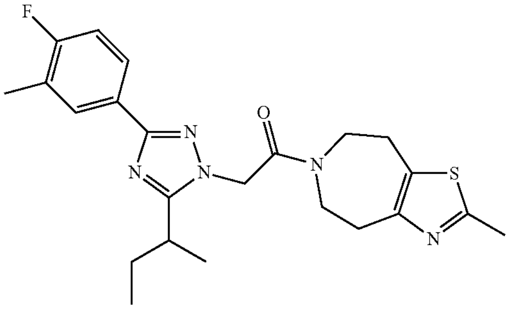 | 442 | method L | 0.90 |
| 7.03.087 | 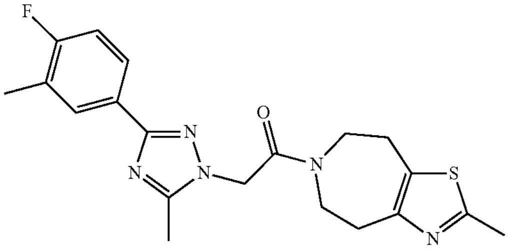 | 400 | method V | 0.74 |
| 7.03.088 | 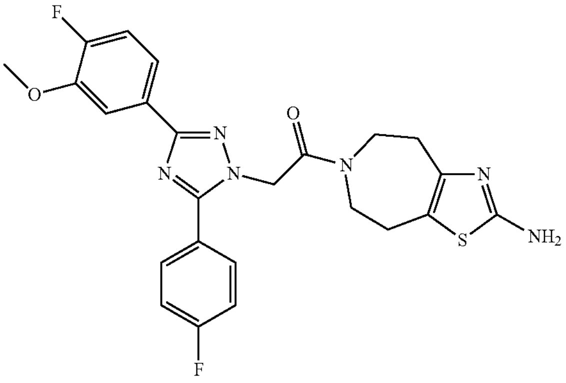 [SMILES: COc1cc(-c2nc(-c3ccc(F)cc3)n(CC(=O)N3CCc4nc(N)sc4CC3)n2)ccc1F] | 497 | method L | 0.78 |

-continued
| Examples | Product | MS m/z [M + H]+ | HPLC Method | Rt min |
|---|---|---|---|---|
| 7.03.089 | 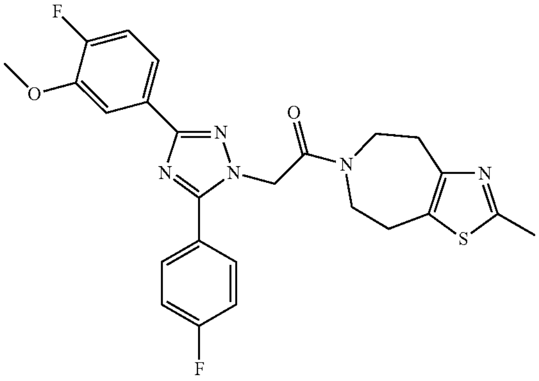 | 496 | method L | 0.87 |
| 7.03.090 | 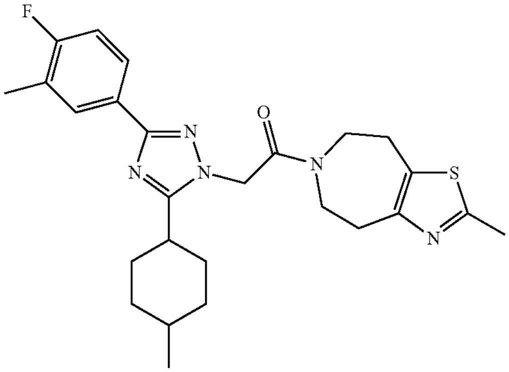 | 482 | method Q | 0.95 |
| 7.03.091 | 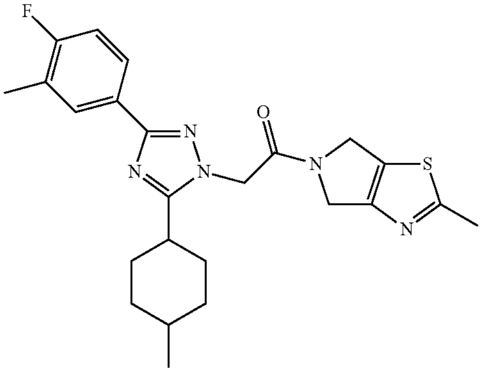 | 454 | method Q | 0.95 |
| 7.03.092 | 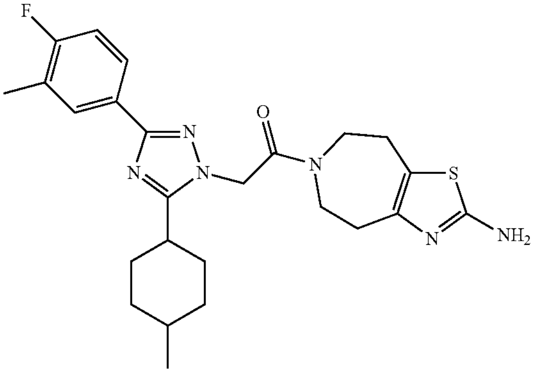 [SMILES: Cc1cc(-c2nc(C3CCC(C)CC3)n(CC(=O)N3CCc4nc(N)sc4CC3)n2)ccc1F] | 483 | method Q | 0.86 |

-continued
| Examples | Product | MS m/z [M + H]+ | HPLC Method | Rt min |
|---|---|---|---|---|
| 7.03.093 | 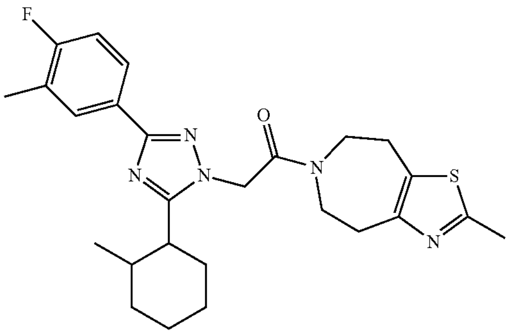 | 482 | method L | 1.01 |
| 7.03.094 | 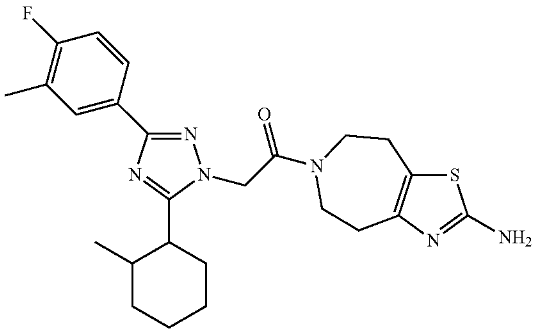 [SMILES: Cc1cc(-c2nc(C3CCCCC3C)n(CC(=O)N3CCc4nc(N)sc4CC3)n2)ccc1F] | 483 | method L | 0.90 |
| 7.03.095 | 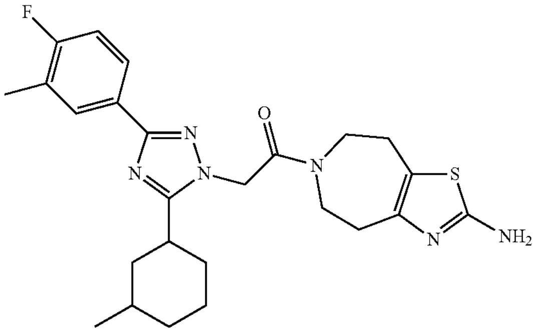 [SMILES: Cc1cc(-c2nc(C3CCCC(C)C3)n(CC(=O)N3CCc4nc(N)sc4CC3)n2)ccc1F] | 483 | method Q | 0.83 |
| 7.03.096 | 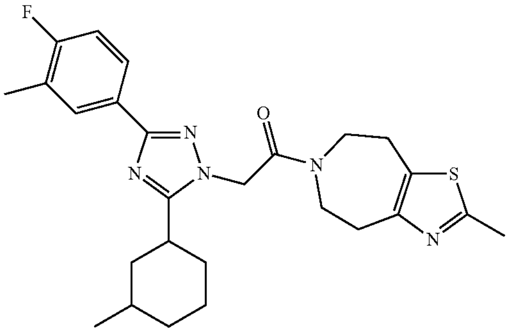 | 482 | method Q | 0.92 |

-continued
| Examples | Product | MS m/z [M + H]$^+$ | HPLC Method | Rt min |
|---|---|---|---|---|
| 7.03.097 | 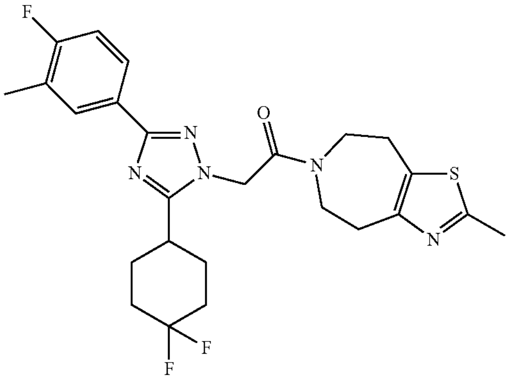 | 504 | method Q | 0.87 |
| 7.03.098 | 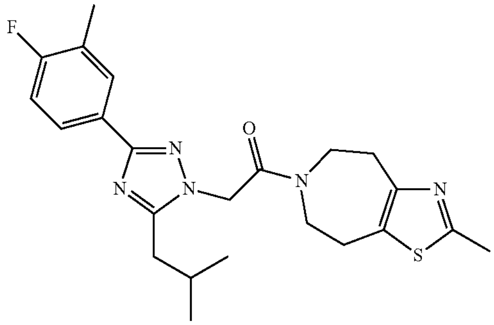 [SMILES: Cc1nc2c(s1)CCN(C(=O)Cn1nc(-c3ccc(F)c(C)c3)nc1CC(C)C)CC2] | 442 | method L | 0.82 |
| 7.03.099 | 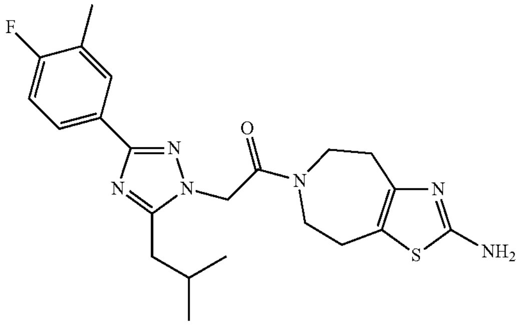 [SMILES: Cc1cc(-c2nc(CC(C)C)n(CC(=O)N3CCc4nc(N)sc4CC3)n2)ccc1F] | 443 | method L | 0.71 |
| 7.03.100 | 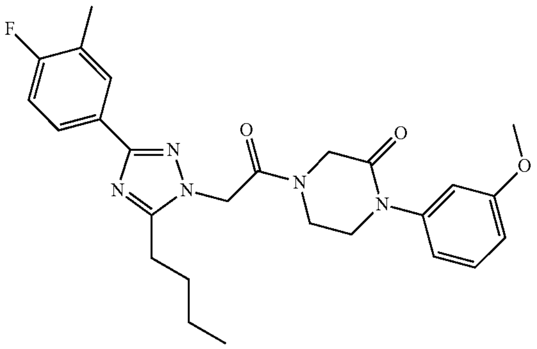 [SMILES: CCCCc1nc(-c2ccc(F)c(C)c2)nn1CC(=O)N1CCN(c2cccc(OC)c2)C(=O)C1] | 480 | method L | 0.86 |

-continued
| Examples | Product | MS m/z $[M + H]^+$ | HPLC Method | Rt min |
|---|---|---|---|---|
| 7.03.101 | 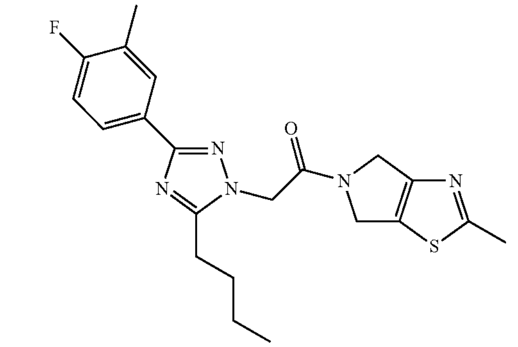 [SMILES: CCCCc1nc(-c2ccc(F)c(C)c2)nn1CC(=O)N1Cc2nc(C)sc2C1] | 414 | method L | 0.87 |
| 7.03.102 | 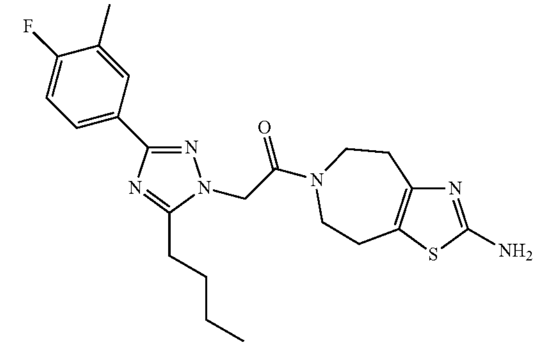 [SMILES: CCCCc1nc(-c2ccc(F)c(C)c2)nn1CC(=O)N1CCc2nc(N)sc2CC1] | 443 | 5.35 (d, 2H, CH2)<br>2.30 (s, 3H, CH3)<br>0.90 (t, 3H,CH3) | |
| 7.03.103 | 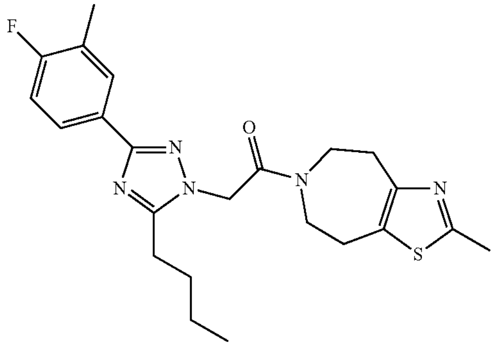 [SMILES: CCCCc1nc(-c2ccc(F)c(C)c2)nn1CC(=O)N1CCc2nc(C)sc2CC1] | 442 | 5.35 (d, 2H, CH2)<br>2.30 (s, 3H, CH3)<br>3.30 (s, 3H, CH3)<br>0.90 (t, 3H, CH3) | |
| 7.03.104 | 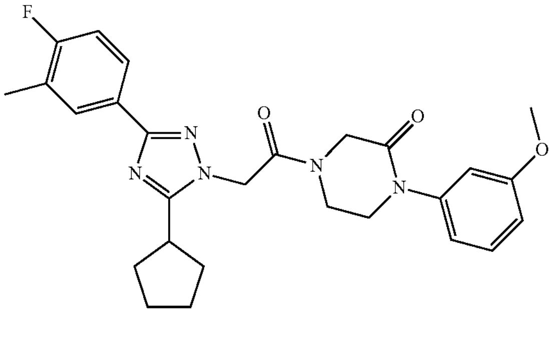 [SMILES: COc1cccc(N2CCN(C(=O)Cn3nc(-c4ccc(F)c(C)c4)nc3C3CCCC3)CC2=O)c1] | 492 | method L | 0.88 |

-continued
| Examples | Product | MS m/z [M + H]+ | HPLC Method | Rt min |
| --- | --- | --- | --- | --- |
| 7.03.105 | 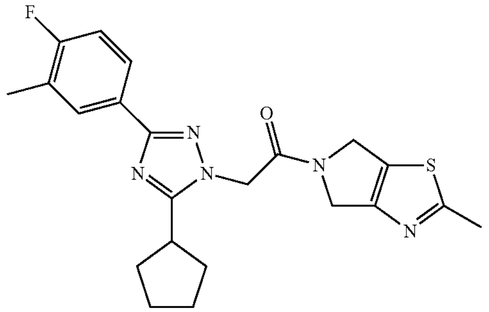 | 426 | method L | 0.88 |
| 7.03.106 | 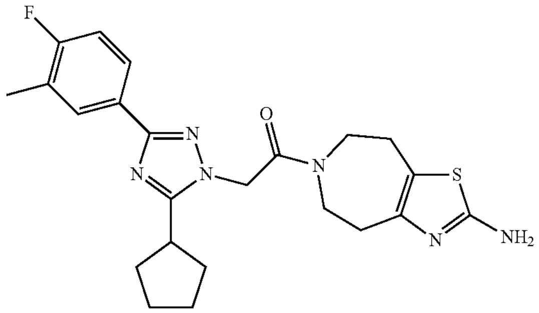 [SMILES: Cc1cc(-c2nc(C3CCCC3)n(CC(=O)N3CCc4nc(N)sc4CC3)n2)ccc1F] | 455 | method L | 0.77 |
| 7.03.107 | 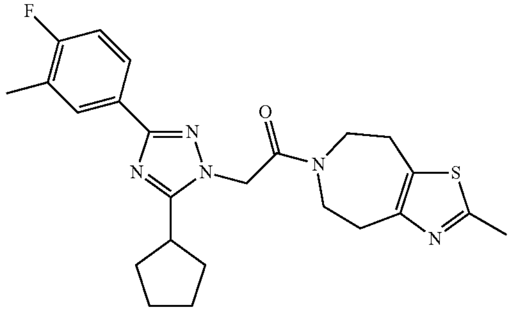 | 454 | method L | 0.86 |
| 7.03.108 | 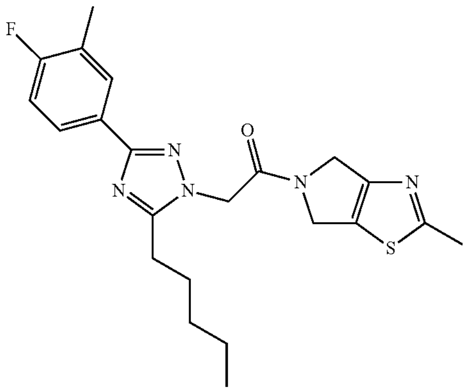 [SMILES: CCCCCc1nc(-c2ccc(F)c(C)c2)nn1CC(=O)N1Cc2nc(C)sc2C1] | 428 | method L | 0.89 |

-continued
| Examples | Product | MS m/z [M + H]$^+$ | HPLC Method | Rt min |
|---|---|---|---|---|
| 7.03.109 | 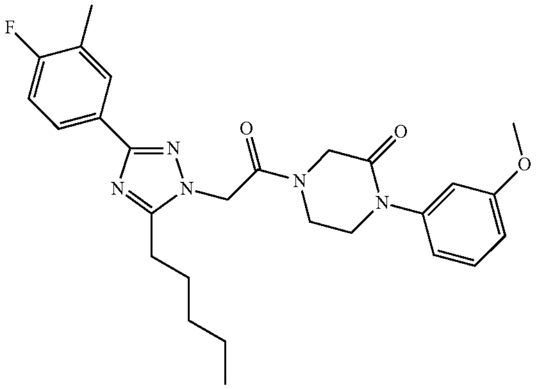 [SMILES: CCCCCc1nc(-c2ccc(F)c(C)c2)nn1CC(=O)N1CCN(c2cccc(OC)c2)C(=O)C1] | 494 | method L | 0.89 |
| 7.03.110 | 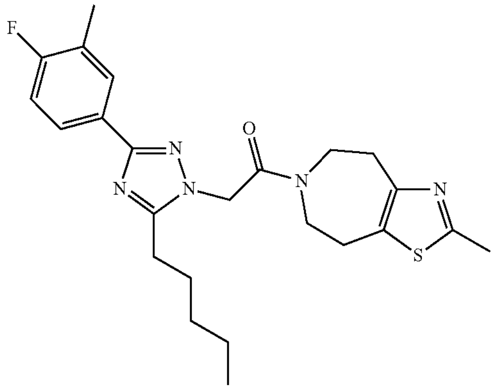 [SMILES: CCCCCc1nc(-c2ccc(F)c(C)c2)nn1CC(=O)N1CCc2nc(C)sc2CC1] | 456 | method L | 0.87 |
| 7.03.111 | 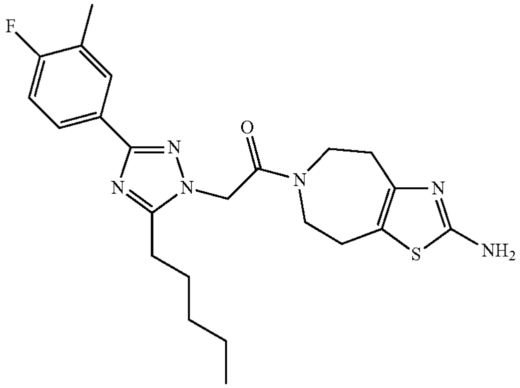 [SMILES: CCCCCc1nc(-c2ccc(F)c(C)c2)nn1CC(=O)N1CCc2nc(N)sc2CC1] | 457 | method L | 0.79 |
| 7.03.112 | 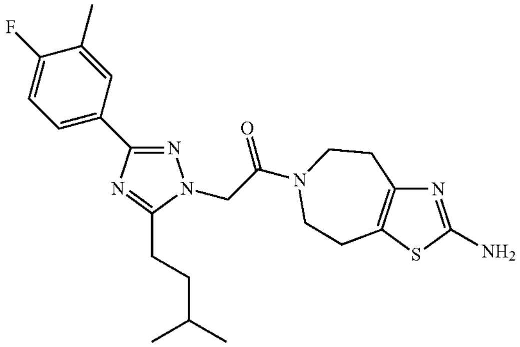 [SMILES: Cc1cc(-c2nc(CCC(C)C)n(CC(=O)N3CCc4nc(N)sc4CC3)n2)ccc1F] | 457 | 5.30 (d, 2H, CH2) 2.30 (s, 3H, CH3) 0.90 (t, 6H, 2/CH3) | |

-continued
| Examples | Product | MS m/z $[M + H]^+$ | HPLC Method | Rt min |
|---|---|---|---|---|
| 7.03.113 | 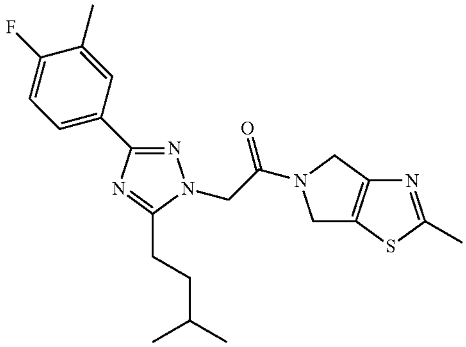 [SMILES: Cc1nc2c(s1)CN(C(=O)Cn1nc(-c3ccc(F)c(C)c3)nc1CCC(C)C)C2] | 428 | method L | 0.92 |
| 7.03.114 | 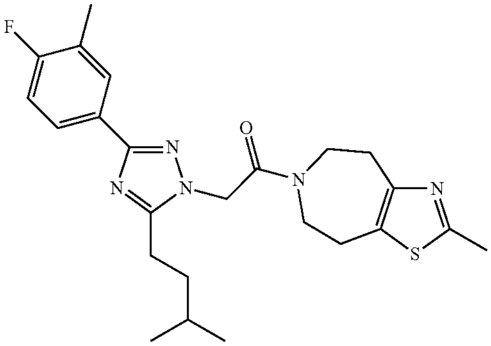 [SMILES: Cc1nc2c(s1)CCN(C(=O)Cn1nc(-c3ccc(F)c(C)c3)nc1CCC(C)C)CC2] | 456 | 5.30 (d, 2H, CH2) 2.30 (s, 3H, CH3) 2.55 (s, 3H, CH3) 0.90 (t, 6H, 2/CH3) | |
| 7.03.115 | 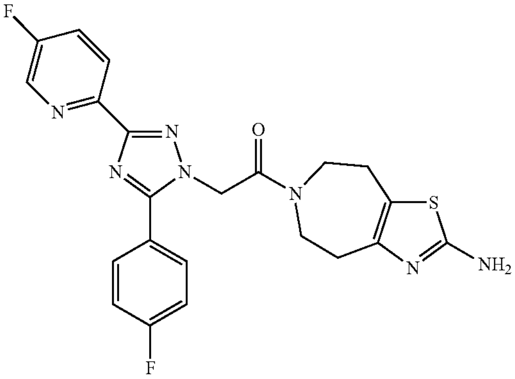 [SMILES: Nc1nc2c(s1)CCN(C(=O)Cn1nc(-c3ccc(F)cn3)nc1-c1ccc(F)cc1)CC2] | 468 | method S | 0.58 |
| 7.03.116 | 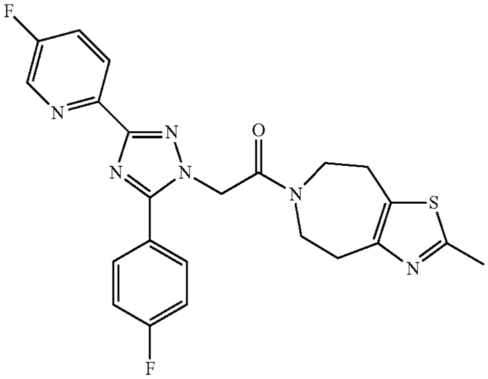 [SMILES: Cc1nc2c(s1)CCN(C(=O)Cn1nc(-c3ccc(F)cn3)nc1-c1ccc(F)cc1)CC2] | 467 | method Y | 0.99 |

-continued
| Examples | Product | MS m/z [M + H]+ | HPLC Method | Rt min |
|---|---|---|---|---|
| 7.03.117 | 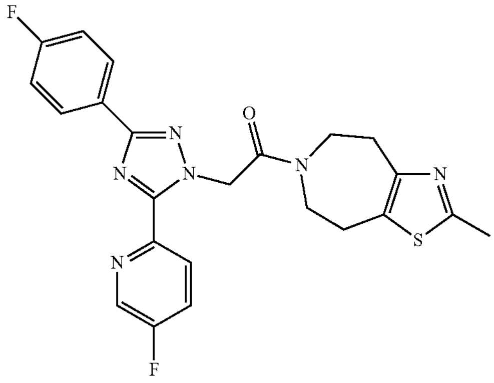 [SMILES: Cc1nc2c(s1)CCN(C(=O)Cn1nc(-c3ccc(F)cc3)nc1-c1ccc(F)cn1)CC2] | 467 | method Y | 1.22 |
| 7.03.118 | 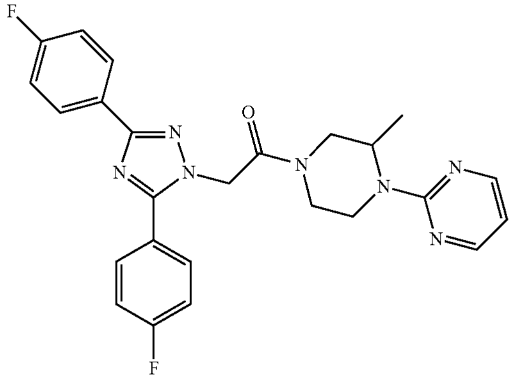 [SMILES: CC1CN(C(=O)Cn2nc(-c3ccc(F)cc3)nc2-c2ccc(F)cc2)CCN1c1ncccn1] | 476 | method B | 1.36 |
| 7.03.119 | 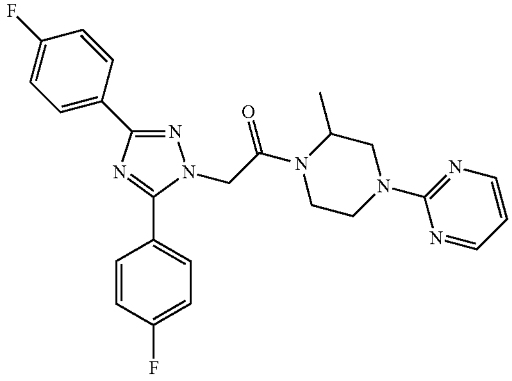 [SMILES: CC1CN(c2ncccn2)CCN1C(=O)Cn1nc(-c2ccc(F)cc2)nc1-c1ccc(F)cc1] | 476 | method B | 1.36 |
| 7.03.121 | 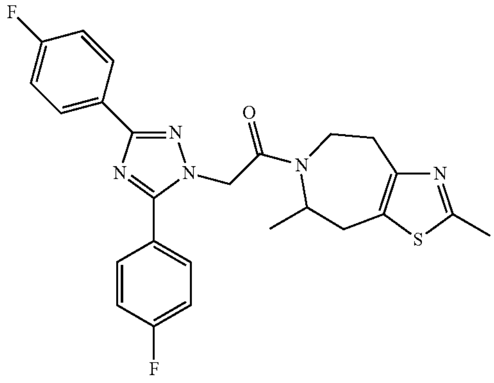 [SMILES: Cc1nc2c(s1)CC(C)N(C(=O)Cn1nc(-c3ccc(F)cc3)nc1-c1ccc(F)cc1)CC2] | 480 | method L | 0.78 |

-continued
| Examples | Product | MS m/z [M + H]+ | HPLC Method | Rt min |
|---|---|---|---|---|
| 7.03.122 | 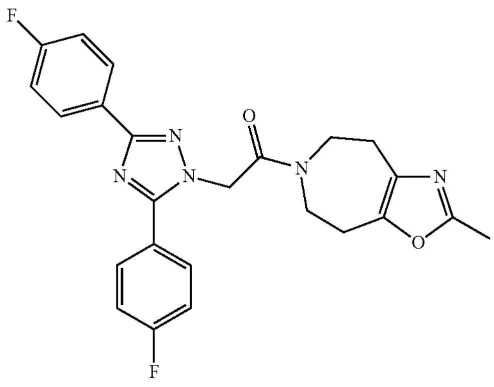 [SMILES: Cc1nc2c(o1)CCN(C(=O)Cn1nc(-c3ccc(F)cc3)nc1-c1ccc(F)cc1)CC2] | 450 | method L | 0.77 |
| 7.03.123 | 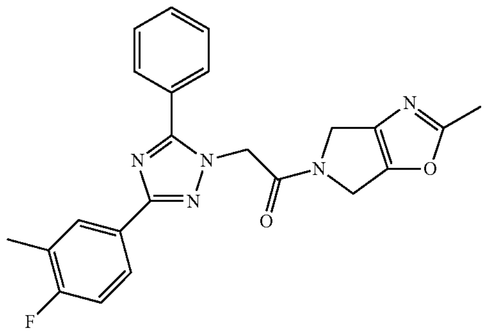 | 418 | method V | 0.87 |
| 7.03.124 | 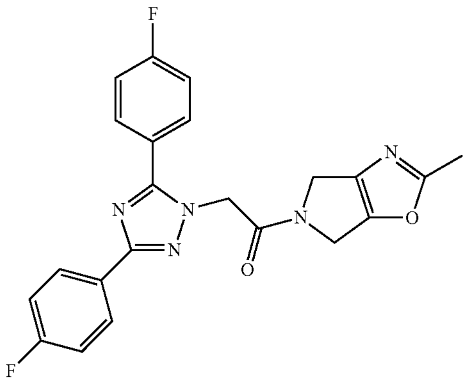 [SMILES: Cc1nc2c(o1)CN(C(=O)Cn1nc(-c3ccc(F)cc3)nc1-c1ccc(F)cc1)C2] | 422 | method V | 0.84 |
| 7.03.125 | 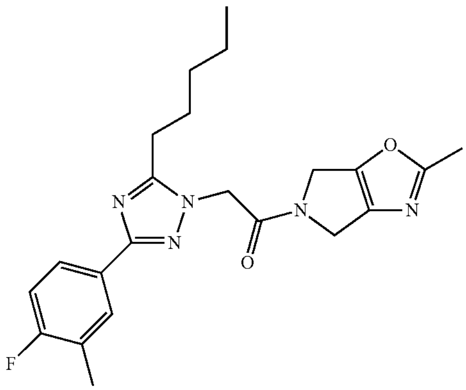 [SMILES: CCCCCc1nc(-c2ccc(F)c(C)c2)nn1CC(=O)N1Cc2nc(C)oc2C1] | 412 | method V | 0.93 |

-continued
| Examples | Product | MS m/z [M + H]+ | HPLC Method | Rt min |
|---|---|---|---|---|
| 7.03.126 | 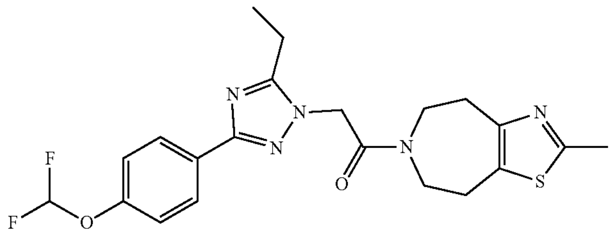 [SMILES: CCc1nc(-c2ccc(OC(F)F)cc2)nn1CC(=O)N1CCc2nc(C)sc2CC1] | 448 | method V | 0.74 |
| 7.03.127 | 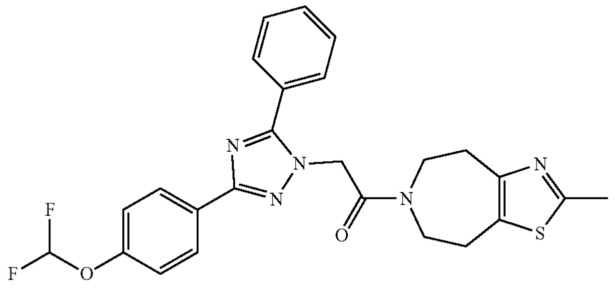 [SMILES: Cc1nc2c(s1)CCN(C(=O)Cn1nc(-c3ccc(OC(F)F)cc3)nc1-c1ccccc1)CC2] | 496 | method V | 0.81 |
| 7.03.128 | 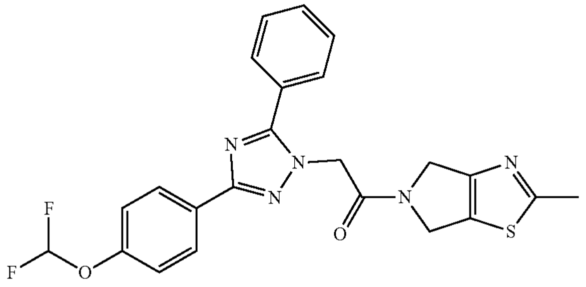 [SMILES: Cc1nc2c(s1)CN(C(=O)Cn1nc(-c3ccc(OC(F)F)cc3)nc1-c1ccccc1)C2] | 468 | method V | 0.85 |
| 7.03.129 | 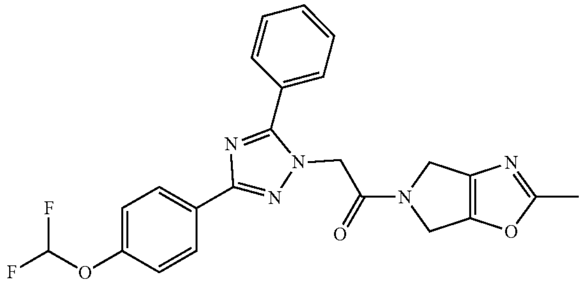 | 452 | method V | 0.83 |
| 7.03.130 | 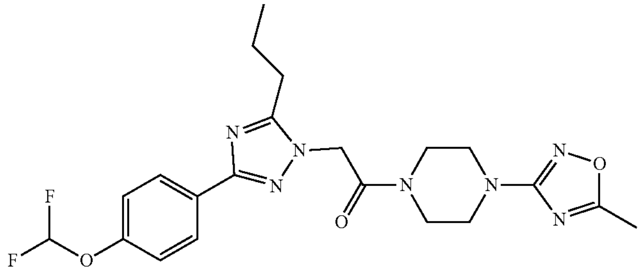 [SMILES: CCCc1nc(-c2ccc(OC(F)F)cc2)nn1CC(=O)N1CCN(c2noc(C)n2)CC1] | 462 | method V | 0.83 |

-continued
| Examples | Product | MS m/z [M + H]+ | HPLC Method | Rt min |
|---|---|---|---|---|
| 7.03.131 | 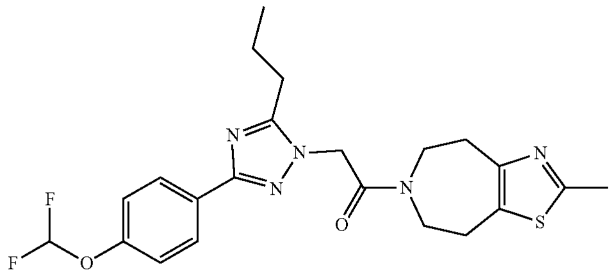 [SMILES: CCCc1nc(-c2ccc(OC(F)F)cc2)nn1CC(=O)N1CCc2nc(C)sc2CC1] | 462 | method V | 0.82 |
| 7.03.132 | 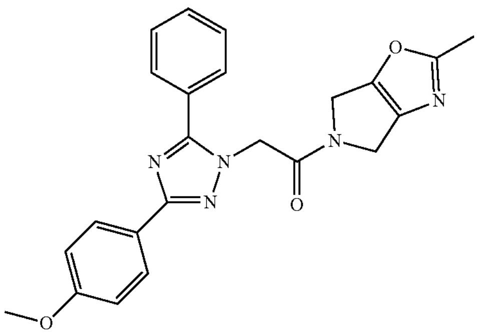 | 416 | method V | 0.76 |
| 7.03.133 | 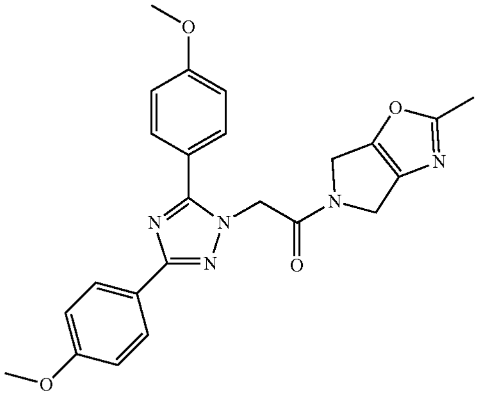 | 446 | method F | 0.65 |
| 7.03.134 | 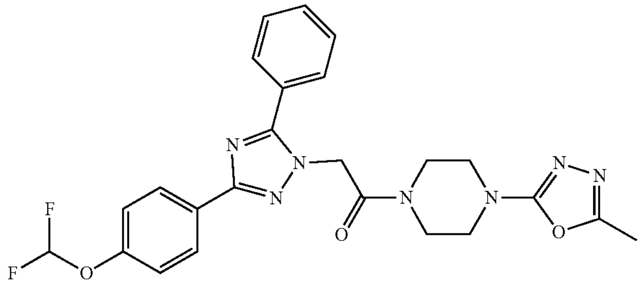 [SMILES: Cc1nnc(N2CCN(C(=O)Cn3nc(-c4ccc(OC(F)F)cc4)nc3-c3ccccc3)CC2)o1] | 496 | method V | 0.79 |

-continued
| Examples | Product | MS m/z [M + H]+ | HPLC Method | Rt min |
|---|---|---|---|---|
| 7.03.135 | 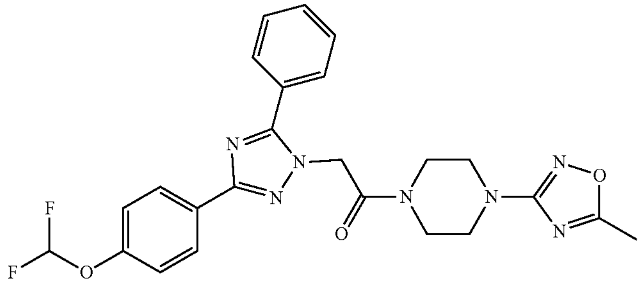 [SMILES: Cc1nc(N2CCN(C(=O)Cn3nc(-c4ccc(OC(F)F)cc4)nc3-c3ccccc3)CC2)no1] | 496 | method V | 0.83 |
| 7.03.136 | 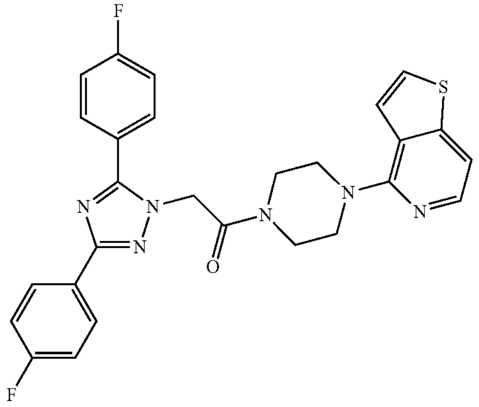 [SMILES: O=C(Cn1nc(-c2ccc(F)cc2)nc1-c1ccc(F)cc1)N1CCN(c2nccc3sccc23)CC1] | 517 | method D | 2.01 |
| 7.03.137 | 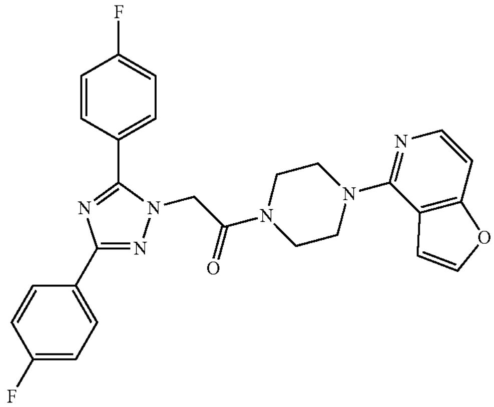 [SMILES: O=C(Cn1nc(-c2ccc(F)cc2)nc1-c1ccc(F)cc1)N1CCN(c2nccc3occc23)CC1] | 501 | method D | 2.00 |
| 7.03.138 | 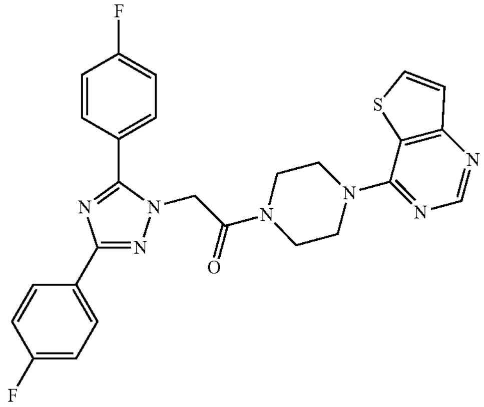 [SMILES: O=C(Cn1nc(-c2ccc(F)cc2)nc1-c1ccc(F)cc1)N1CCN(c2ncnc3ccsc23)CC1] | 518 | Method N | 1.83 |

-continued
| Examples | Product | MS m/z [M + H]+ | HPLC Method | Rt min |
|---|---|---|---|---|
| 7.03.139 | 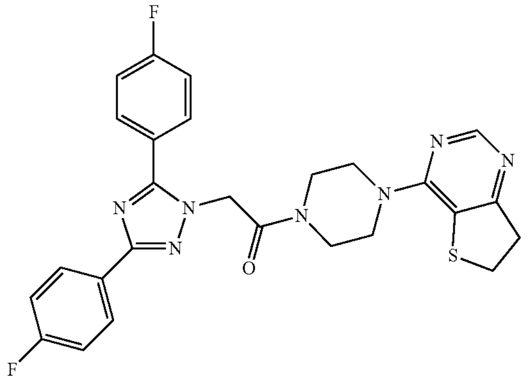 [SMILES: O=C(Cn1nc(-c2ccc(F)cc2)nc1-c1ccc(F)cc1)N1CCN(c2ncnc3c2SCC3)CC1] | 518 | Method K | 2.54 |
| 7.03.140 | 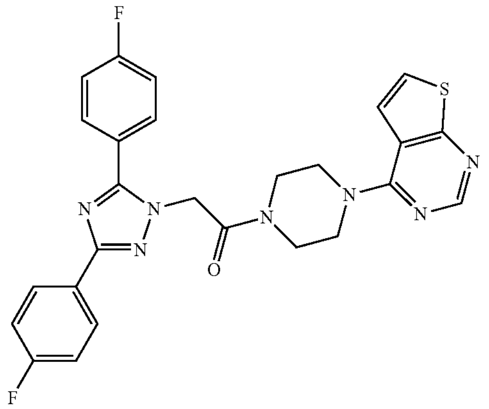 [SMILES: O=C(Cn1nc(-c2ccc(F)cc2)nc1-c1ccc(F)cc1)N1CCN(c2ncnc3sccc23)CC1] | 518 | Method N | 1.83 |
| 7.03.141 | 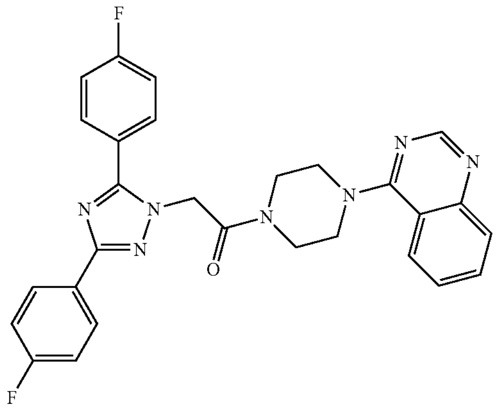 [SMILES: O=C(Cn1nc(-c2ccc(F)cc2)nc1-c1ccc(F)cc1)N1CCN(c2ncnc3ccccc23)CC1] | 512 | Method N | 1.84 |

7.04.01. 2-[3,5-bis-(4-Fluoro-phenyl)-(1,2,4)triazol-1-yl)-1-(2-pyrrolidin-1-yl-4,5,7,8-tetrahydro-thiazolo[4,5-d]azepin-6-yl)-ethanone

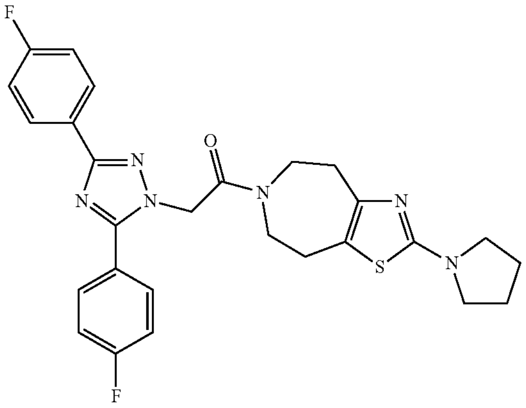 [SMILES: O=C(Cn1nc(-c2ccc(F)cc2)nc1-c1ccc(F)cc1)N1CCc2nc(N3CCCC3)sc2CC1]

37 mg 1-(2-bromo-4,5,7,8-tetrahydro-thiazolo[4,5-d]azepin-6-yl)-2-(5-(4-fluoro-phenyl)-3-p-tolyl-(1,2,4)triazol-1-yl)-ethanone and 29 μl pyrrolidine in 1 mL N-methyl-pyrrolidinon were stirred for 10 min at 100° C. in a microwave. The mixture was purified by HPLC to yield 26 mg of the desired product. $R_t$: 1.70 (method I), $(M+H)^+$: 521

By using the same synthesis strategy as for 2-[3,5-bis-(4-fluoro-phenyl)-(1,2,4)triazol-1-yl)-1-(2-pyrrolidin-1-yl-4,5,7,8-tetrahydro-thiazolo[4,5-d]azepin-6-yl)-ethanone the following compounds were obtained:

| Examples | Product | MS m/z $[M+H]^+$ | HPLC Method | Rt min |
|---|---|---|---|---|
| 7.04.02 | 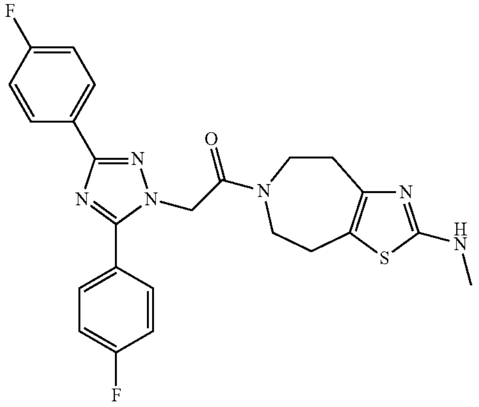 [SMILES: CNc1nc2c(s1)CCN(C(=O)Cn1nc(-c3ccc(F)cc3)nc1-c1ccc(F)cc1)CC2] | 481 | method I | 1.68 |
| 7.04.03 | 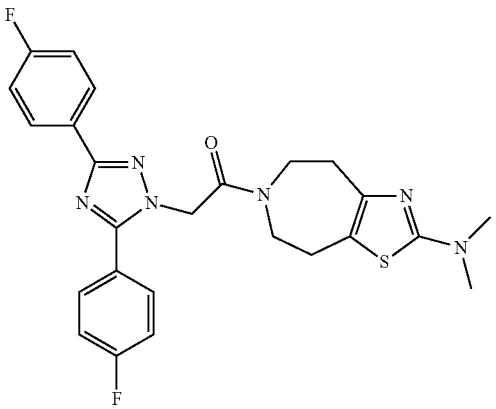 [SMILES: CN(C)c1nc2c(s1)CCN(C(=O)Cn1nc(-c3ccc(F)cc3)nc1-c1ccc(F)cc1)CC2] | 495 | method I | 1.66 |

-continued

| Examples | Product | MS m/z [M + H]+ | HPLC Method | Rt min |
|---|---|---|---|---|
| 7.04.04 | 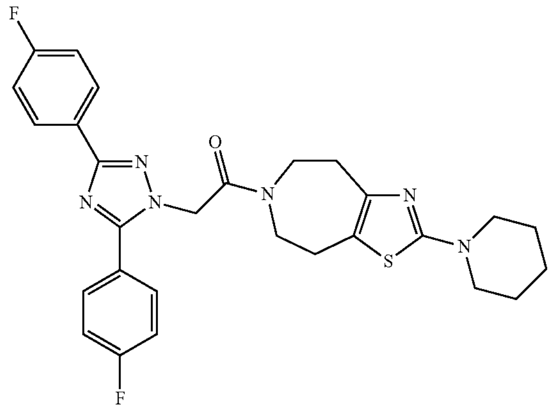 [SMILES: O=C(Cn1nc(-c2ccc(F)cc2)nc1-c1ccc(F)cc1)N1CCc2nc(N3CCCCC3)sc2CC1] | 535 | method I | 1.79 |
| 7.04.05 | 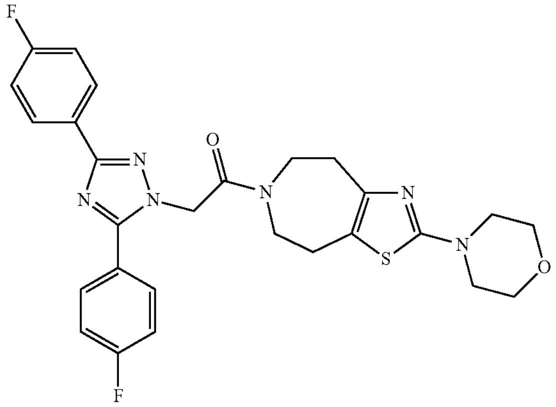 [SMILES: O=C(Cn1nc(-c2ccc(F)cc2)nc1-c1ccc(F)cc1)N1CCc2nc(N3CCOCC3)sc2CC1] | 537 | method I | 1.79 |

7.05.01 2-(3,5-bis-(4-Fluoro-phenyl)-(1,2,4)triazol-1-yl]-1-[4-(5,6-dihydro-4H-(1,3) thiazin-2-yl)-piperazin-1-yl]-ethanone

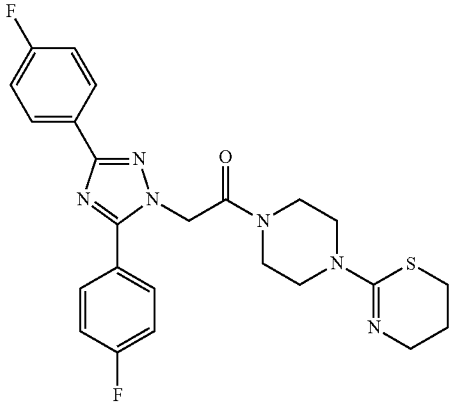 [SMILES: O=C(Cn1nc(-c2ccc(F)cc2)nc1-c1ccc(F)cc1)N1CCN(C2=NCCCS2)CC1]

0.08 mL 1-bromo-3-isothiocyanato-propane and 305 mg sodium carbonate were added to 250 mg 2-(3,5-Bis-(4-fluoro-phenyl)-(1,2,4)triazol-1-yl)-1-piperazin-1-yl-ethanone in 5 mL chloroform. The reaction was stirred over night at 60° C. The reaction was filtered over silicagel and the solvent was evaporated. The residue was crystallized from diethylether to yield 206 mg of the desired compound. $R_t$: 1.17 min (method B), $(M+H)^+$: 483

7.06.01. 2-(3,5-bis-(4-Fluoro-phenyl)-(1,2,4)triazol-1-yl]-1-(4,5,7,8-tetrahydro-thiazolo[4,5-d]azepin-6-yl)-ethanone

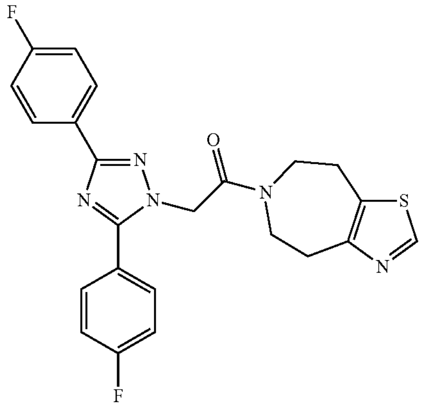 [SMILES: O=C(Cn1nc(-c2ccc(F)cc2)nc1-c1ccc(F)cc1)N1CCc2ncsc2CC1]

32 mg (3,5-bis-(4-fluoro-phenyl)-(1,2,4)triazol-1-yl)-acetic acid was dissolved in 1.5 mL DMF. 32 mg HATU and 15 µL triethylamine were added to this solution and the mixture was stirred for 5 min. at RT. Then, 15 mg 5,6,7,8-tetrahydro-4H-thiazolo[4,5-d]azepine and 15 μL triethylamine in 0.5 mL DMF were added. The mixture was stirred over night at RT. The reaction solution was purified by HPLC to yield 23 mg of the desired compound.

$R_t$: 0.44 (method T), $(M+H)^+$: 452

The invention claimed is:

1. A compound of formula I

I

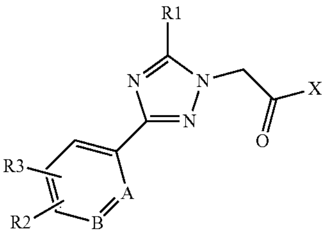

in which

A and B independently represent CH or N;

$R^1$ represents phenyl, $C_{1-5}$alkyl or $C_{3-6}$cycloalkyl which are optionally substituted with one or more substituents selected from fluoro, $C_{1-3}$alkyl and —O—$C_{1-3}$alkyl;

$R^2$ and $R^3$ independently represent —H, halogen, —CN, —COO—$C_{1-4}$alkyl, $C_{1-5}$alkyl, $C_{3-5}$cycloalkyl or —O—$C_{1-5}$alkyl which latter four groups are optionally substituted with one or more fluorine atoms;

X represents

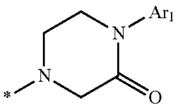 , 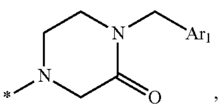 ,

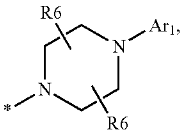 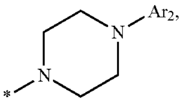

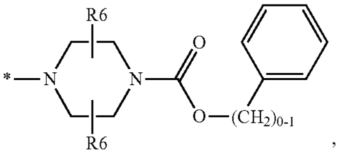 , 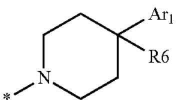 ,

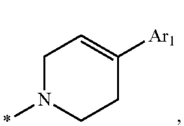 , 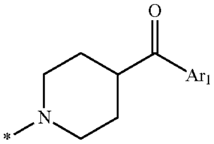 ,

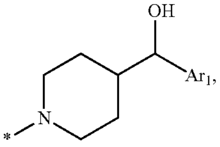 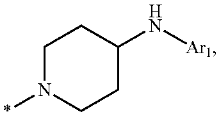

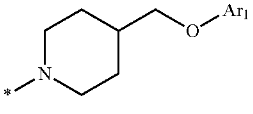 , 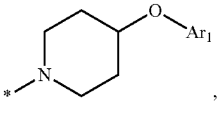 ,

-continued

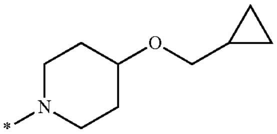 , 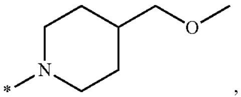 ,

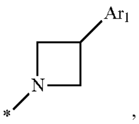 , 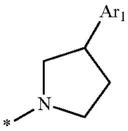 , 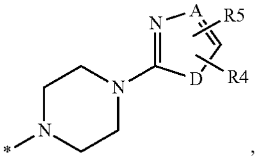 ,

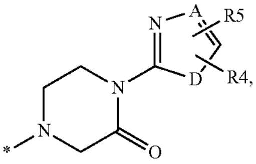 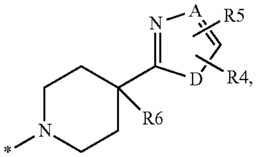

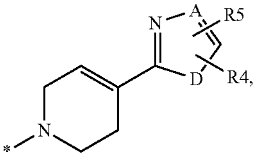 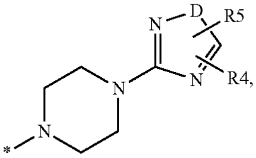

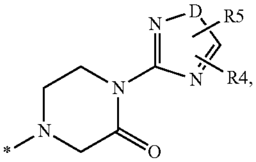 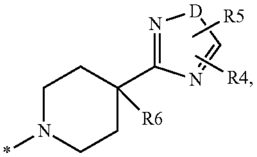

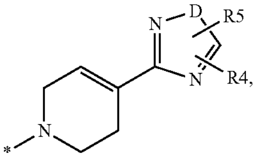

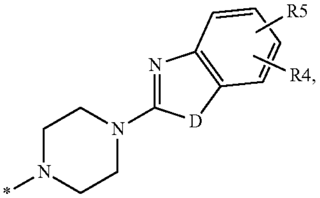

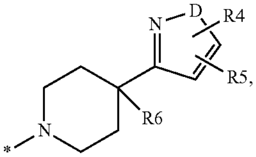

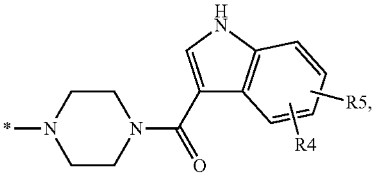

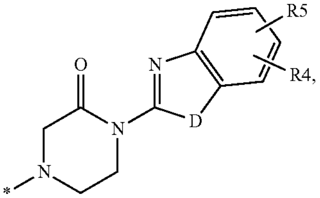

-continued
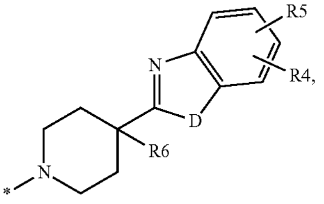
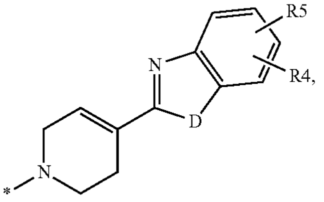
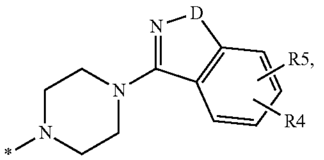
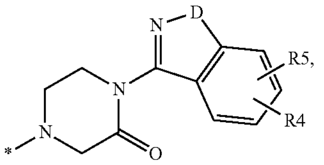
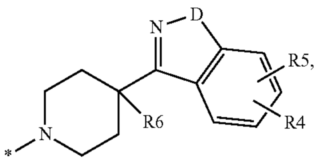
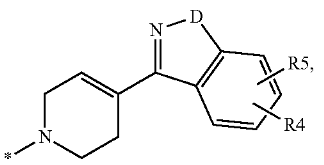
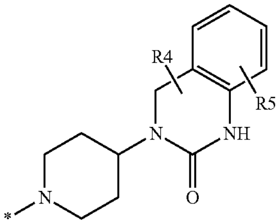
,
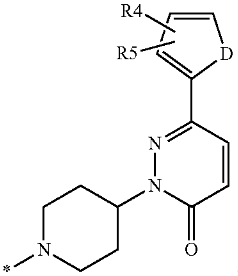
,
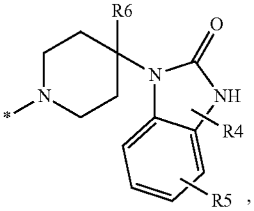
,
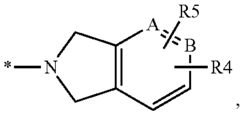
,
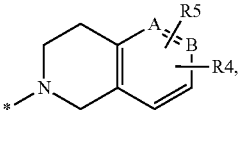
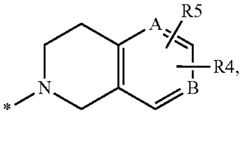
-continued
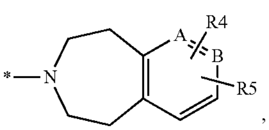
,
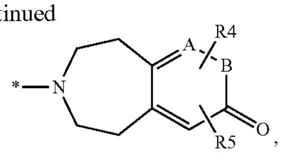
,
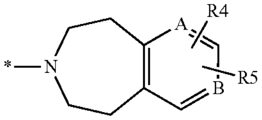
,
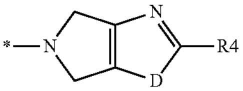
,
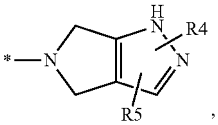
,
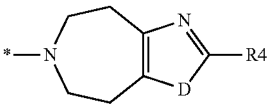
,
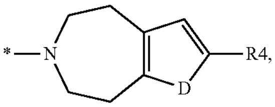
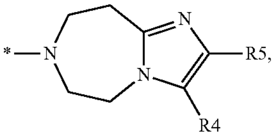
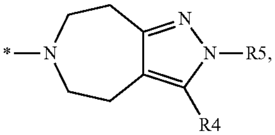
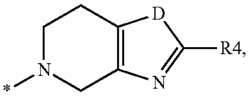
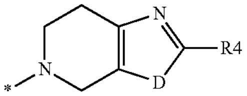
or
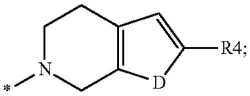
$Ar_1$ represents
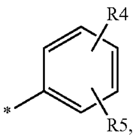
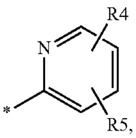
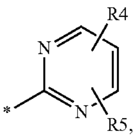
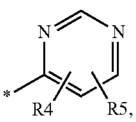
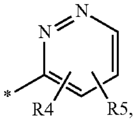
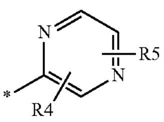
,
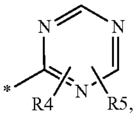
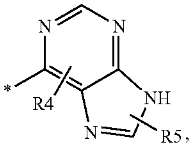
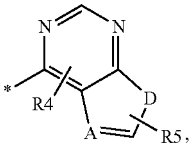
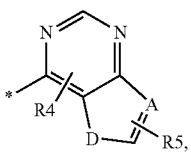
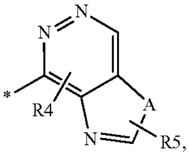
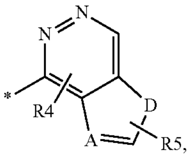
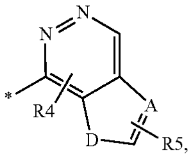
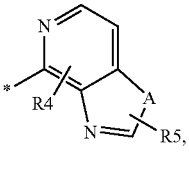
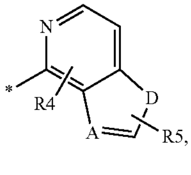

-continued

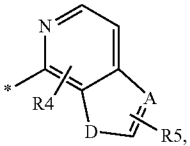
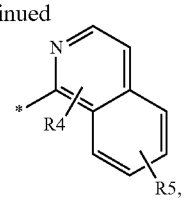
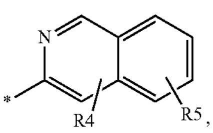
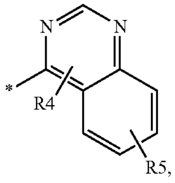
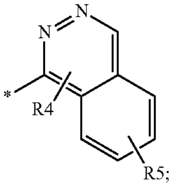

$Ar_2$ represents

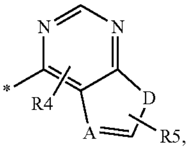
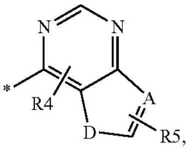
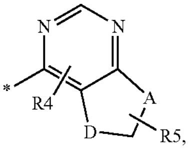
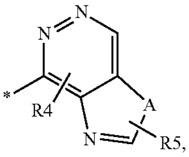
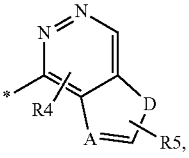
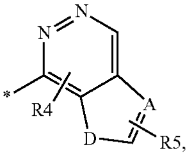
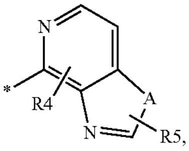
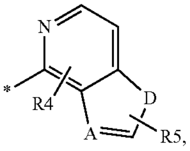
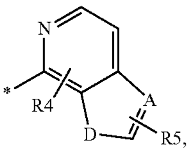
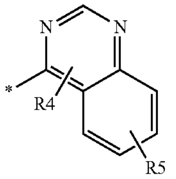

or

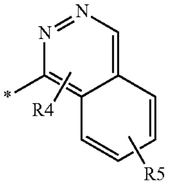

D represents S or O;

$R^4$ and $R^5$ independently represent —H, halogen, —OH, —CN, —$NH_2$, $C_{1-5}$alkyl, 3-7 membered heterocycloalkyl, phenyl, —NH-phenyl, —NH—$C_{1-5}$alkyl, —N($C_{1-5}$alkyl)$_2$, —O—$C_{1-5}$alkyl, —COO—$C_{1-5}$alkyl, —CONH($C_{1-5}$alkyl), —CON($C_{1-5}$alkyl)$_2$, —NH-CONH—$C_{1-5}$alkyl, —NHCON($C_{1-5}$alkyl)$_2$, —NH-CONH—$C_{3-5}$alkenyl, —NHCON($C_{3-5}$alkenyl)$_2$ or —NHCO—$C_{1-5}$alkyl which latter fifteen groups are optionally substituted with one or more substituents selected from halogen, —OH;

or together with the the aromatic ring they are attached to form an 1,3-dioxolane ring;

$R^6$ represents —H or $C_{1-3}$alkyl;

or a physiologically acceptable salt thereof.

2. The compound according to claim 1, wherein

X represents

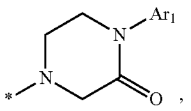
,
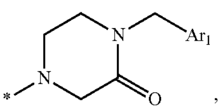
,
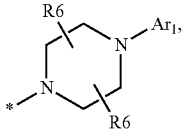
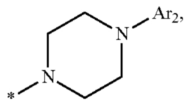
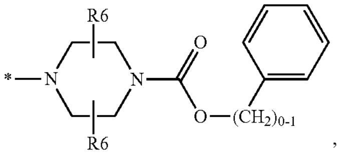
,
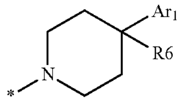
,
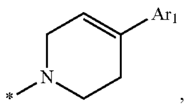
,
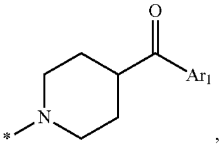
,
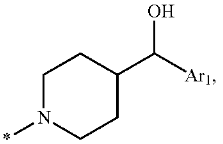
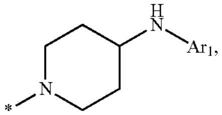
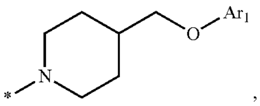
,
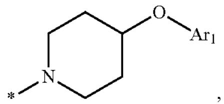
,
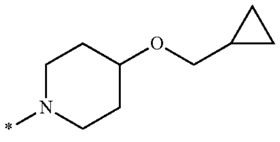
,
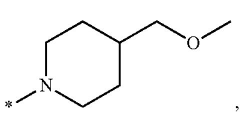
,
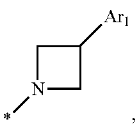
,
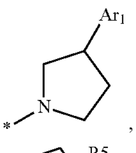
,
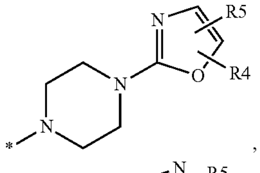
,
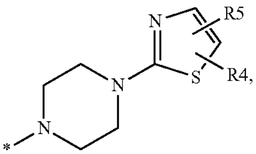
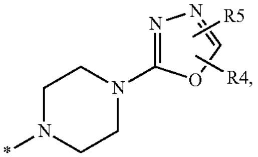

-continued
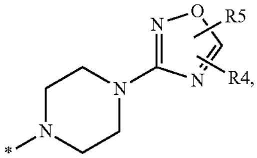
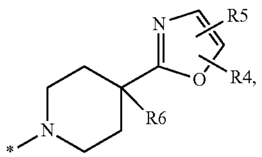
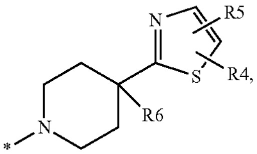
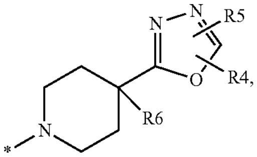
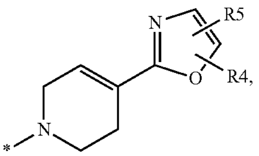
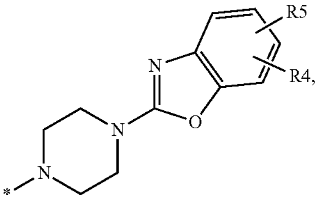
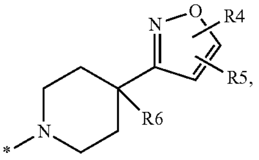
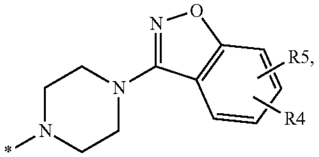
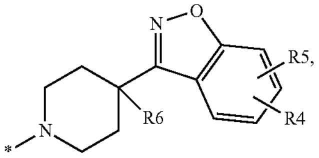
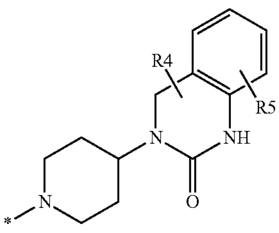
,
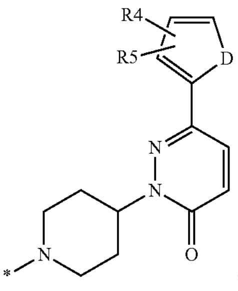
,
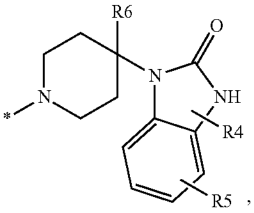
,
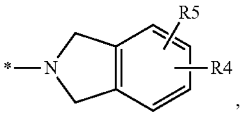
,
-continued
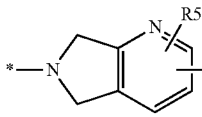
,
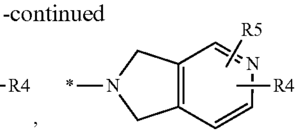
,
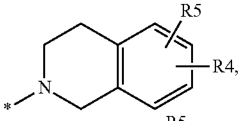
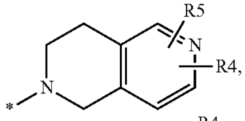
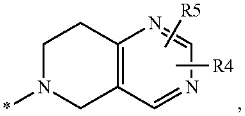
,
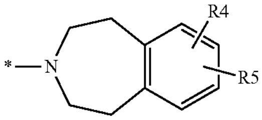
,
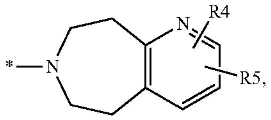
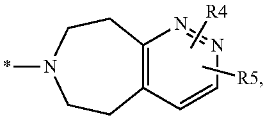
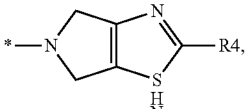
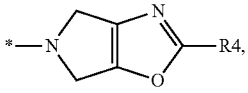
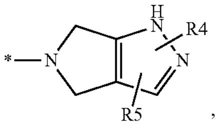
,
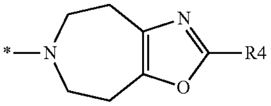
,
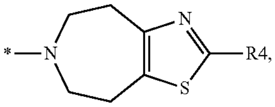
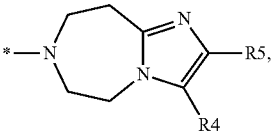
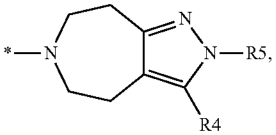
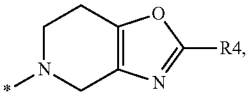
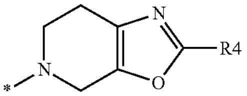
or
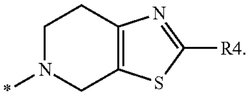
3. The compound according to claim 2, wherein $Ar_1$ represents
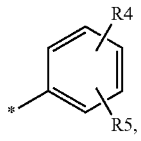
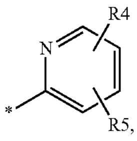
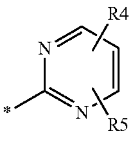
or
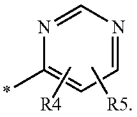
4. The compound according to claim 3, wherein $Ar_2$ represents
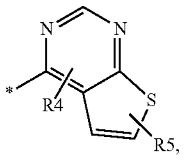
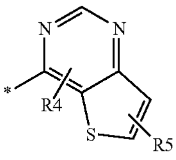
or -continued

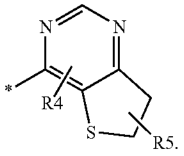

5. The compound according to claim 4, wherein the group

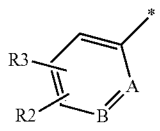

represents phenyl or 2-pyridyl which latter two groups are optionally substituted with one or more substituents selected from fluoro, chloro, bromo, —CN, $C_{1-3}$alkyl, $C_{3-5}$cycloalkyl, —O—$C_{1-3}$alkyl and —COO—$C_{1-4}$alkyl which latter four groups are optionally substituted with one or more fluorine atoms.

6. The compound according to claim 5, wherein $R^1$ represents phenyl, methyl, ethyl, propyl, iso-propyl, butyl, pentyl, cyclopentyl, cyclohexyl,

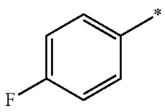 , 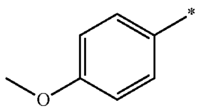 ,

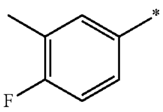 , 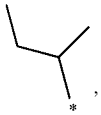 , 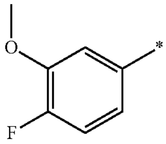 ,

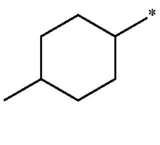 , 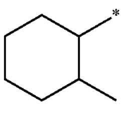 , 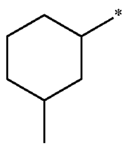 ,

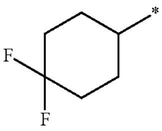 , 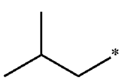 or 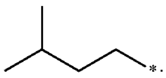.

7. The compound according to claim 6, wherein

X represents

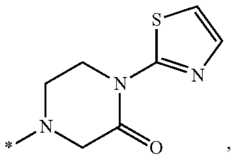 , 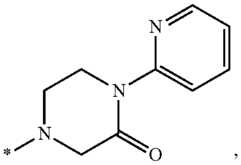 ,

-continued

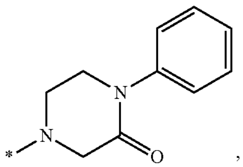 , 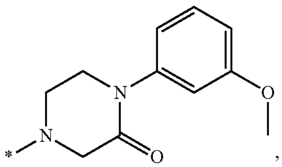 ,

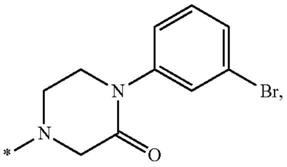 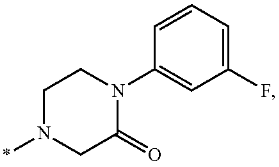

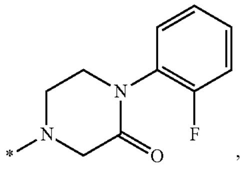 , 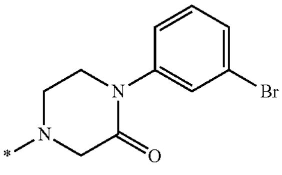 ,

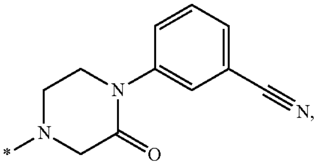

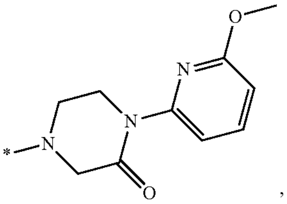 , 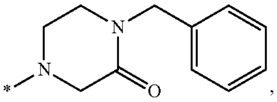 ,

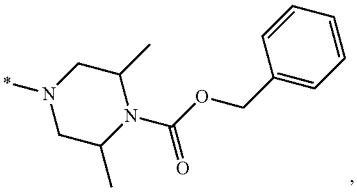 ,

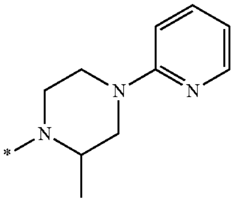 , 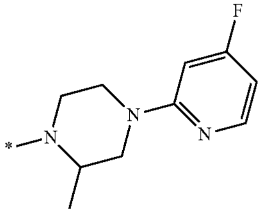 ,

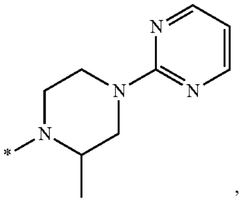 , 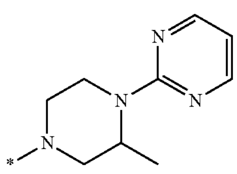 ,

-continued
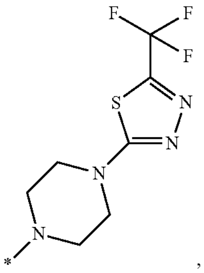,
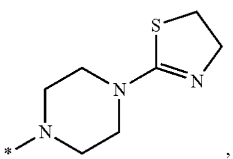,
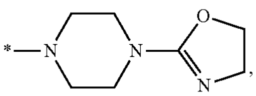,
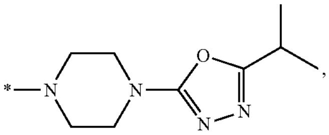,
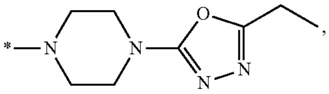,
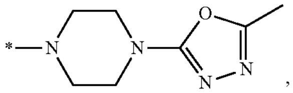,
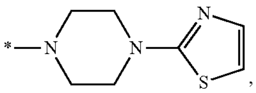,
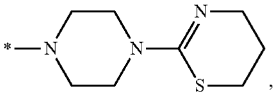,
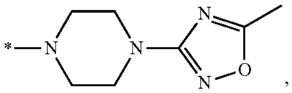,
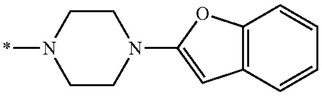,
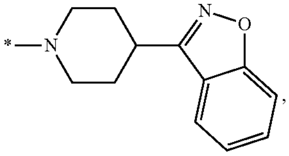,
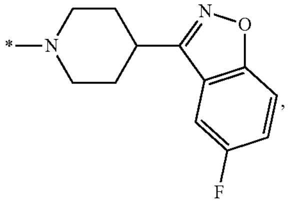,
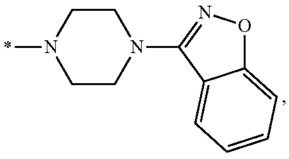,
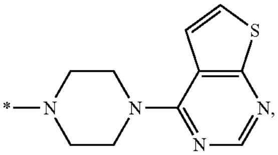,
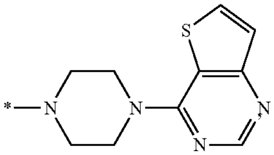,
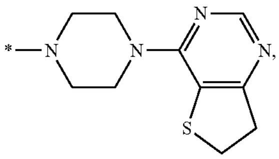
-continued
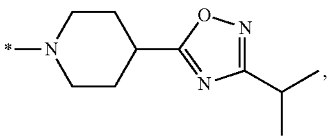,
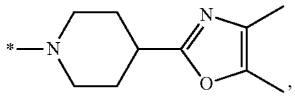,
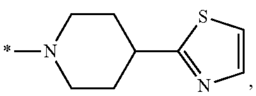,
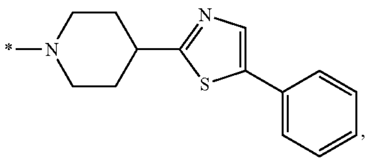,
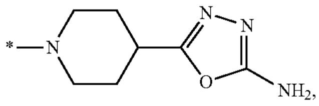,
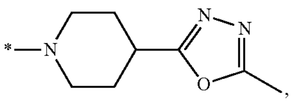,
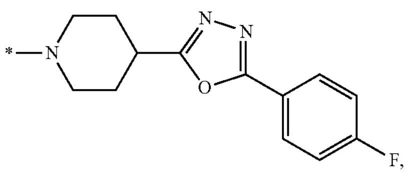,
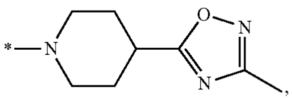,
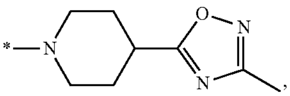,
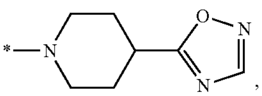,
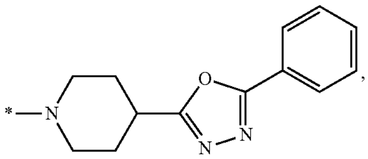,
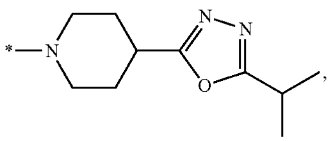,
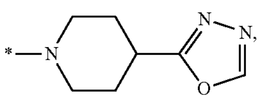,
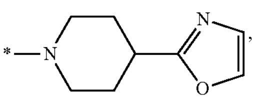,
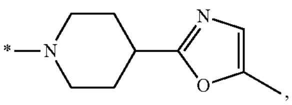,
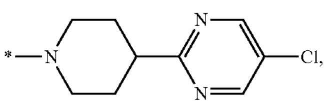,
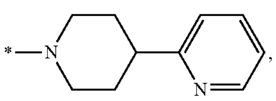,
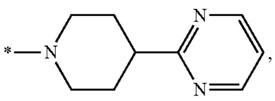, -continued
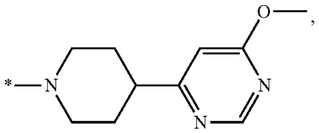
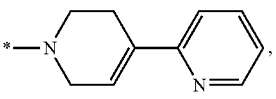
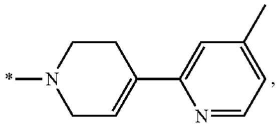
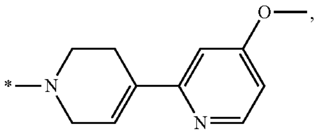
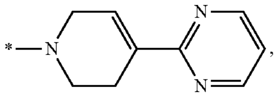
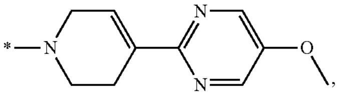
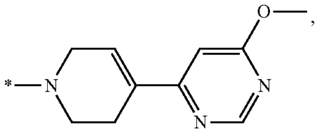
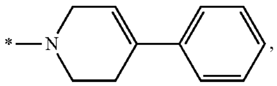
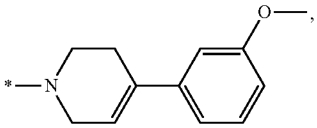
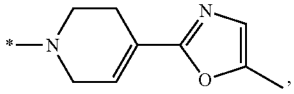
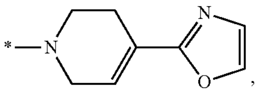
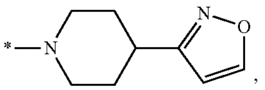
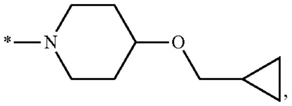
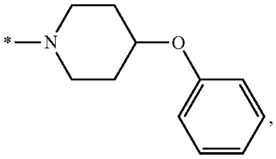
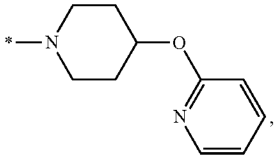
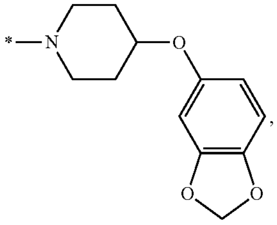
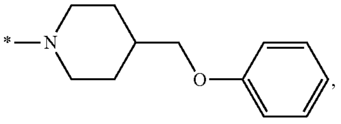
-continued
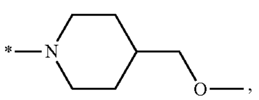
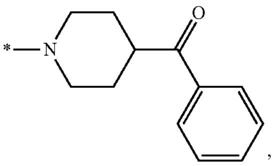
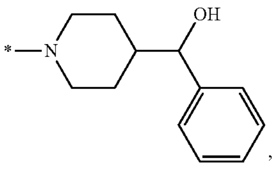
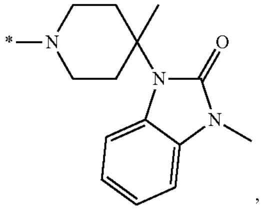
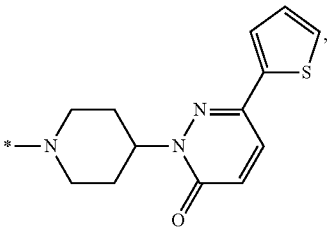
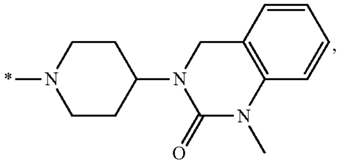
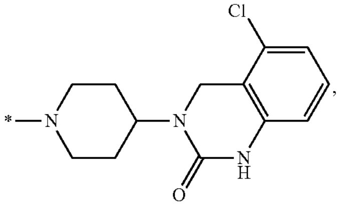
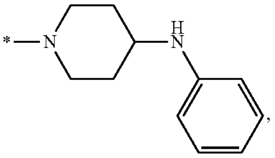
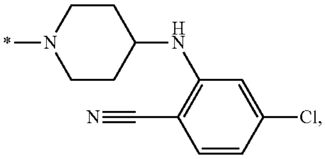
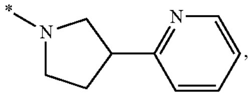
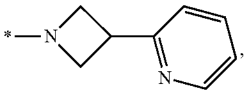
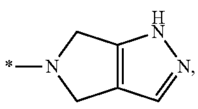
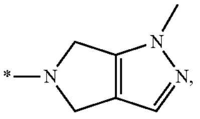
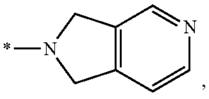
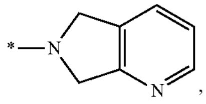

-continued
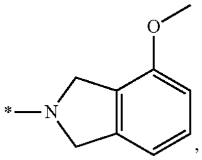, 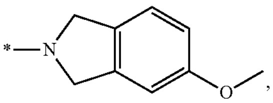,
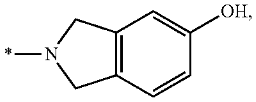
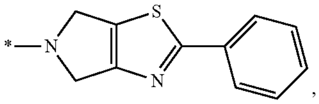, 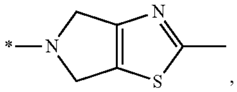,
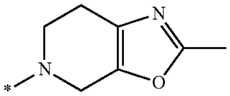, 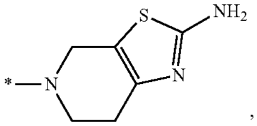,
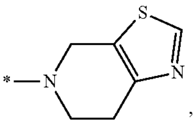, 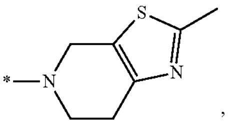,
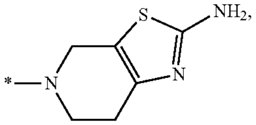
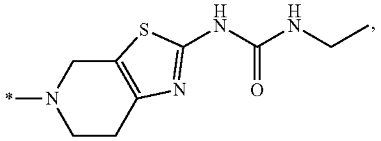
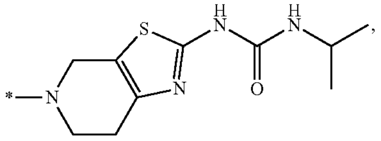
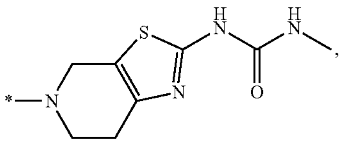
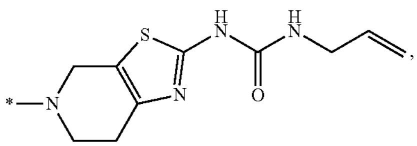
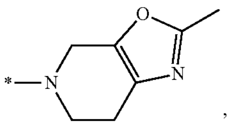, 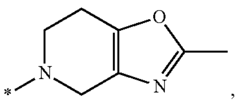,
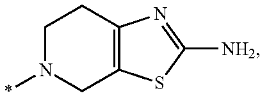
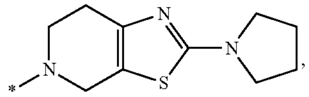
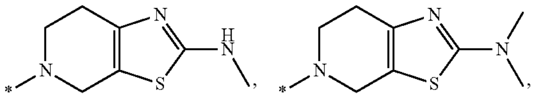
-continued
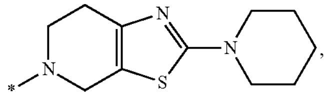
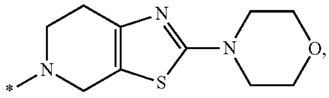
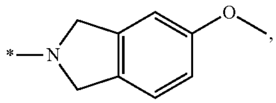 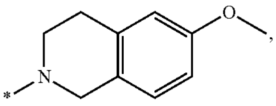
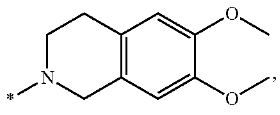 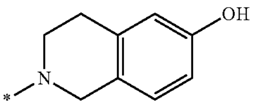,
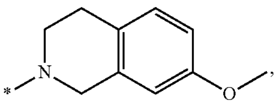 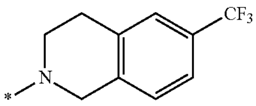,
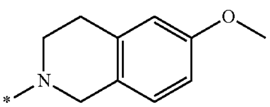 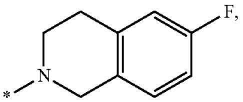
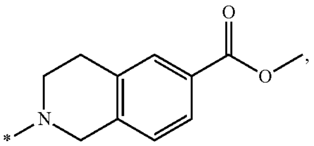
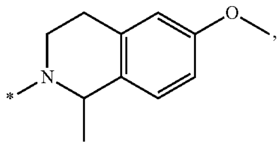
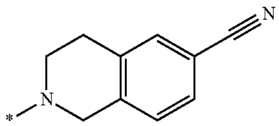, 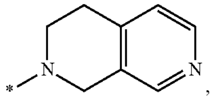
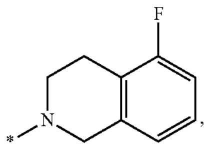 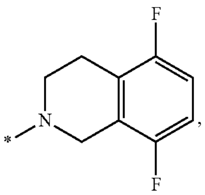
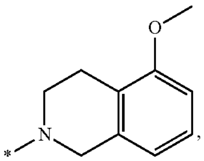 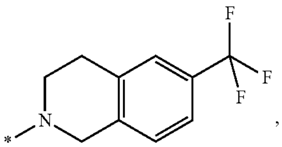,
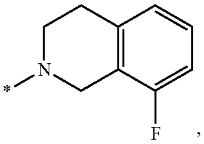, 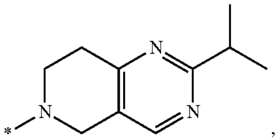,
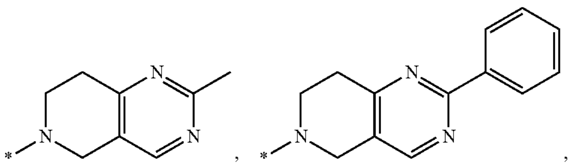, -continued
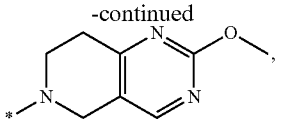
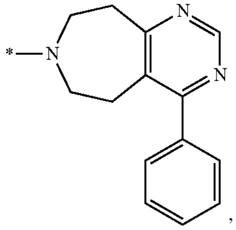
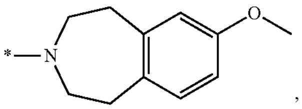
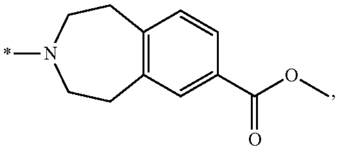
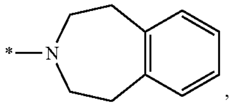
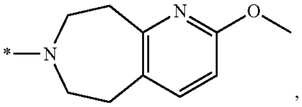
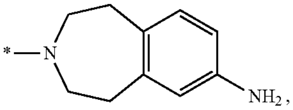
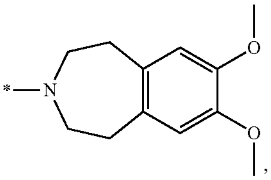
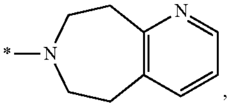
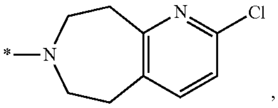
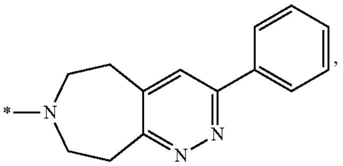
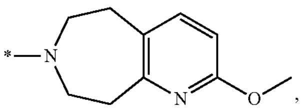
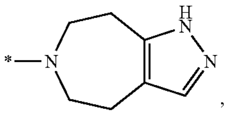
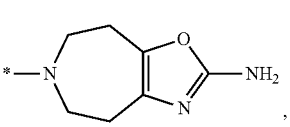
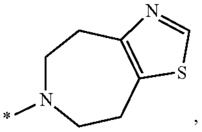
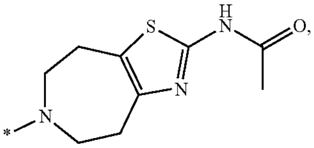
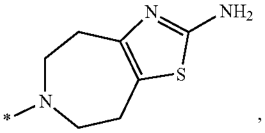
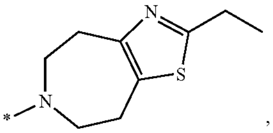
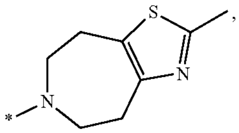
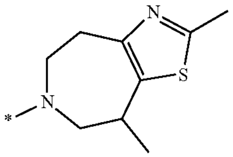
-continued
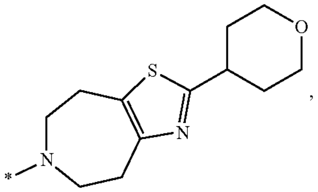
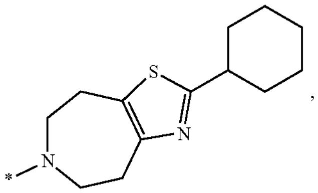
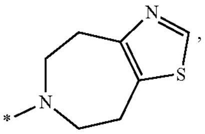
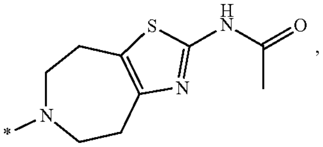
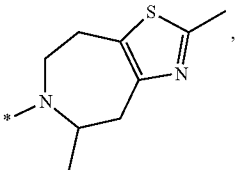
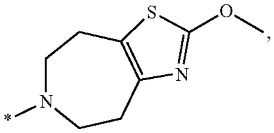
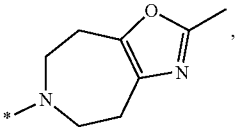
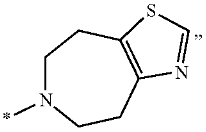
or
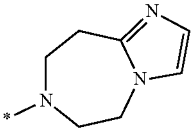
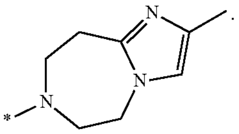
8. A compound according to claim 5, wherein the group represents
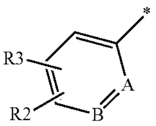
represents
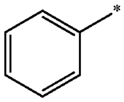
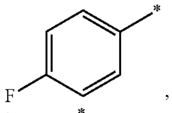
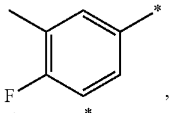
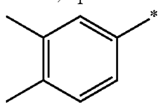
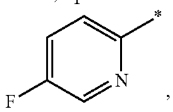
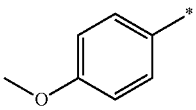
or
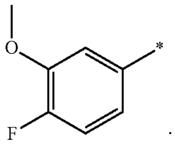

9. A compound of formula I
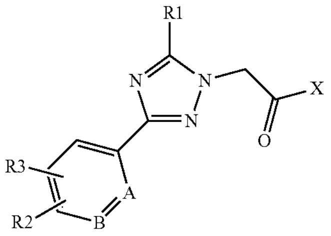
in which
A represents N or CH;
B represents CH;
$R^1$ represents phenyl, methyl, ethyl, propyl, iso-propyl, butyl, pentyl, cyclopentyl, cyclohexyl,
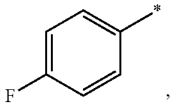, 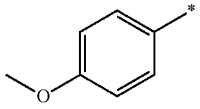,
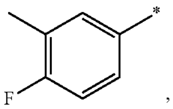, 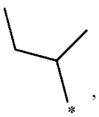, 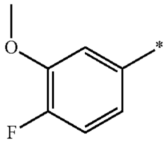,
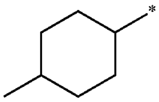, 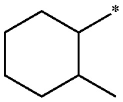, 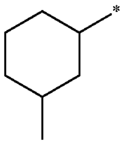,
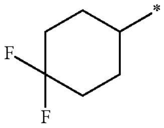, 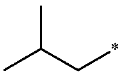 or 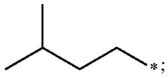;
X represents
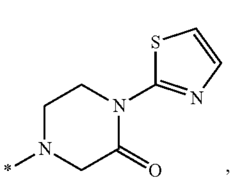, 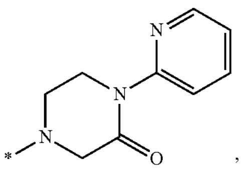,
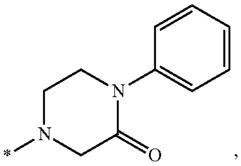, 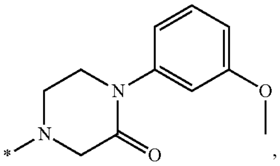,
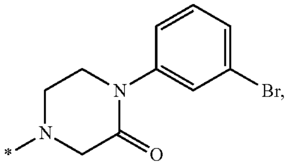 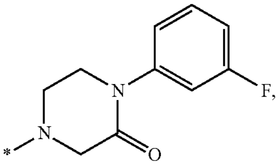
-continued
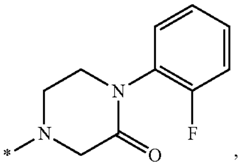, 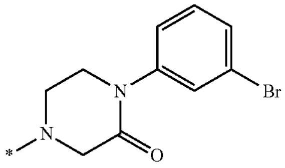,
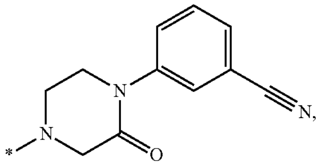
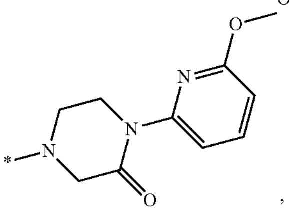, 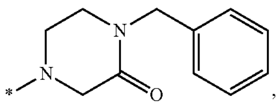,
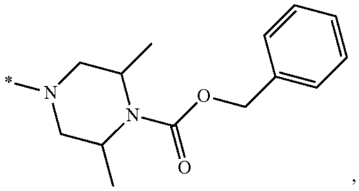,
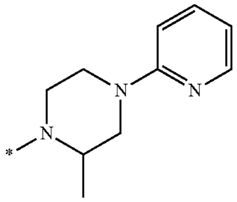, 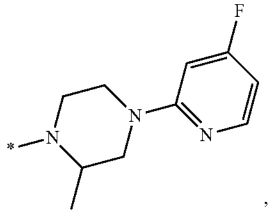,
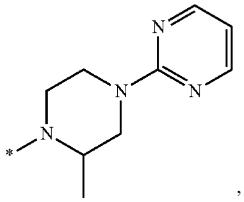, 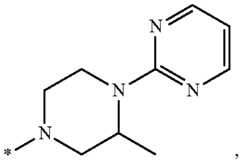,
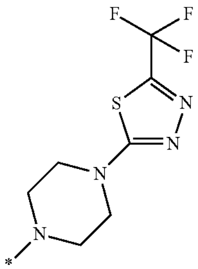, 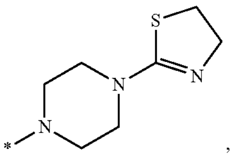,
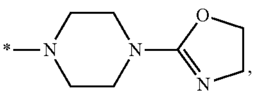
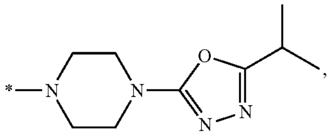
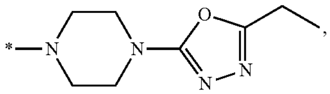

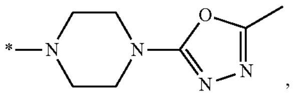,
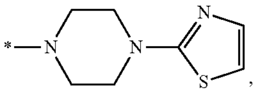,
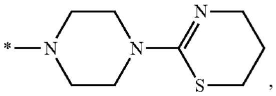,
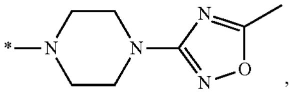,
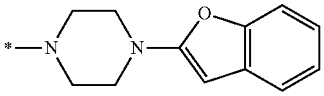,
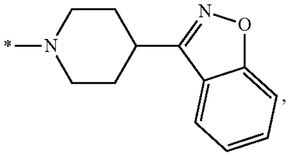,
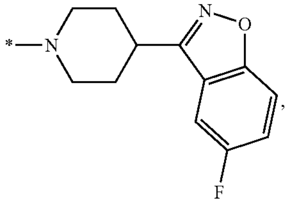,
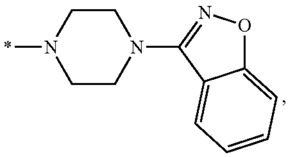,
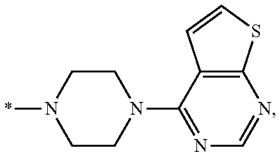,
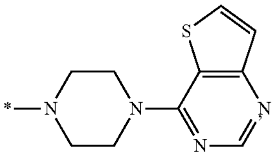
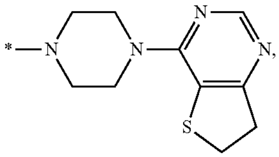,
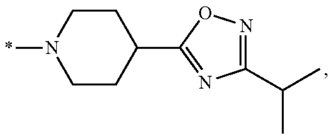,
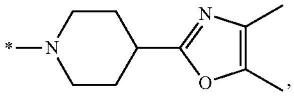,
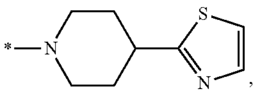,
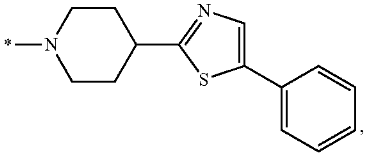,
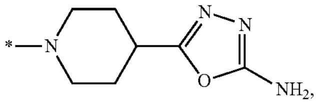,
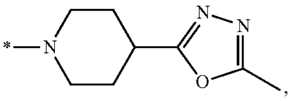,
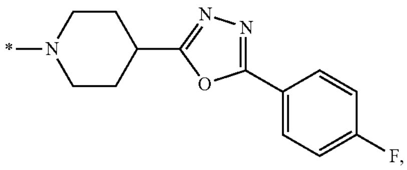,
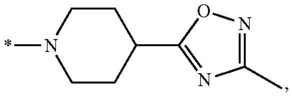,
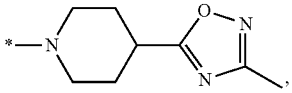,
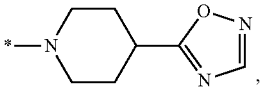,
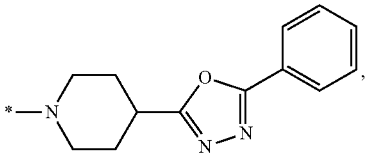,
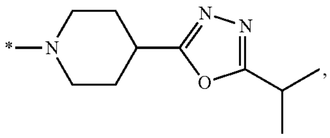,
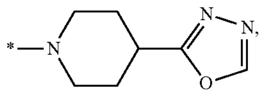,
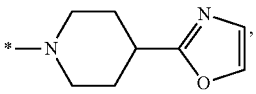,
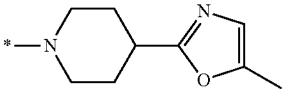,
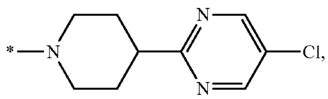,
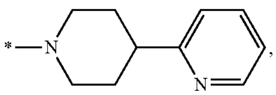,
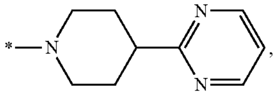,
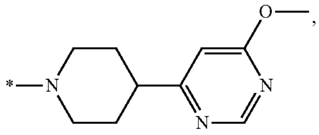,
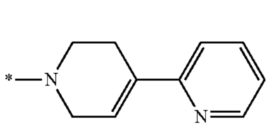,
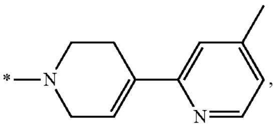,
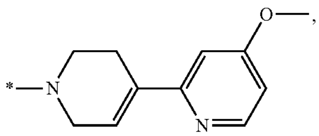,
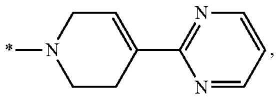,
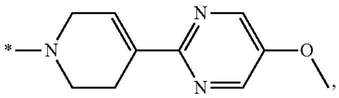, -continued
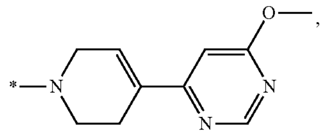,
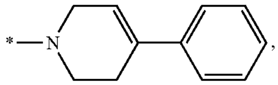,
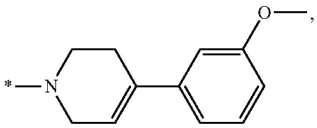,
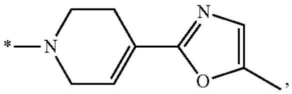,
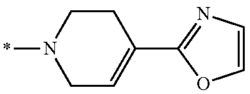,
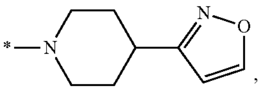,
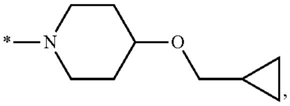,
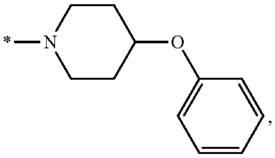,
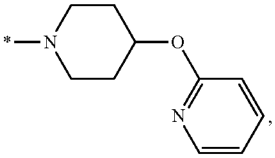,
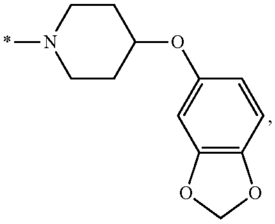,
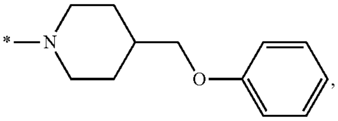,
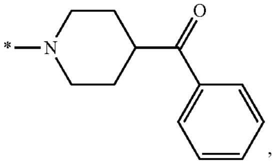,
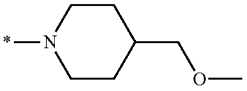,
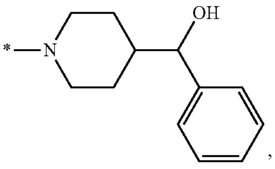,
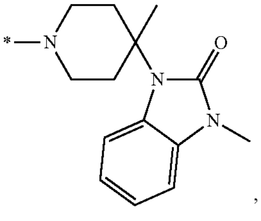,
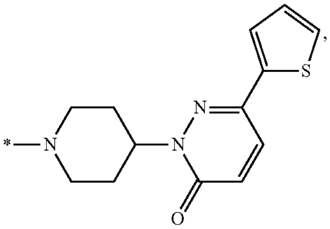,
-continued
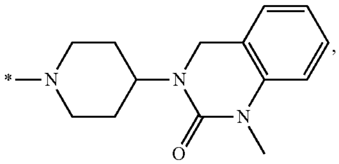,
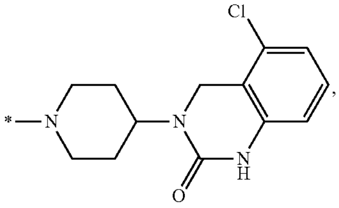,
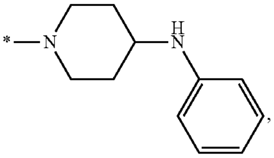,
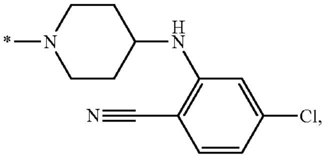,
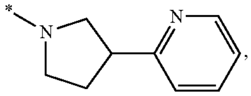,
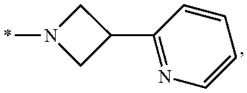,
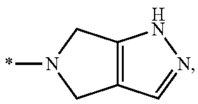,
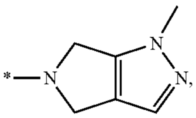,
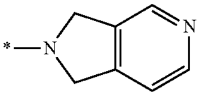,
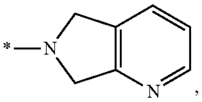,
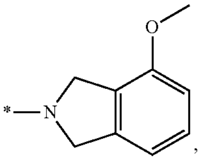,
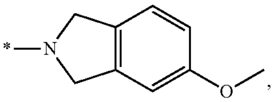,
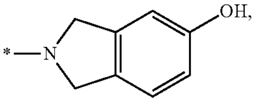,
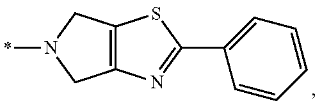,
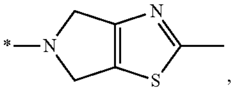,
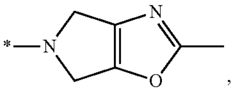,
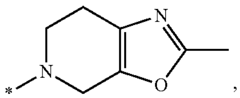,
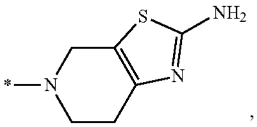,
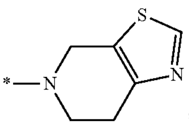,
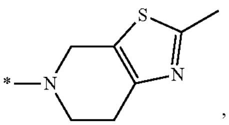, -continued
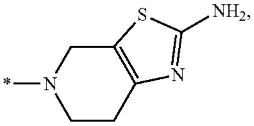
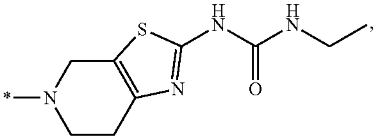
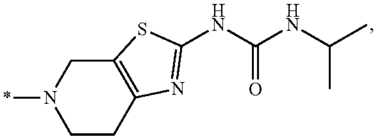
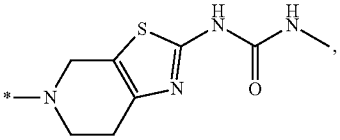
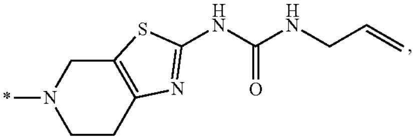
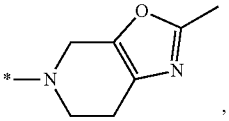
,
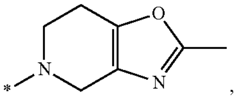
,
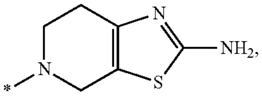
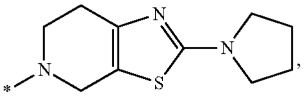
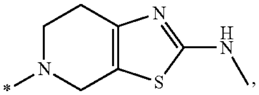
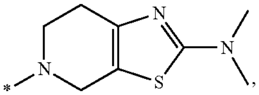
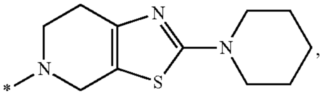
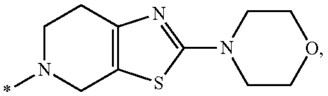
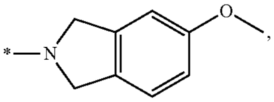
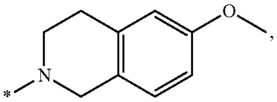
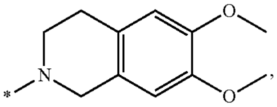
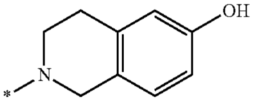
,
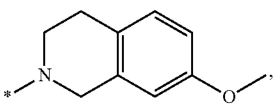
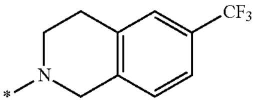
,
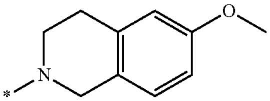
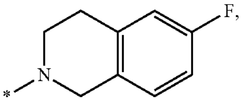
-continued
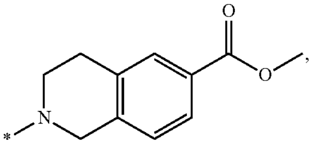
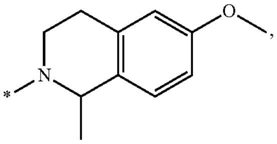
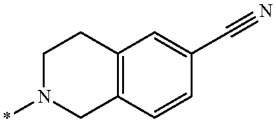
,
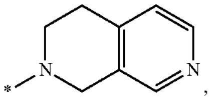
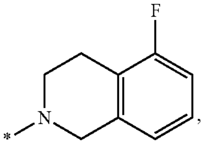
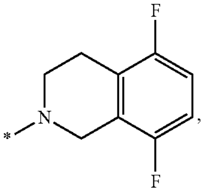
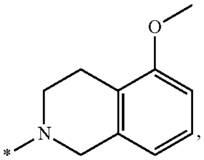
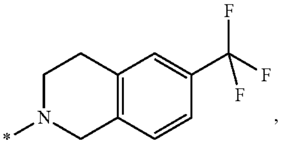
,
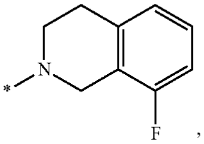
,
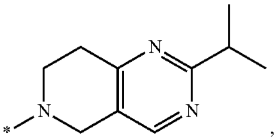
,
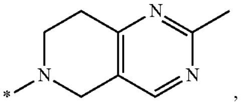
,
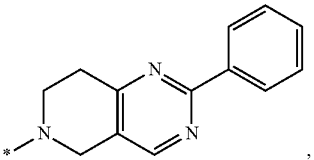
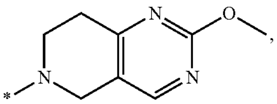
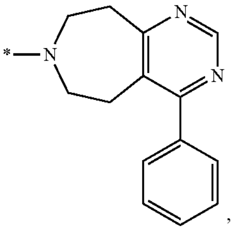
,
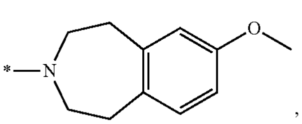
,
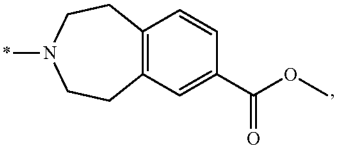
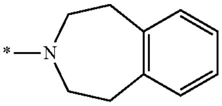
,
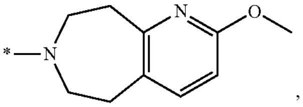
, -continued
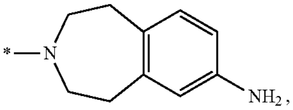,
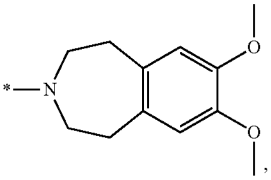,
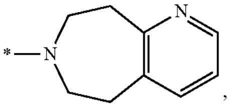,
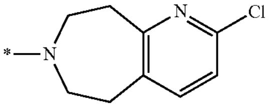,
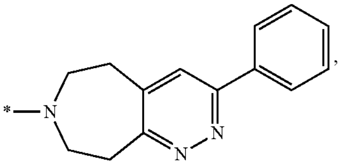,
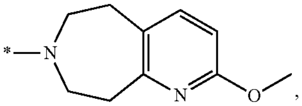,
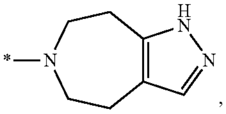,
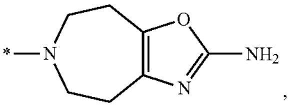,
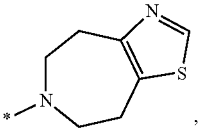,
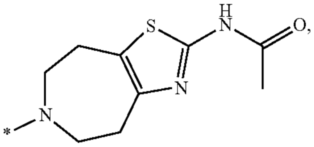
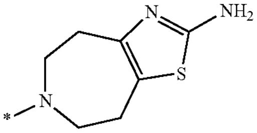,
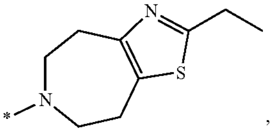,
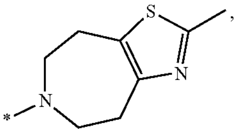,
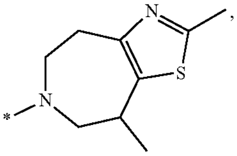,
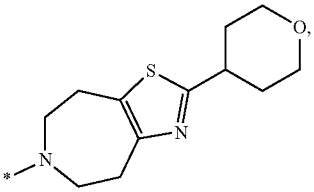
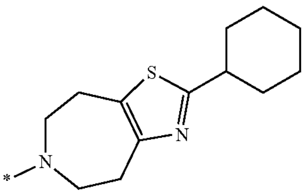
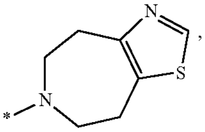,
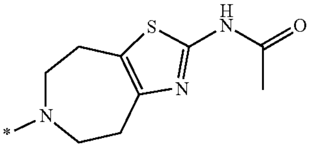,
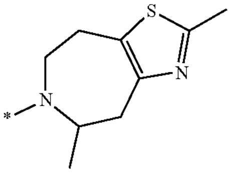,
-continued
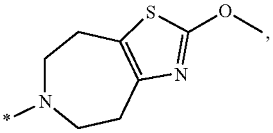,
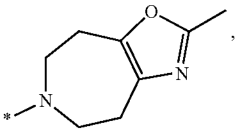,
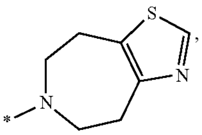,
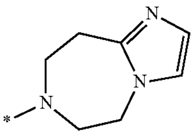 or
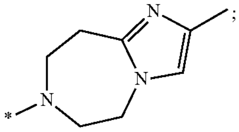;
the group
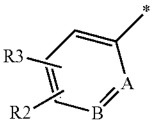
represents
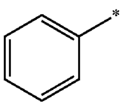,
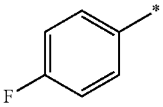,
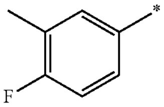,
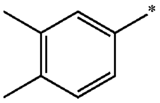,
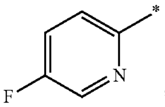,
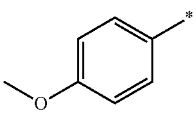 or
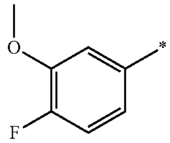;
or a physiologically acceptable salt thereof.
10. A compound selected from the group consisting of
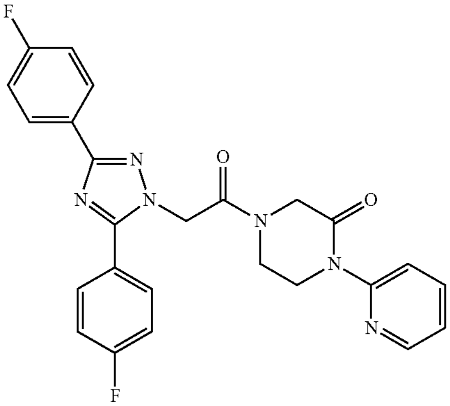

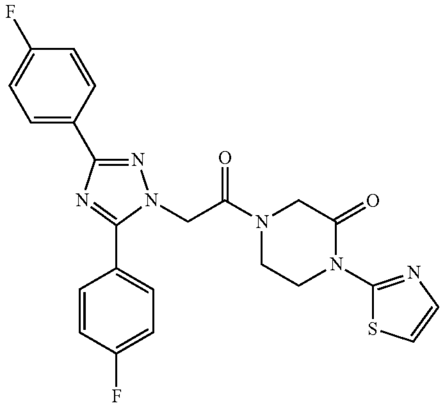
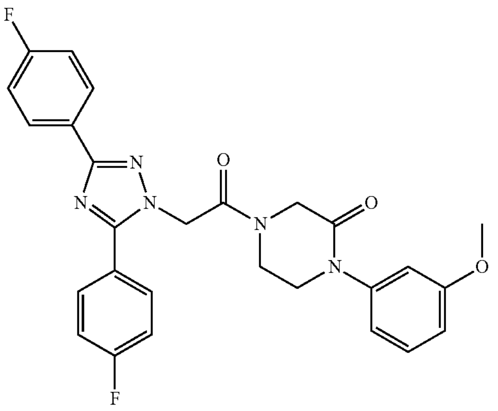
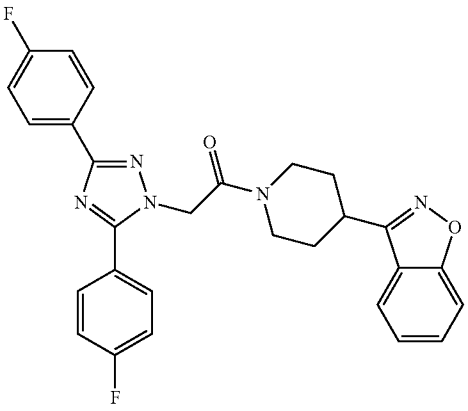
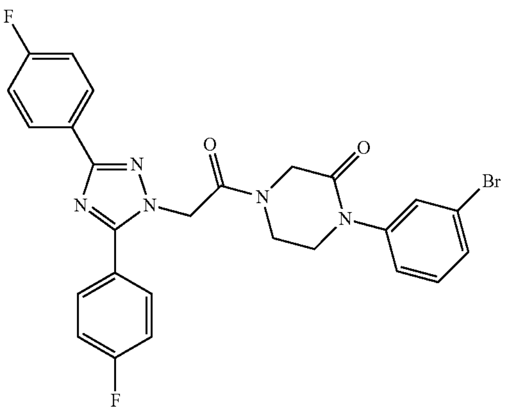
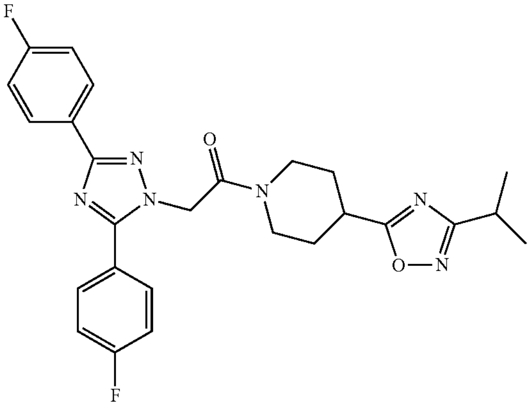
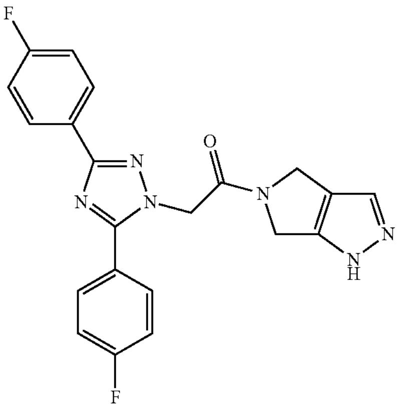
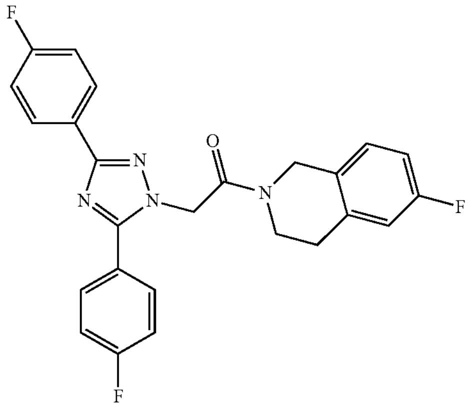
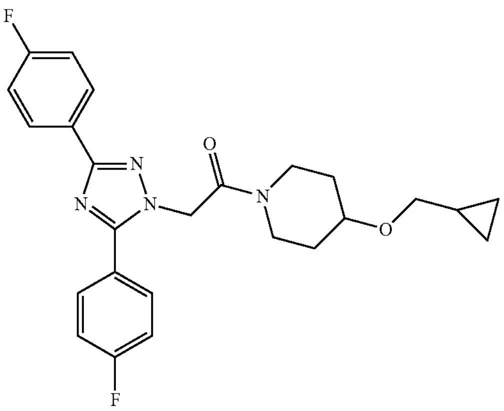

-continued
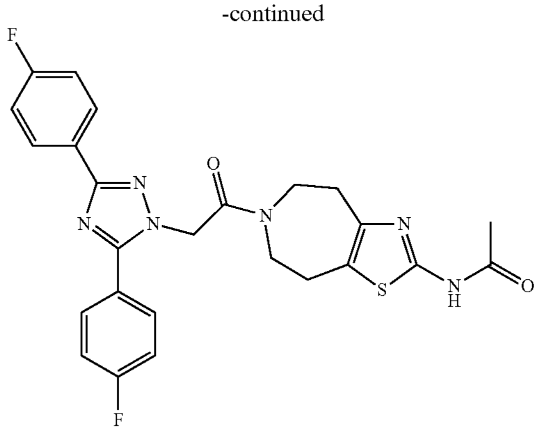
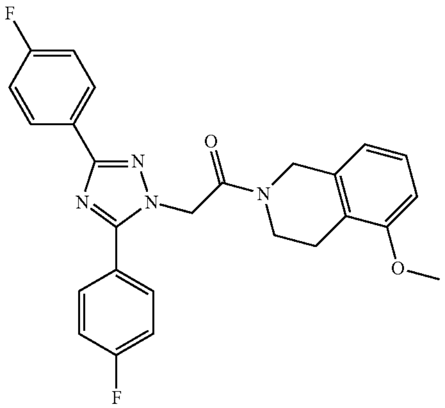
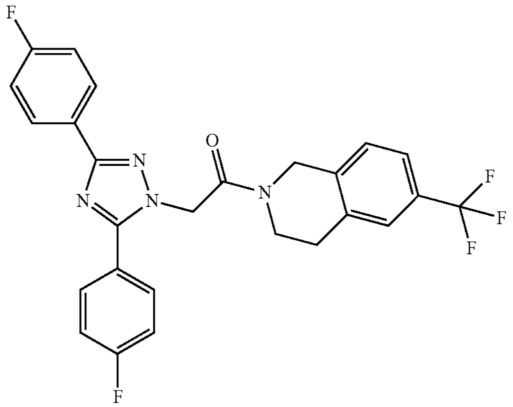
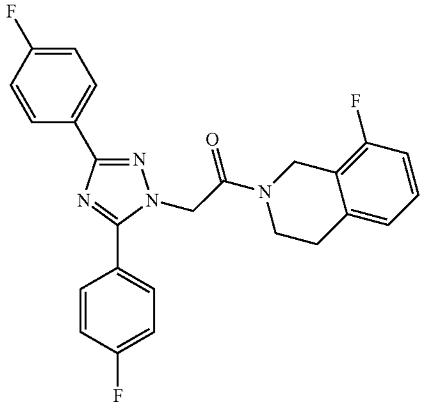
-continued
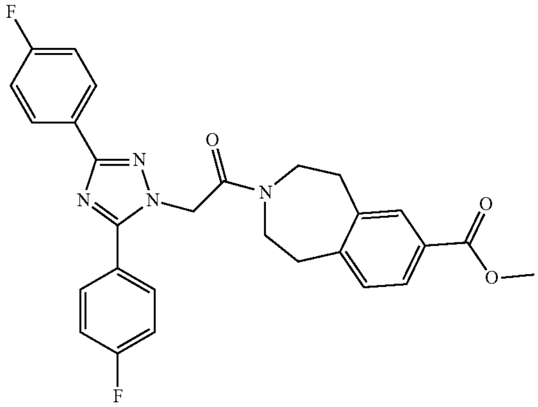
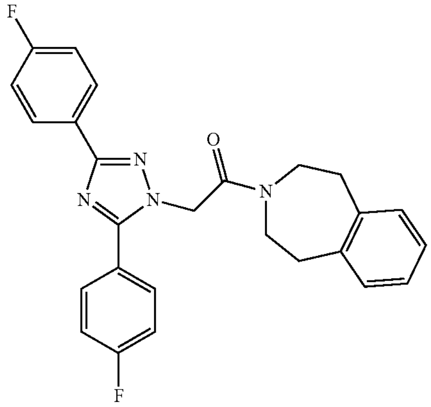
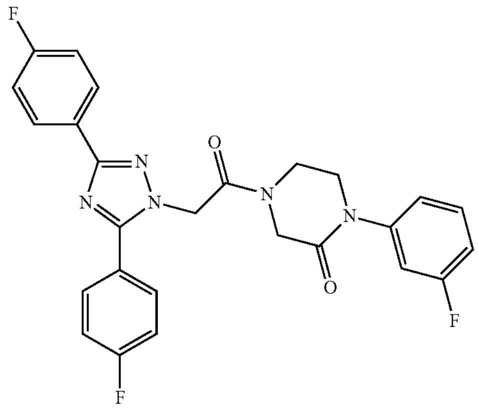
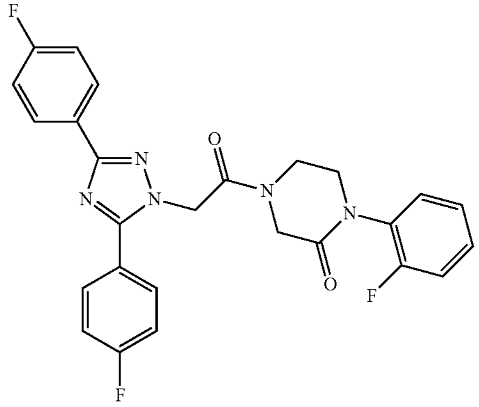

-continued
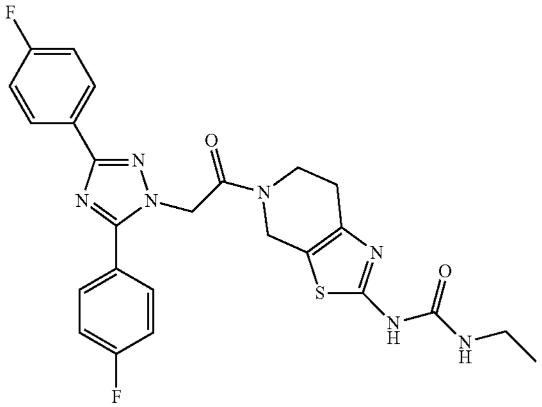
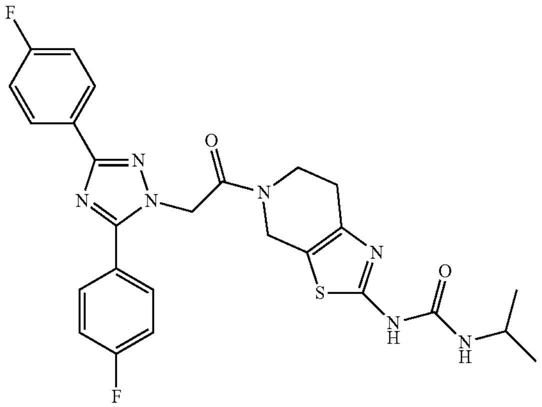
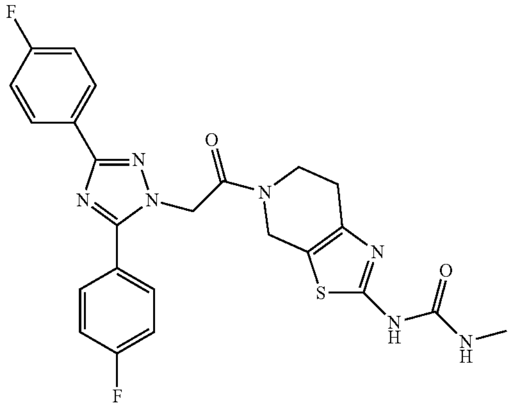
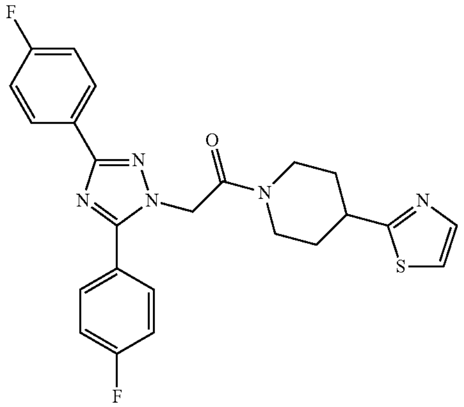
-continued
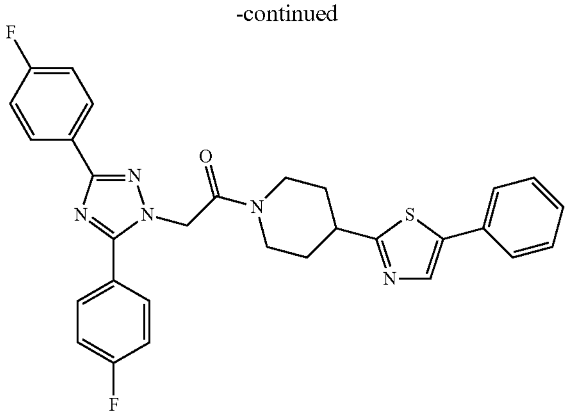
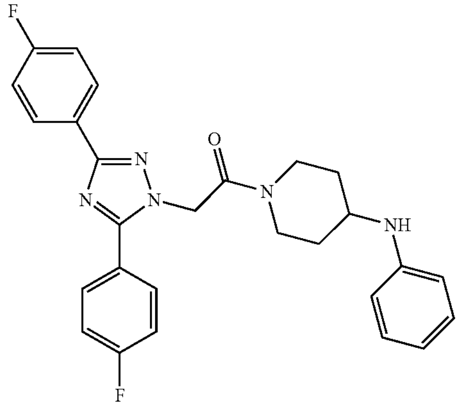
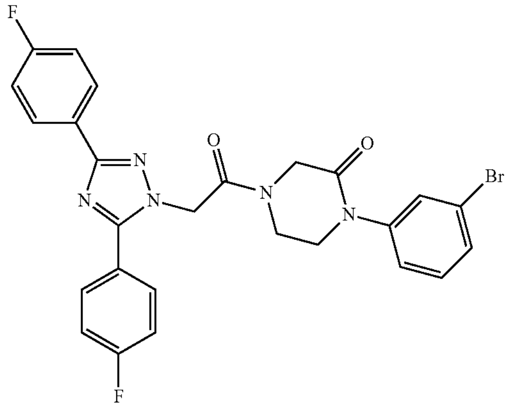
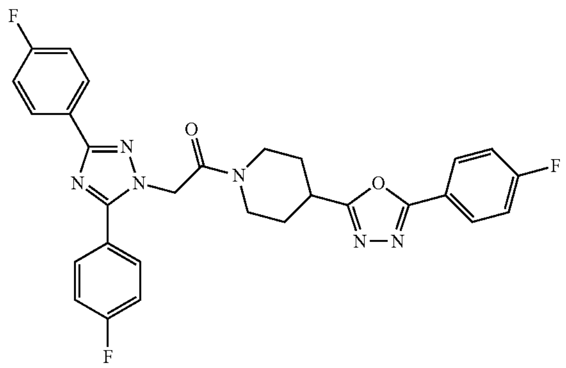

-continued
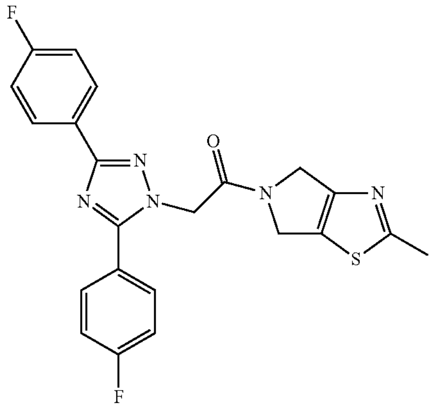
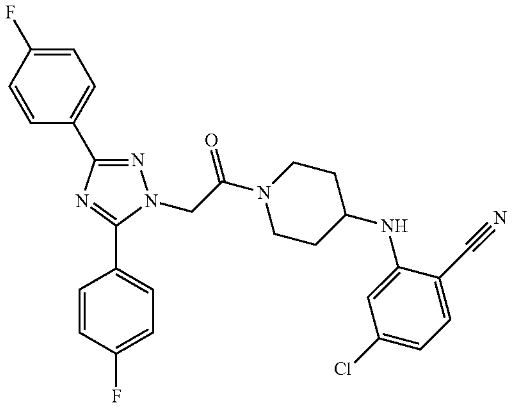
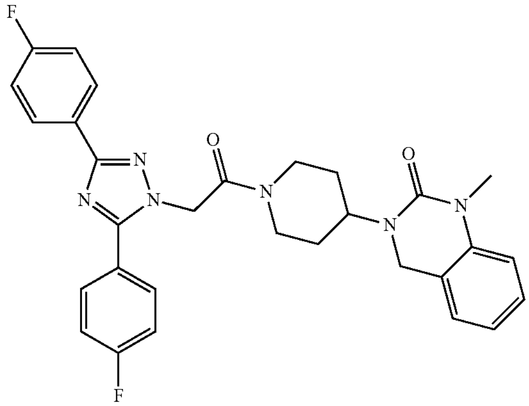
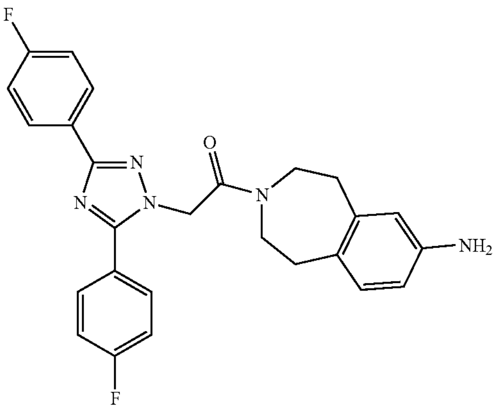
-continued
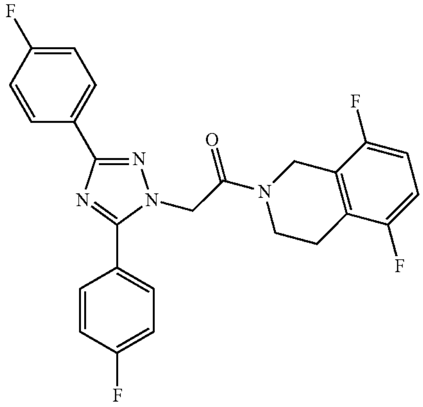
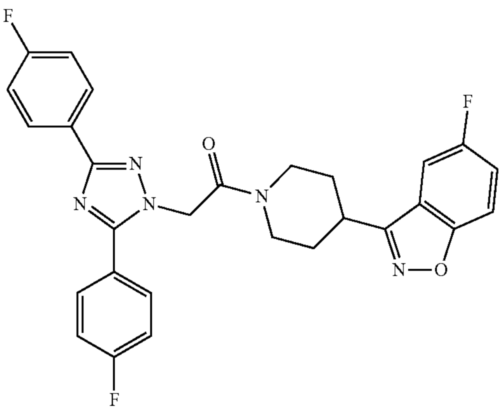
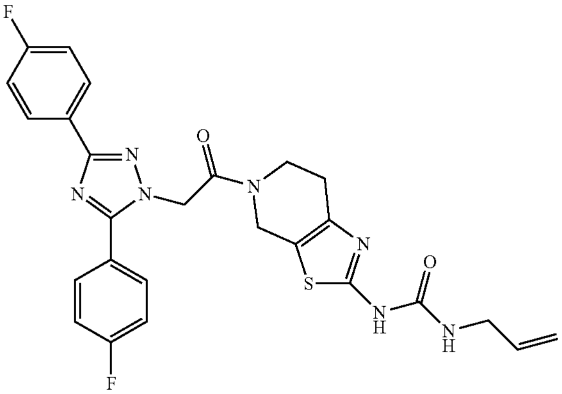
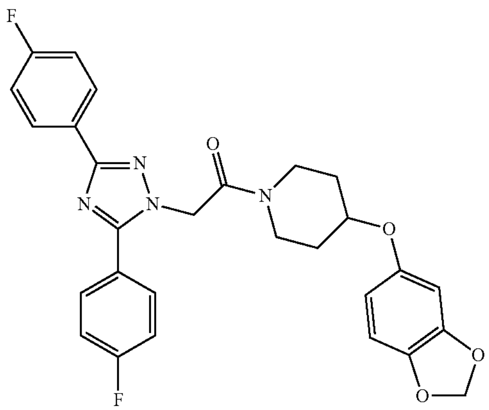

-continued
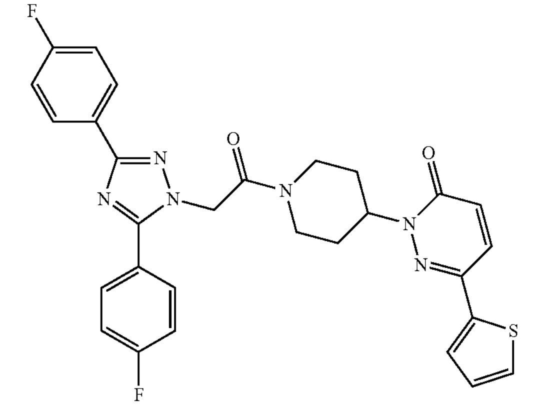
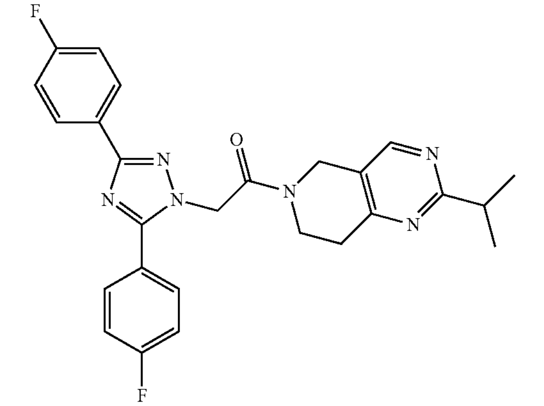
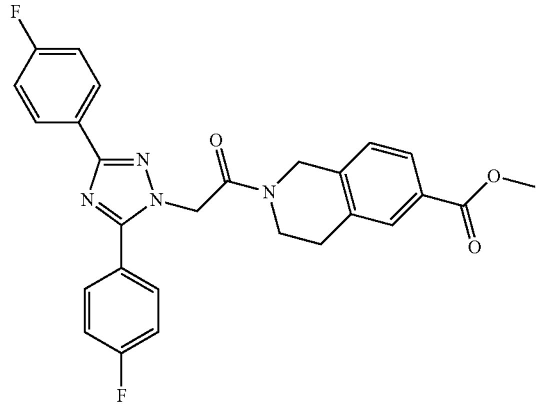
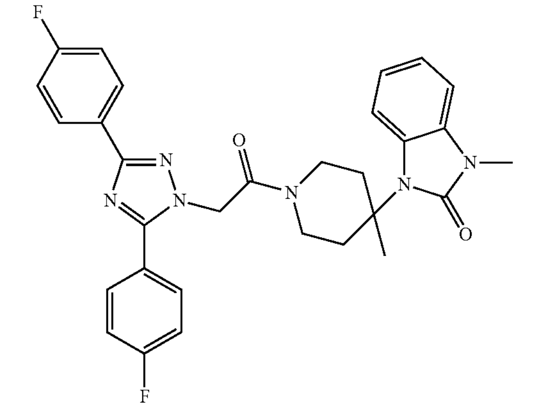
-continued
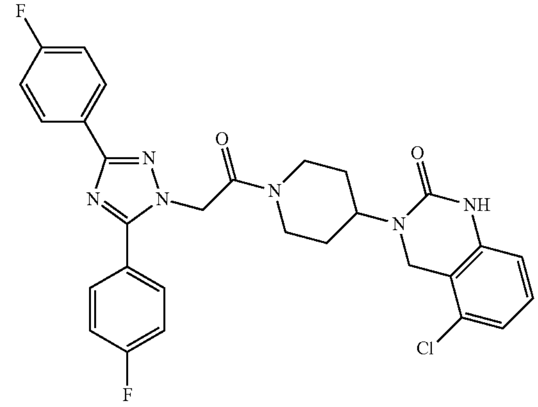
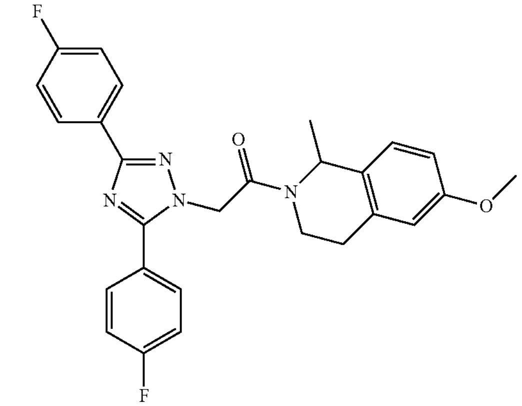
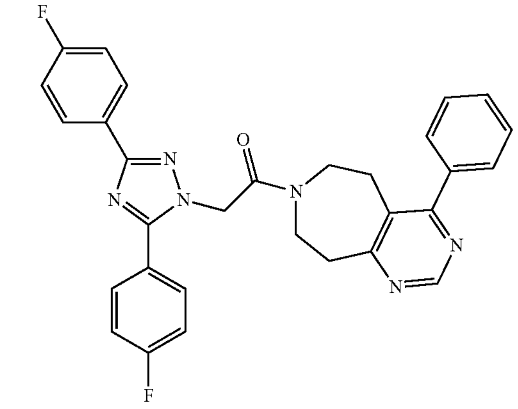
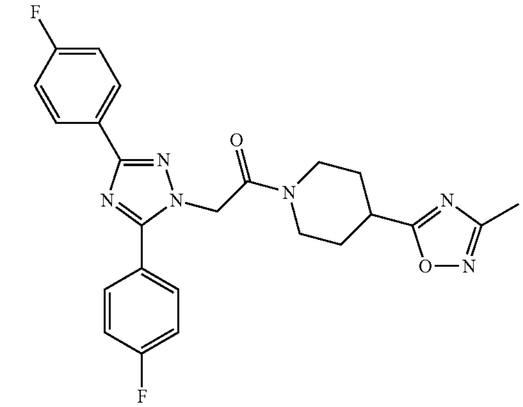

-continued
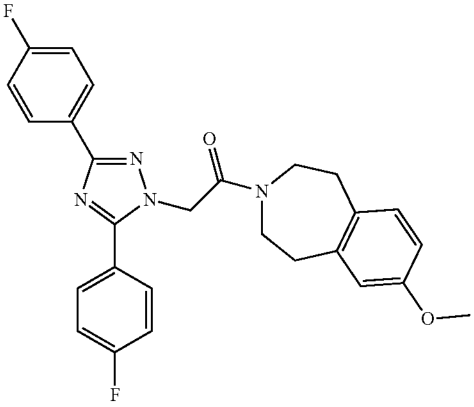
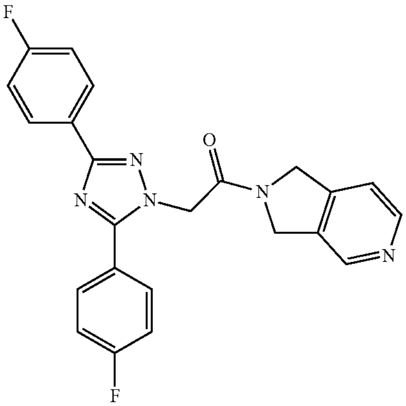
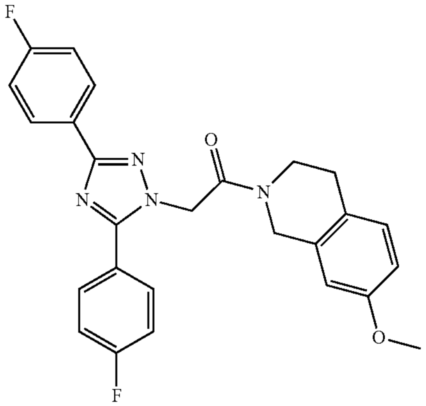
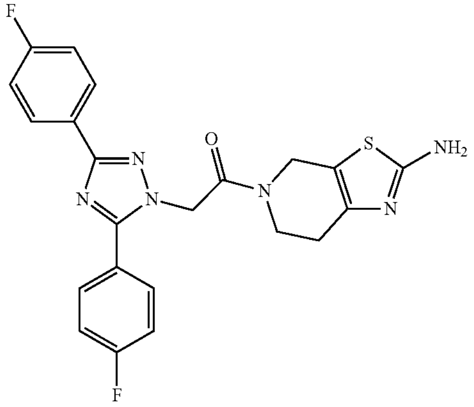
-continued
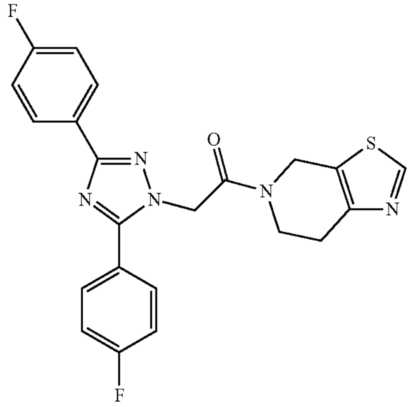
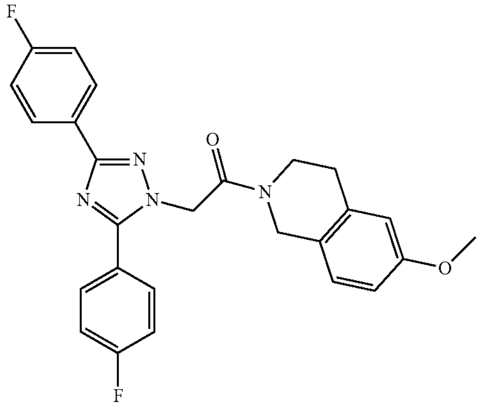
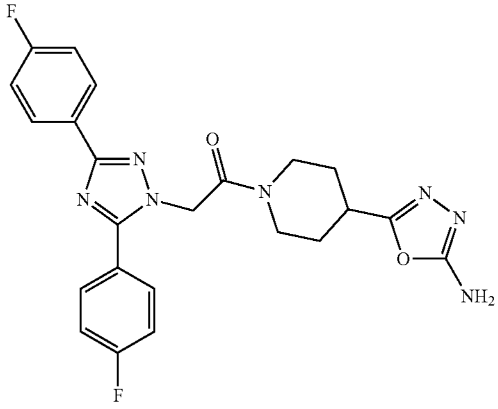
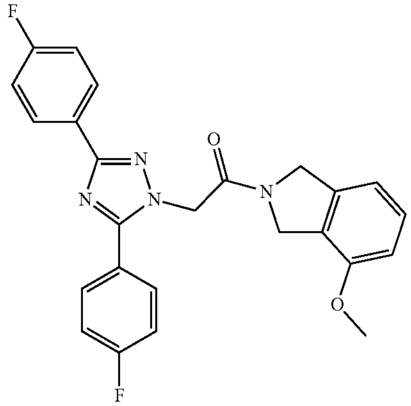

-continued
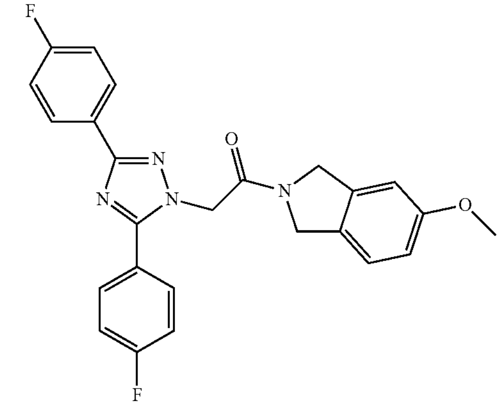
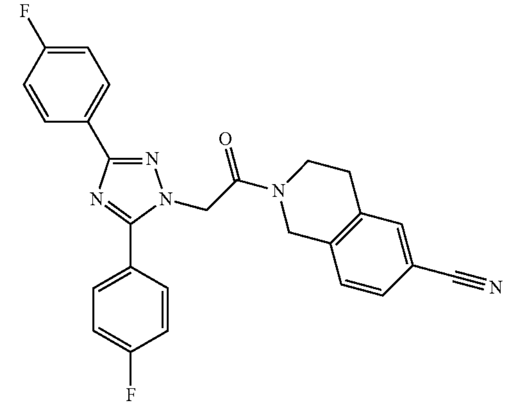
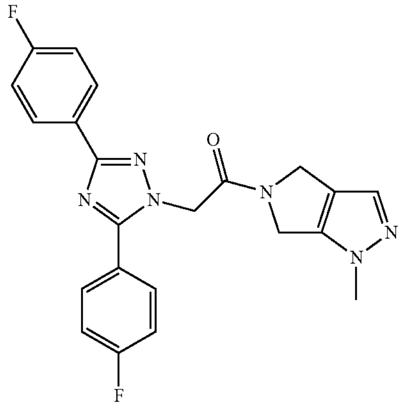
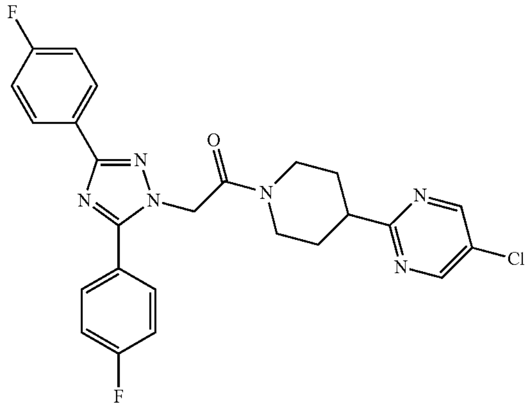
-continued
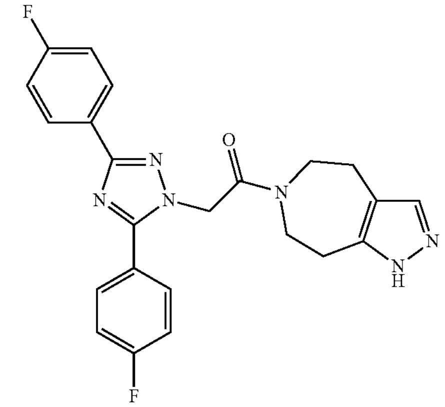
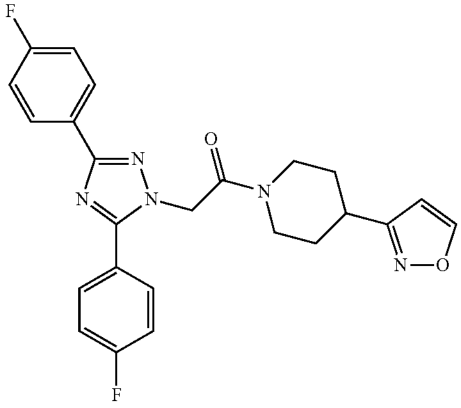
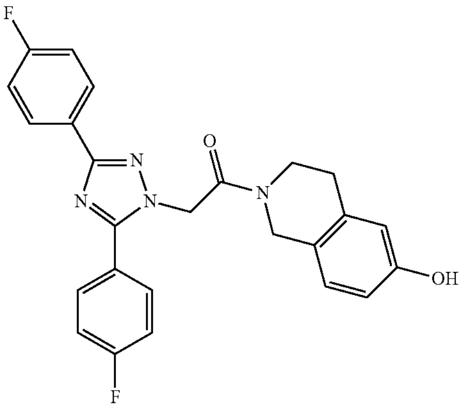
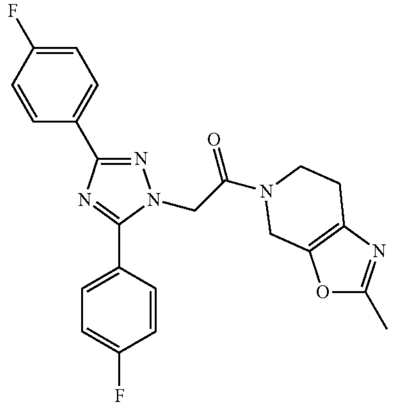

-continued
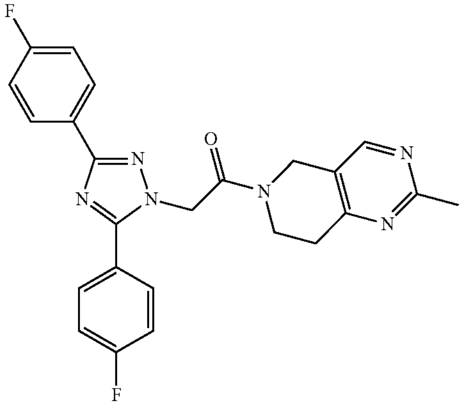
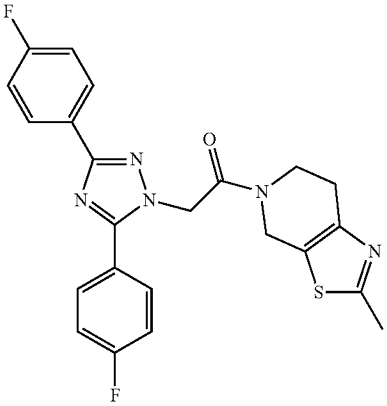
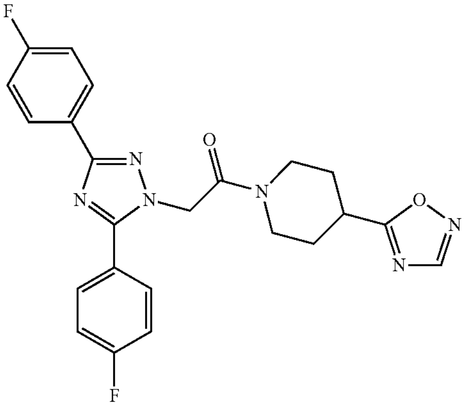
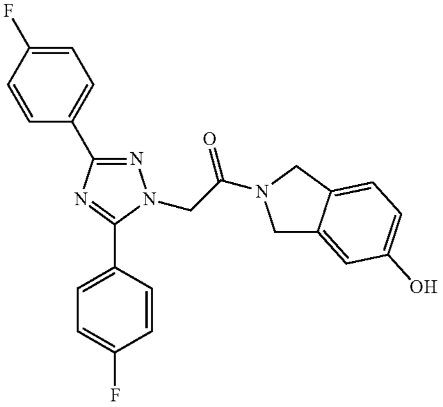
-continued
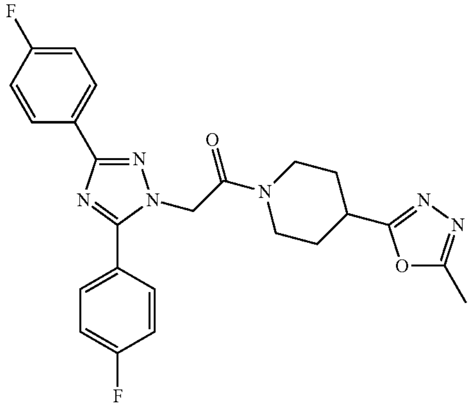
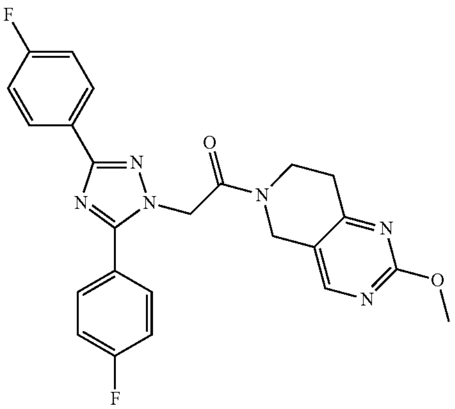
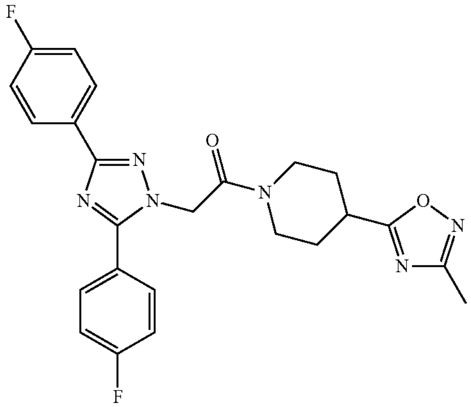
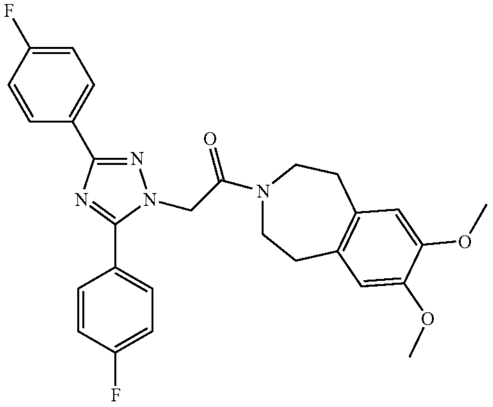

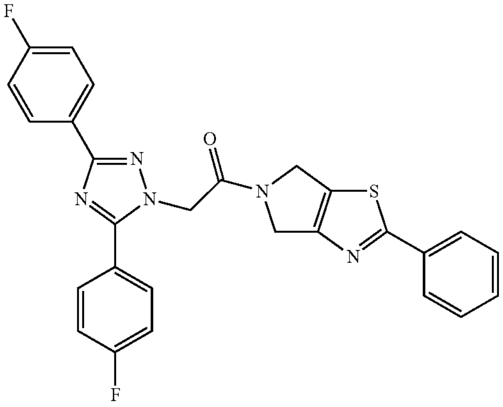
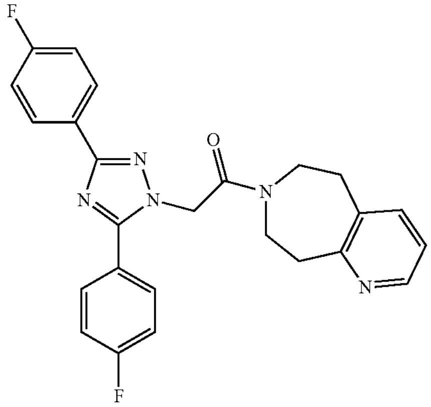
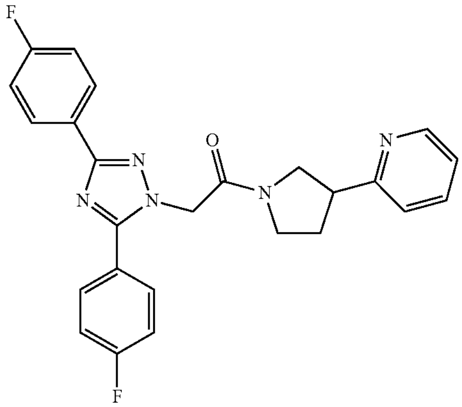
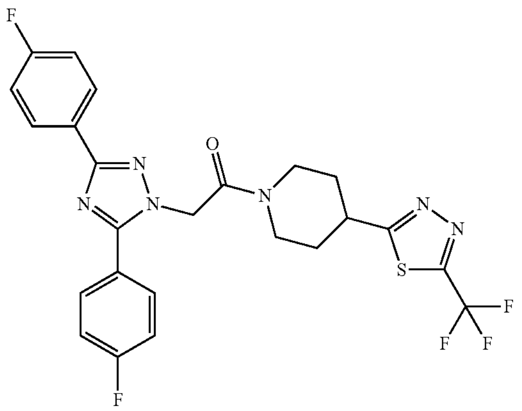
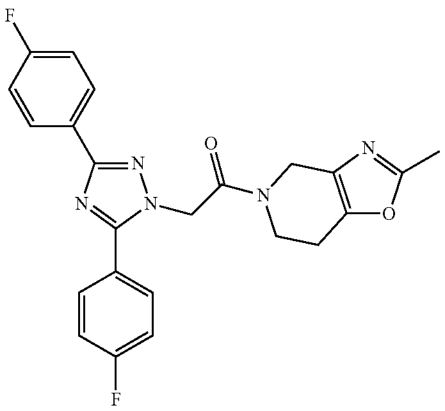
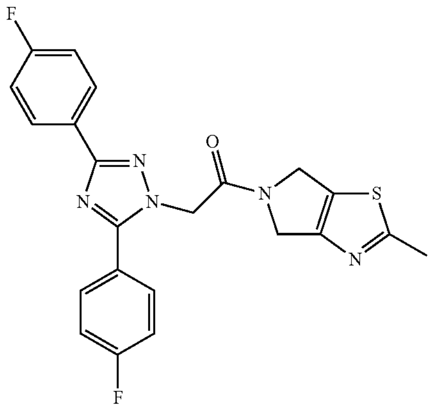
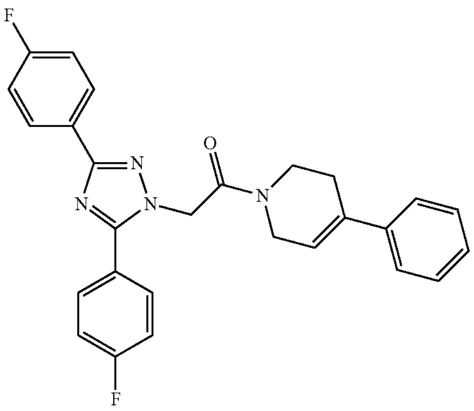
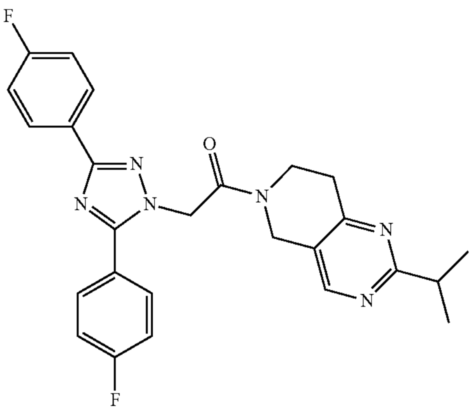

-continued
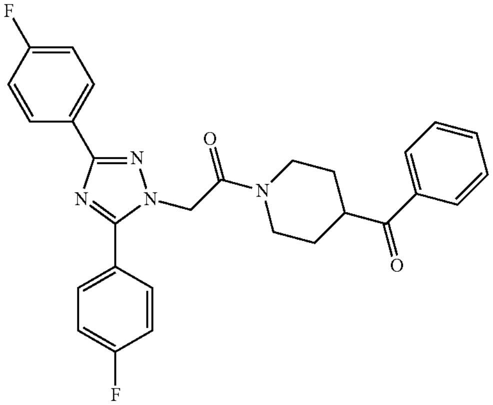
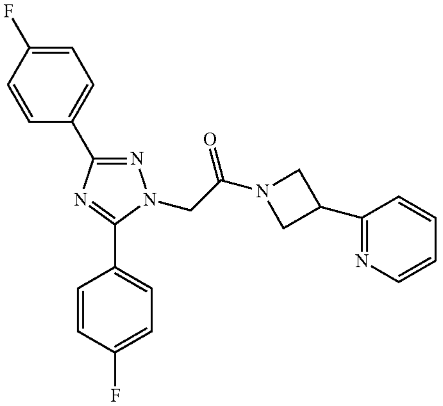
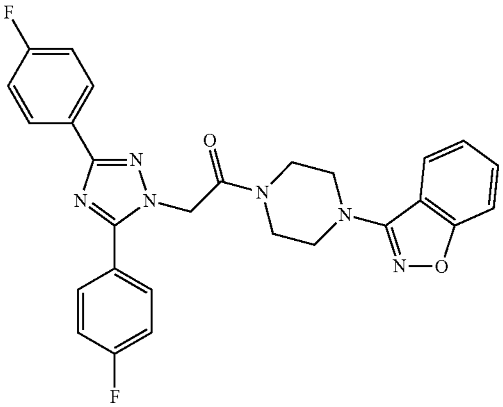
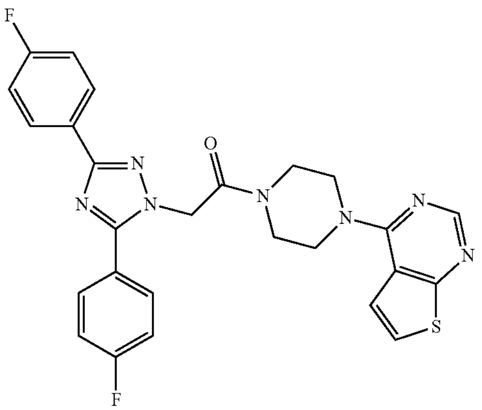
-continued
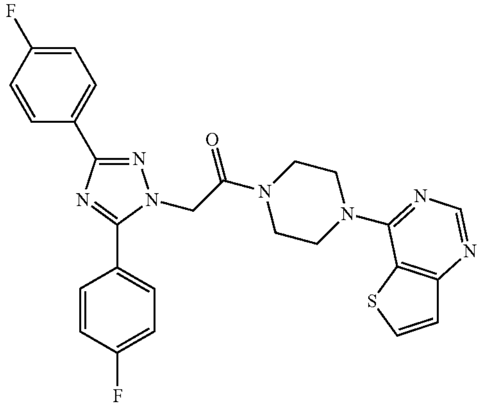
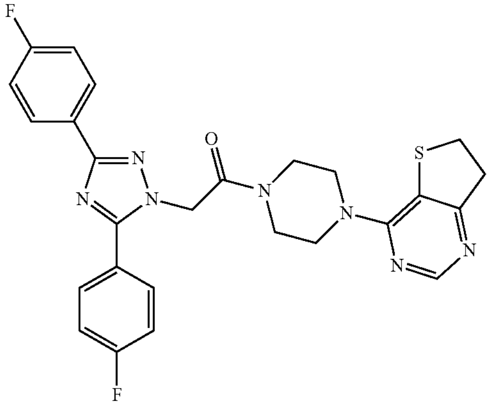
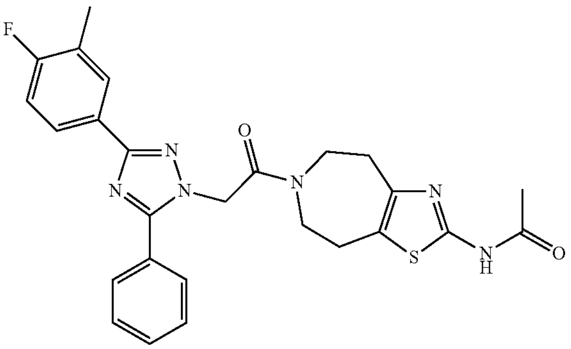
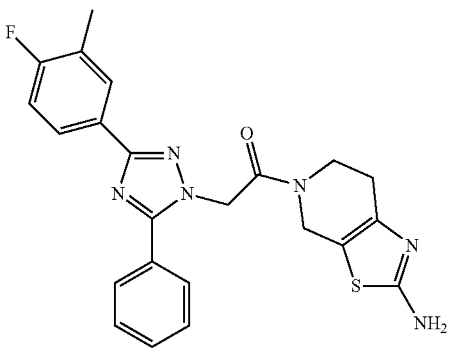

-continued
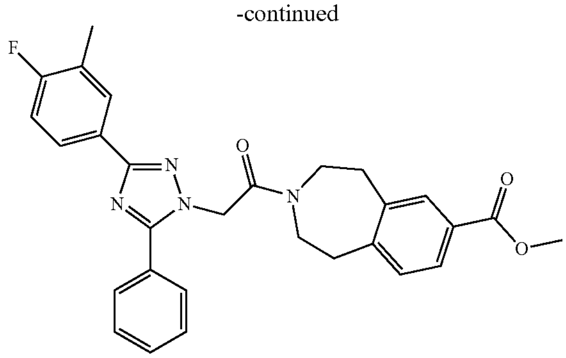
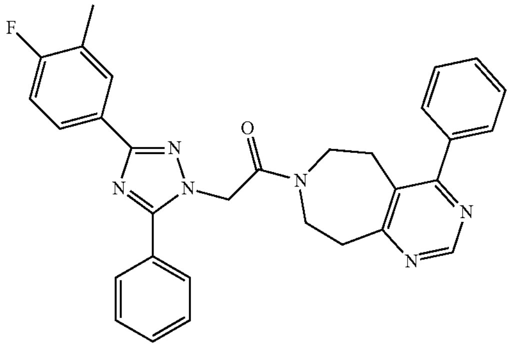
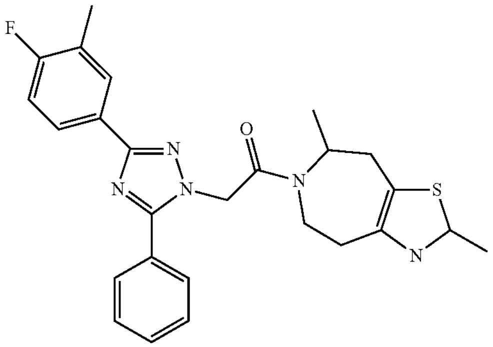
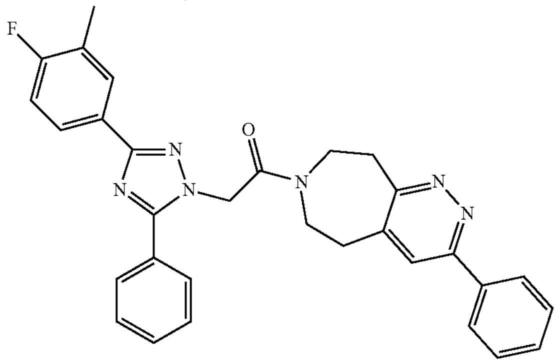
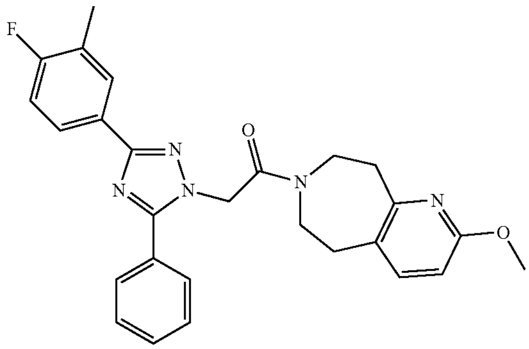
-continued
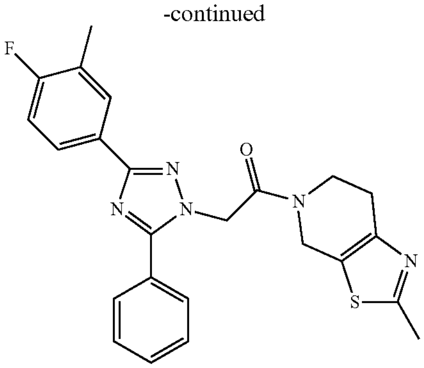
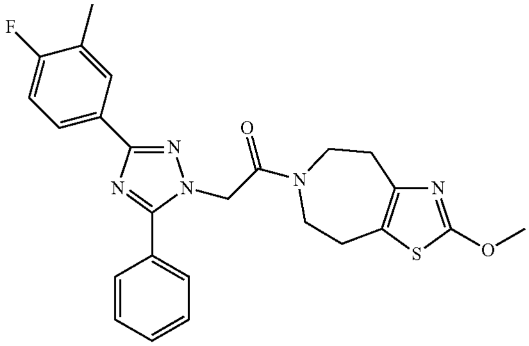
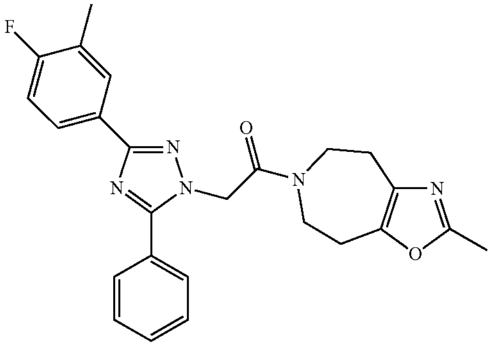
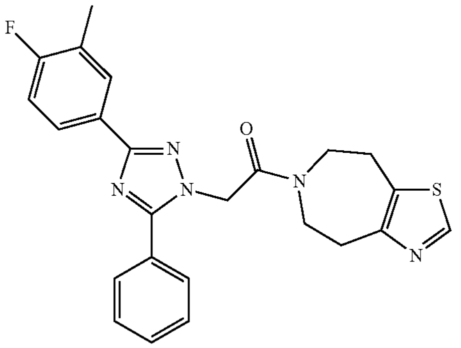
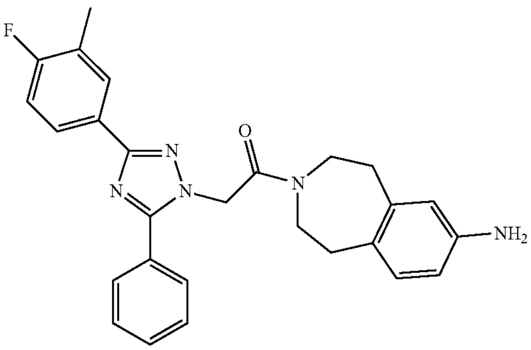

-continued
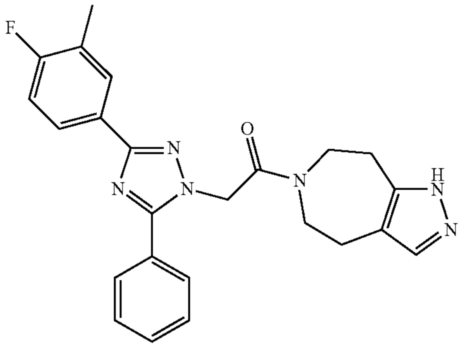
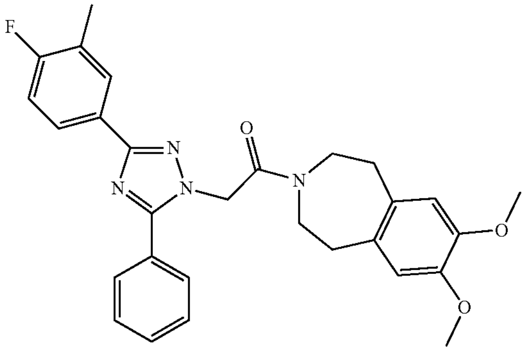
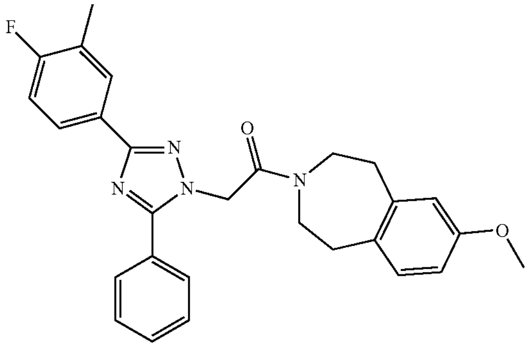
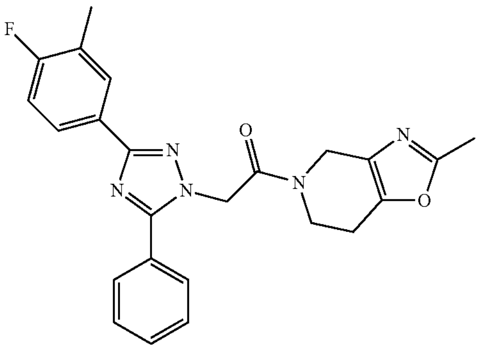
-continued
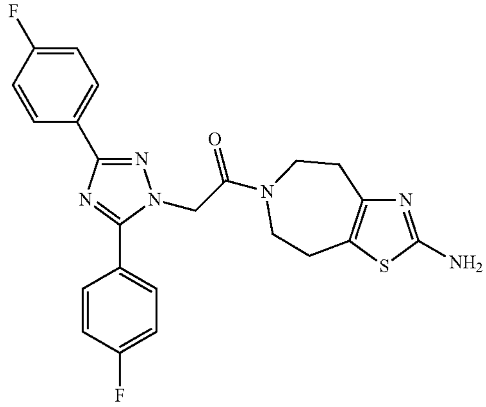
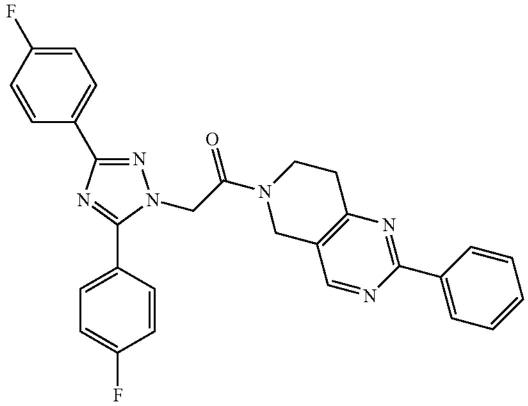
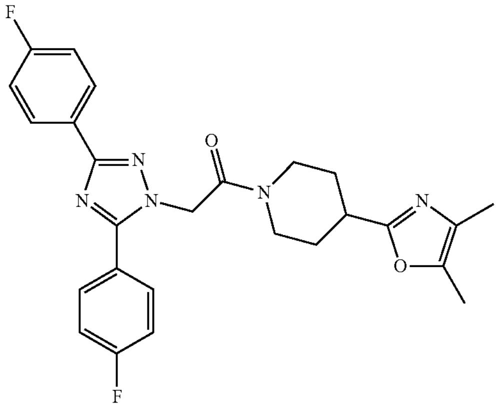
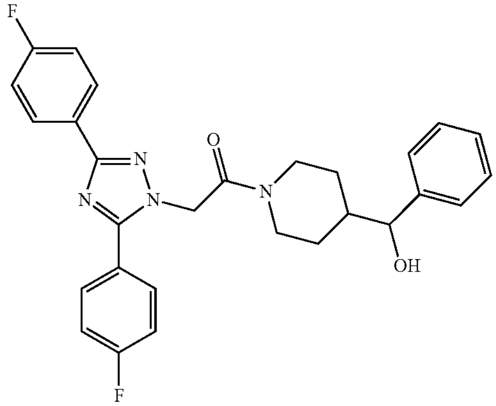

-continued
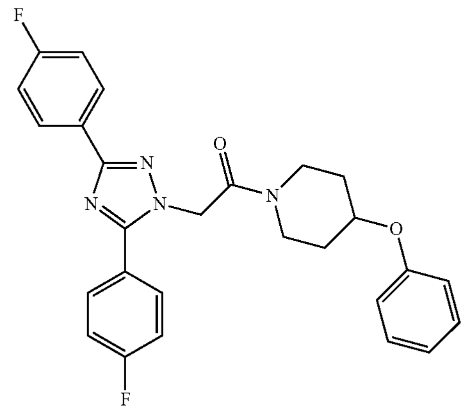
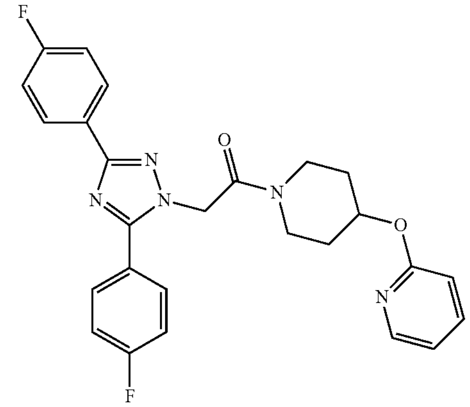
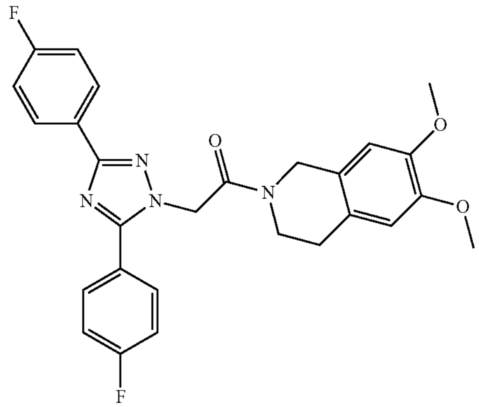
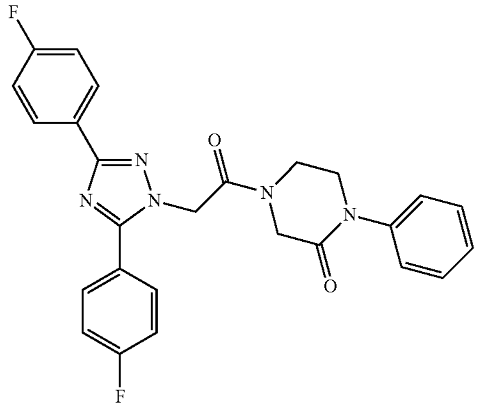
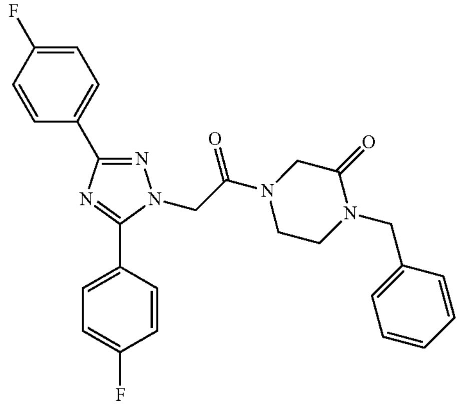
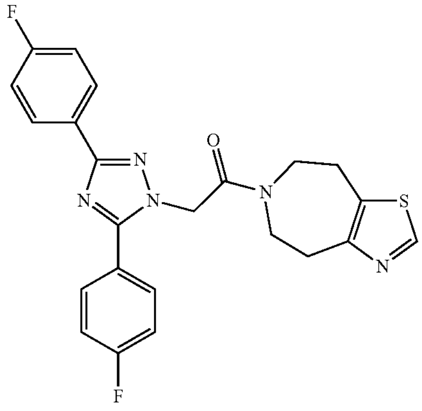
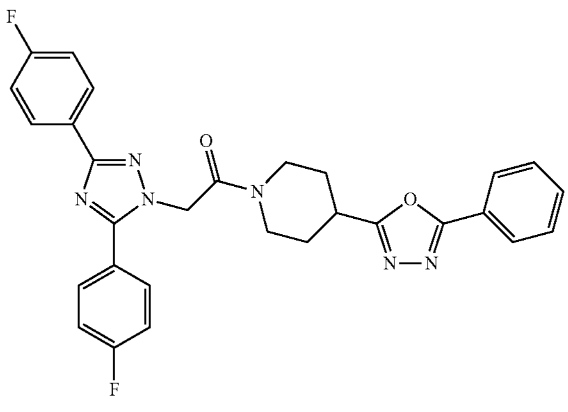
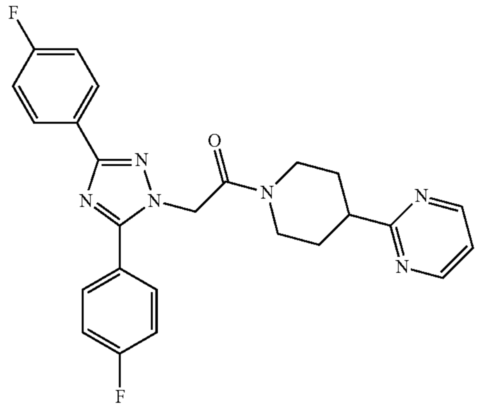
-continued -continued
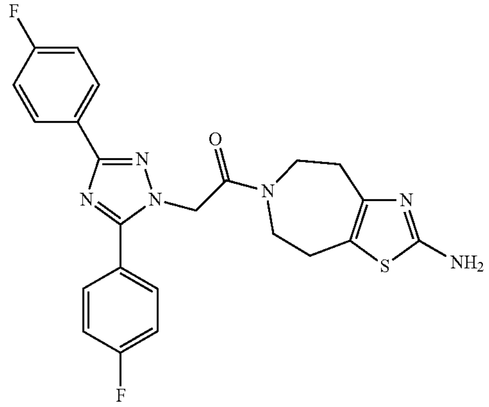
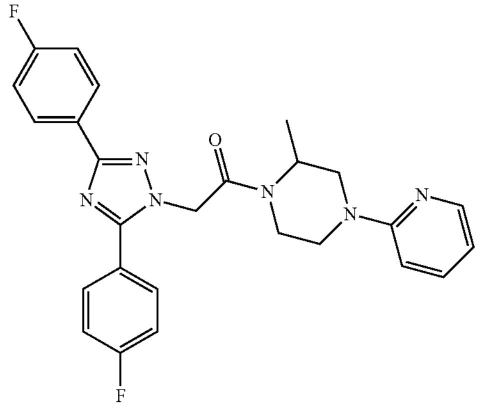
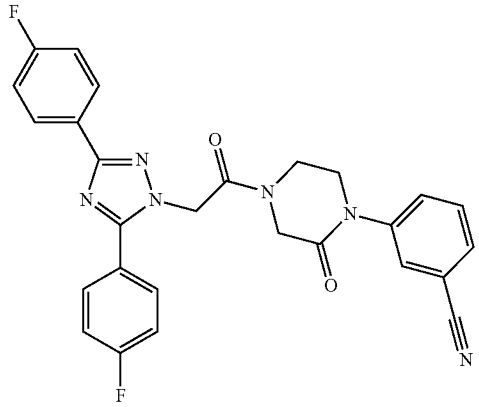
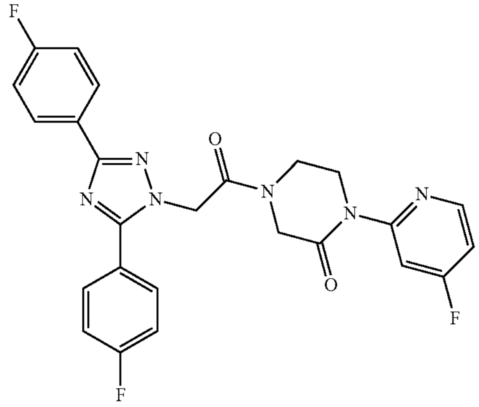
-continued
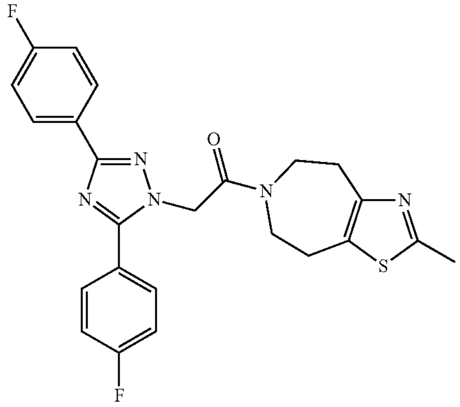
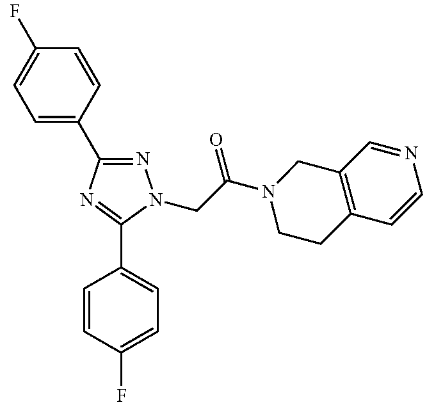
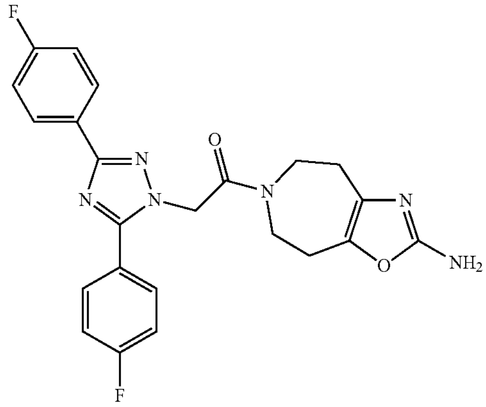
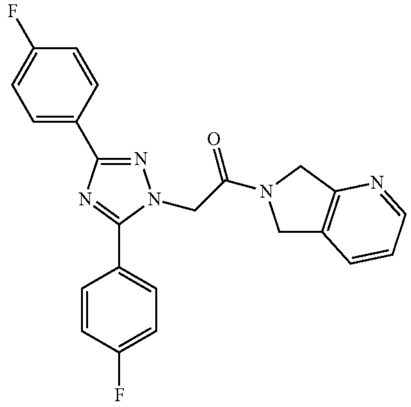

-continued
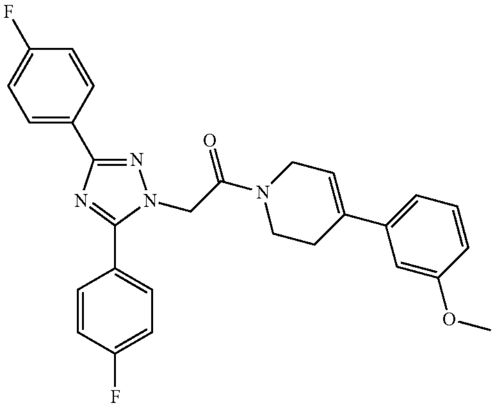
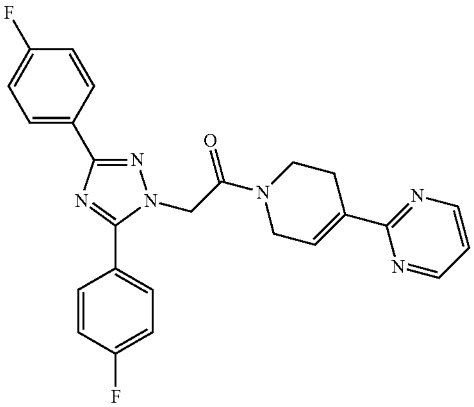
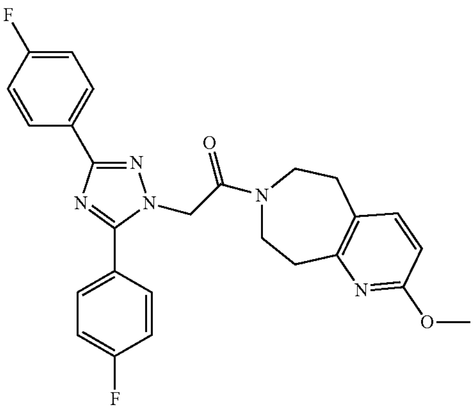
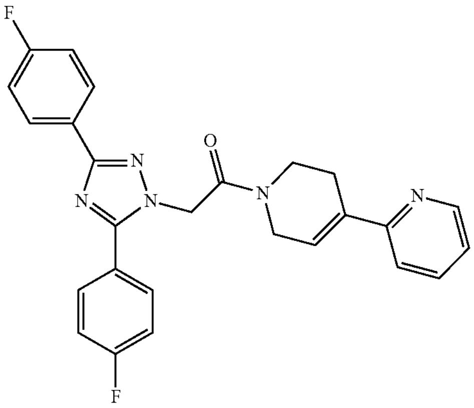
-continued
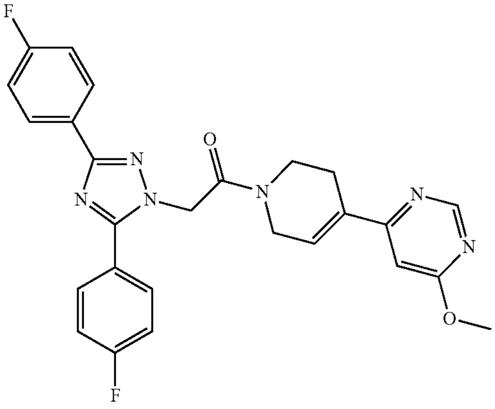
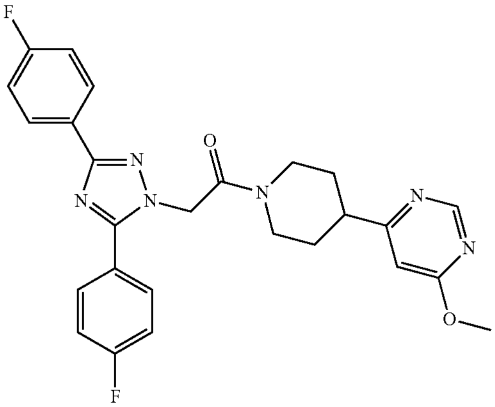
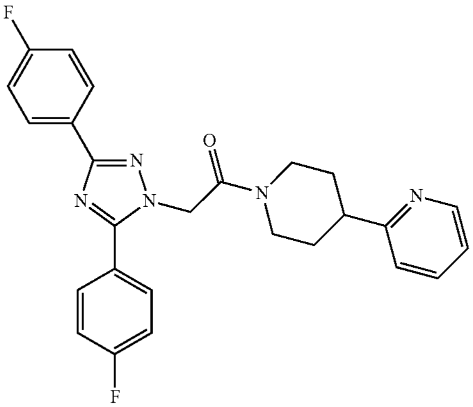
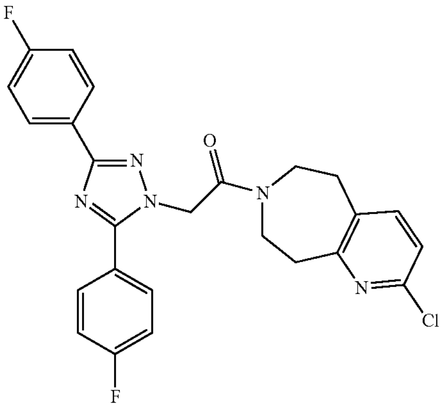

-continued
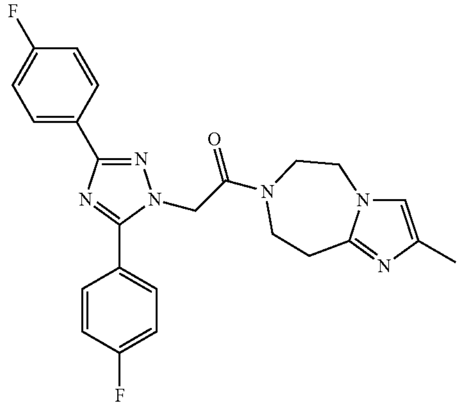
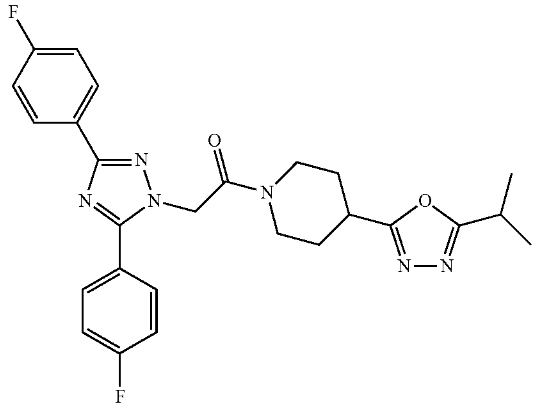
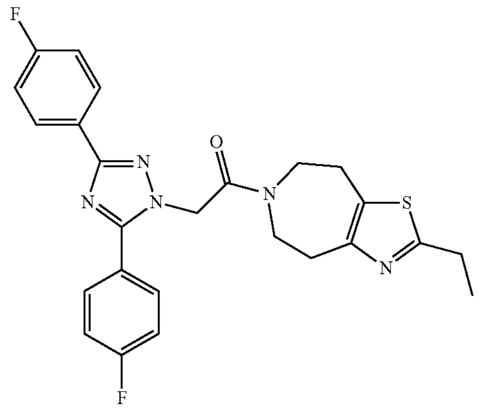
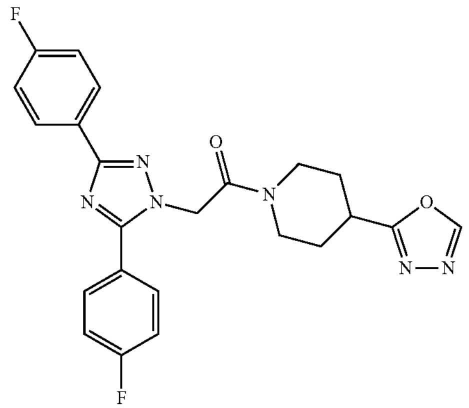
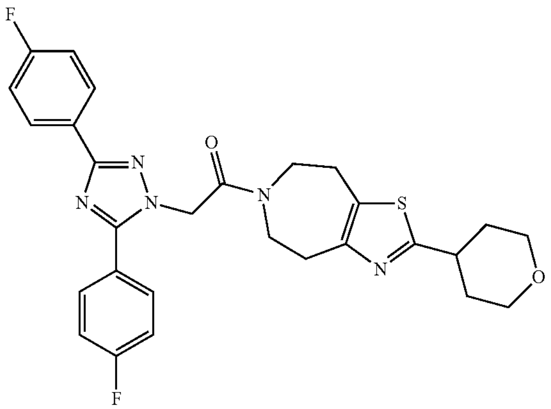
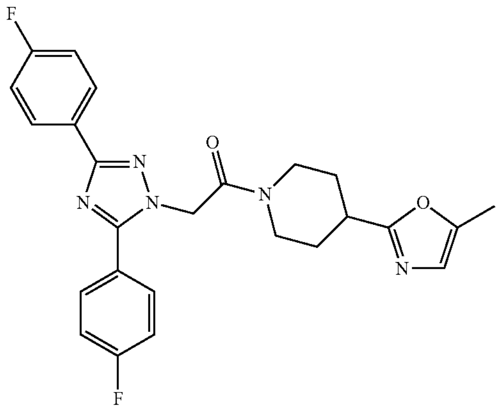
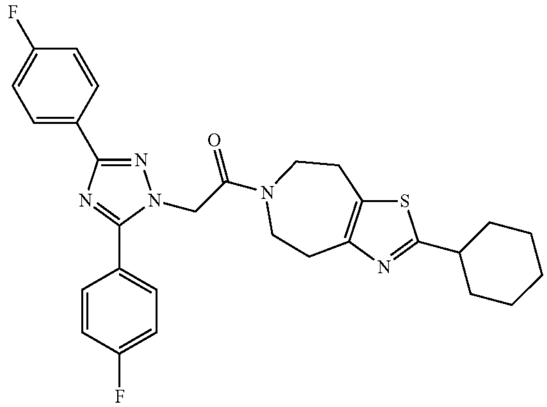
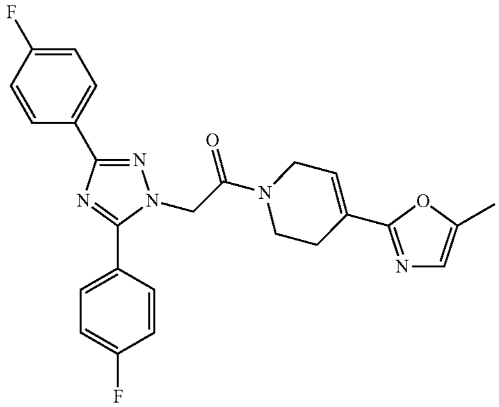
-continued -continued
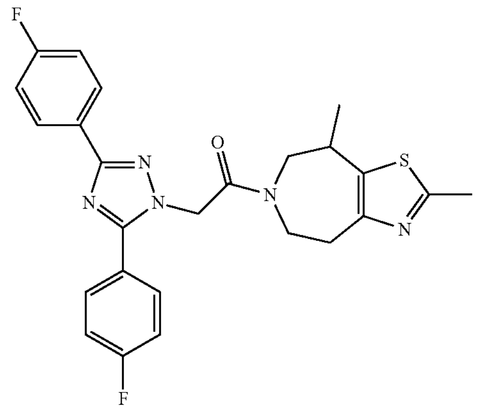
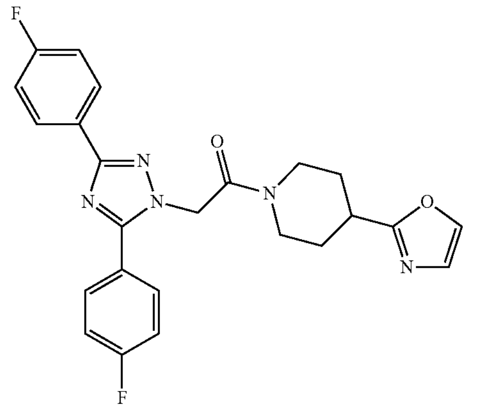
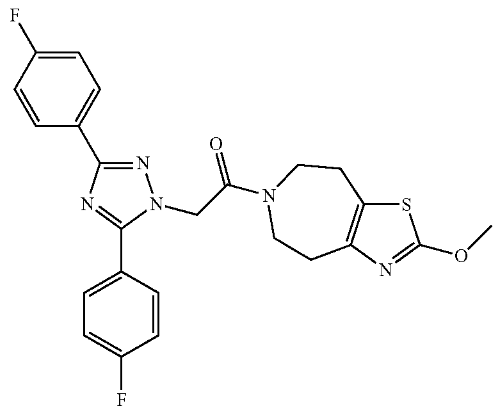
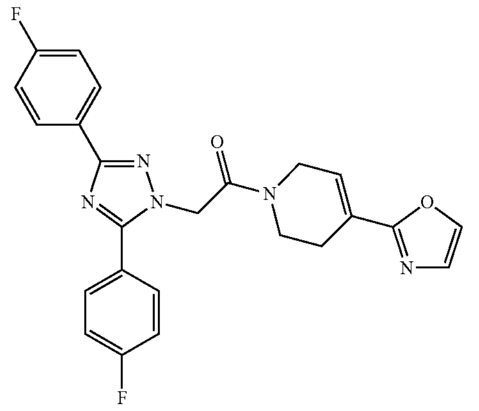
-continued
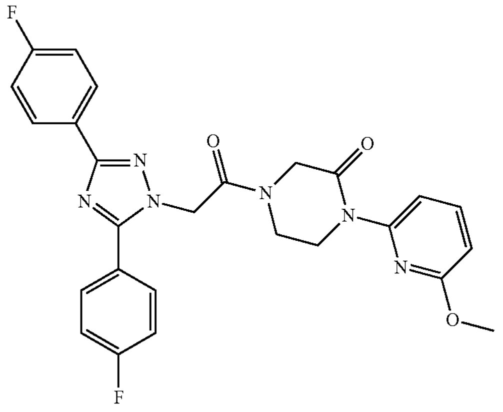
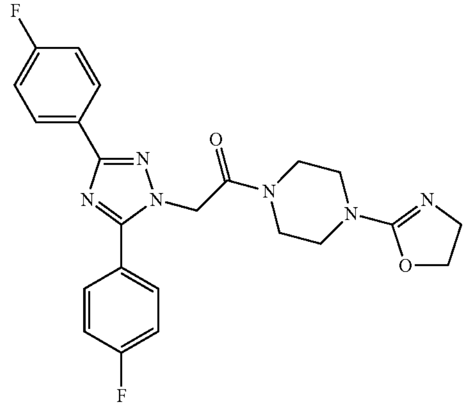
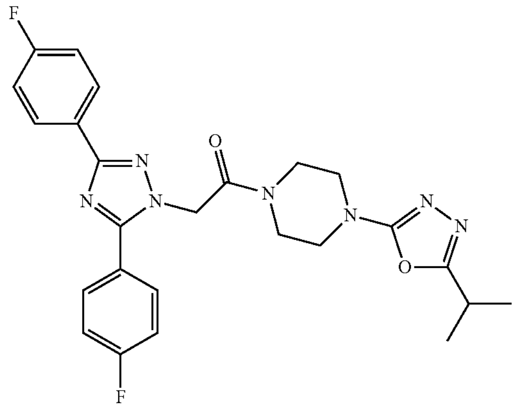
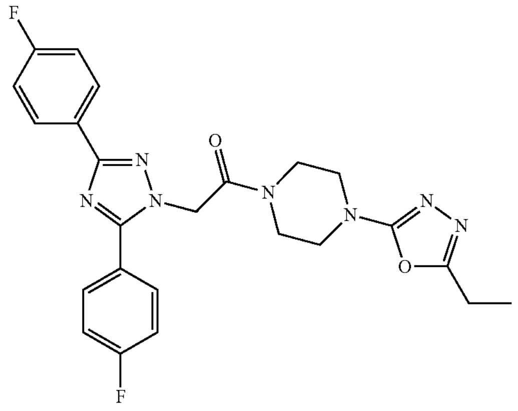

-continued
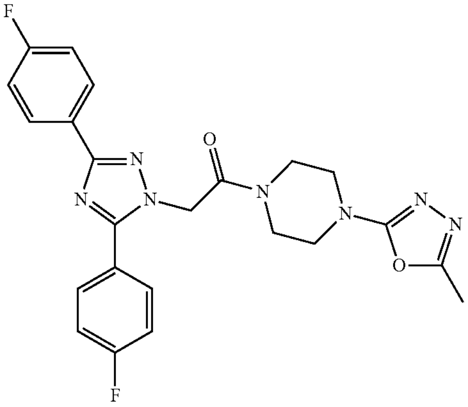
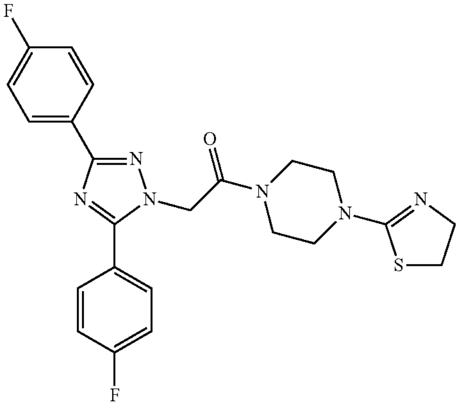
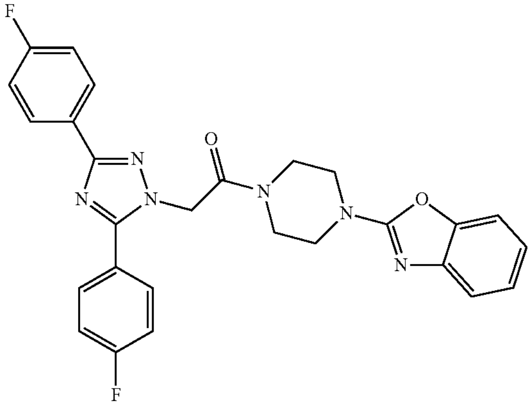
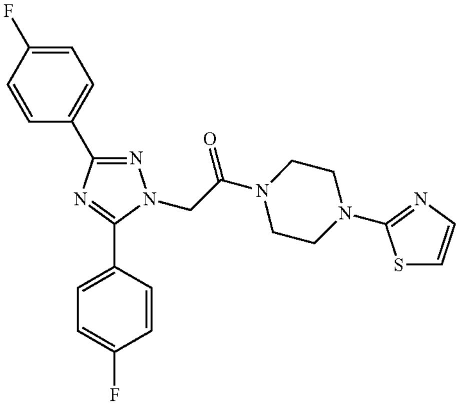
-continued
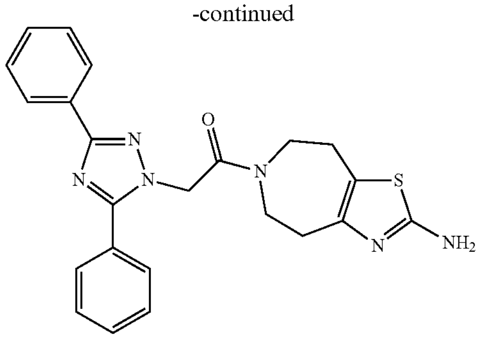
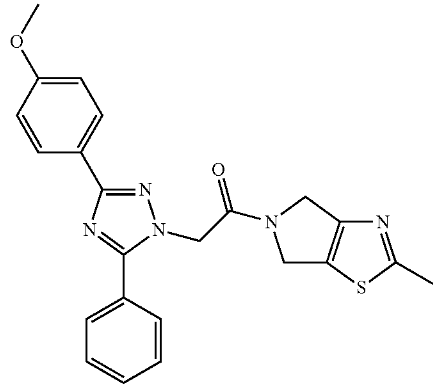
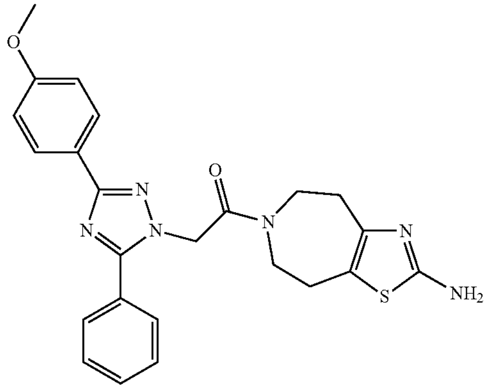
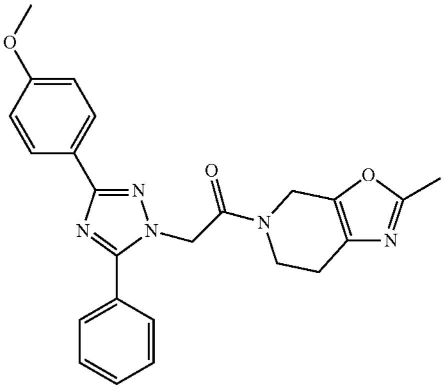

-continued
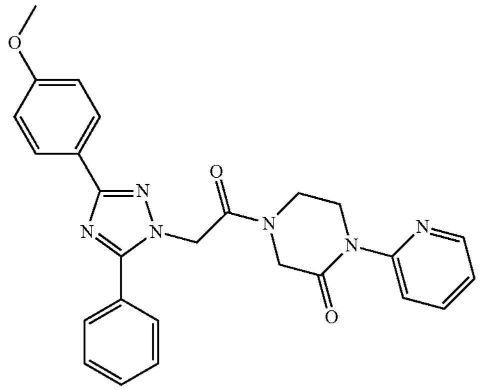
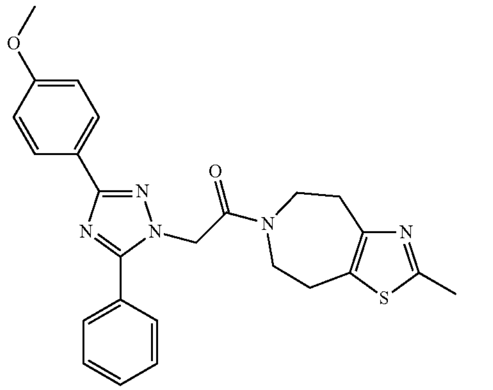
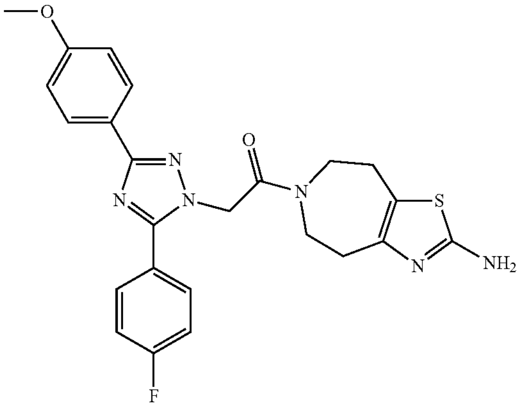
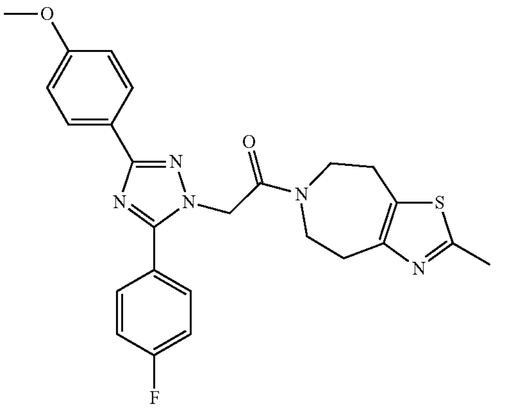
-continued
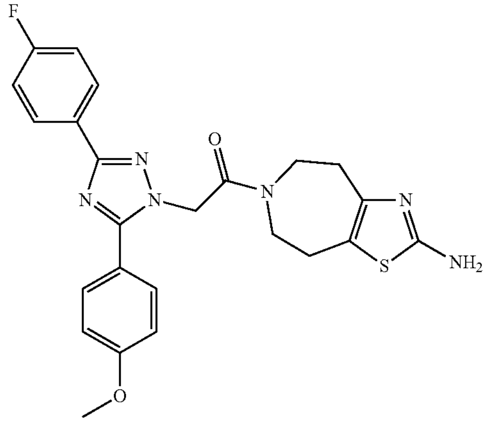
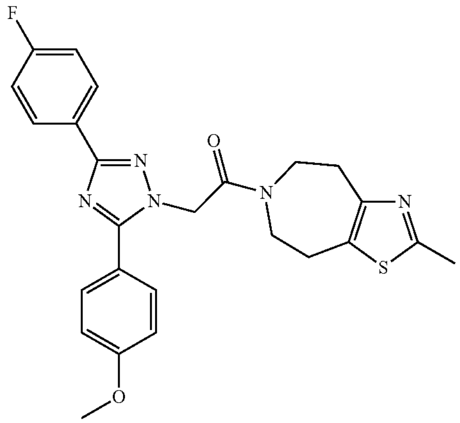
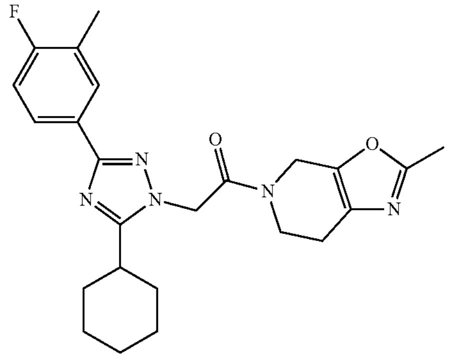
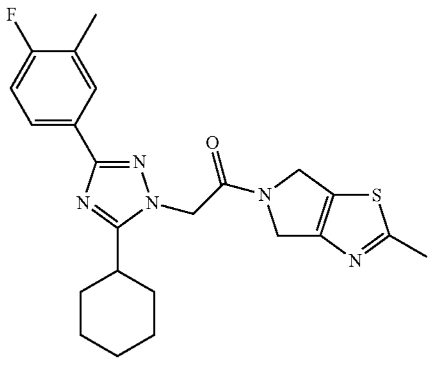

-continued
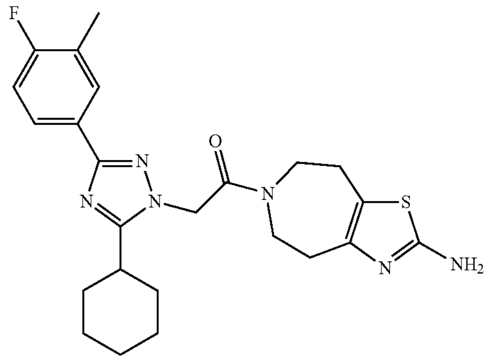
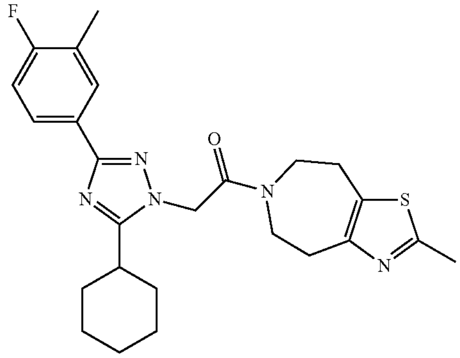
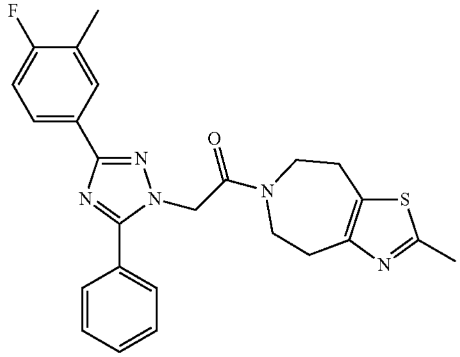
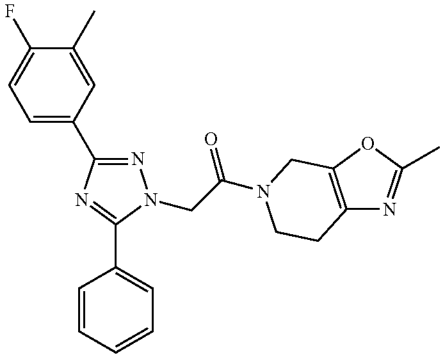
-continued
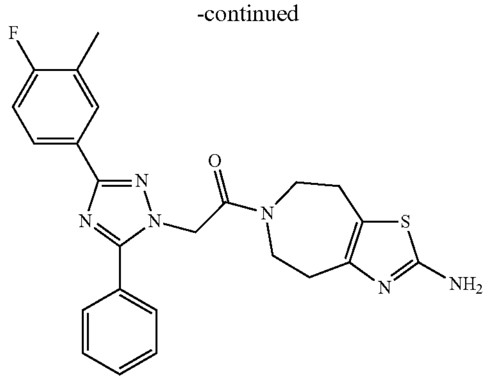
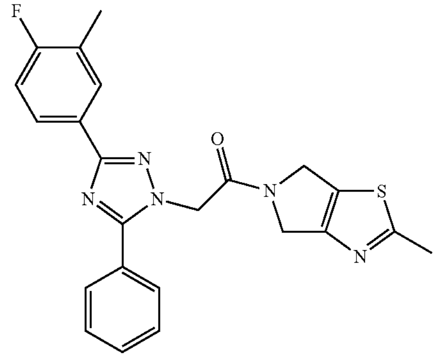
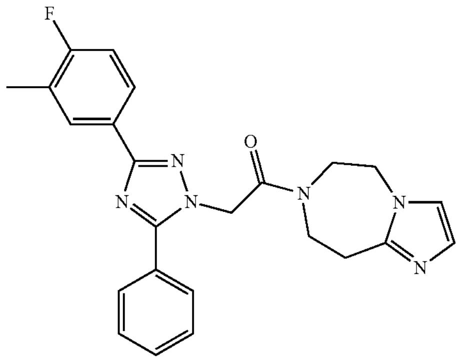
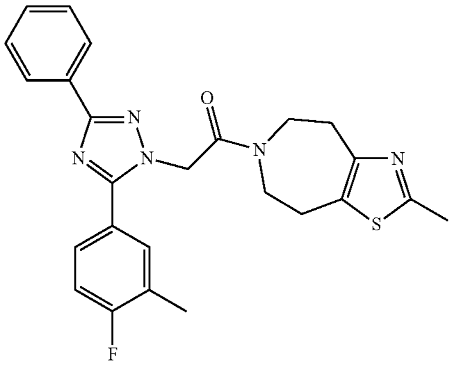

-continued
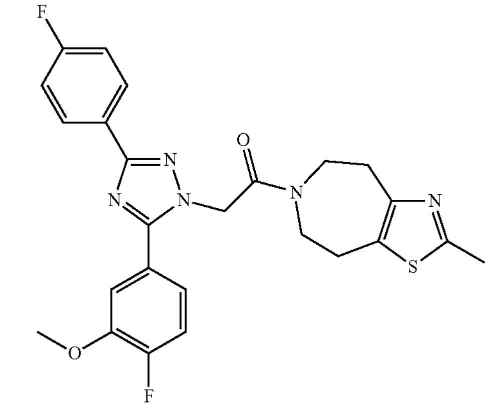
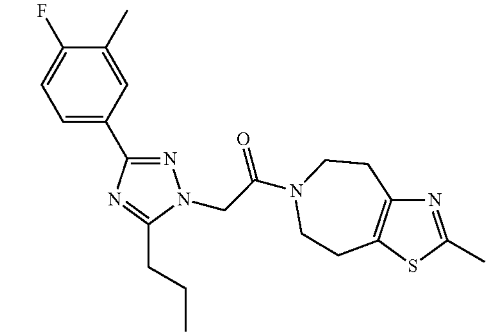
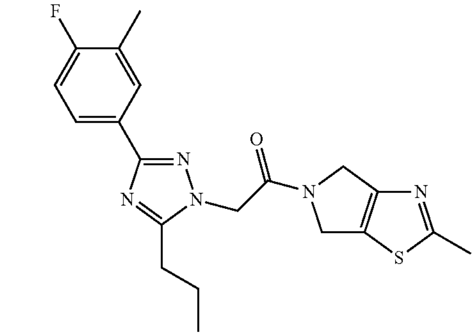
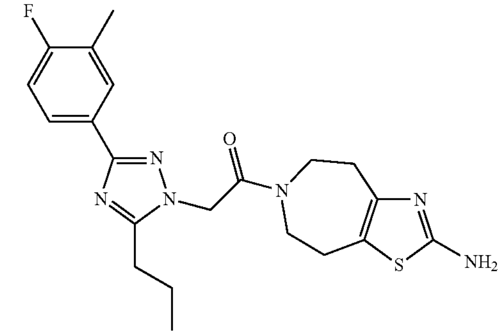
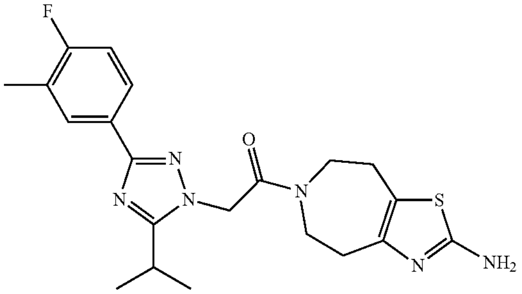
-continued
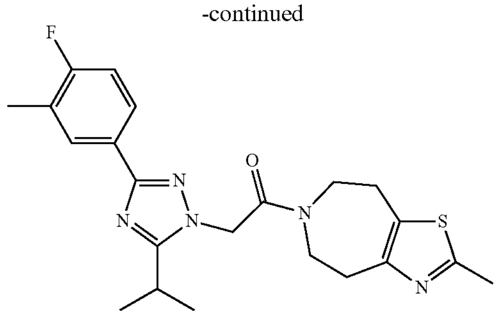
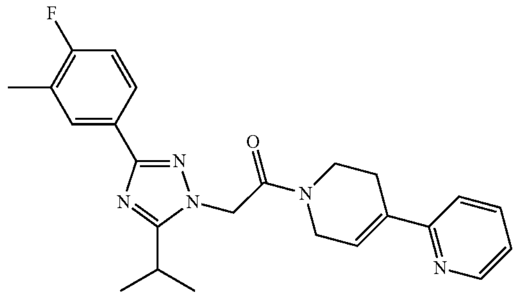
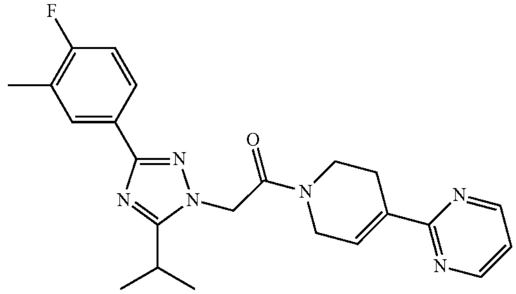
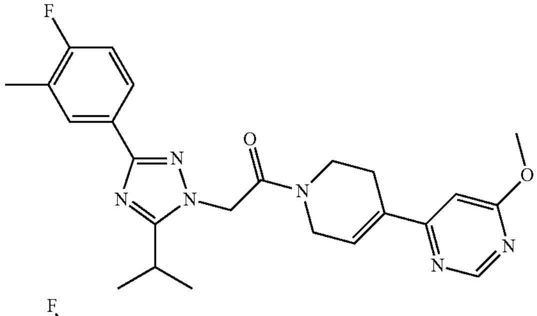
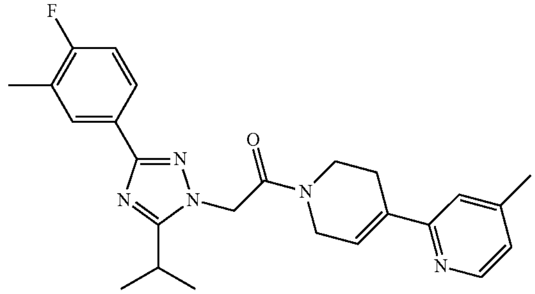

-continued
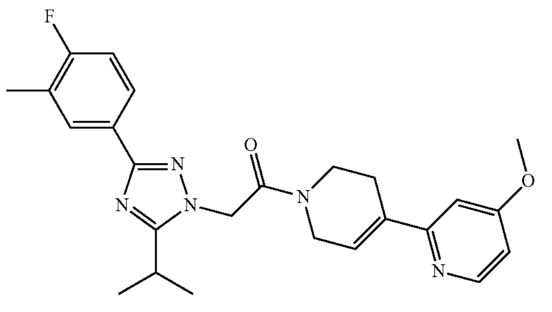
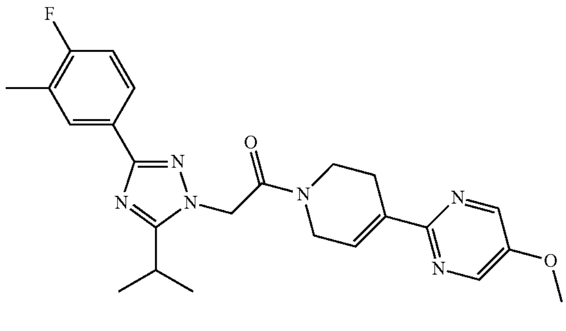
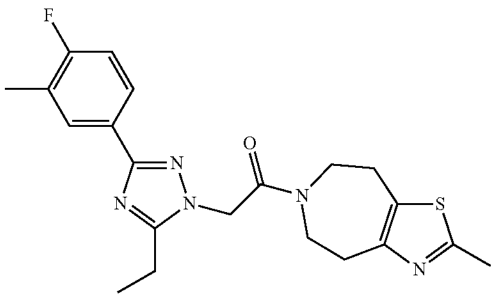
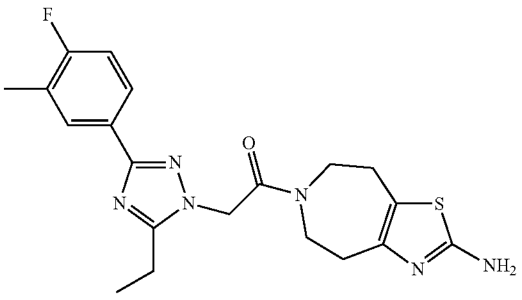
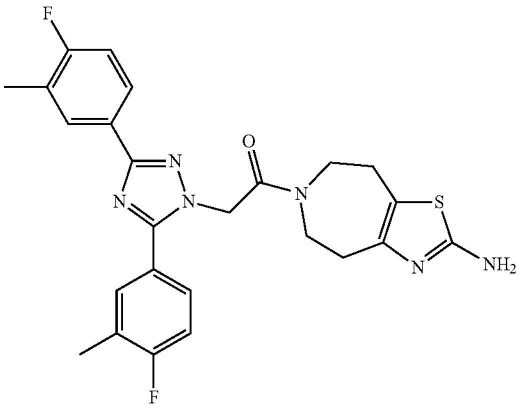
-continued
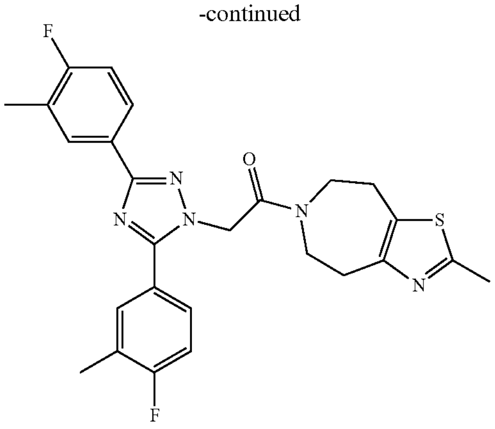
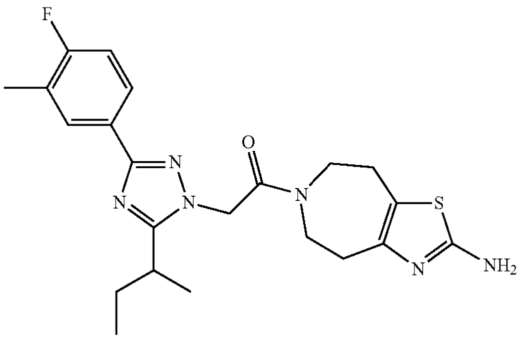
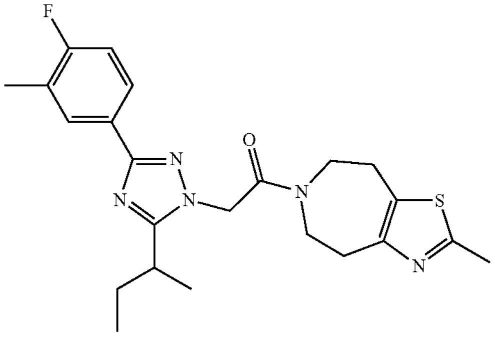
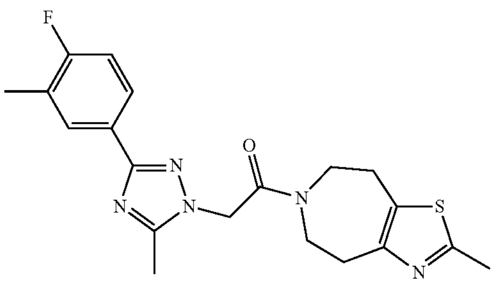

-continued
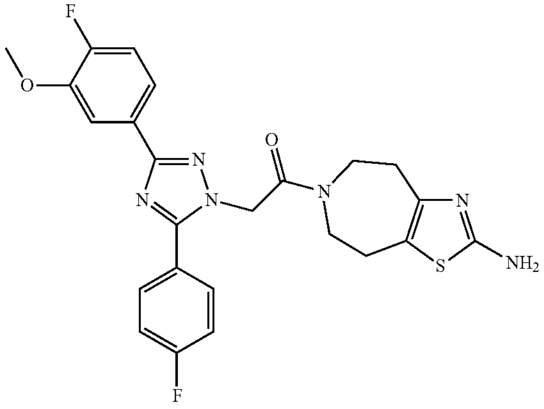
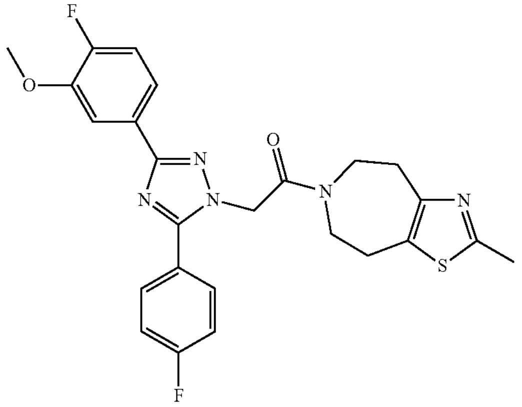
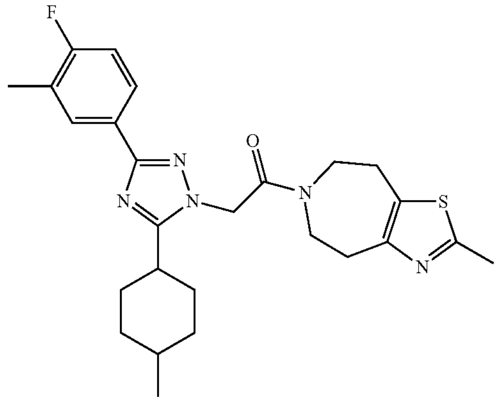
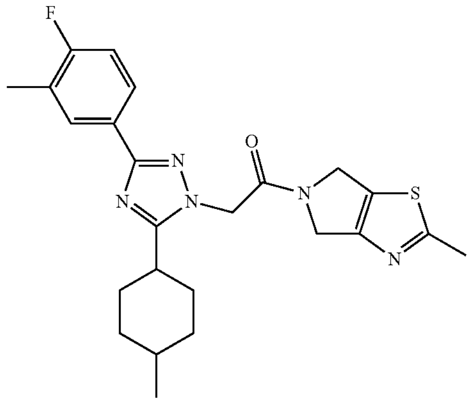
-continued
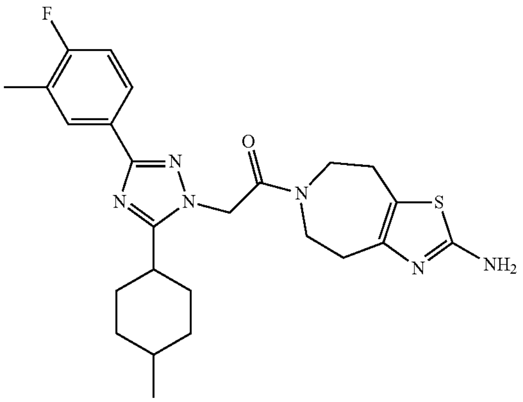
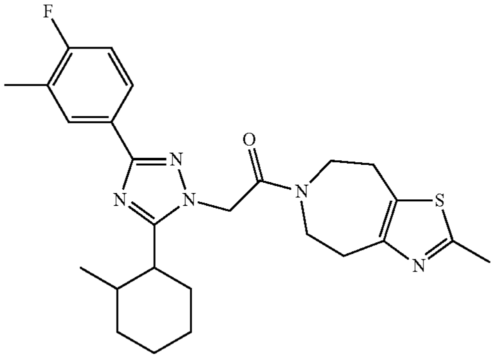
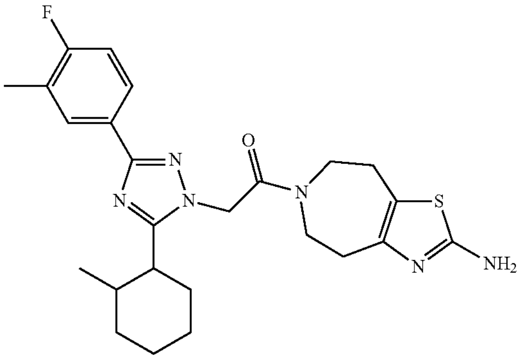
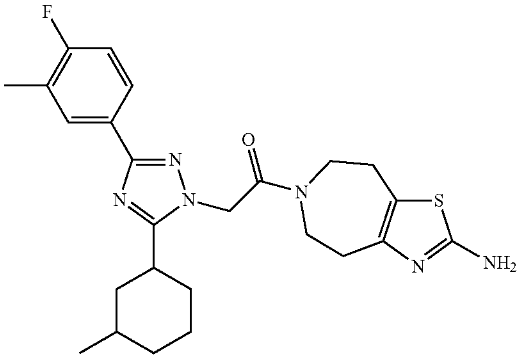

-continued
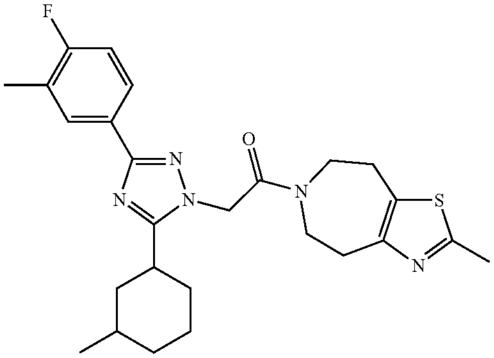
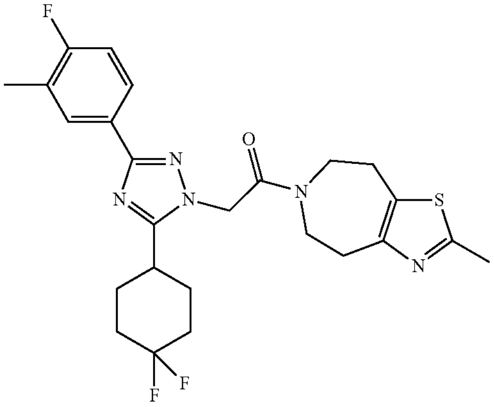
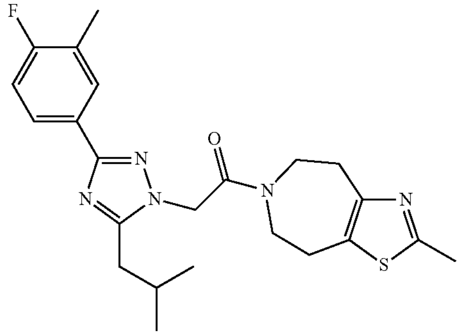
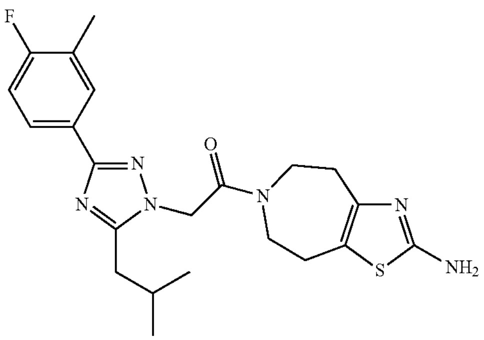
-continued
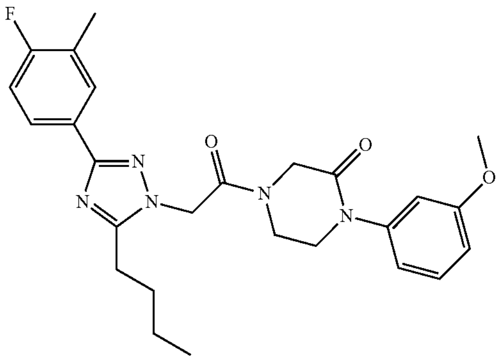
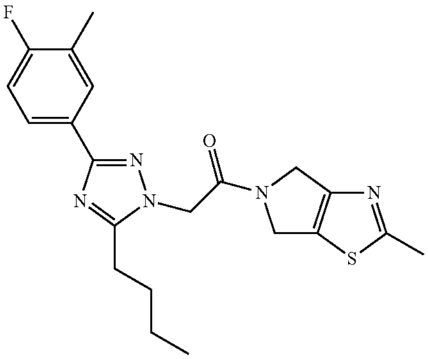
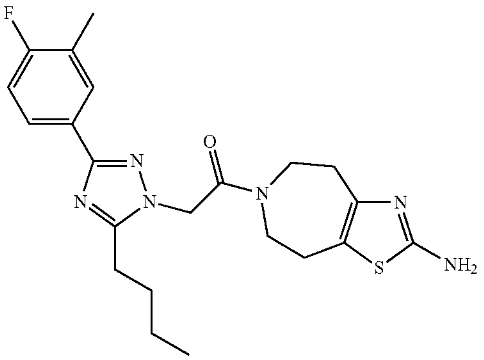
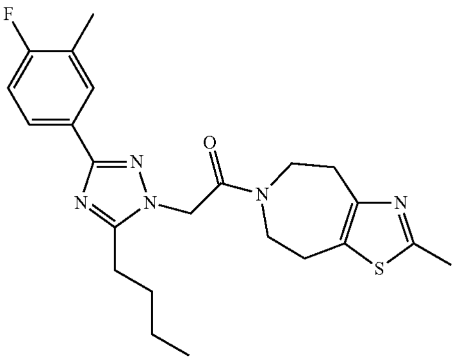

-continued
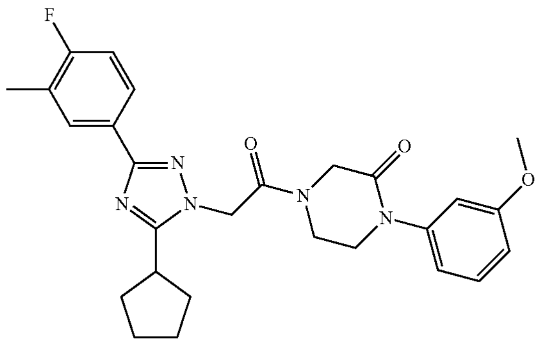
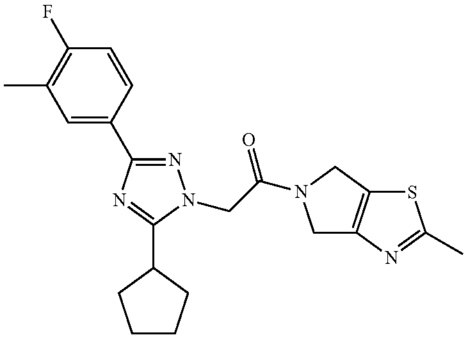
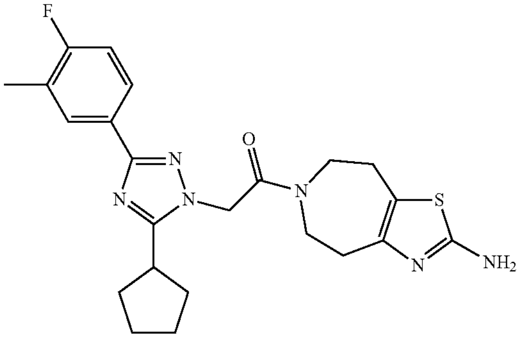
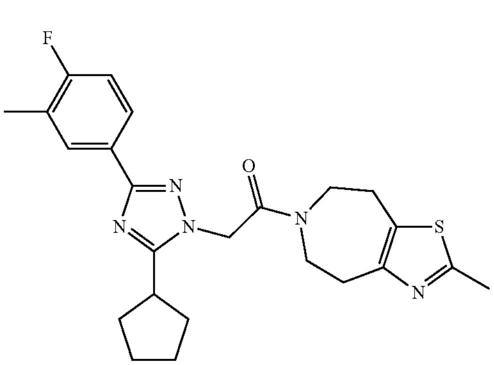
-continued
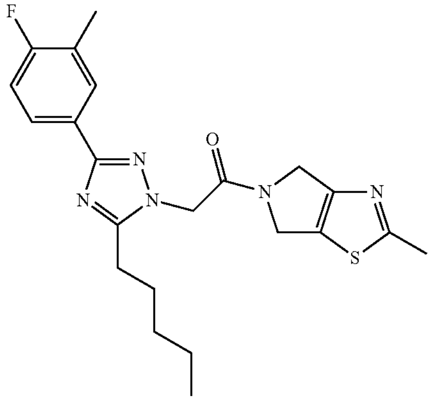
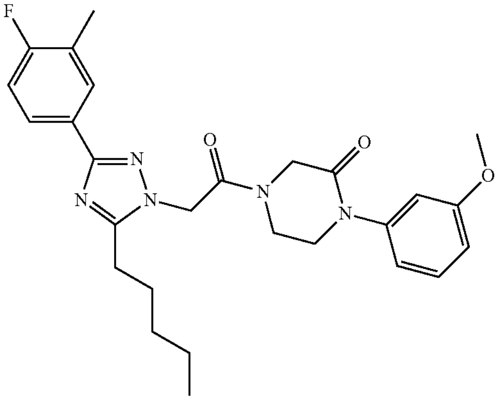
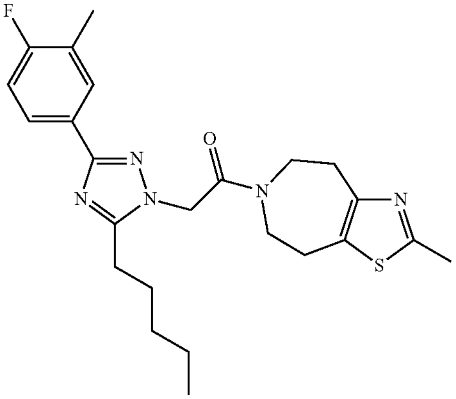
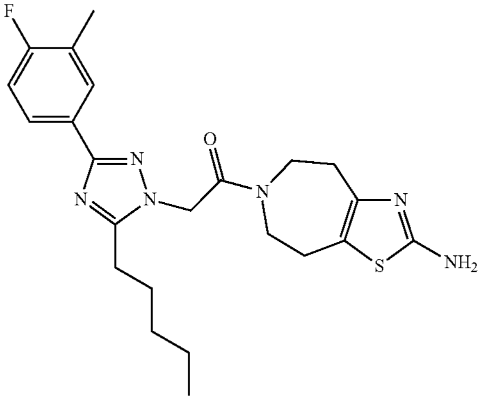

-continued
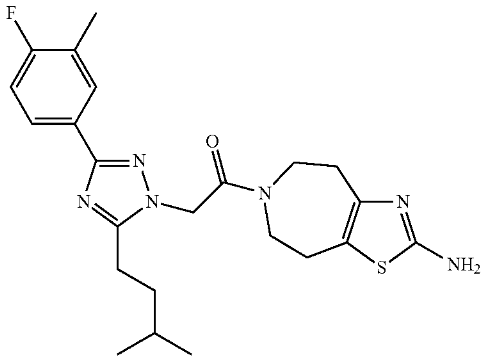
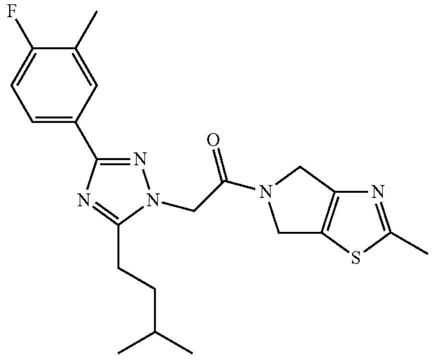
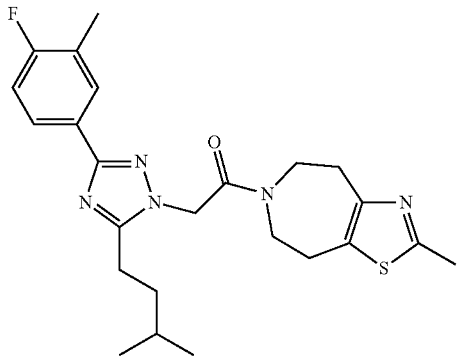
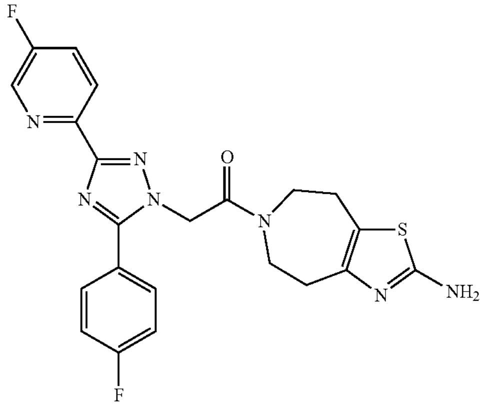
-continued
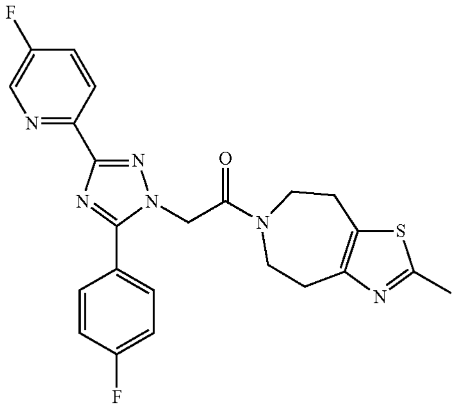
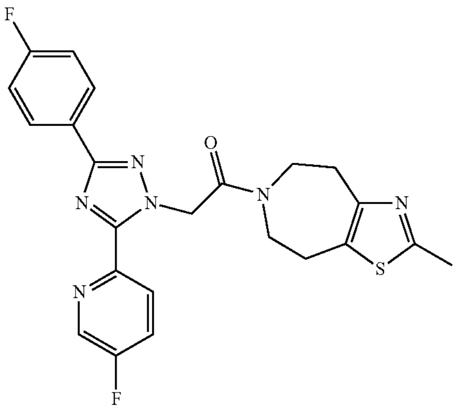
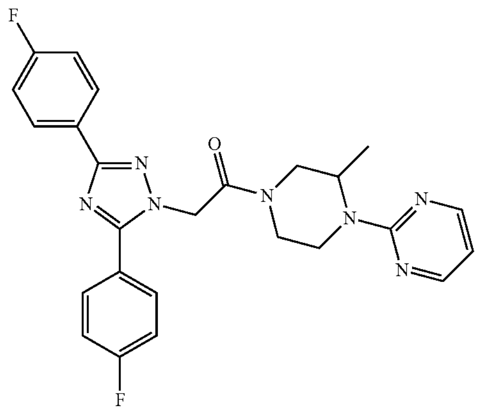
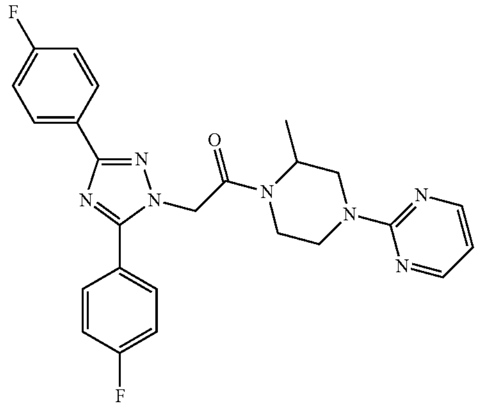

-continued
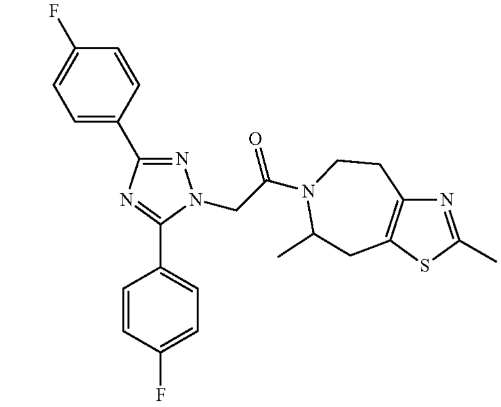
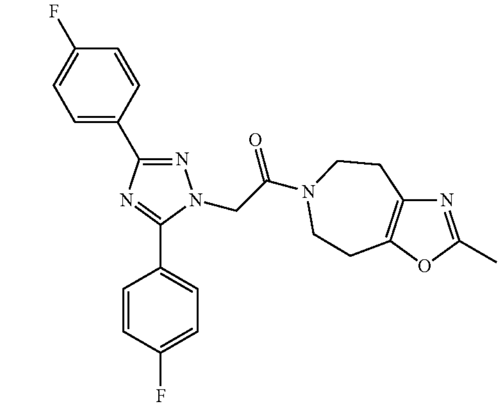
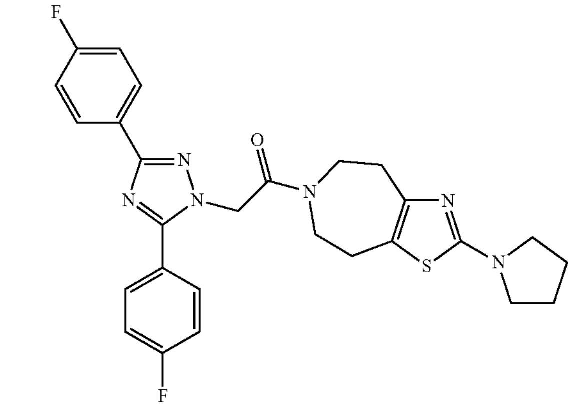
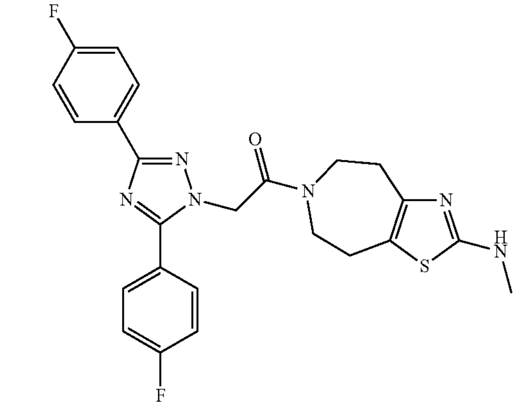
-continued
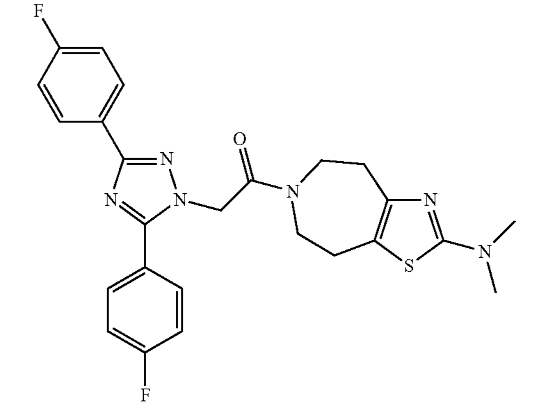
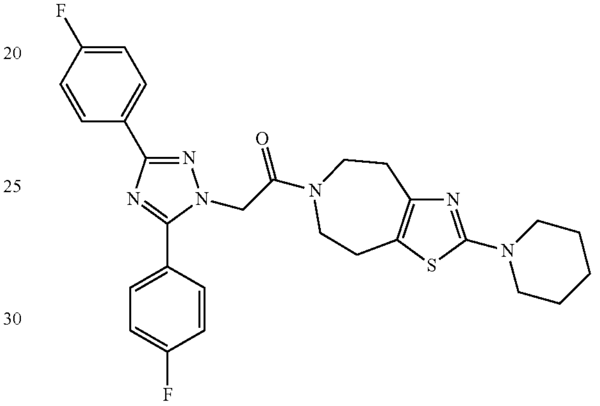
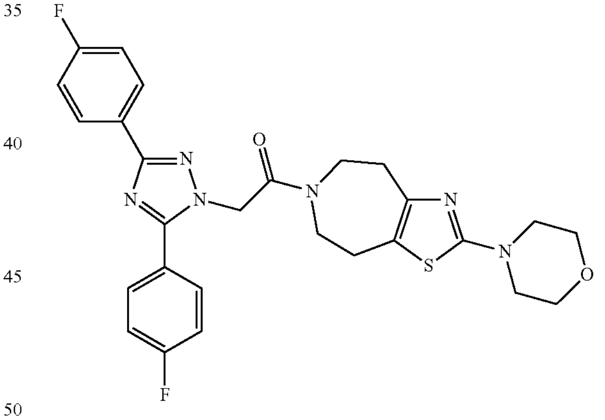
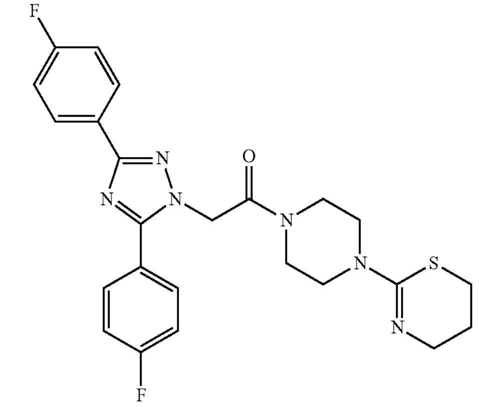

-continued
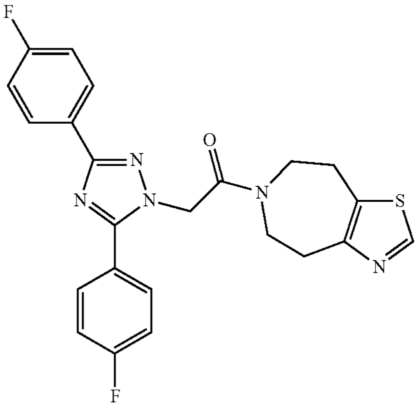
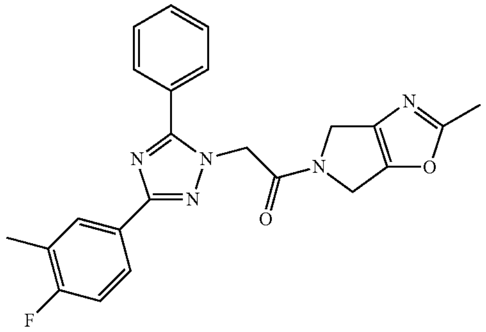
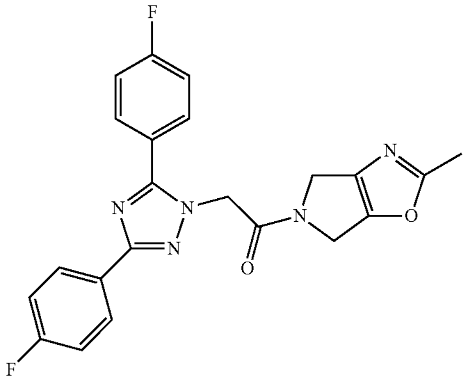
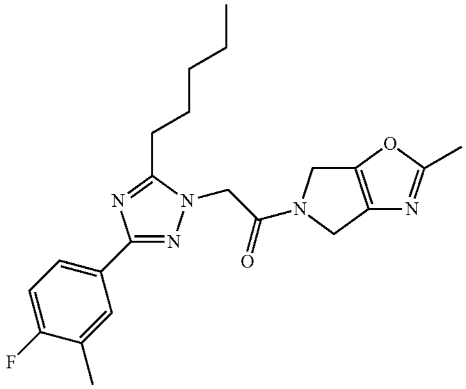
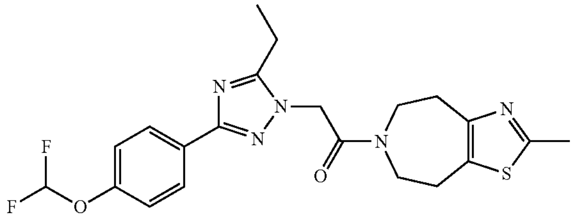
-continued
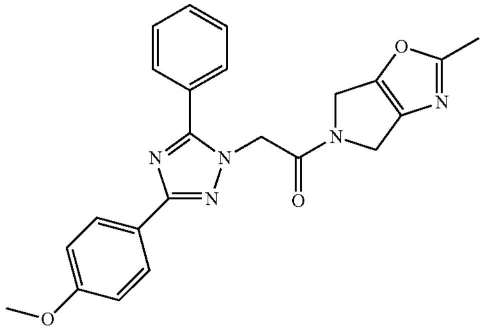
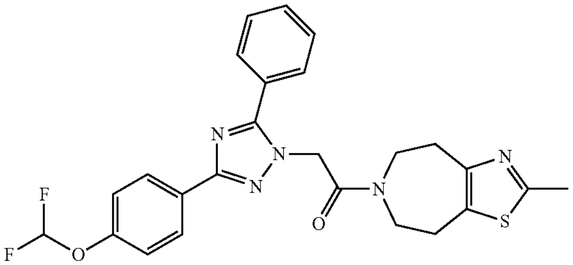
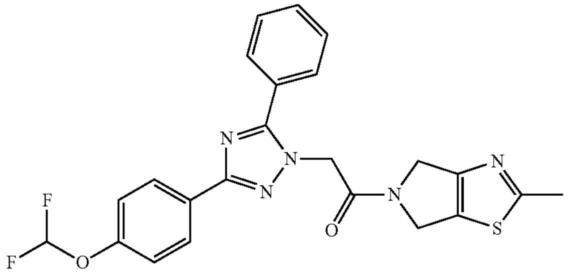
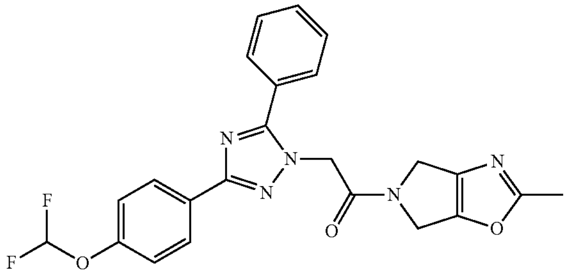
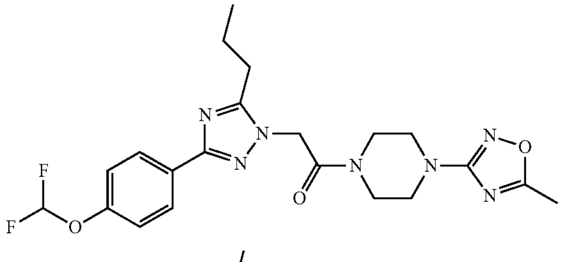
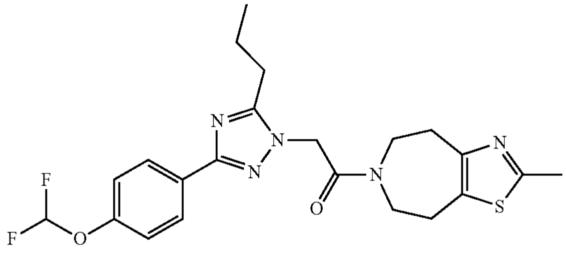

-continued
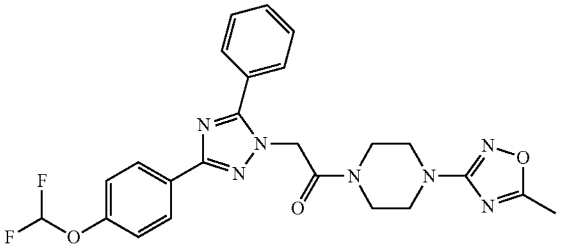
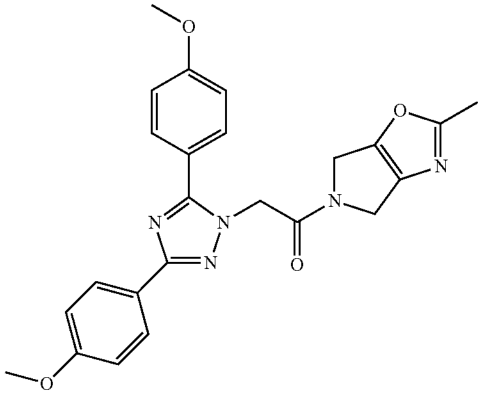
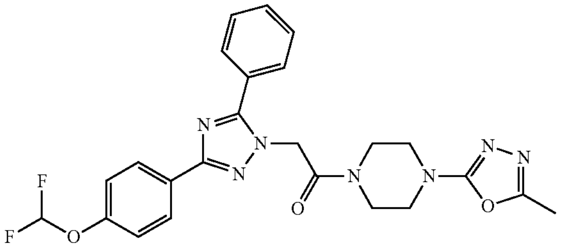
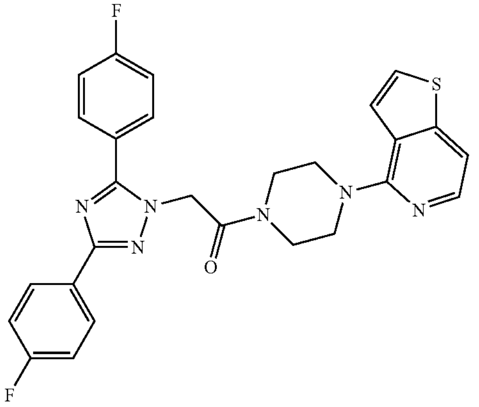
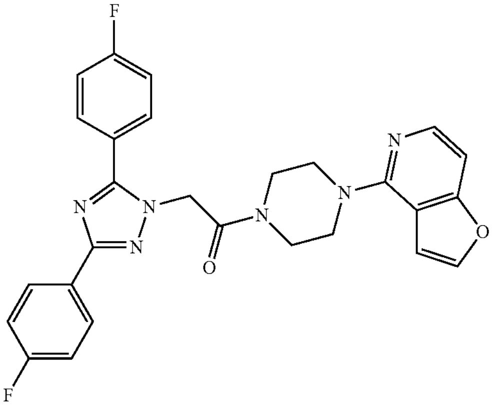
-continued
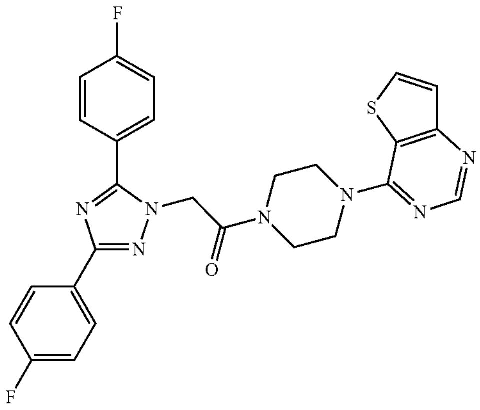
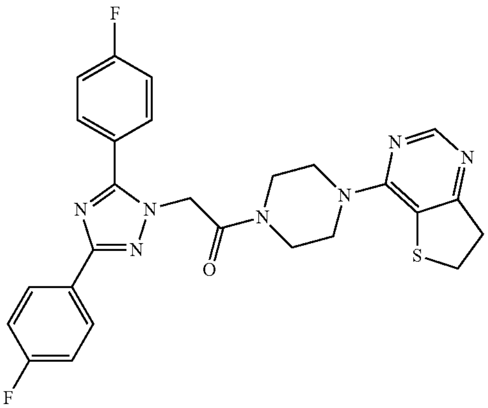
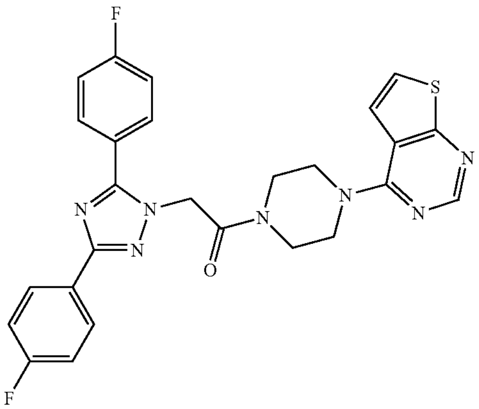
and
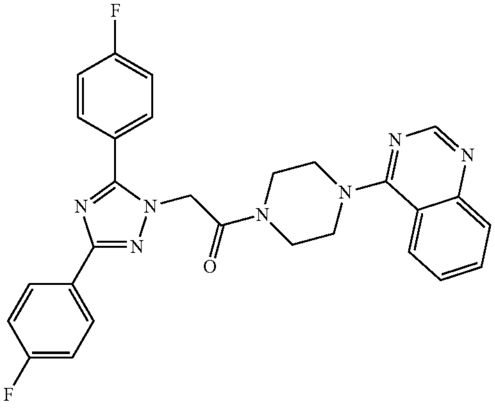
or a physiologically acceptable salt thereof.

11. A pharmaceutical composition comprising a therapeutically effective amount of a compound according to claim 1 or a pharmaceutically acceptable salt thereof in admixture with a pharmaceutically acceptable adjuvant, diluent and/or carrier.

* * * * *